United States Patent
Nomura et al.

(10) Patent No.: US 10,790,451 B2
(45) Date of Patent: Sep. 29, 2020

(54) TRIAZOLE DERIVATIVE, AND LIGHT-EMITTING ELEMENT, LIGHT-EMITTING DEVICE, AND ELECTRONIC DEVICE WITH THE USE OF TRIAZOLE DERIVATIVE

(71) Applicant: Semiconductor Energy Laboratory Co., Ltd., Atsugi-shi, Kanagawa-ken (JP)

(72) Inventors: Hiroko Nomura, Isehara (JP); Sachiko Kawakami, Atsugi (JP); Nobuharu Ohsawa, Zama (JP); Satoshi Seo, Kawasaki (JP)

(73) Assignee: Semiconductor Energy Laboratory Co., Ltd., Kanagawa-ken (JP)

(*) Notice: Subject to any disclaimer, the term of this patent is extended or adjusted under 35 U.S.C. 154(b) by 232 days.

(21) Appl. No.: 15/161,568

(22) Filed: May 23, 2016

(65) Prior Publication Data

US 2016/0268515 A1   Sep. 15, 2016

Related U.S. Application Data

(63) Continuation of application No. 14/064,658, filed on Oct. 28, 2013, now Pat. No. 9,397,299, which is a continuation of application No. 13/450,726, filed on Apr. 19, 2012, now Pat. No. 8,592,056, which is a continuation of application No. 12/153,228, filed on May 15, 2008, now Pat. No. 8,178,217.

(30) Foreign Application Priority Data

May 17, 2007 (JP) ................. 2007-131228

(51) Int. Cl.
| | | |
|---|---|---|
| H01L 51/00 | (2006.01) | |
| C09K 11/06 | (2006.01) | |
| C07D 215/38 | (2006.01) | |
| C07D 249/08 | (2006.01) | |
| C07D 403/14 | (2006.01) | |
| C07D 401/14 | (2006.01) | |
| C07D 403/10 | (2006.01) | |
| C09K 11/02 | (2006.01) | |
| H01L 51/50 | (2006.01) | |
| H01L 51/52 | (2006.01) | |

(52) U.S. Cl.
CPC ........ *H01L 51/0067* (2013.01); *C07D 215/38* (2013.01); *C07D 249/08* (2013.01); *C07D 401/14* (2013.01); *C07D 403/10* (2013.01); *C07D 403/14* (2013.01); *C09K 11/025* (2013.01); *C09K 11/06* (2013.01); *H01L 51/0052* (2013.01); *H01L 51/0058* (2013.01); *H01L 51/0072* (2013.01); *H01L 51/5012* (2013.01); *H01L 51/5016* (2013.01); *H01L 51/5072* (2013.01); *H01L 51/5092* (2013.01); *H01L 51/5203* (2013.01); *Y10S 428/917* (2013.01)

(58) Field of Classification Search
None
See application file for complete search history.

(56) References Cited

U.S. PATENT DOCUMENTS

| | | | |
|---|---|---|---|
| 2,884,424 | A | 4/1959 | Klingsberge |
| 2,888,461 | A | 5/1959 | Klingsberge |
| 5,834,130 | A | 11/1998 | Kido |
| 5,869,199 | A | 2/1999 | Kido |
| 5,935,721 | A | 8/1999 | Shi et al. |
| 6,333,326 | B1 | 12/2001 | Stobie et al. |
| 6,376,490 | B1 | 4/2002 | Bull et al. |
| 6,830,833 | B2 | 12/2004 | Li |
| 7,034,047 | B2 | 4/2006 | Tobe et al. |
| 7,084,164 | B2 | 8/2006 | Tobe et al. |
| 7,094,902 | B2 | 8/2006 | Roberts et al. |
| 7,318,966 | B2 | 1/2008 | Tominaga et al. |
| 7,442,760 | B2 | 10/2008 | Roberts et al. |
| 7,629,060 | B2 | 12/2009 | Oshiyama et al. |
| 7,965,032 | B2 | 6/2011 | Bae et al. |

(Continued)

FOREIGN PATENT DOCUMENTS

| | | |
|---|---|---|
| CN | 001956237 A | 5/2007 |
| DE | 1001992 | 2/1957 |

(Continued)

OTHER PUBLICATIONS

STN Registry database entry for CAS RN 332848-71-2, entry date Apr. 26, 2001, Accessed Mar. 31, 2018.*

(Continued)

*Primary Examiner* — Alicia L Otton
(74) *Attorney, Agent, or Firm* — Robinson Intellectual Property Law Office; Eric J. Robinson

(57) ABSTRACT

It is an object of the present invention to provide a novel triazole derivative. Further, it is another object of the present invention to provide a light-emitting element having high luminous efficiency with the use of the novel triazole derivative. Moreover, it is still another object of the present invention to provide a light-emitting device and electronic devices which have low power consumption. A light-emitting element having high luminous efficiency can be manufactured with the use of a triazole derivative which is a 1,2,4-triazole derivative, in which an aryl group or a heteroaryl group is bonded to each of 3-position, 4-position, and 5-position, and in which any one of the aryl group or heteroaryl group has a 9H-carbazol-9-yl group.

10 Claims, 57 Drawing Sheets

(56) References Cited

U.S. PATENT DOCUMENTS

| | | | |
|---|---|---|---|
| 7,990,046 B2 | 8/2011 | Iwakuma et al. |
| 8,178,217 B2 | 5/2012 | Nomura et al. |
| 8,425,194 B2 | 4/2013 | Liotta et al. |
| 8,580,391 B2 | 11/2013 | Iwakuma et al. |
| 8,580,398 B2 | 11/2013 | Iwakuma et al. |
| 8,592,056 B2 | 11/2013 | Nomura et al. |
| 8,685,543 B2 | 4/2014 | Iwakuma et al. |
| 8,741,450 B2 | 6/2014 | Iwakuma et al. |
| 2002/0182441 A1 | 12/2002 | Lamansky et al. |
| 2003/0216385 A1 | 11/2003 | Tobe et al. |
| 2004/0086745 A1 | 5/2004 | Iwakuma et al. |
| 2005/0031899 A1 | 2/2005 | Nomura et al. |
| 2005/0048310 A1 | 3/2005 | Cocchi et al. |
| 2007/0122655 A1 | 5/2007 | Deaton et al. |
| 2007/0222376 A1 | 9/2007 | Ohsawa et al. |
| 2007/0257600 A1 | 11/2007 | Matsuura et al. |
| 2007/0296328 A1 | 12/2007 | Matsuura et al. |
| 2009/0036623 A1 | 2/2009 | Tsuda et al. |
| 2009/0102361 A1 | 4/2009 | Miki et al. |
| 2009/0160324 A1 | 6/2009 | Nomura et al. |
| 2012/0298975 A1 | 11/2012 | Iwakuma et al. |
| 2013/0285025 A1 | 10/2013 | Miki et al. |
| 2014/0001460 A1 | 1/2014 | Iwakuma et al. |
| 2014/0048787 A1 | 2/2014 | Miki et al. |

FOREIGN PATENT DOCUMENTS

| | | |
|---|---|---|
| DE | 2133159 | 1/1973 |
| DE | 272860 | 10/1989 |
| DE | 102005000903 | 7/2006 |
| DE | 102005000904 | 8/2006 |
| EP | 0647694 A | 4/1995 |
| EP | 0712916 A | 5/1996 |
| EP | 1293503 A | 3/2003 |
| EP | 1341403 A | 9/2003 |
| EP | 1424381 A | 6/2004 |
| EP | 1486550 A | 12/2004 |
| EP | 1489155 A | 12/2004 |
| EP | 1715728 A | 10/2006 |
| EP | 1718121 A | 11/2006 |
| EP | 1942107 A | 7/2008 |
| EP | 2169028 A | 3/2010 |
| EP | 2248870 A | 11/2010 |
| EP | 2364964 A | 9/2011 |
| EP | 2365735 A | 9/2011 |
| EP | 2770036 A | 8/2014 |
| GB | 1096600 | 12/1967 |
| JP | 57-090635 A | 6/1982 |
| JP | 63-013049 A | 1/1988 |
| JP | 07-090260 A | 4/1995 |
| JP | 09-188756 A | 7/1997 |
| JP | 09-291274 A | 11/1997 |
| JP | 10-270166 A | 10/1998 |
| JP | 11-506123 | 6/1999 |
| JP | 2000-068059 A | 3/2000 |
| JP | 2002-352957 A | 12/2002 |
| JP | 2003-007467 A | 1/2003 |
| JP | 2004-014440 A | 1/2004 |
| JP | 2004-071380 A | 3/2004 |
| JP | 2004-152527 A | 5/2004 |
| JP | 2004-182737 A | 7/2004 |
| JP | 2004-185967 A | 7/2004 |
| JP | 2004-214050 A | 7/2004 |
| JP | 2004-217557 A | 8/2004 |
| JP | 2004-220931 A | 8/2004 |
| JP | 2004-253298 A | 9/2004 |
| JP | 2004-311410 A | 11/2004 |
| JP | 2004-325749 A | 11/2004 |
| JP | 2004-335427 A | 11/2004 |
| JP | 2005-044790 A | 2/2005 |
| JP | 2006-514148 | 4/2006 |
| JP | 2006-143765 A | 6/2006 |
| JP | 2006-193706 A | 7/2006 |
| JP | 2008-234902 A | 10/2008 |
| JP | 2009-024698 A | 2/2009 |
| JP | 2009-529035 | 8/2009 |
| WO | WO-1997/032873 | 9/1997 |
| WO | WO-1998/038186 | 9/1998 |
| WO | WO-2001/087855 | 11/2001 |
| WO | WO-2003/007394 | 1/2003 |
| WO | WO-2003/078541 | 9/2003 |
| WO | WO-2003/080760 | 10/2003 |
| WO | WO-2004/102615 | 11/2004 |
| WO | WO-2005/076668 | 8/2005 |
| WO | WO-2005/076669 | 8/2005 |
| WO | WO-2006/126439 | 11/2006 |
| WO | WO-2007/026847 | 3/2007 |
| WO | WO-2007/102683 | 9/2007 |

OTHER PUBLICATIONS

STN Registry database entry for CAS RN 482625-90-1, entry date Jan. 29, 2003, Accessed Mar. 31, 2018.*
STN Registry database entry for CAS RN 332910-38-0 (Published in STN Registry Apr. 26, 2001); Accessed Aug. 20, 2018.*
STN Registry database entry for CAS RN 29091-56-3 (Published in STN Registry Nov. 16, 1984); Accessed Aug. 20, 2018.*
STN Registry database entry for CAS RN 197078-73-2, Entry Date Nov. 11, 1997, Accessed Mar. 13, 2019.*
STN Registry database entry for CAS RN 15944-28-2, Entry Date Nov. 16, 1984, Accessed Mar. 13, 2019.*
STN Registry database entry for CAS RN 28194-01-6, Entry Date Nov. 16, 1984, Accessed Aug. 30, 2019.*
STN Registry database entry for CAS RN 29091-61-0, Entry Date Nov. 16, 1984, Accessed Jan. 6, 2020.*
Kim.J et al., "New host materials with high triplet energy level for blue-emitting electrophosphorescent device", Synthetic Metals, 2007, vol. 157, No. 18-20, pp. 743-750.
International Search Report (Application No. PCT/JP2008/058584) dated Jun. 10, 2008.
Written Opinion (Application No. PCT/JP2008/058584) dated Jun. 10, 2008.
Lange.J et al., "4(H)-1,2,4-Triazole Derivatives With Expected Biological Activity. Part 1. Preparation of 3,5-Diphenyl-4-Aryl-4(H)-1,2,4-Triazoles From Bis-(α-Chlorobenzylidene)-Hydrazine and Substituted Anilines", Diss. Pharm. Pharmacol. (Dissertationes Pharmaceuticae et Pharmacologicae), 1970, vol. 22, No. 4, pp. 217-221.
Deshmukh.M et al., "New Route to Synthesis and QSAR Study of 1,2,4-Aryl Substituted Triazoles", Synthetic Communications, Jul. 1, 2004, vol. 34, No. 14, pp. 1-4.
Liu.Z et al., "5-(4-Chlorophenyl)-4-(4-methoxyphenyl)-3-(2-pyridyl)-4H-1,2,4-triazole", Acta. Cryst.(Acta Crystallographica Section E: Structure Reports Online), Dec. 1, 2007, vol. 63, No. 12, p. o4634.
Artamonova.T et al., "Synthesis of 3,4,5-Trisubstituted 1,2,4-Triazoles from 5-Aryltetrazoles", Russian Journal of Organic Chemistry, Feb. 27, 1998, vol. 34, No. 7, pp. 1040-1042.
Tartakovsky.V et al., "New approaches to synthesis of tris[1,2,4]triazolo[1,3,5]triazines", Russian Chemical Bulletin, Mar. 1, 2005, vol. 54, No. 3, pp. 719-725.
O.A.Yasinskii et al., "Elektronnaya provodimost i vliyanie mostikovyh grupp v n-nitroaromaticheskih soedineniyah", Zhurnal Obshchei Khimii, 1977, vol. 47, pp. 211-217.
Heller.G, "Umwandlung von Chinazolonen in Triazolderivate", Journal Fur Praktische Chemie, 1928, vol. 120, No. 1, pp. 49-63.
Nuriev.V et al., "Synthetic pathways to a family of pyridine-containing azoles—promising ligands for coordination chemistry", ARKIVOC, 2005, vol. 2005, No. 4, pp. 208-224.
Hu.J et al., "4-(4-Chlorophenyl)-3-phenyl-5-(4-pyridyl)-4H-1,2,4-triazole", Acta. Cryst.(Acta Crystallographica Section E: Structure Reports Online), Dec. 1, 2007, vol. 63, No. 12, p. o4671.
Zhang.S et al., "4-(4-Chlorophenyl)-5-(4-methylphenyl)-3-(2-pyridyl)-4H-1,2,4-triazole", Acta. Cryst.(Acta Crystallographica Section E: Structure Reports Online), Apr. 1, 2006, vol. 62, No. 4, pp. o1279-o1280.
Chen.W et al., "4-(p-Bromophenyl)-3,5-bis(2-pyridyl)-4H-1,2,4-triazole", Acta. Cryst.(Acta Crystallographica Section C), Jun. 1, 1998, vol. 54, No. 6, pp. 851-852.

(56) References Cited

OTHER PUBLICATIONS

Wang.Z et al., "3,5-Bis(2-pyridyl)-4-p-chlorophenyl-4H-1,2,4-triazole", Acta. Cryst.(Acta Crystallographica Section C), Mar. 1, 1998, vol. 54, No. 3, pp. 438-439.

Chiriac.C, "A New Method for the Preparation of Triaryl-s-Triazoles From Diaroylhydrazines", Rev. Roum. Chim. (Revue Roumaine De Chimie), May 1, 1982, vol. 27, No. 5, pp. 645-649.

Bender.M et al., "Infrared Absorption of Aryl-Substituted 1,2,4-(H)-Triazoles in the Triazole-Ring Stretching Vibrations Region", Bulletin De L'Academie Polonaise Des Sciences, 1980, vol. 28, No. 11-12, pp. 701-708.

Carter.K, "Aryl Fluoride Monomers in Nucleophilic Aromatic Substitution Polymerization:Evaluation of Monomer Reactivity by 19F NMR Spectroscopy", Macromolecules, 1995, vol. 28, No. 19, pp. 6462-6470, American Chemical Society.

Huisgen.R et al., "Die Synthese von 1.2.4-Triazolen aus 5-substituierten Tetrazolen and Carbonsaure-imidchloriden", Chem.Ber. (Chemische Berichte), 1960, vol. 93, pp. 2885-2891.

Grimshaw.J et al., "Electrochemical Reactions. Part 25. A Comparison of the Reductive and Photochemical Cyclization of Some i-(2-Chlorophenyl)-j-Phenyltriazoles", Proc. R. IR. Acad. (Proceedings of the Royal Irish Academy. Section B: Biological, Geological, and Chemical Science), 1983, vol. 83, pp. 93-101.

Li.Z et al., "Synthesis and Light-Emitting Properties of Bipolar Oligofluorenes Containing Triarylamine and 1,2,4-Triazole Moieties", Organic Letters, Aug. 15, 2006, vol. 8, No. 19, pp. 4271-4274.

Chen.S et al., "Luminescent copoly(aryl ether)s with new electron-transporting bis(3-(trifluoromethyl)phenyl)-1,3,4-oxadiazole or bis(3-(trifluoromethyl)phenyl)-4-(4-hexyloxyphenyl)-4H-1,2,4-triazole segments", Journal of Polymer Science Part A: Polymer Chemistry, Dec. 1, 2004, vol. 42, No. 23, pp. 5900-5910.

Chen.S et al., "Connector Effect in Electroluminescent Properties of Poly(p-phenylene vinylene) Derivatives Containing Triazole Chromophores", Macromol. Chem. Phys.(Macromolecular Chemistry and Physics), Jun. 24, 2006, vol. 207, No. 12, pp. 1070-1079.

Lu.J et al., "Novel Soluble and Fluorescent Poly(arylene ether)s Containing p-Quaterphenyl, 2,5-Bis(4-phenylphenyl)oxadiazole, or 2,5-Bis(4-phenylphenyl)triazole Groups", Macromolecules, 2001, vol. 34, No. 17, pp. 5860-5867, American Chemical Society.

Tsai.L et al., "Novel Hyperbranched Polyfluorenes Containing Electron-Transporting Aromatic Triazole as Branch Unit", Macromolecules, May 1, 2007, vol. 40, No. 9, pp. 2984-2992, American Chemical Society.

Chen.S et al., "Synthesis and Optical and Electrochemical Properties of Copolymers Consisting of 9,9-Dihexylfluorene and Aromatic Triazole Chromophores", Journal of Polymer Science Part A: Polymer Chemistry, 2007, vol. 45, No. 1, pp. 136-146.

Chinese Office Action (Application No. 201710158441.8) dated Oct. 25, 2018.

Gautun.O et al., "Regioselectivity in the Thermal Rearrangement of Unsymmetrical 4-Methyl-4H-1,2,4-triazoles to 1-Methyl-1H-1,2,4-triazoles", Molecules, Nov. 30, 2001, vol. 6, pp. 969-978.

\* cited by examiner

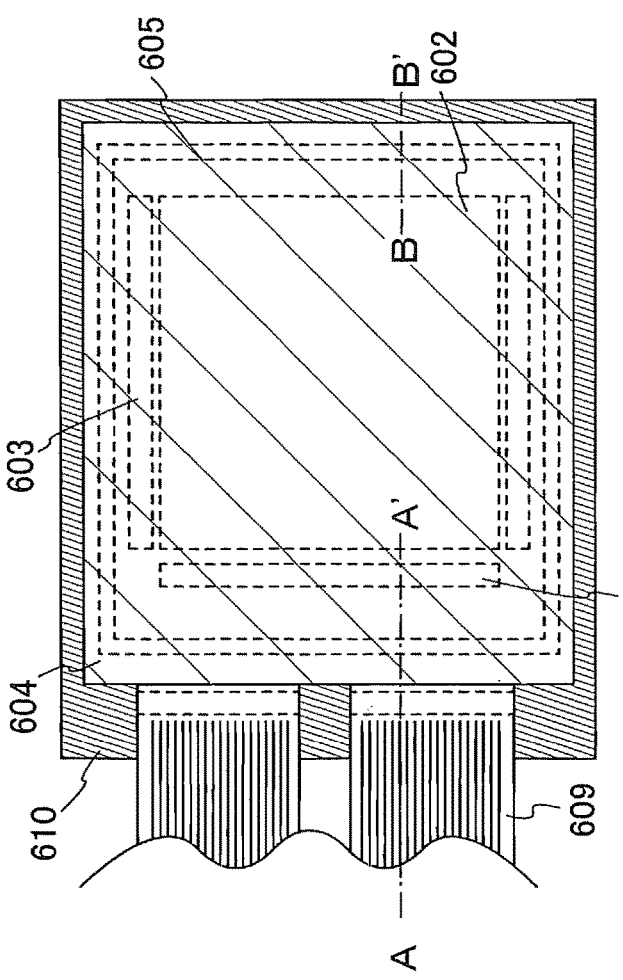
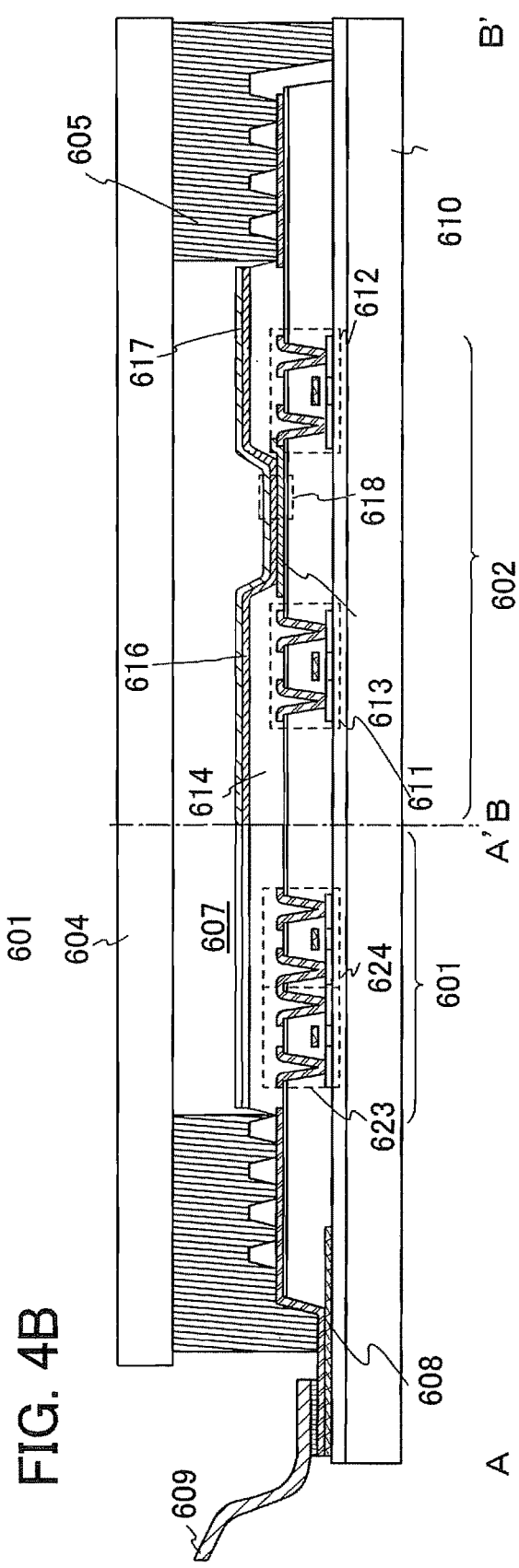
FIG. 4A
FIG. 4B

TRIAZOLE DERIVATIVE, AND LIGHT-EMITTING ELEMENT, LIGHT-EMITTING DEVICE, AND ELECTRONIC DEVICE WITH THE USE OF TRIAZOLE DERIVATIVE

TECHNICAL FIELD

The present invention relates to a triazole derivative. In addition, the present invention relates to current-excitation type light-emitting elements, and a light-emitting device and electronic devices having the light-emitting element.

BACKGROUND ART

In recent years, research and development have been extensively conducted on light-emitting elements which utilize electroluminescence. In a basic structure of such a light-emitting element, a substance having a light-emitting property is interposed between a pair of electrodes. By application of voltage to the element, light emission can be obtained from the substance having a light-emitting property.

Since such a light-emitting element is a self light-emitting type, there are advantages that visibility of a pixel is better than visibility of a liquid crystal display, that a backlight is not necessary, and the like. Accordingly, such a light-emitting element is suitable for a flat panel display element. In addition, other advantages of such a light-emitting element are that the element can be manufactured to be thin and lightweight and the response speed is very high.

Since the light-emitting element can be formed into a film shape, surface light emission can be easily obtained by formation of a large-area element. This is a feature which is difficult to be obtained by point light sources typified by an incandescent lamp and an LED or linear light sources typified by a fluorescent lamp. Accordingly, the light-emitting element has a high utility value as a surface light source applicable to a lighting system and the like.

Light-emitting elements which utilize electroluminescence are classified broadly according to whether they use an organic compound or an inorganic compound as a light-emitting substance.

When an organic compound is used as a light-emitting substance, electrons and holes are injected into a layer containing a light-emitting organic compound from a pair of electrodes by voltage application to a light-emitting element, so that current flows therethrough. The electrons and holes (i.e., carriers) are recombined; thus, the light-emitting organic compound becomes in an excited state. The light-emitting organic compound returns to a ground state from the excited state, thereby emitting light. Based on such a mechanism, such a light-emitting element is referred to as a current-excitation type light-emitting element.

As types of excited states of the organic compound, there are a singlet excited state (S*) and a triplet excited state (T*). The statistical generation ratio thereof in the light-emitting element is S*:T*=1:3.

In a compound which converts a singlet excited state into light emission (hereinafter referred to as a fluorescent compound), light emission from a triplet excited state (phosphorescence) is not observed at a room temperature but only light emission from a singlet excited state (fluorescence) is observed. Therefore, in a light-emitting element with the use of a fluorescent compound, the theoretical limit of internal quantum efficiency (the ratio of generated photons to injected carriers) is considered to be 25% based on S*:T*=1:3.

On the other hand, when a compound which converts a triplet excited state into light emission (hereinafter referred to as a phosphorescent compound) is used, internal quantum efficiency can be theoretically improved from 75 to 100%. That is, luminous efficiency can be three to four times as high as that of a fluorescent compound. From such a reason, in order to achieve a high efficiency light-emitting element, a light-emitting element with the use of a phosphorescent compound has been actively developed recently.

When a light-emitting layer of a light-emitting element is formed with the use of the above phosphorescent compound, in order to suppress concentration quenching of the phosphorescent compound or quenching due to triplet-triplet annihilation (T-T annihilation), the light-emitting layer is often formed so that the phosphorescent compound is dispersed in a matrix of another substance. At this time, the substance which serves as a matrix is referred to as a host material, and the substance which is dispersed in a matrix such as a phosphorescent substance is referred to as a guest material.

When the phosphorescent compound is used as a guest material, a host material is needed to have higher triplet excitation energy (an energy difference between a ground state and a triplet excited state) than that of the phosphorescent compound. In Patent Document 1 (Japanese Published Patent Application No. 2002-352957), TAZ is used as a host material of a phosphorescent compound, which emits green light.

DISCLOSURE OF INVENTION

A compound having such high triplet excitation energy (an energy difference between a ground state and a triplet excited state) as TAZ is useful as a host material for a phosphorescent compound.

On the other hand, TAZ has high singlet excitation energy (an energy difference between a ground state and a singlet excited state) and is also used as a hole blocking material. That is, TAZ has a feature that holes are extremely difficult to be injected into TAZ. Thus, when TAZ is used as a host material of a light-emitting layer, holes are difficult to be injected into the light-emitting layer, and thus there is a possibility that a light-emitting region exists close to an interface between the light-emitting layer and a hole-transporting layer. When the light-emitting region locally exist close to the interface, concentration quenching of a light-emitting substance or quenching due to triplet-triplet annihilation (T-T annihilation) arises, which results in decrease of luminous efficiency.

In view of the above-described problem, it is an object of the present invention to provide a novel triazole derivative.

Further, it is another object of the present invention to provide a light-emitting element having high luminous efficiency with the use of the novel triazole derivative. Moreover, it is still another object of the present invention to provide a light-emitting device and electronic devices which have low power consumption.

A triazole derivative which includes, in the same molecule, a triazole skeleton having an electron transport property and high triplet excitation energy, and a carbazole skeleton having a hole-transporting property, was synthesized by the present inventors. Then, it was found that the triazole derivative has high triplet excitation energy, and an electron-transporting property and a hole-transporting property. More specifically, it was found that the triazole derivative which is a 1,2,4-triazole derivative, in which an aryl group or a heteroaryl group is bonded to each of 3-position, 4-position, and 5-position, and in which any one of the aryl group or heteroaryl group has a 9H-carbazol-9-yl group, has high triplet excitation energy, and an electron-transporting property and a hole-transporting property.

Thus, one aspect of the present invention is a triazole derivative where any one of $Ar^1$ to $Ar^3$ of a triazole derivative which is represented by a general formula (G1) is bonded with a 9H-carbazol-9-yl group which is represented by a general formula (G2).

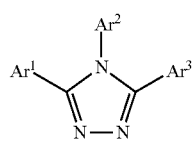
(G1)

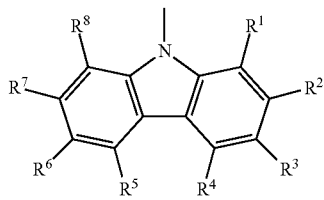
(G2)

In the formula, $Ar^1$ to $Ar^3$ each represent an aryl group or a heteroaryl group, and $R^1$ to $R^8$ each represent hydrogen, an alkyl group, an alkoxy group, or an aryl group.

In addition, another aspect of the present invention is a triazole derivative which is represented by a general formula (G3).

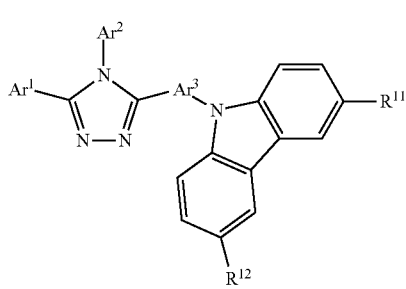
(G3)

In the formula, $Ar^1$ and $Ar^2$ each represent an aryl group or a heteroaryl group, $Ar^3$ represents an arylene group or a heteroarylene group, and $R^{11}$ and $R^{12}$ each represent hydrogen, an alkyl group, an alkoxy group, or an aryl group.

In addition, another aspect of the present invention is a triazole derivative which is represented by a general formula (G4).

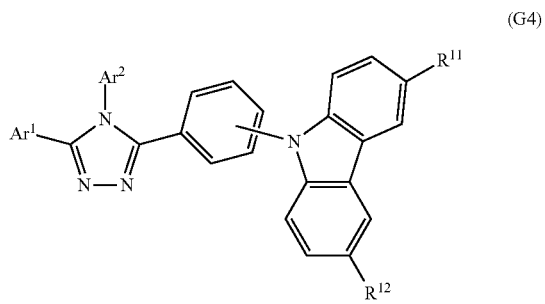
(G4)

In the formula, $Ar^1$ and $Ar^2$ each represent an aryl group or a heteroaryl group, and $R^{11}$ and $R^{12}$ each represent hydrogen, an alkyl group, an alkoxy group, or an aryl group.

In addition, another aspect of the present invention is a triazole derivative which is represented by a general formula (G5).

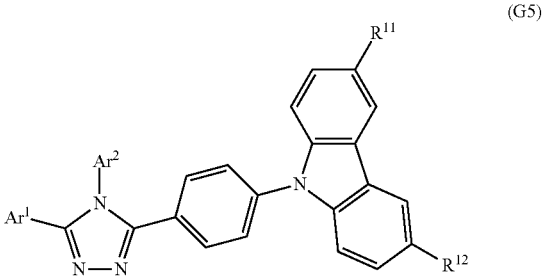
(G5)

In the formula, $Ar^1$ and $Ar^2$ each represent an aryl group or a heteroaryl group, and $R^{11}$ and $R^{12}$ each represent hydrogen, an alkyl group, an alkoxy group, or an aryl group.

In any of the above-described structures, it is preferable that $Ar^1$ and $Ar^2$ be each a phenyl group or a pyridyl group.

In addition, another aspect of the present invention is a triazole derivative which is represented by a general formula (G6).

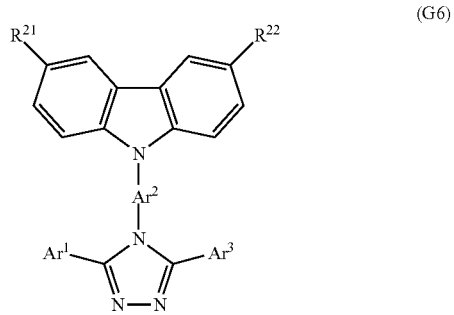
(G6)

In the formula, $Ar^1$ and $Ar^3$ each represent an aryl group or a heteroaryl group, $Ar^2$ represents an arylene group or a heteroarylene group, and $R^{21}$ and $R^{22}$ each represent hydrogen, an alkyl group, an alkoxy group, or an aryl group.

In addition, another aspect of the present invention is a triazole derivative which is represented by a general formula (G7).

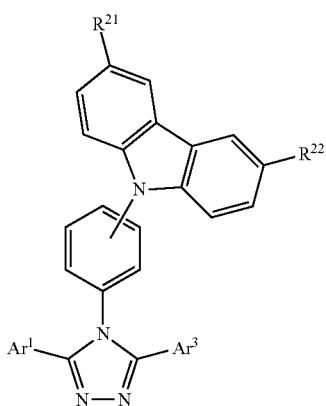

(G7)

In the formula, $Ar^1$ and $Ar^3$ each represent an aryl group or a heteroaryl group, and $R^{21}$ and $R^{22}$ each represent hydrogen, an alkyl group, an alkoxy group, or an aryl group.

In addition, another aspect of the present invention is a triazole derivative which is represented by a general formula (G8).

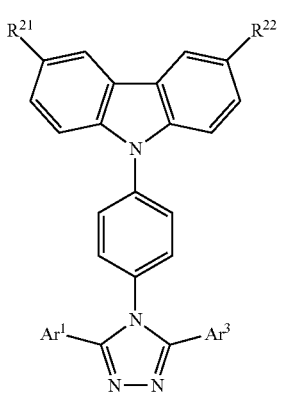

(G8)

In the formula, $Ar^1$ and $Ar^2$ each represent an aryl group or a heteroaryl group, and $R^{21}$ and $R^{22}$ each represent hydrogen, an alkyl group, an alkoxy group, or an aryl group.

In any of the above-described structures, it is preferable that $Ar^1$ and $Ar^3$ be each a phenyl group or a pyridyl group.

In addition, another aspect of the present invention is a light-emitting element with any of the above-described triazole derivatives. Specifically, it is a light-emitting element including any of the above-described triazole derivatives between a pair of electrodes.

In addition, another aspect of the present invention is a light-emitting element which includes a light-emitting layer between a pair of electrodes, where the light-emitting layer has any of the above-described triazole derivatives.

Since any of the above-described triazole derivatives has high triplet excitation energy, more advantageous effect can be obtained when a light-emitting layer has any of the above-described triazole derivatives and a substance that emits phosphorescence in its structure. In particular, light emission of high luminous efficiency can be obtained with the use of any of the above-described triazole derivatives, even in a case where a substance is used that emits phosphorescence which shows light emission of a short wavelength, the light emission peak wavelength of which is greater than or equal to 400 nm and less than or equal to 500 nm.

In addition, a light-emitting device of the present invention includes a light-emitting element having any of the above-described triazole derivatives and a control circuit which controls light emission of the light-emitting element. The category of the light-emitting device in this specification includes image display devices, light-emitting devices, and light sources (including lighting systems). Further, the category of the light-emitting device also includes all of the following: modules in each of which a connector, for example, a flexible printed circuit (FPC), a tape automated bonding (TAB) tape, or a tape carrier package (TCP) is attached to a panel; modules in each of which a printed wiring board is provided at an end of a TAB tape or a TCP; and modules in each of which an integrated circuit (IC) is directly mounted on the light-emitting element by a chip on glass (COG) method.

Furthermore, the present invention covers an electronic device in which the light-emitting element of the present invention is used in its display portion. Therefore, one aspect of the present invention is an electronic device that includes a display portion, and the display portion includes the above-described light-emitting element and a control circuit which controls light emission of the light-emitting element.

A triazole derivative of the present invention has high triplet excitation energy.

In addition, a light-emitting element having high luminous efficiency can be obtained with the use of a triazole derivative of the present invention. Moreover, a light-emitting device and electronic devices which have low power consumption can be obtained.

BRIEF DESCRIPTION OF DRAWINGS

In the accompanying drawings:

FIGS. 4A and 4B are a top view and a cross-sectional view showing a light-emitting device of the present invention, respectively;

BEST MODE FOR CARRYING OUT THE INVENTION

Figure 1:
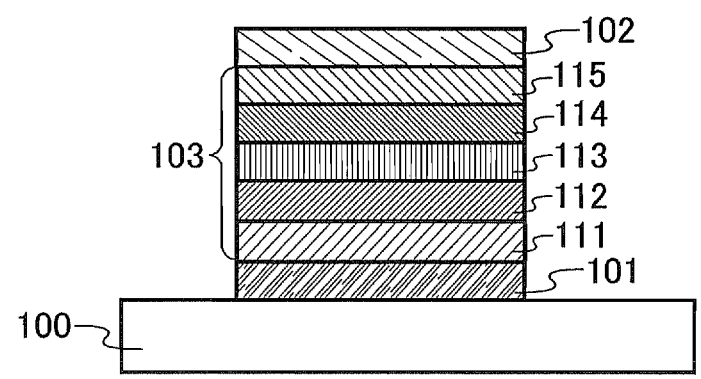
FIG. 1 is a cross-sectional view showing a light-emitting element of the present invention.

Embodiment modes and Embodiments of the present invention will be described in detail with reference to the drawings. Note that the present invention is not limited to the description below, and it is easily understood by those skilled in the art that various changes and modifications can be made without departing from the spirit and scope of the present invention. Accordingly, the present invention should not be interpreted as being limited to the content of the embodiment modes and embodiments described below

Embodiment Mode 1

This embodiment mode will describe a triazole derivative of the present invention.

A triazole derivative of the present invention includes, in the same molecule, a triazole skeleton having an electron transport property and high triplet excitation energy, and a carbazole skeleton having hole-transporting property.

Specifically, the triazole derivative of the present invention is a triazole derivative, which is 1,2,4-triazole derivative in which an aryl group or a heteroaryl group is bonded to each of 3-position, 4-position, and 5-position, in which any one of the aryl group or heteroaryl group has a 9H-carbazol-9-yl group.

That is, the triazole derivative of the present invention is a triazole derivative where any one of $Ar^1$ to $Ar^3$ of a triazole derivative which is represented by a general formula (G1) is bonded with a 9H-carbazol-9-yl group which is represented by a general formula (G2).

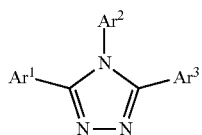

(G1)

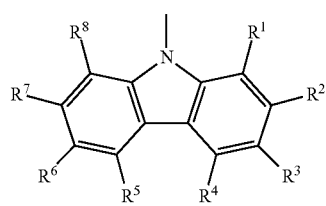

(G2)

In the general formulas (G1) and (G2), $Ar^1$ to $Ar^3$ each represent an aryl group or a heteroaryl group, and $R^1$ to $R^8$ each represent hydrogen, an alkyl group, an alkoxy group, or an aryl group.

As the above-described triazole derivative, triazole derivatives which are represented by general formulas (G3) and (G6) can be given.

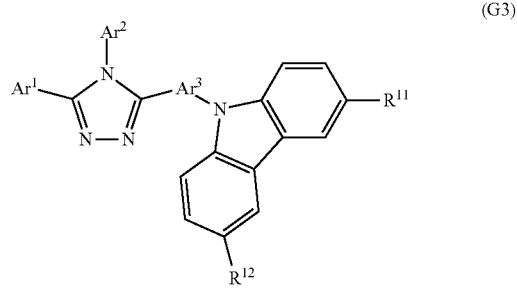

(G3)

In the general formula (G3), $Ar^1$ and $Ar^2$ each represent an aryl group or a heteroaryl group, $Ar^3$ represents an arylene group or a heteroarylene group, and $R^{11}$ and $R^{12}$ each represent hydrogen, an alkyl group, an alkoxy group, or an aryl group.

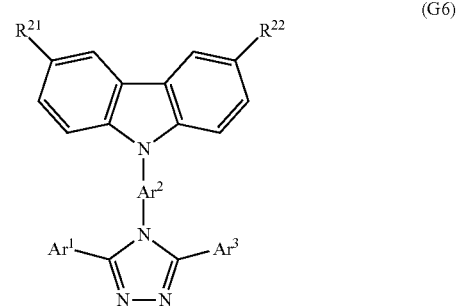

(G6)

In the general formula (G6), $Ar^1$ and $Ar^3$ each represent an aryl group or a heteroaryl group, $Ar^2$ represents an arylene group or a heteroarylene group, and $R^{21}$ and $R^{22}$ each represent hydrogen, an alkyl group, an alkoxy group, or an aryl group.

The aryl group may have a substituent. In addition, an aryl group having 6 to 25 carbon atoms is preferable for ease of synthesis. For example, the following can be given: a phenyl group, an o-tolyl group, a m-tolyl group, a p-tolyl group, a 4-tert-butylphenyl group, a 1-naphthyl group, a 2-naphthyl group, a 2-biphenyl group, a 3-biphenyl group, a 4-biphenylyl group, a 9,9-dimethylfluoren-2-yl group, a spiro-9,9'-bifluoren-2-yl group, and the like. Part of these substituents are shown in structural formulas (11-1) to (11-9).

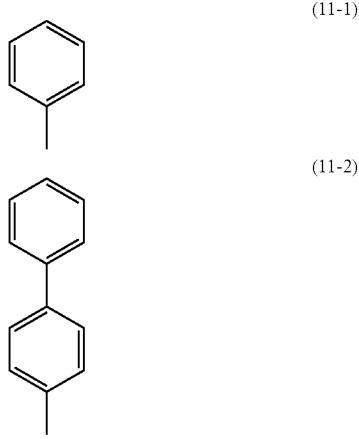

(11-1)

(11-2)

a pyrimidin-4-yl group, a pyrazin-2-yl group, a 2-pyridyl group, a 3-pyridyl group, a 4-pyridyl group, and the like. Part of these substituents are shown in structural formulas (12-1) to (12-14).

The heteroaryl group may have a substituent. In addition, a heteroaryl group having 3 to 9 carbon atoms is preferable for ease of synthesis. For example, the following can be given: a 1,3,5-triazin-2-yl group, a 1,2,4-triazin-3-yl group, (12-10)
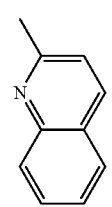

(12-11)
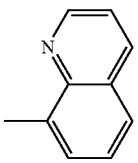

(12-12)
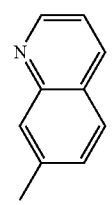

(12-13)
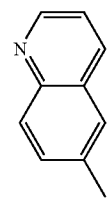

(12-14)
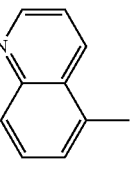

The arylene group may have a substituent. In addition, an arylene group having 6 to 25 carbon atoms is preferable for ease of synthesis. For example, the following can be given: a 1,2-phenylene group, a 1,3-phenylene group, a 1,4-phenylene group, a 2,5-dimethyl-1,4-phenylene group, a 1,4-naphthylene group, a 1,5-naphthylene group, a 4,4'-biphenylene group, a 9,9-dimethylfluorene-2,7-diyl group, a spiro-9,9'-bifluorene-2,7-diyl group, and the like. Part of these substituents are shown in structural formulas (13-1) to (13-9).

(13-1)
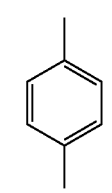

(13-2)
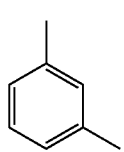

(13-3)
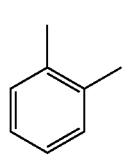

(13-4)
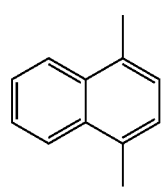

(13-5)
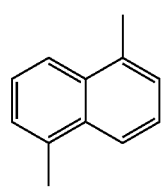

(13-6)
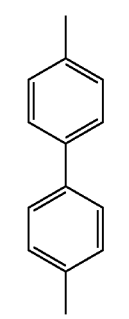

(13-7)
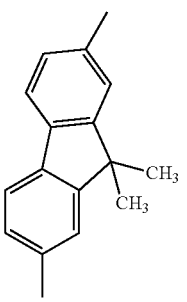

(13-8)
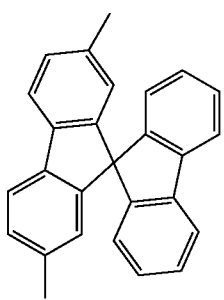

-continued (13-9)

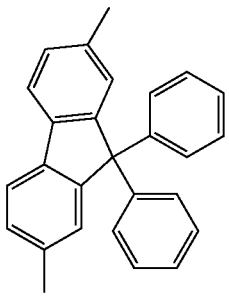

The heteroarylene group may have a substituent. In addition, a hetero arylene group having 3 to 9 carbon atoms is preferable for ease of synthesis. For example, a pyridin-2,5-diyl group, a pyridin-2,6-diyl group, and the like can be given. Part of these substituents are shown in structural formulas (14-1) and (14-2).

(14-1)

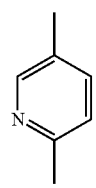

(14-2)

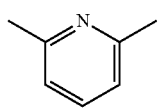

The alkyl group is preferably an alkyl group having 1 to 4 carbon atoms for ease of synthesis. For example, as the alkyl group having 1 to 4 carbon atoms, a methyl group, an ethyl group, an isopropyl group, an n-propyl group, an isobutyl group, a sec-butyl group, an n-butyl group, a tert-butyl group, and the like can be given.

The alkoxy group is preferably an alkoxy group having 1 to 4 carbon atoms for ease of synthesis. For example, as the alkoxy group having 1 to 4 carbon atoms, a methoxy group, an ethoxy group, an isopropoxy group, an isobutoxy group, a tert-butoxy group, and the like can be given.

The triazole derivative which is represented by the general formula (G3) is preferably a triazole derivative which is represented by a general formula (G4) for ease of synthesis.

(G4)

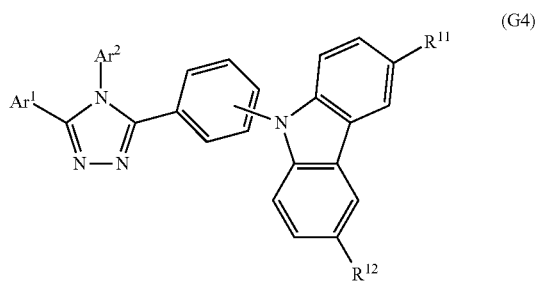

In the general formula (G4), $Ar^1$ and $Ar^2$ each represent an aryl group or a heteroaryl group, and $R^{11}$ and $R^{12}$ each represent hydrogen, an alkyl group, an alkoxy group, or an aryl group.

Having less steric hindrance, where synthesis is performed with ease, the triazole derivative which is represented by the general formula (G4) is preferably a triazole derivative which is represented by a general formula (G5).

(G5)

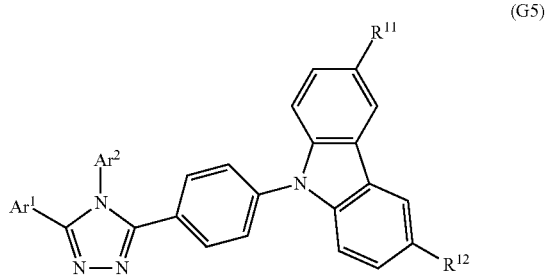

In the general formula (G5), $Ar^1$ and $Ar^2$ each represent an aryl group or a heteroaryl group, and $R^{11}$ and $R^{12}$ each represent hydrogen, an alkyl group, an alkoxy group, or an aryl group.

In any of the general formulas (G3) to (G5), it is preferable that $Ar^1$ and $Ar^2$ be each a phenyl group or a pyridyl group for ease of synthesis. Since triplet excitation energy is high, it is preferable that $Ar^1$ and $Ar^2$ be each a phenyl group or a pyridyl group. In particular, a pyridyl group is preferable. When $Ar^1$ and $Ar^2$ are each a pyridyl group, an electron-transporting property of the triazole derivative of the present invention increases, so that carrier balance improves. Thus, the triazole derivative of the present invention can be preferably used for a light-emitting element. Particularly when being used for a light-emitting layer of a light-emitting element, a pyridyl group is more preferable because the balance between injected electrons and holes is important.

A triazole derivative which is represented by a general formula (G6) is preferably a triazole derivative which is represented by a general formula (G7) for ease of synthesis.

(G7)

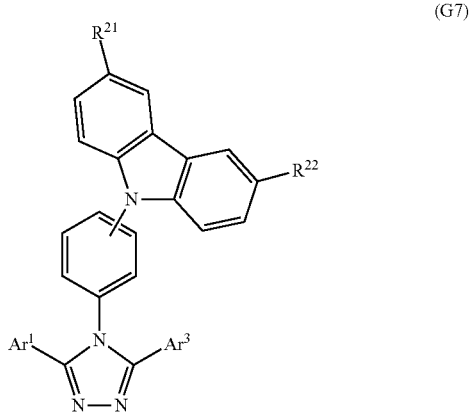

In the general formula (G7), $Ar^1$ and $Ar^3$ each represent an aryl group or a heteroaryl group, and $R^{21}$ and $R^{22}$ each represent hydrogen, an alkyl group, an alkoxy group, or an aryl group.

Having less steric hindrance, where synthesis is performed with ease, the triazole derivative which is represented by the general formula (G7) is preferably a triazole derivative which is represented by a general formula (G8).

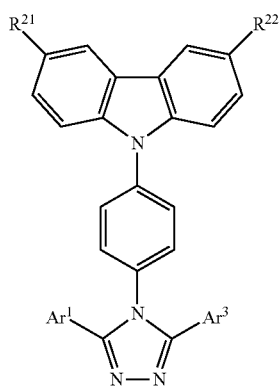

(G8)

In the general formula (G8), $Ar^1$ and $Ar^3$ each represent an aryl group or a heteroaryl group, and $R^{21}$ and $R^{22}$ each represent hydrogen, an alkyl group, an alkoxy group, or an aryl group.

In any of the general formulas (G6) to (G8), it is preferable that $Ar^1$ and $Ar^3$ be each a phenyl group or a pyridyl group for ease of synthesis. Since triplet excitation energy is high, it is preferable that $Ar^1$ and $Ar^3$ be each a phenyl group or a pyridyl group. In particular, a pyridyl group is preferable. When $Ar^1$ and $Ar^3$ are each a pyridyl group, an electron-transporting property of a triazole derivative increases, so that carrier balance improves. Thus, the triazole derivative of the present invention can be preferably used for a light-emitting element. Particularly when being used for a light-emitting layer of a light-emitting element, a pyridyl group is more preferable because the balance between injected electrons and holes is important.

As the triazole derivatives which are represented by the general formulas (G3) and (G6), specifically, triazole derivatives which are represented by structural formulas (101) to (195) and triazole derivatives which are represented by structural formulas (201) to (248) can be given. However, the present invention is not limited thereto.

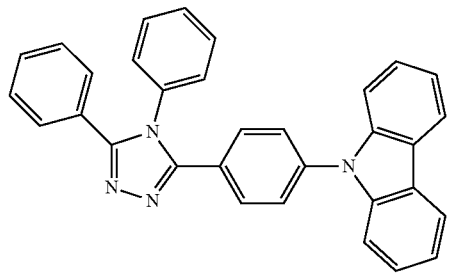

(101)

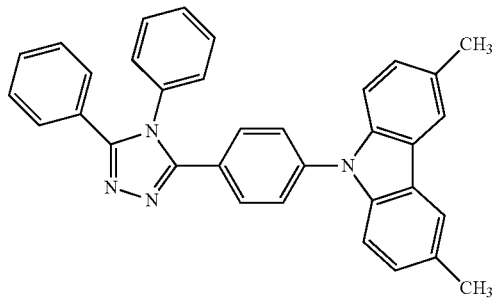

(102)

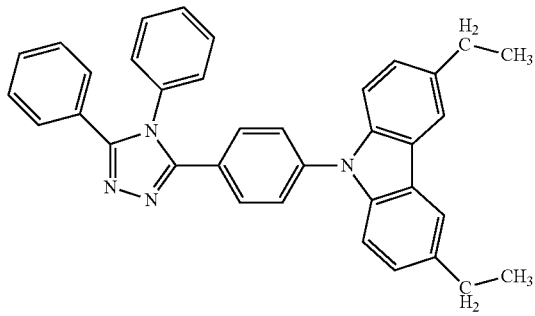

(103)

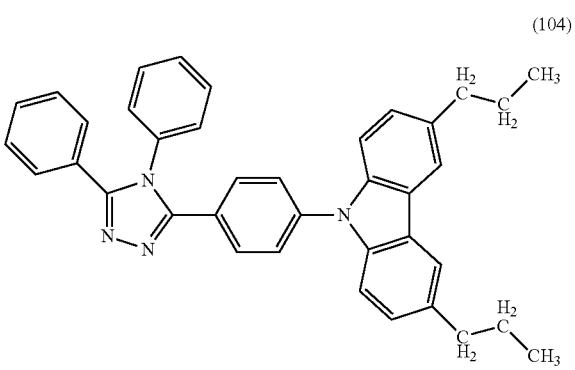

(104)

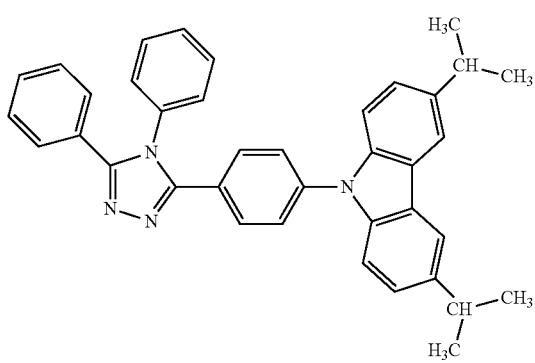

(105)

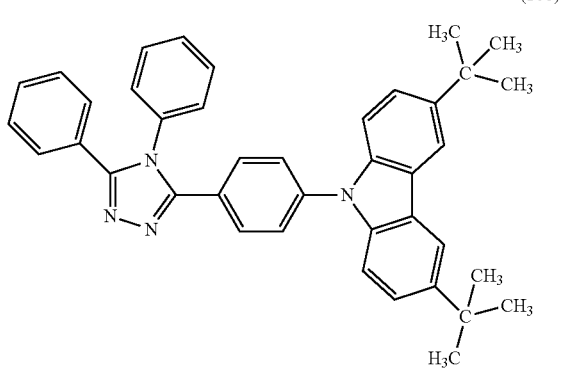

(106)

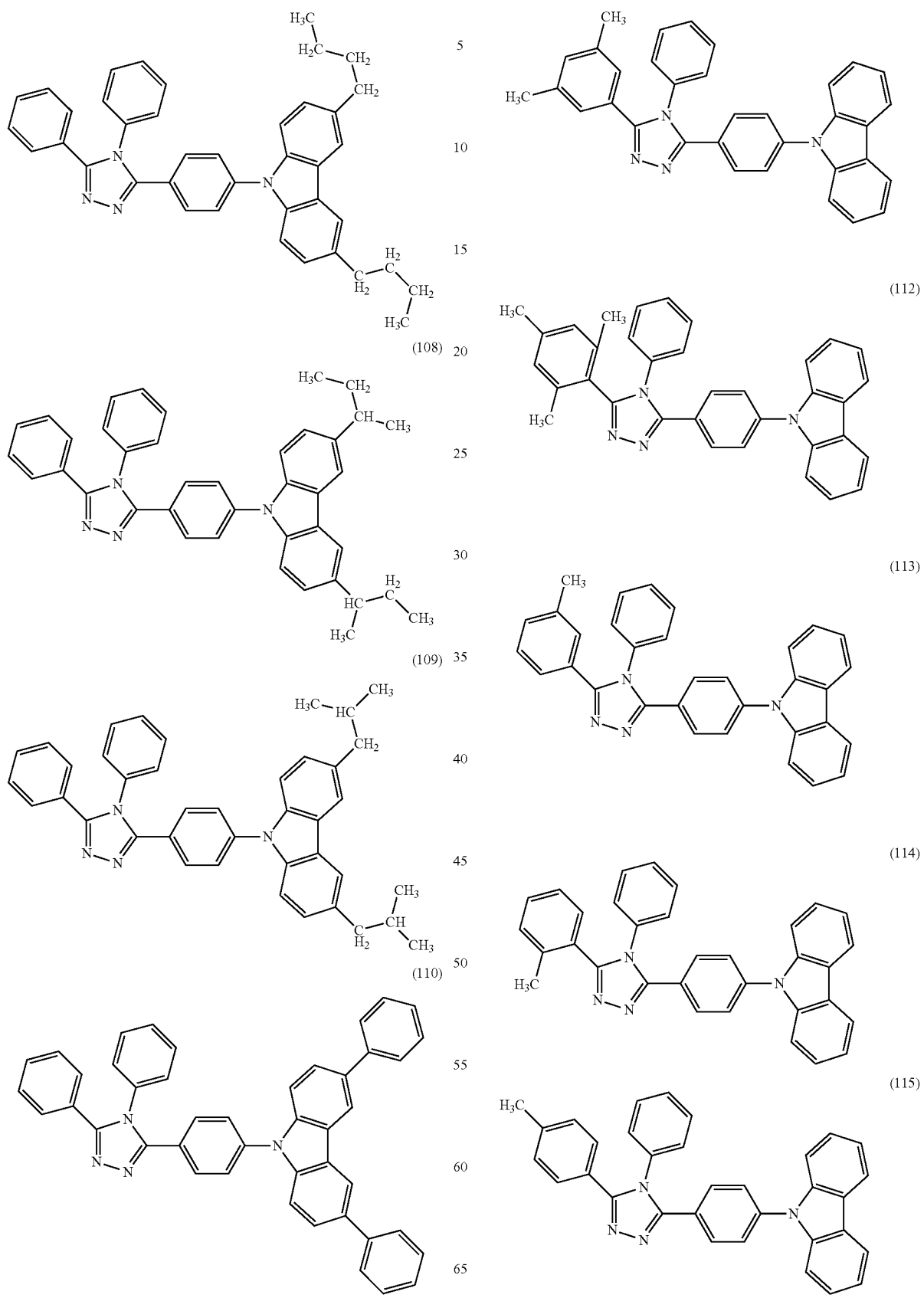

(116)
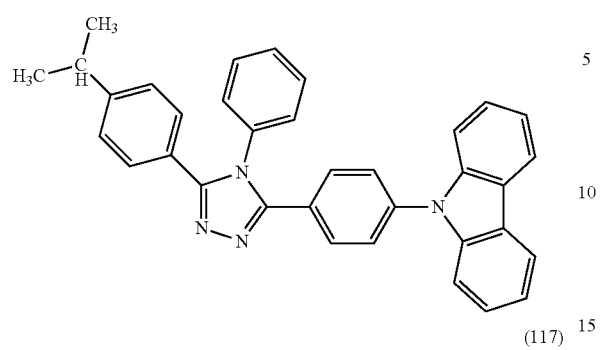
(121)
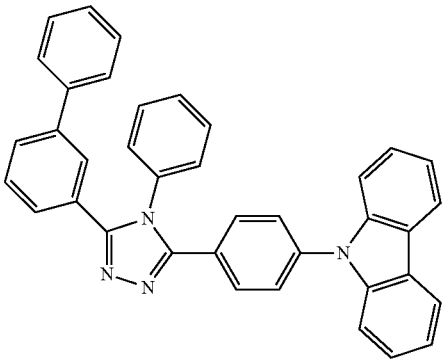
(117)
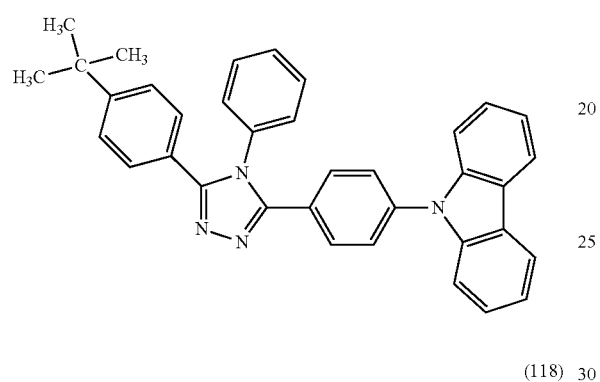
(122)
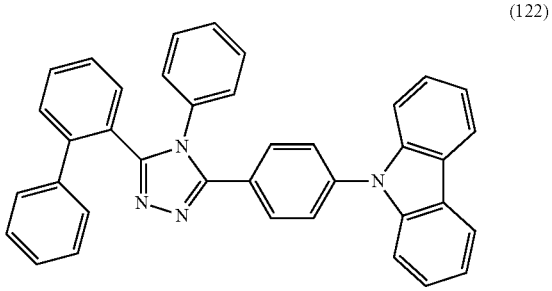
(118)
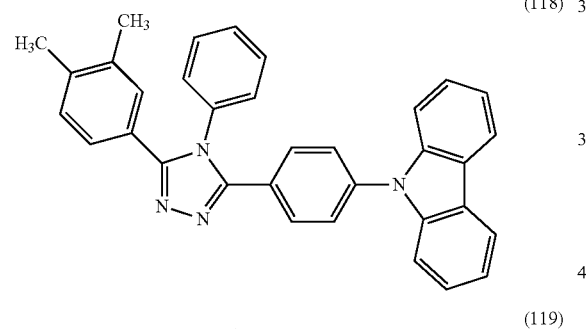
(123)
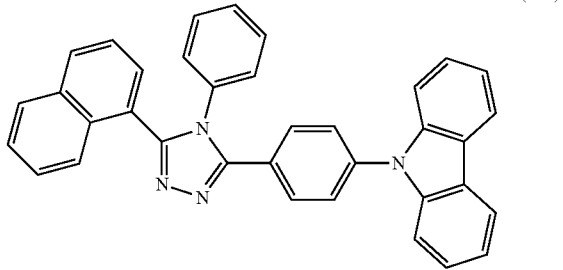
(119)
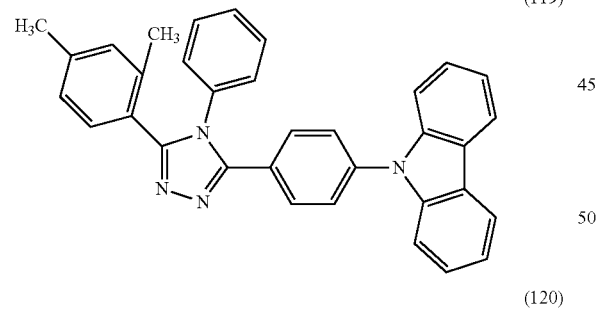
(124)
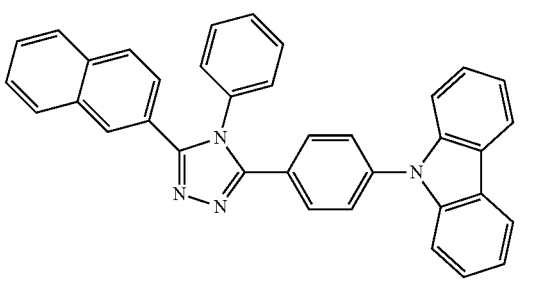
(120)
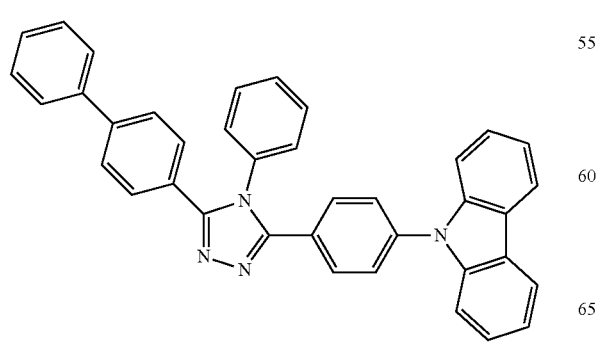
(125)
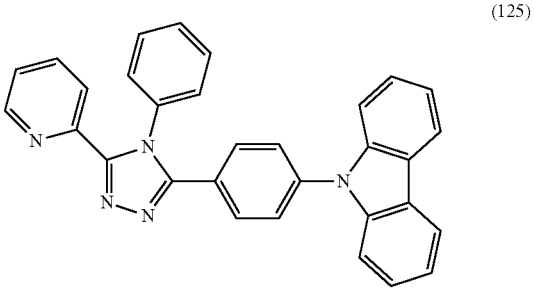

(126)
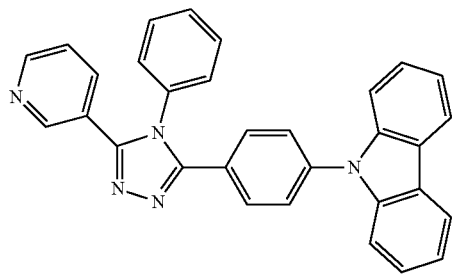
(131)
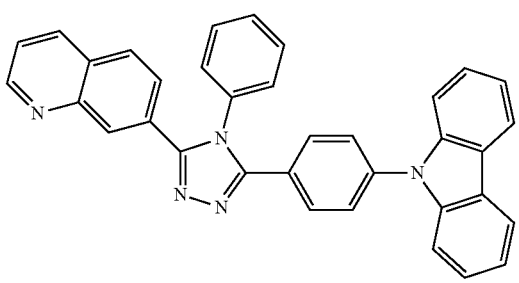
(127)
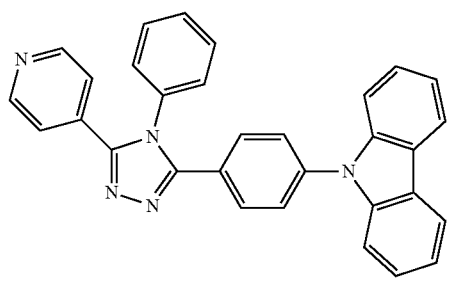
(132)
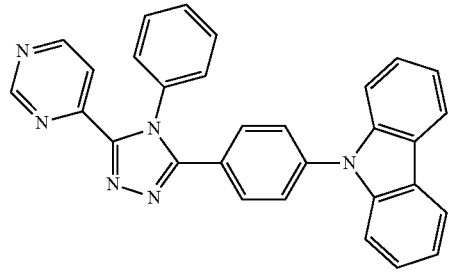
(128)
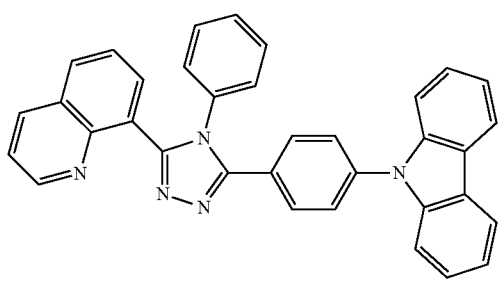
(133)
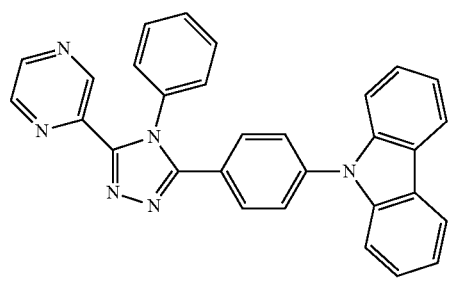
(129)
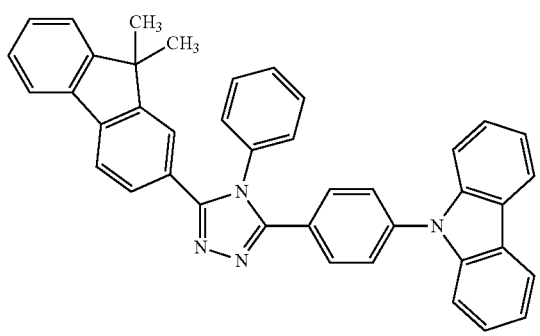
(134)
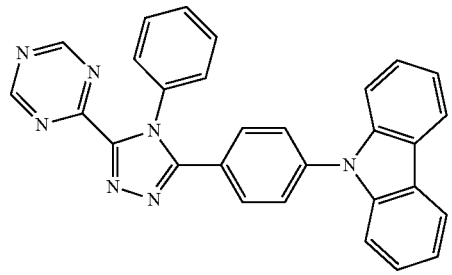
(130)
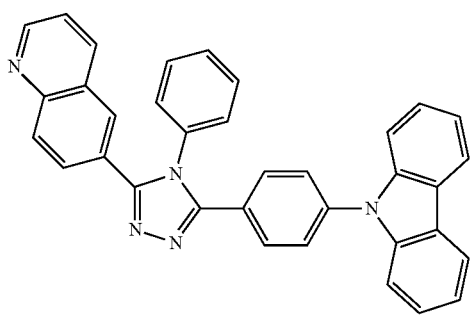
(135)
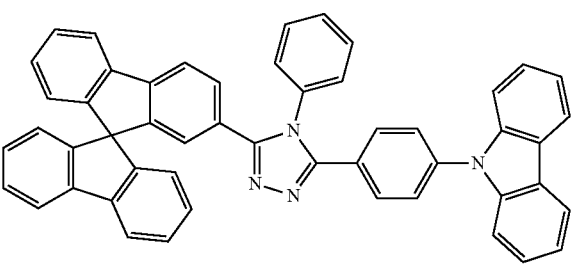

-continued
(136)
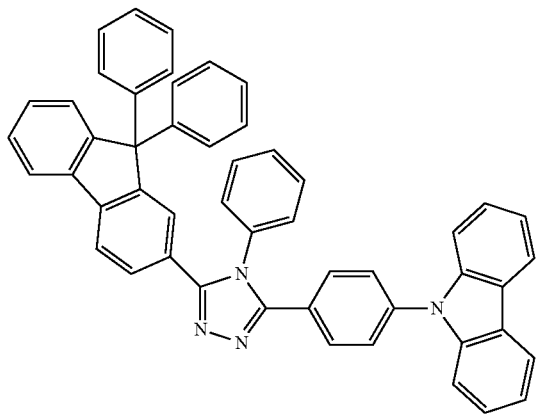
(137)
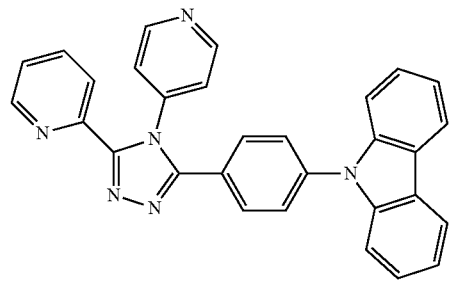
(138)
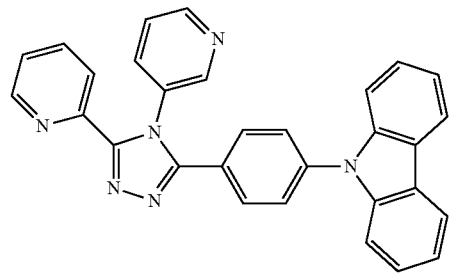
(139)
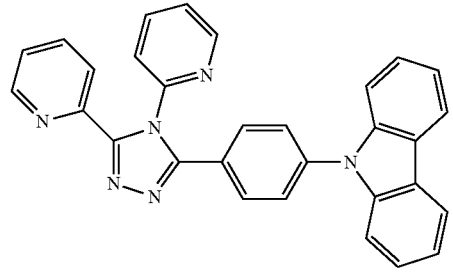
(140)
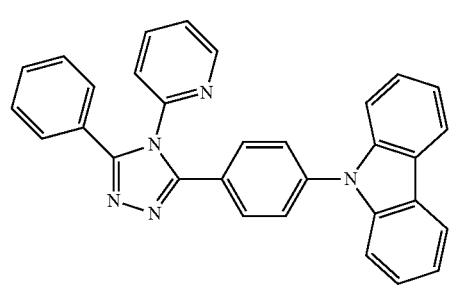
-continued
(141)
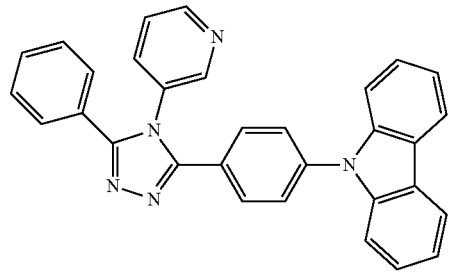
(142)
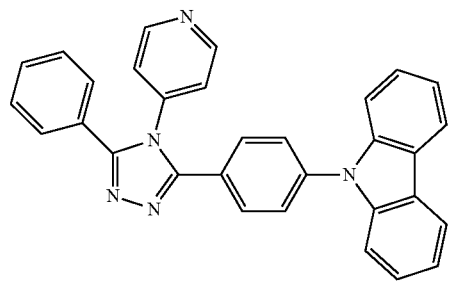
(143)
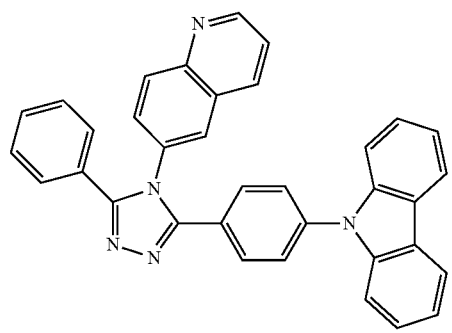
(144)
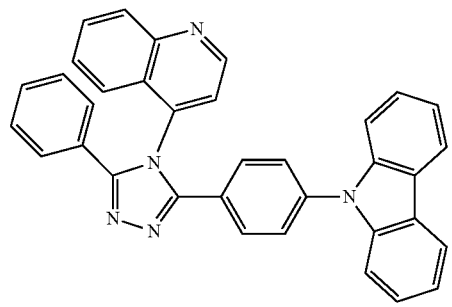
(145)
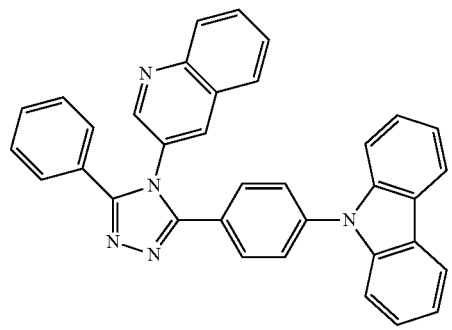

(146)
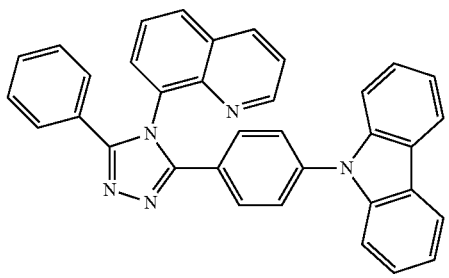
(147)
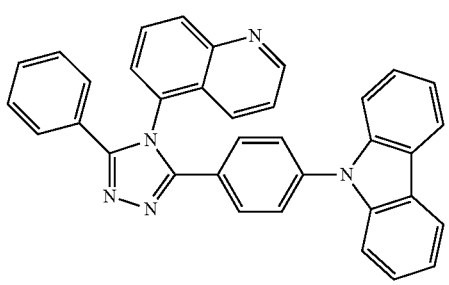
(148)
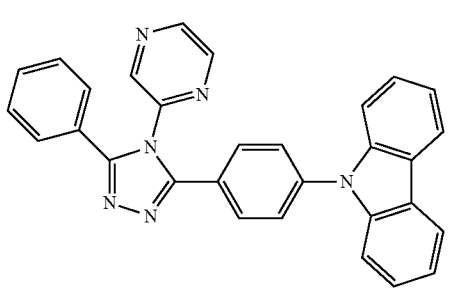
(149)
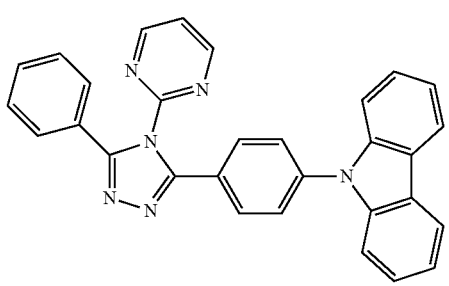
(150)
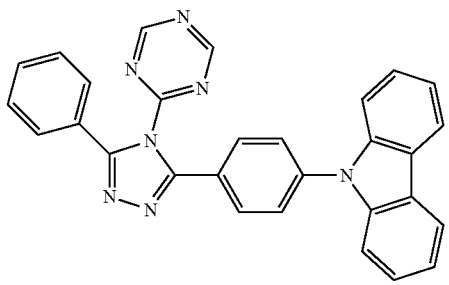
(151)
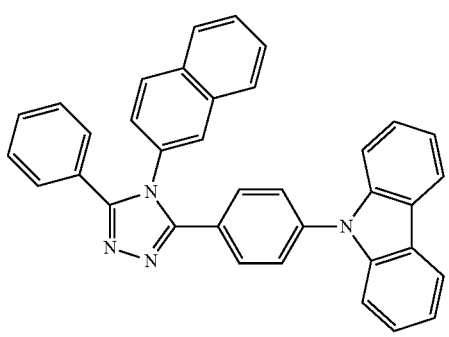
(152)
(153)
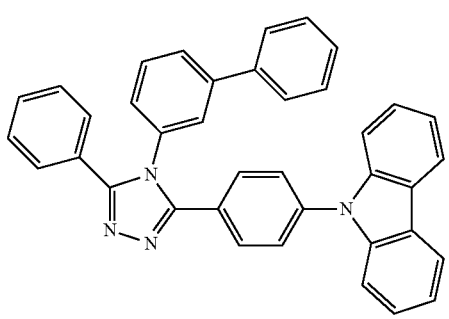
(154)
(155)
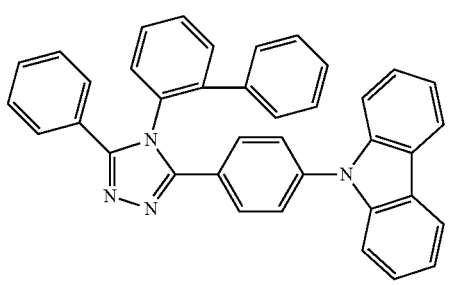

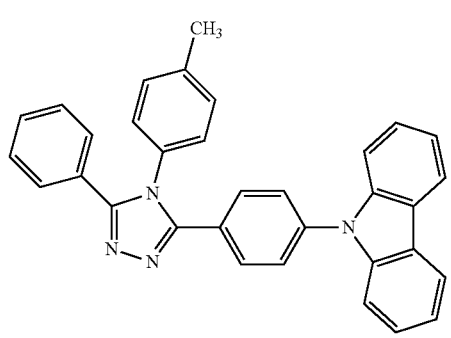 (156)
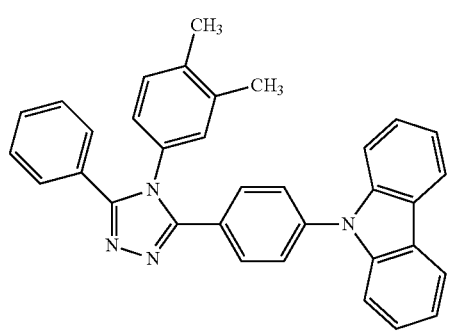 (161)
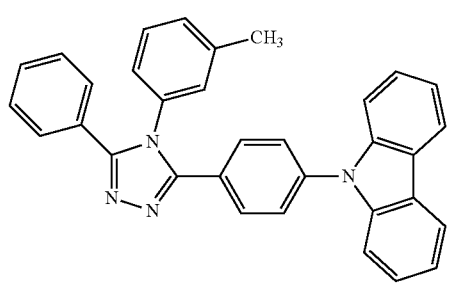 (157)
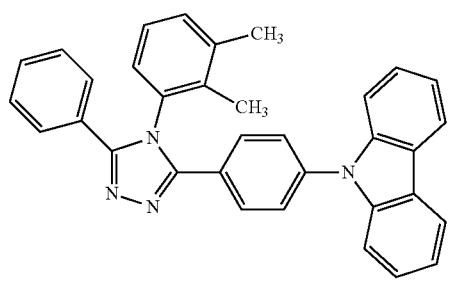 (162)
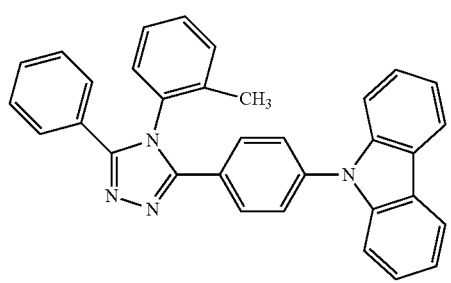 (158)
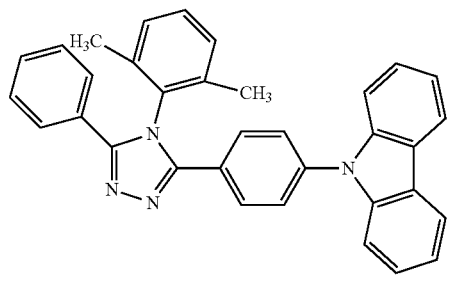 (163)
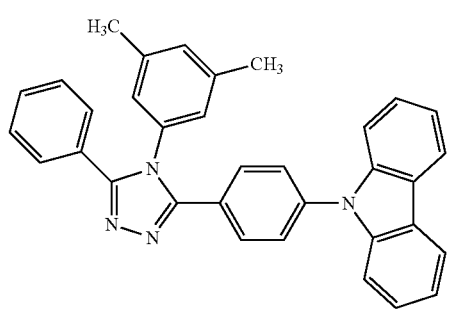 (159)
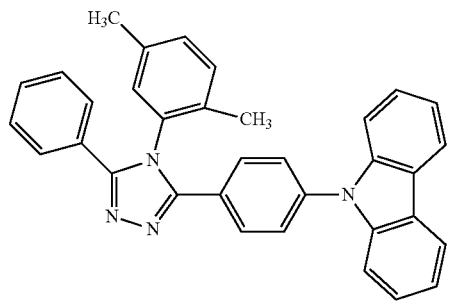 (164)
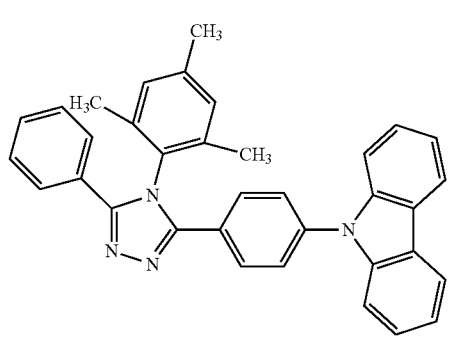 (160)
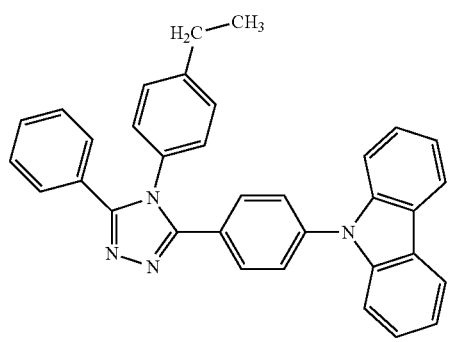 (165)

-continued
(166)
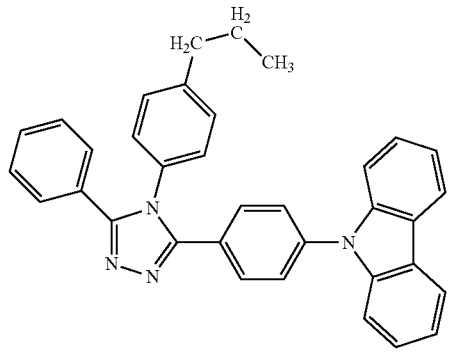
(167)
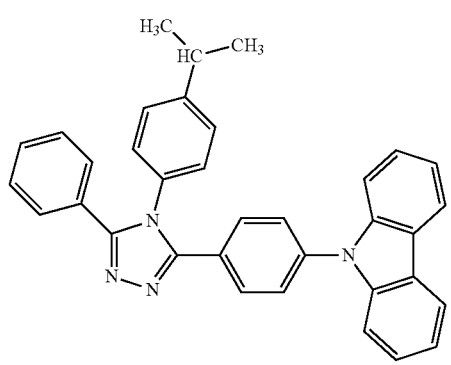
(168)
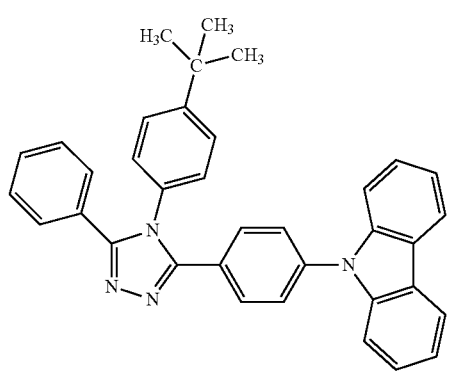
(169)
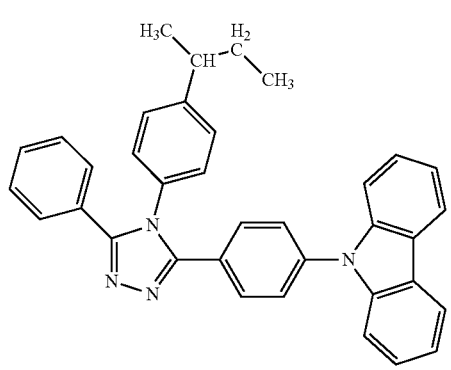
-continued
(170)
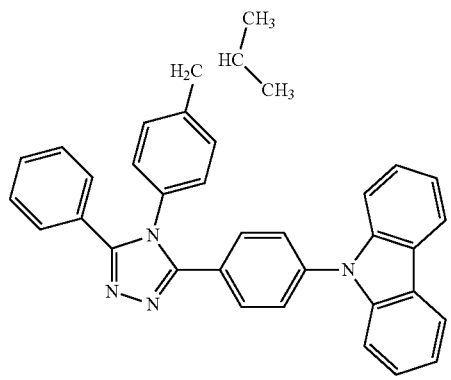
(171)
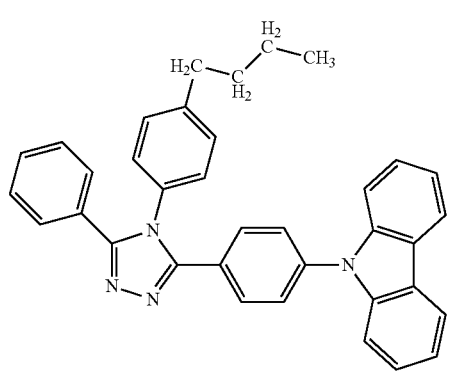
(172)
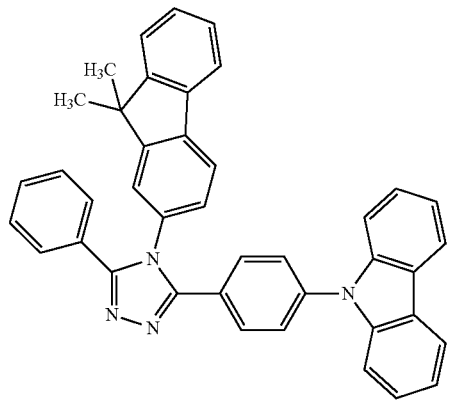
(173)
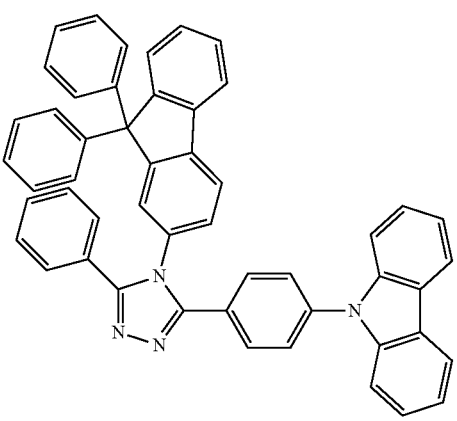

(174) 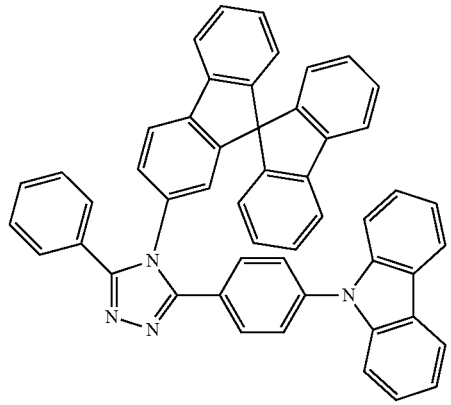
(175) 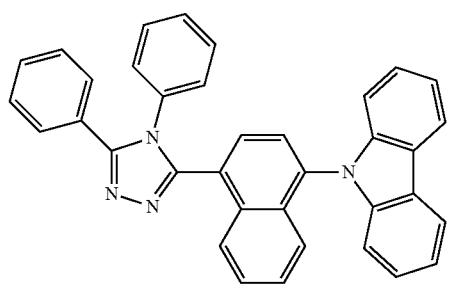
(176) 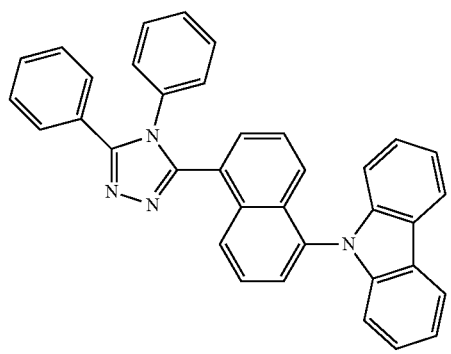
(177) 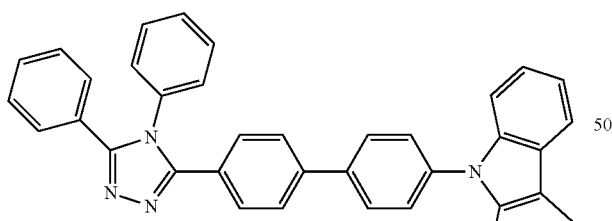
(178) 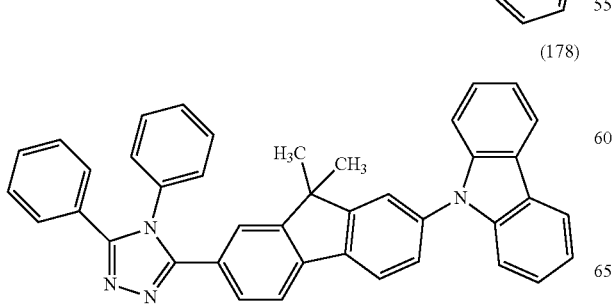
(179) 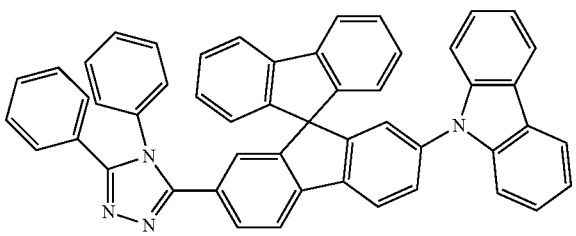
(180) 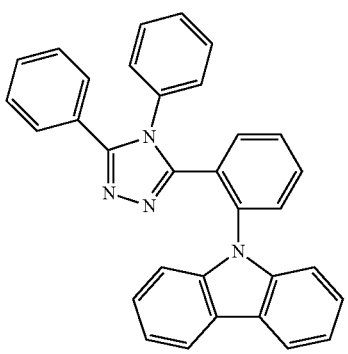
(181) 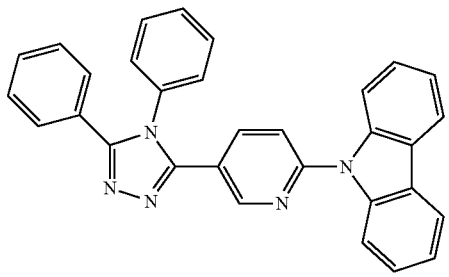
(182) 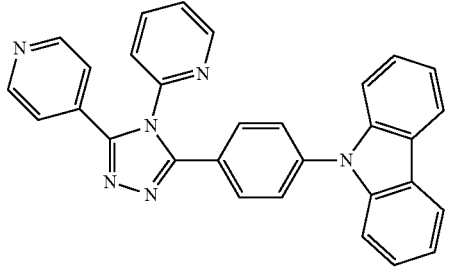
(183) 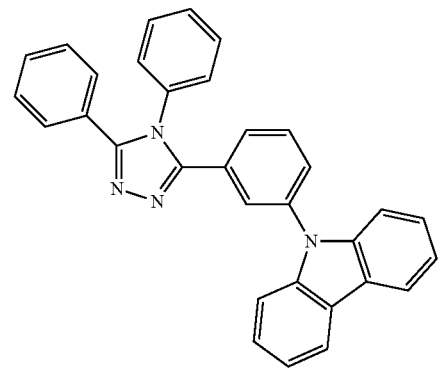

(184)
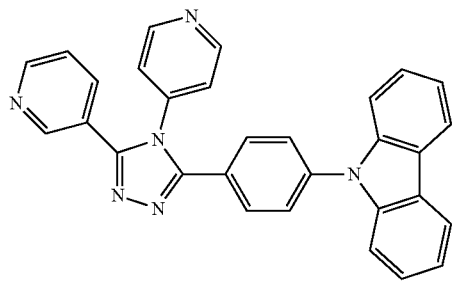
(185)
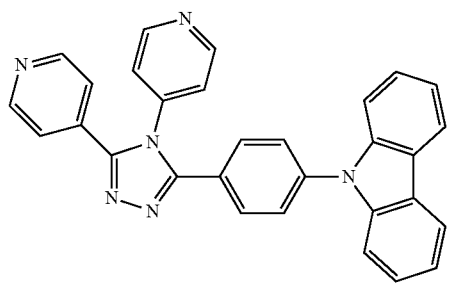
(186)
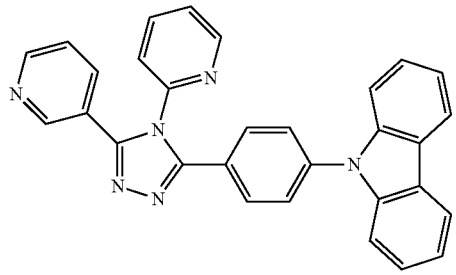
(187)
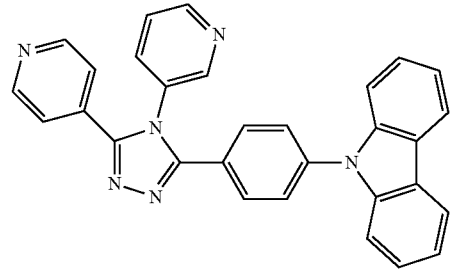
(188)
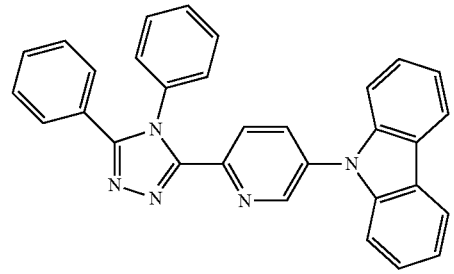
(189)
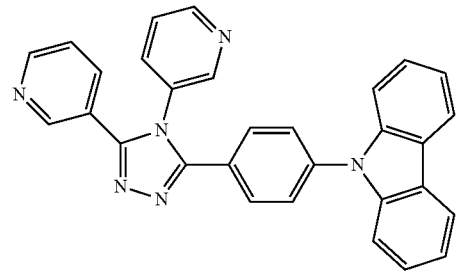
(190)
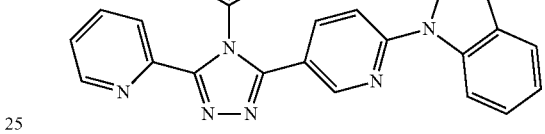
(191)
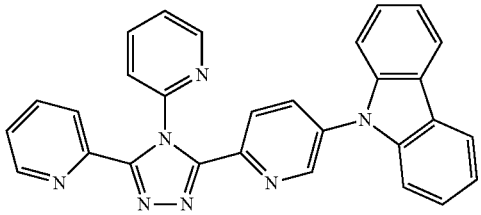
(192)
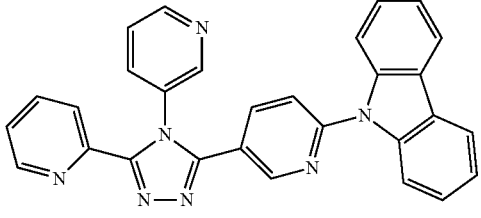
(193)
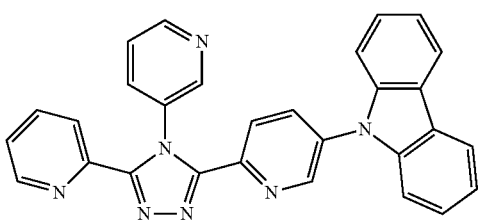
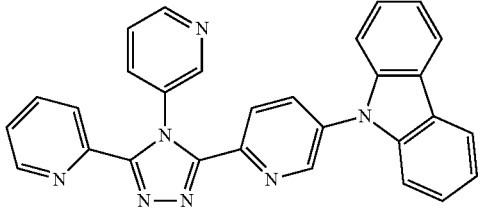
(194)
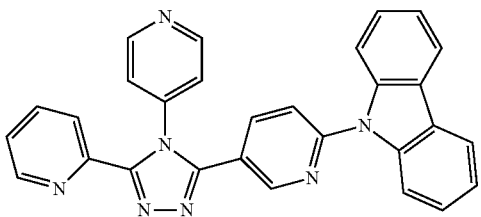

(195)
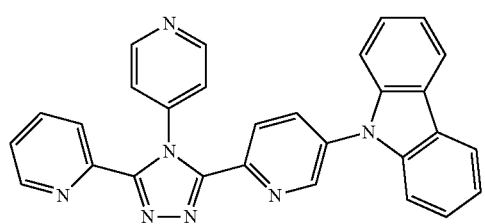
(201)
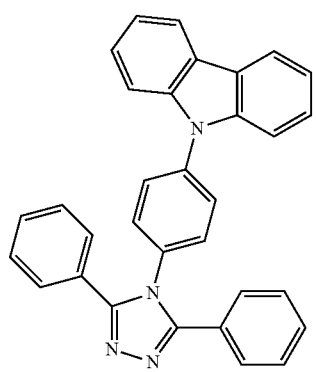
(202)
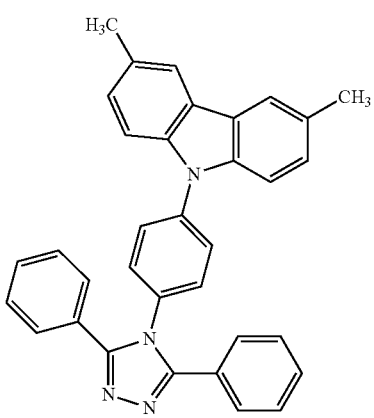
(203)
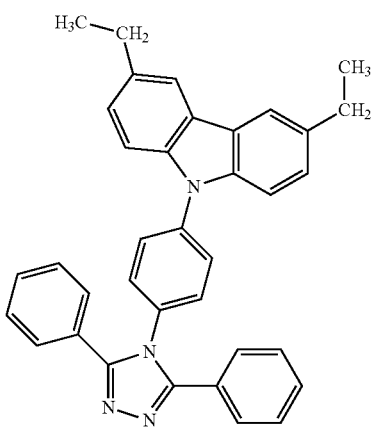
(204)
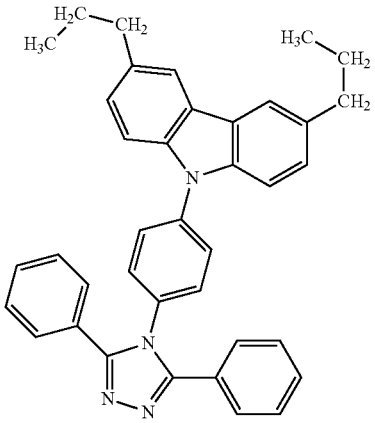
(205)
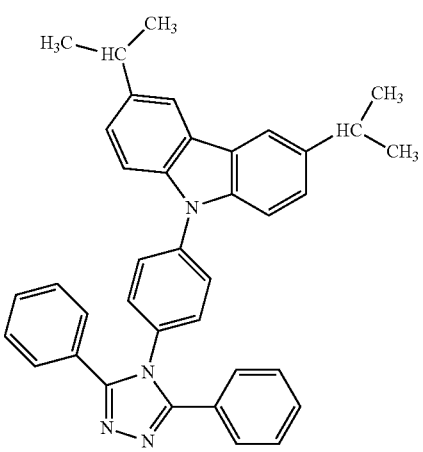
(206)
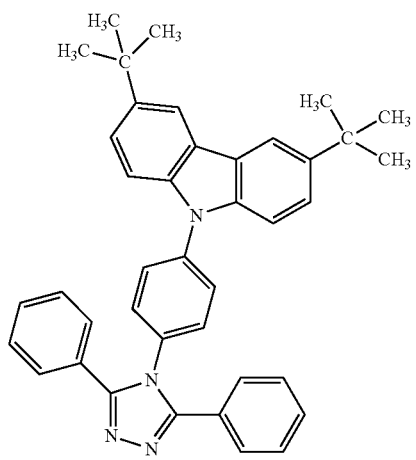

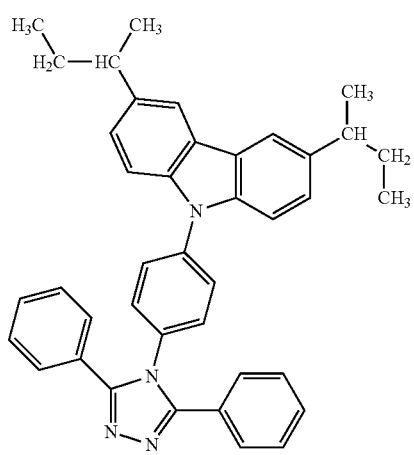
(207)
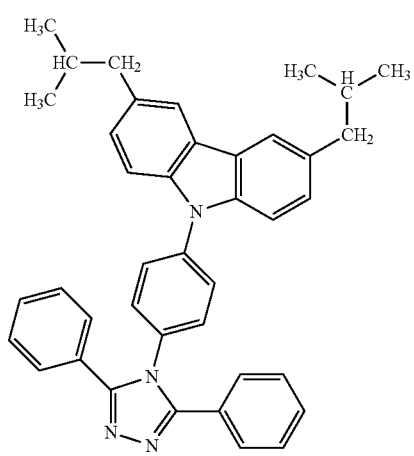
(208)
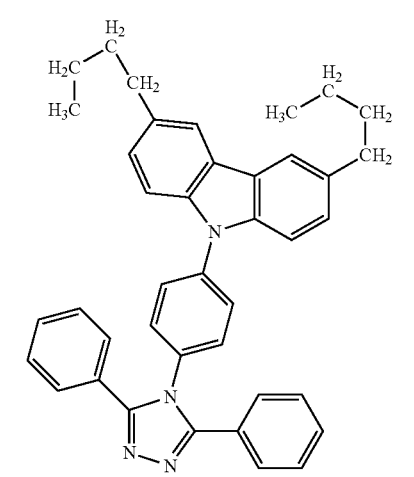
(209)
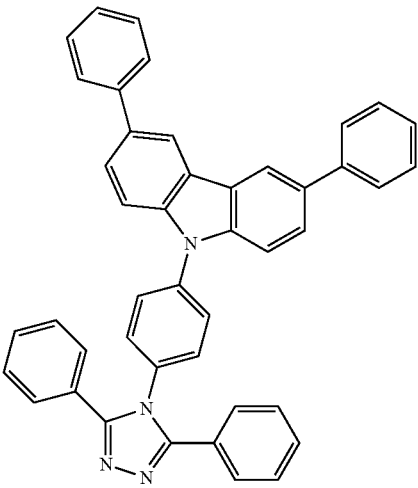
(210)
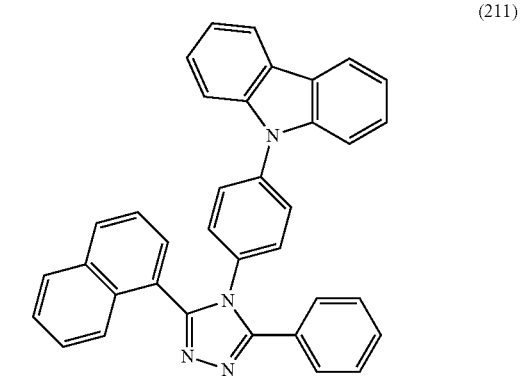
(211)
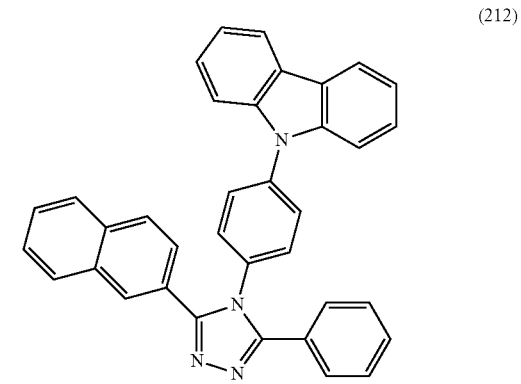
(212)
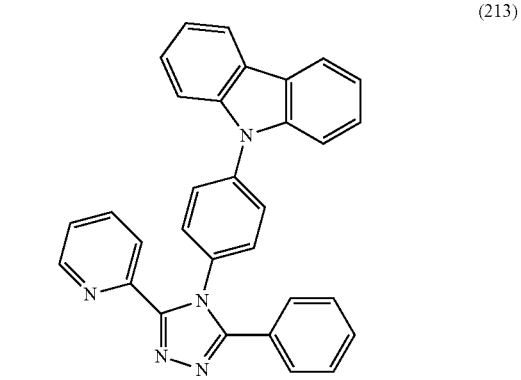
(213)

(214)
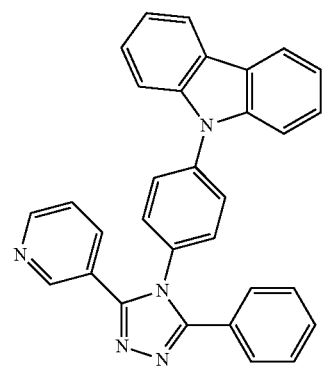
(215)
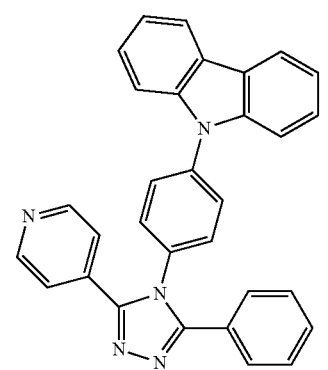
(216)
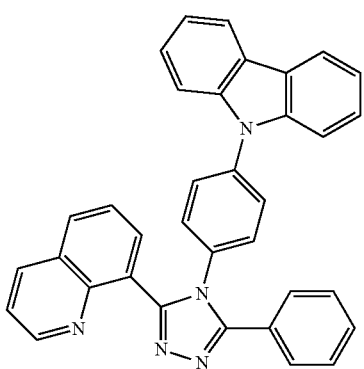
(217)
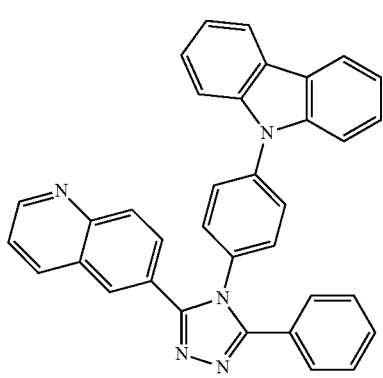
(218)
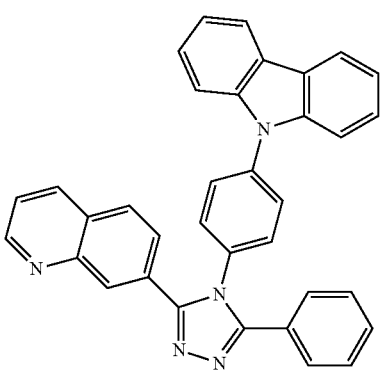
(219)
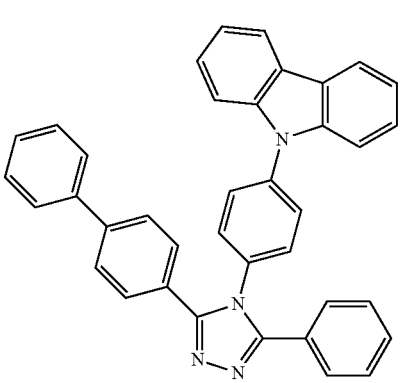
(220)
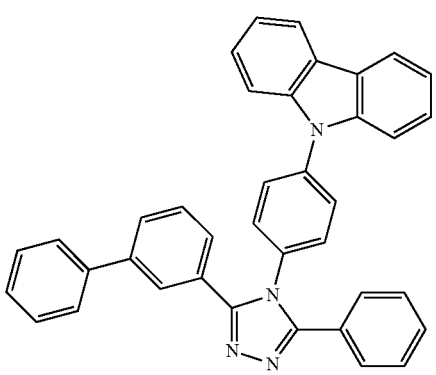
(221)
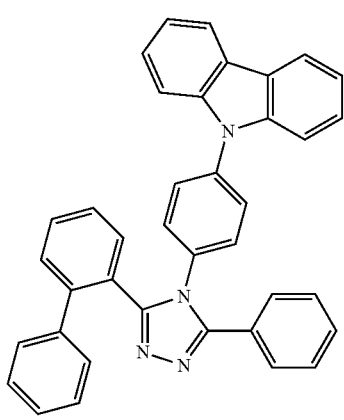

(222)
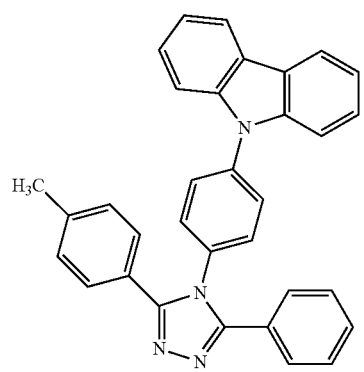
(223)
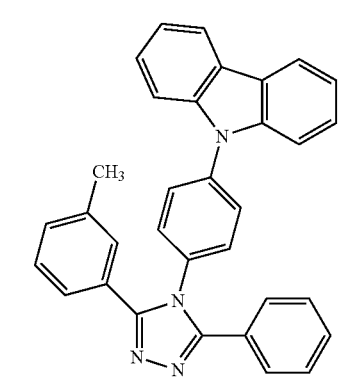
(224)
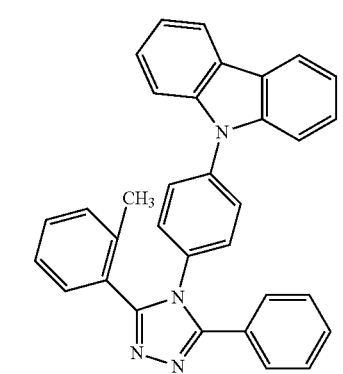
(225)
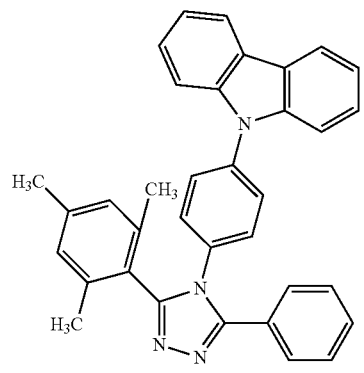
(226)
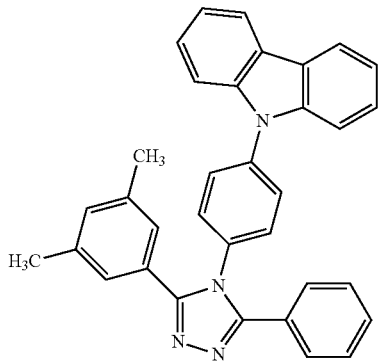
(227)
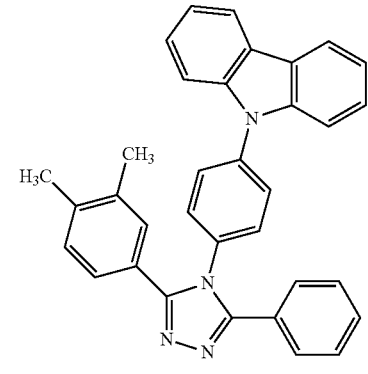
(228)
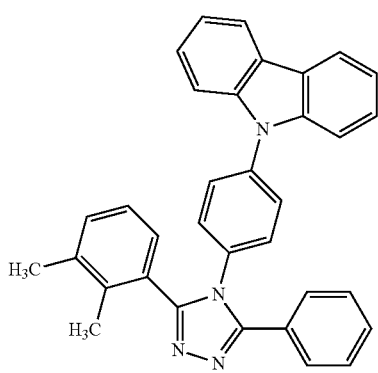
(229)
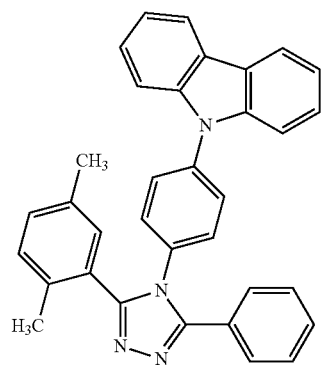

(230) 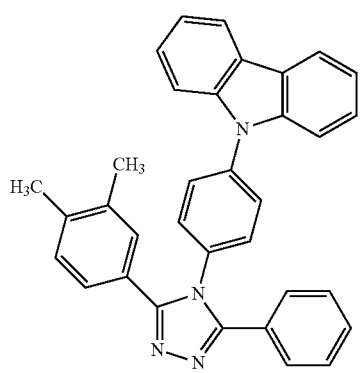
(234) 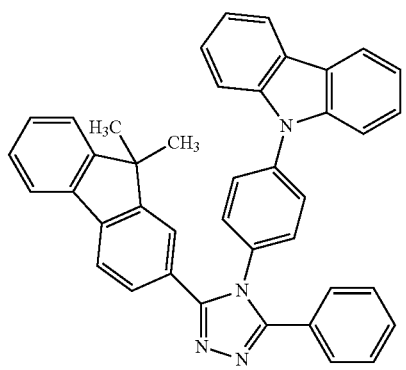
(231) 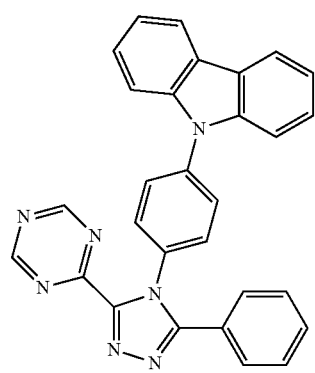
(235) 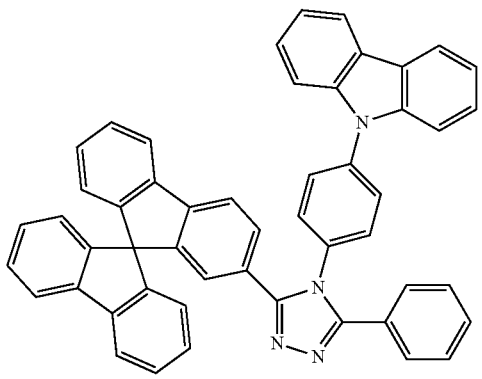
(232) 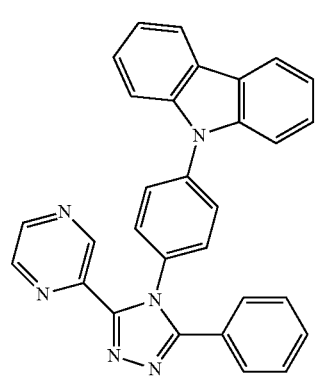
(236) 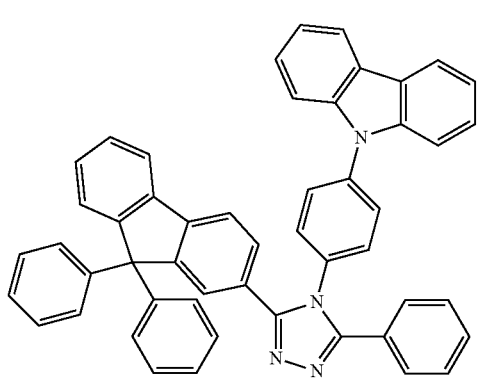
(233) 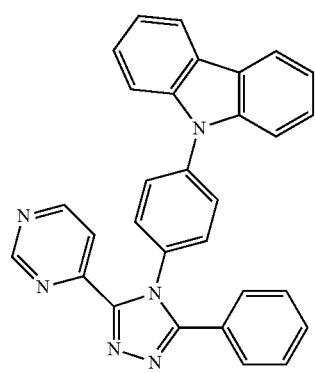
(237) 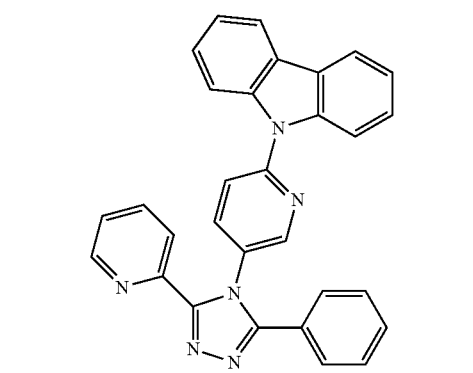

(238) 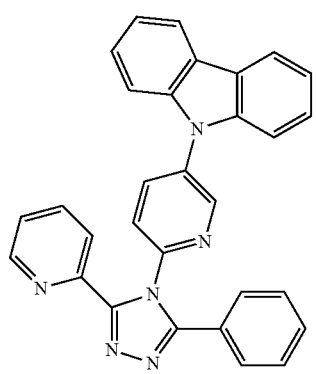
(239) 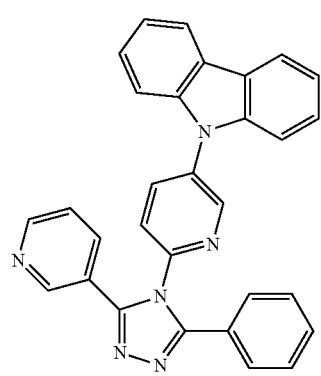
(240) 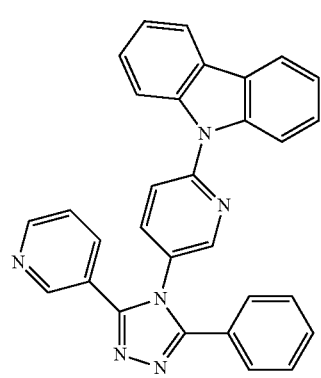
(241) 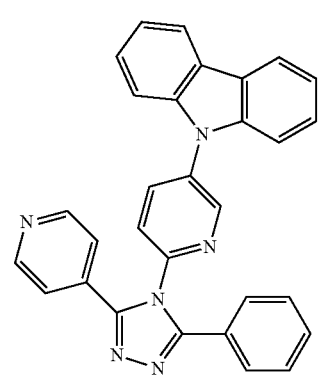
(242) 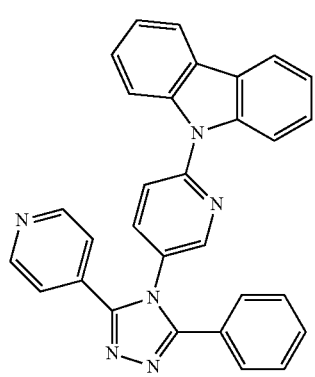
(243) 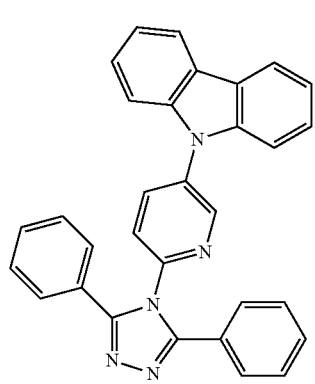
(244) 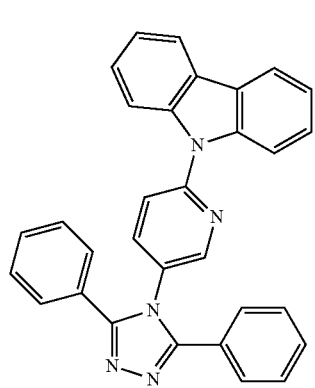
(245) 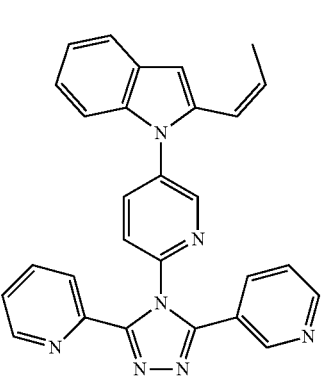

-continued

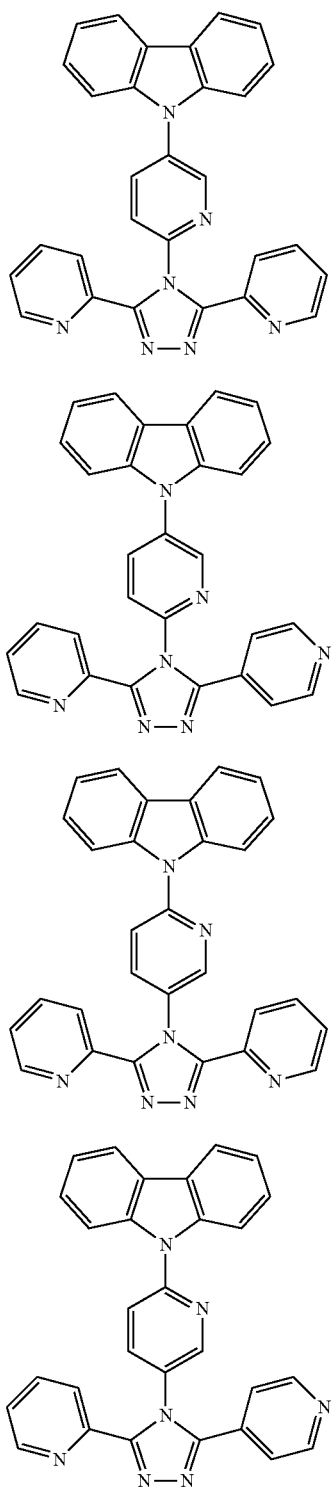

(246)

(247)

(248)

(249)

As a synthesis method of the triazole derivative of the present invention, various reactions can be applied. For example, the triazole derivative of the present invention can be synthesized by synthetic reactions shown below. Note that the synthetic method of the triazole derivative of the present invention is not limited to the following synthetic methods.

<<Synthetic Methods of Halogenated Triazole Derivatives (TAZ-1) and (TAZ-2)>>
<A Synthetic Method of a Halogenated Triazole Derivative (TAZ-1)>
A synthesis scheme of a halogenated triazole derivative (TAZ-1) is shown in (A-1).

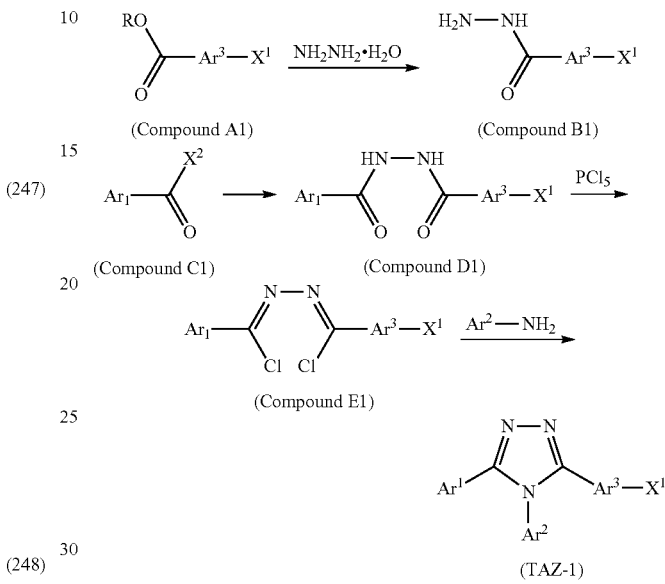

First, a compound A1 (ester of halogenated aryl carboxylic acid or ester of halogenated heteroaryl carboxylic acid) and hydrazine are reacted to synthesize a compound B1 (haglogenated aryl hydrazide or halogenated heteroaryl hydrazide). Next, the compound B1 (haglogenated aryl hydrazide or halogenated heteroaryl hydrazide) and a compound C1 (aryl carboxylic acid halide or heteroaryl carboxylic acid halide) are reacted to obtain a compound D1 (a diacyl hydrazine derivative). Then, the compound D1 (diacyl hydrazine derivative) is reacted with phosphorus pentachloride to obtain a compound E1 (a hydrazone derivative). Further, the compound E1 (hydrazone derivative) and arylamine or heteroaryl are reacted to form a 1,2,4-triazole ring, so that a halogenated triazole derivative (TAZ-1) can be obtained.

In the synthesis scheme (A-1), $Ar^1$ and $Ar^2$ each represent an aryl group or a heteroaryl group, $Ar^3$ represents an arylene group or a heteroarylene group, and $R^1$ to $R^8$ each represent hydrogen, an alkyl group, an alkoxy group, or an aryl group. In addition, $X^1$ and $X^2$ each represent a halogen group. $X^1$ is preferably a bromo group or an iodo group, and $X^2$ is preferably a choloro group.

Note that a synthetic method of the halogenated triazole derivative (TAZ-1) is not limited to the above-described scheme (A-1), and various methods can be used. For example, the halogenated triazole derivative (TAZ-1) can be synthesized with a method shown in a synthesis scheme (A-5).

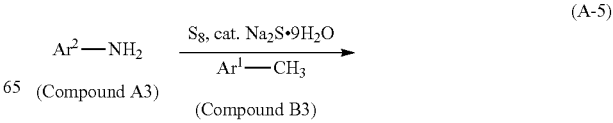

-continued

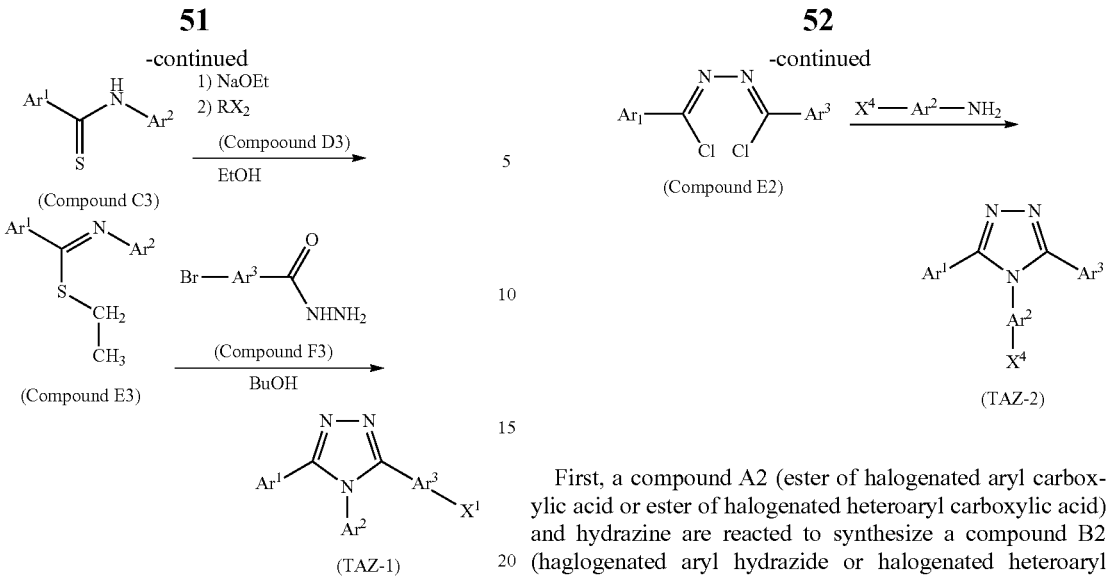

(TAZ-1)

First, arylamine or heteroarylamine (a compound A3), methyl aryl or methyl heteroaryl (a compound B3), and sulfur are reacted in the presence of a catalyst to obtain a thiocarboxyamide compound (a compound C3). Next, the thiocarboxyamide compound (compound C3) and halogenated alkyl (a compound D3) are reacted in the presence of a base to be able to obtain a carboximidoethioate compound (a compound E3). Next, the carboximidoethioate compound (compound E3) and halogenated aryl hydrazide or halogenated heteroaryl hydrazide (a compound F3) are reacted to form a 1,2,4-triazole ring, so that the halogenated triazole derivative (TAZ-1) can be obtained.

In the synthesis scheme (A-5), R represents an alkyl group having 1 to 4 carbon atoms. In addition, $Ar^1$ and $Ar^2$ each represent an aryl group or a heteroaryl group, and $Ar^3$ represents an arylene group or a heteroarylene group. $X^1$ and X each represent a halogen group, and $X^1$ is preferably a bromo group or an iodo group.

<A Synthetic Method of a Halogenated Triazole Derivative (TAZ-2)>

A synthesis scheme of a halogenated triazole derivative (TAZ-2) is shown in (A-2).

(TAZ-2)

First, a compound A2 (ester of halogenated aryl carboxylic acid or ester of halogenated heteroaryl carboxylic acid) and hydrazine are reacted to synthesize a compound B2 (haglogenated aryl hydrazide or halogenated heteroaryl hydrazide). Next, the compound B2 (haglogenated aryl hydrazide or halogenated heteroaryl hydrazide) and a compound C2 (aryl carboxylic acid halide or heteroaryl carboxylic acid halide) are reacted to obtain a compound D2 (a diacyl hydrazine derivative). Then, the compound D2 (diacyl hydrazine derivative) and phosphorus pentachloride are reacted to obtain a compound E2 (a hydrazone derivative). Further, the compound E2 (hydrazone derivative) and arylamine or heteroaryl are reacted to form a 1,2,4-triazole ring, so that a halogenated triazole derivative (TAZ-2) can be obtained.

In the synthesis scheme (A-2), $Ar^1$ and $Ar^3$ each represent an aryl group or a heteroaryl group, $Ar^2$ represents an arylene group or a heteroarylene group, and $R^1$ to $R^8$ each represent hydrogen, an alkyl group, an alkoxy group, or an aryl group. In addition, $X^3$ and $X^4$ each represent a halogen group. $X^3$ is preferably a bromo group or an iodo group, and $X^4$ is preferably a choloro group.

<<A Synthetic Method of a Triazole Derivative of the Present Invention>>

Any of the halogenated triazole derivative (TAZ-1) or (TAZ-2) which is obtained by the above-described synthesis scheme (A-1) or (A-2), respectively, is coupled with a carbazole derivative (Cz1) in the presence of a base with the use of a metal calayst. Accordingly, the triazole derivative of the present invention can be obtained, which is shown in each of synthesis schemes (A-3) and (A-4).

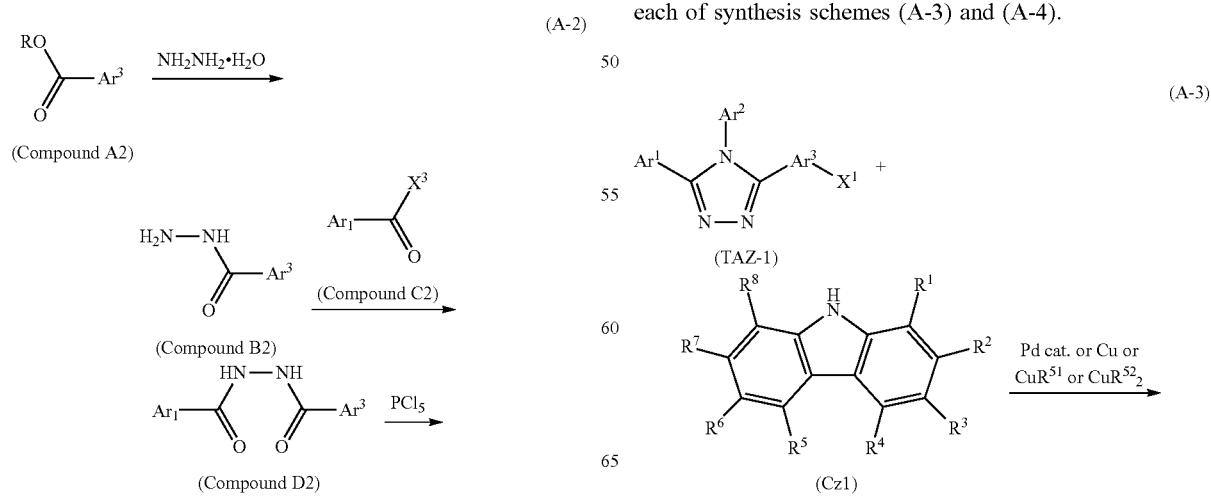

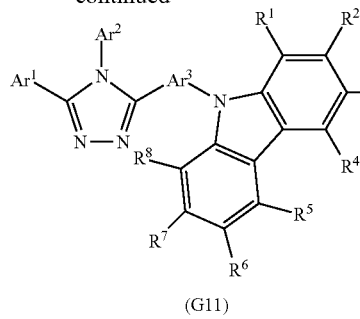

(G11)

As shown in the synthesis scheme (A-3), a carbazole derivative (Cz1) is coupled with the halogenated triazole derivative (TAZ-1) by a Buchwald-Hartwig reaction with a palladium catalyst or an Ullman reaction with copper or a copper compound, so that a triazole derivative which is represented by a general formula (G11) can be obtained.

In the synthesis scheme (A-3), $Ar^1$ and $Ar^2$ each represent an aryl group or a heteroaryl group, $Ar^3$ represents an arylene group or a heteroarylene group, and $R^1$ to $R^8$ each represent hydrogen, an alkyl group, an alkoxy group, or an aryl group. In addition, $X^1$ and $X^2$ each represent a halogen group. $X^1$ is preferably a bromo group or an iodo group, and $X^2$ is preferably a choloro group.

In the case where a Buchwald-Hartwig reaction is performed, as the palladium catalyst which can be used in the synthesis scheme (A-3), bis(dibenzylideneacetone)palladium(0), palladium(II) acetate, and the like, can be given, but the pallarium catalyst which can be used is not limited thereto. As a ligand in the palladium catalyst which can be used in the synthesis scheme (A-3), tri(tert-butyl)phosphine, tri(n-hexyl)phosphine, tricyclohexylphosphine, and the like can be given, but the ligand which can be used is not limited thereto. As a base which can be used in the synthesis scheme (A-3), an organic base such as sodium tert-butoxide, an inorganic base such as potassium carbonate, and the like can be given, but the base which can be used is not limited thereto. As a solvent which can be used in the synthesis scheme (A-3), toluene, xylene, benzene, tetrahydrofuran, and the like can be given, but the solvent which can be used is not limited thereto.

The case in which an Ullmann reaction is performed in the synthesis scheme (A-3) is described. In the synthesis scheme (A-3), $R^{51}$ and $R^{52}$ each represent a halogen group, an acetyl group, or the like, and chlorine, bromine, and iodine can be given as the halogen group. It is preferable that $R^{51}$ be iodine to form copper(I) iodide or that $R^{52}$ be an acetyl group to form copper(II) acetate. The copper compound used for the reaction is not limited thereto, and copper can be used as an alternative to the copper compound. As a base which can be used in the synthesis scheme (A-3), an inorganic base such as potassium carbonate can be given, but the base which can be used is not limited thereto. As a solvent which can be used in the synthesis scheme (A-3), 1,3-dimethyl-3,4,5,6-tetrahydro-2(1H)pyrimidinone (abbreviation: DMPU), toluene, xylene, benzene, and the like can be given, but the solvent which can be used is not limited thereto. DMPU or xylene which has a high boiling point is preferably used because, by an Ullmann reaction, an object can be obtained in a shorter time and at a higher yield when the reaction temperature is greater than or equal to 100° C. Since it is further preferable that the reaction temperature be a temperature greater than or equal to 150° C., DMPU is more preferably used.

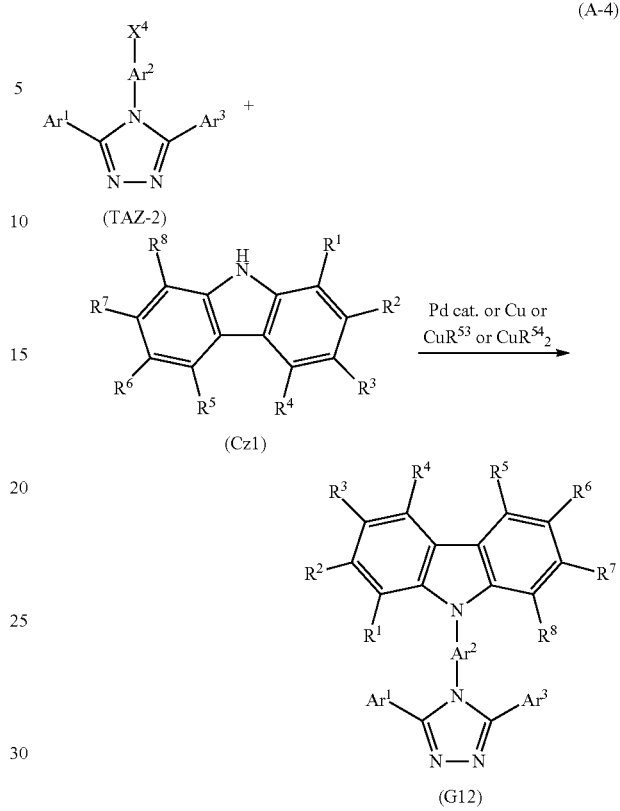

As shown in the synthesis scheme (A-4), a carbazole derivative (Cz1) is coupled with the halogenated triazole derivative (TAZ-2) by a Buchwald-Hartwig reaction with a palladium catalyst or an Ullman reaction with copper or a copper compound, so that a triazole derivative which is represented by a general formula (G12) can be obtained.

In the synthesis scheme (A-4), $Ar^1$ and $Ar^3$ each represent an aryl group or a heteroaryl group, $Ar^2$ represents an arylene group or a heteroarylene group, and $R^1$ to $R^8$ each represent hydrogen, an alkyl group, an alkoxy group, or an aryl group. In addition, $X^3$ and $X^4$ each represent a halogen group. $X^3$ is preferably a bromo group or an iodo group, and $X^4$ is preferably a choloro group.

In the case where a Buchwald-Hartwig reaction is performed, as the palladium catalyst which can be used in the synthesis scheme (A-4), bis(dibenzylideneacetone)palladium(0), palladium(II) acetate, and the like, can be given, but the pallarium catalyst which can be used is not limited thereto. As a ligand in the palladium catalyst which can be used in the synthesis scheme (A-4), tri(tert-butyl)phosphine, tri(n-hexyl)phosphine, tricyclohexylphosphine, and the like can be given, but the ligand which can be used is not limited thereto. As a base which can be used in the synthesis scheme (A-4), an organic base such as sodium tert-butoxide, an inorganic base such as potassium carbonate, and the like can be given, but the base which can be used is not limited thereto. As a solvent which can be used in the synthesis scheme (A-4), toluene, xylene, benzene, tetrahydrofuran, and the like can be given, but the solvent which can be used is not limited thereto.

The case in which an Ullmann reaction is performed in the synthesis scheme (A-4) is described. In the synthesis scheme (A-4), $R^{53}$ and $R^{54}$ each represent a halogen group, an acetyl group, or the like, and chlorine, bromine, and iodine can be given as the halogen group. It is preferable that $R^{53}$ be iodine to form copper(I) iodide or that $R^{54}$ be an acetyl group to form copper(II) acetate. The copper compound used for the reaction is not limited thereto, and copper can be used as an alternative to the copper compound. As a base which can be used in the synthesis scheme (A-4), an inorganic base such as potassium carbonate can be given, but the base which can be used is not limited thereto. As a solvent which can be used in the synthesis scheme (A-4), 1,3-dimethyl-3,4,5,6-tetrahydro-2(1H)pyrimidinone (abbreviation: DMPU), toluene, xylene, benzene, and the like can be given, but the solvent which can be used is not limited thereto. DMPU or xylene which has a high boiling point is preferably used because, by an Ullmann reaction, an object can be obtained in a shorter time and at a higher yield when the reaction temperature is greater than or equal to 100° C. Since it is further preferable that the reaction temperature be a temperature greater than or equal to 150° C., DMPU is more preferably used.

The triazole derivative of the present invention has high triplet excitation energy, and an electron-transporting property and a hole-transporting property. Thus, the triazole derivative of the present invention can be preferably used for a light-emitting element. In particular, when being used for a light-emitting layer of a light-emitting element, the triazole derivative of the present invention is preferably used for the light-emitting layer because the balance between injected electrons and holes is important. Having high triplet excitation energy, the triazole derivative of the present invention can be used for a light-emitting layer, along with a substance that emits phosphorescence. In particular, high luminous efficiency can be achieved even in a case where the triazole derivative of the present invention is used for a light-emitting layer, along with a substance that emits phosphorescence which shows light emission of a short wavelength, the light emissiong peak wavelength of which is greater than or equal to 400 nm and less than or equal to 500 nm.

Since singlet excitation energy (an energy difference between a ground state and a singlet excited state) is higher than triplet excitation energy, a substance having high triplet excitation energy also has high singlet excitation energy. Therefore, the triazole derivative of the present invention having high triplet excitation energy is useful even in a case of being used for a light-emitting layer, along with a substance that emits fluorescence.

In addition, the triazole derivative of the present invention can be used as a carrier-transporting layer in a light-emitting element because it is possible to transport carriers. In particular, the triazole derivative of the present invention has high triplet excitation energy; therefore, energy transfer from a light-emitting layer does not easily occur even in a case where the triazole derivative of the present invention is used for a layer in contact with the light-emitting layer. Accordingly, high luminous efficiency can be achieved.

Embodiment Mode 2

Figure 2:
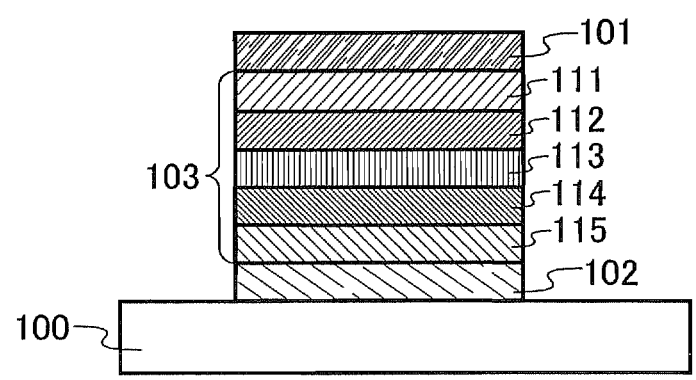
FIG. 2 is a cross-sectional view showing a light-emitting element of the present invention.

This embodiment mode will describe one mode of a light-emitting element using the triazole derivative of the present invention with reference to FIGS. 1 and 2.

The light-emitting element of the present invention has a plurality of layers between a pair of electrodes. The plurality of layers are formed by stacking layers formed of a substance having a high carrier-injecting property or a substance having a high carrier-transporting property. These layers are stacked so that a light-emitting region is formed in a region away from the electrodes, in other words, so that recombination of carriers is performed in a region away from the electrodes.

In FIG. 1, a substrate 100 is used as a support of the light-emitting element. For the substrate 100, a substrate of glass, plastic, or the like may be used, for example. Note that any other materials may be used as long as the substrate 100 functions as a support of the light-emitting element.

In this embodiment mode, the light-emitting element includes a first, a second electrode 102, and an EL layer 103 provided between the first electrode 101 and the second electrode 102. Note that in this embodiment mode, description is made below with an assumption that the first electrode 101 functions as an anode and the second electrode 102 functions as a cathode. That is, description is made below with an assumption that light emission is obtained when voltage is applied to the first electrode 101 and the second electrode 102 so that the potential of the first electrode 101 gets higher than that of the second electrode 102.

It is preferable that the first electrode 101 be formed with a metal, an alloy, or a conductive compound each having a high work function (specifically greater than or equal to 4.0 eV), a mixture thereof, or the like. Specifically, for example, the following can be given: indium tin oxide (ITO), ITO containing silicon or silicon oxide, indium zinc oxide (IZO), indium oxide containing tungsten oxide and zinc oxide (IWZO), and the like. Such conductive metal oxide films are normally deposited by a sputtering method, but may also be deposited by application of a sol-gel process or the like. For example, indium zinc oxide (IZO) can be deposited by a sputtering method, with a target in which 1 to 20 wt % of zinc oxide is added to indium oxide. Indium oxide containing tungsten oxide and zinc oxide (IWZO) can be deposited by a sputtering method, with a target in which 0.5 to 5 wt % of tungsten oxide and 0.1 to 1 wt % of zinc oxide are added to indium oxide. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), and the like can be given as the material of the first electrode 101.

In addition, when a layer containing a composite material which will be described later is used as a layer in contact with the first electrode 101, the first electrode 101 can be formed with any of a variety of metals, alloys, or conductive compounds, a mixture of them, or the like, regardless of respective work functions. For example, aluminum (Al), silver (Ag), an alloy containing aluminum (AlSi), or the like can be used. Alternatively, any of the following low work function materials can be used: Group 1 and Group 2 elements of the periodic table, in other words, an alkali metal such as lithium (Li) or cesium (Cs), an alkaline earth metal such as magnesium (Mg), calcium (Ca), or strontium (Sr), or alloys thereof (e.g., MgAg or A111); a rare earth metal such as europium (Eu) or ytterbium (Yb), or alloys thereof; or the like. Films containing an alkali metal, an alkaline earth metal, or an alloy thereof can be formed by a vacuum evaporation method. Alternatively, films containing an alloy of an alkali metal or an alkaline earth metal can be formed by a sputtering method. Further alternatively, a film can be formed with a silver paste or the like by an ink-jet method or the like.

There is no particular limitation on a stacked-layer structure of the EL layer 103. It is acceptable as long as the EL layer 103 is formed by any combination of the light-emitting layer described in this embodiment mode, as appropriate, with layers each containing a substance having a high electron-transporting property, a substance having a high hole-transporting property, a substance having a high electron-injecting property, a substance having a high hole-injecting property, a bipolar substance (a substance having a high electron-transporting and hole-transporting property), or the like. For example, any combination of a hole-injecting layer, a hole-transporting layer, a light-emitting layer, an electron-transporting layer, an electron-injecting layer, or the like, as appropriate, can be employed. Materials for forming each layer are specifically shown below.

A hole-injecting layer 111 is a layer containing a substance having a high hole-injecting property. As a substance having a high hole-injecting property, molybdenum oxide, vanadium oxide, ruthenium oxide, tungsten oxide, manganese oxide, or the like can be used. Alternatively, the hole-injecting layer 111 can be formed with a phthalocyanine compound such as phthalocyanine ($H_2Pc$) or copper phthalocyanine (CuPc), a high molecular compound such as poly(3,4-ethylenedioxythiophene)/poly(styrenesulfonic acid) (PEDOT/PSS), or the like.

Alternatively, the hole-injecting layer 111 can be formed with a composite material in which an acceptor substance is mixed into a substance having a high hole-transporting property. Note that a material for forming the electrode can be selected regardless of its work function with the use of the composite material in which an acceptor substance is mixed into a substance having a high hole-transporting property. That is, not only a high-work function material, but also a low-work function material can be used for the first electrode 101. As the acceptor substance, the following can be given: 7,7,8,8-tetracyano-2,3,5,6-tetrafluoroquinodimethane (abbreviation: $F_4$-TCNQ), chloranil, transition metal oxide, and oxide of metals that belong to Group 4 to Group 8 of the periodic table. Specifically, any of vanadium oxide, niobium oxide, tantalum oxide, chromium oxide, molybdenum oxide, tungsten oxide, manganese oxide, or rhenium oxide is preferably used because of their high electron accepting property. In particular, molybdenum oxide is more preferable because of its stability in the atmosphere, low hygroscopic property, and easiness of handling.

Note that in this specification, being composite refer not only to a state in which two materials are simply mixed but a state in which charges are transferred between a plurality of materials by mixture of the materials.

As the substance having a high hole-transporting property used for the composite material, any of a variety of compounds such as an aromatic amine compound, a carbazole derivative, aromatic hydrocarbon, or a high molecular compound (e.g., an oligomer, a dendrimer, or a polymer) can be used. A substance having a hole mobility of $10^{-6}$ cm$^2$/Vs or more is preferably used as substance having a high hole-transporting property used for the composite material. However, any other substances may also be used as long as it is a substance in which the hole-transporting property is higher than the electron-transporting property. Organic compounds that can be used for the composite material are specifically shown below.

For example, as the aromatic amine compound that can be used for the composite material, the following can be given: N,N'-bis(4-methylphenyl)-N,N'-diphenyl-p-phenylenediamine (abbreviation: DTDPPA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), and the like.

As the carbazole derivative which can be used for the composite material, specifically, the following can be given: 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphtyl)-N-(9-phenylcarbazol-3-yl)amino]-9-phenylcarbazole (abbreviation: PCzPCN1), and the like.

As the carbazole derivative which can be used for the composite material, the following can be given: 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), 1,4-bis[4-(N-carbazolyl)phenyl]-2,3,5,6-tetraphenylbenzene, and the like.

As the aromatic hydrocarbon which can be used for the composite material, for example, the following can be given: 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 9,10-bis[2-(1-naphthyl)phenyl]-2-tert-butyl-anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Alternatively, pentacene, coronene, or the like can be used. As described above, an aromatic hydrocarbon having a hole mobility of $1 \times 10^{-6}$ cm$^2$/Vs or more and having 14 to 42 carbon atoms is more preferably used.

The aromatic hydrocarbon which can be used for the composite material may have a vinyl skeleton. As the aromatic hydrocarbon having a vinyl skeleton, for example, the following can be given: 4,4'-bis(2,2-diphenylvinyl)biphenyl (abbreviation: DPVBi) 9,10-bis[4-(2,2-diphenylvinyl)phenyl]anthracene (abbreviation: DPVPA), and the like.

As the hole-injecting layer 111, a high molecular compound (e.g., an oligomer, a dendrimer, or a polymer) can be used. For example, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), or poly[N,N'-bis(4-butylphenyl)-N,N'-bis(phenyl)benzidine] (abbreviation: Poly-TPD) can be given. Alternatively, a high molecular compound mixed with acid, such as poly(3,4-ethylenedioxythiophene)/poly(styrenesulfonic acid) (PEDOT/PSS) or polyaniline/poly(styrenesulfonic acid) (PAni/PSS) can be used.

Note that the hole-injecting layer 111 may be formed with a composite material of the above-described high molecular compound, such as PVK, PVTPA, PTPDMA, or Poly-TPD, and the above-described acceptor substance.

A hole-transporting layer 112 is a layer containing a substance having a high hole-transporting property. As the substance having a high hole-transporting property, for example, an aromatic amine compound such as 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4',4"-tris(N, N-diphenylamino)triphenylamine (abbreviation: TDATA), 4,4',4''-tris[N-(3-methylphenyl)-N-phenylamino]triphenylamine (abbreviation: MTDATA), or 4,4'-bis[N-(spiro-9,9'-bifluoren-2-yl)-N-phenylamino]-1,1'-biphenyl (abbreviation: BSPB). These substances described here are mainly substances each having a hole mobility of $10^{-6}$ cm$^2$/Vs or more. Any other substances may also be used as long as it is a substance in which the hole-transporting property is higher than the electron-transporting property. The hole-transporting layer 112 is not limited to a single layer, and may be a stack of two or more layers each containing any of the above-described substances.

Alternatively, as the hole-transporting layer 112, a high molecular compound such as PVK, PVTPA, PTPDMA, or Poly-TPD can be used.

Note that the hole-transporting layer 112 in contact with a light-emitting layer is preferably formed with a substance having higher excitation energy than that of a light-emitting substance of the light-emitting layer. Specifically, when the light-emitting substance is a fluorescent compound, the hole-transporting layer 112 is preferably formed with a substance having higher singlet excitation energy than that of a fluorescent compound. In addition, when the light-emitting substance is a phosphorescent compound, the hole-transporting layer 112 is preferably formed with a substance having higher triplet excitation energy than that of a phosphorescent compound. With such structures, energy transfer from the light-emitting layer to the hole-transporting layer 112 can be suppressed, and high luminous efficiency can be achieved. As a substance having a hole transporting property which is higher than an electron-transporting property and having high triplet excitation energy, the following can be given: 4,4',4''-tris(N-carbazolyl)triphenylamine (an abbreviation: TCTA), 1,1-bis[4-(diphenylamino)phenyl]cyclohexane (abbreviation: TPAC), 9,9-bis[4-(diphenylamino)phenyl]fluorene (abbreviation: TPAF), 4,4'-di(N-carbazolyl)biphenyl (abbreviation: CBP), and the like.

A light-emitting layer 113 is a layer containing a substance having a high light-emitting property. The light-emitting layer 113 can be formed with the triazole derivative which is shown in Embodiment Mode 1. Emitting purple light, the triazole derivative which is shown in Embodiment Mode 1 can be used for the light-emitting layer 113, as a substance having high light-emitting property.

Alternatively, a structure in which a substance having a high light-emitting property is dispersed in the triazole derivative which is shown in Embodiment Mode 1 can be applied. Since the triazole derivative which is shown in Embodiment Mode 1 has high triplet excitation energy and high singlet excitation energy, it is particularly preferable to apply the structure in which a substance having a high light-emitting property is dispersed in the triazole derivative which is shown in Embodiment Mode 1.

As the substance having a high light-emitting property which is dispersed in the triazole derivative which is shown in Embodiment Mode 1, a substance which emits fluorescence or a substance which emits phosphorescence can be used.

When the substance which emits phosphorescence (a phosphorescent compound) is used, a substance having lower triplet excitation energy than that of the triazole derivative which is shown in Embodiment Mode 1 is preferably used. Since the triazole derivative which is shown in Embodiment Mode 1 has high triplet excitation energy, the selection range of the phosphorescent compound which is used for the light-emitting layer 113 is extended. In particular, high luminous efficiency can be achieved even in a case where the triazole derivative which is shown in Embodiment Mode 1 is used for the light-emitting layer 113, along with a substance that emits phosphorescence which shows light emission (blue light emission) of a short wavelength, the light emission peak wavelength of which is greater than or equal to 400 nm and less than or equal to 500 nm.

As the phosphorescent compound which can be used for the light-emitting layer 113, along with the triazole derivative which is shown in Embodiment Mode 1, any of the following organic metal complexes can be used. For example, as a blue light-emitting material, the following can be given: bis[2-(4',6'-difluorophenyl)pyridinato-N,C$^{2'}$] iridium(III)tetrakis(1-pyrazolyl)borate (abbreviation: FIr6); bis[2-(4',6'-difluorophenyl)pyridinato-N,C$^{2'}$]iridium(III)picolinate (abbreviation: FIrpic); bis {2-[3,5'-bis(trifluoromethyl)phenyl]pyridinato-N,C$^{2'}$}iridium (III) picolinate (abbreviation: Ir(CF$_3$ppy)$_2$(pic)); bis[2-(4',6'-difluorophenyl)pyridinato-N,C$^{2'}$]iridium(III)acetylacetonate (abbreviation: FIr(acac)); and the like. As a green light-emitting material, the following can be given: tris(2-phenylpyridinato-N,C$^{2'}$) iridium(III) (abbreviation: Ir(ppy)$_3$); bis(2-phenylpyridinato-N,C$^{2'}$)iridium(III)acetylacetonate (abbreviation: Ir(ppy)$_2$(acac)); bis(1,2-diphenyl-1H-benzimidazolato) iridium(III)acetylacetonate (abbreviation: Ir(pbi)$_2$(acac)); bis(benzo[h]quinolinato)iridium(III)acetylacetonate (abbreviation: Ir(bzq)$_2$(acac)); and the like. As a yellow light-emitting material, the following can be given: bis(2,4-diphenyl-1,3-oxazolato-N,C$^{2'}$)iridium(III)acetylacetonate (abbreviation: Ir(dpo)$_2$(acac)); bis[2-(4'-perfluorophenyl-phenyl)pyridinato]iridium(III)acetylacetonate (abbreviation: Ir(p-PF-ph)$_2$(acac)); bis(2-phenylbenzothiazolato-N, C$^{2'}$)iridium(III)acetylacetonate (abbreviation: Ir(bt)$_2$(acac)); and the like. As an orange light-emitting material, the following can be given: tris(2-phenylquinolinato-N,C$^{2'}$) iridium(III) (abbreviation: Ir(pq)$_3$); bis(2-phenylquinolinato-N,C$^{2'}$)iridium(III)acetylacetonate (abbreviation: Ir(pq)$_2$ (acac)); and the like. As a red light-emitting material, the following can be given: bis[2-(2'-benzo[4,5-α]thienyl) pyridinato-N,C$^{3'}$)iridium(III)acetylacetonate (abbreviation: Ir(btp)$_2$(acac)); bis(1-phenylisoquinolinato-N,C$^{2'}$)iridium (III)acetylacetonate (abbreviation: Ir(piq)$_2$(acac)); (acetylacetonato)bis[2,3-bis(4-fluorophenyl)quinoxalinato] (abbreviation: Ir(Fdpq)$_2$(acac)); (2,3,7,8,12,13,17,18-octaethyl-21H,23H-porphyrinato)platinum(II) (abbreviation: PtOEP); and the like. In addition, a rare-earth metal complex such as tris(acetylacetonato)(monophenanthroline)terbium(III) (abbreviation: Tb(acac)$_3$(Phen)); tris(1,3-diphenyl-1,3-propanedionato)(monophenanthroline)europium(III) (abbreviation: Eu(DBM)$_3$(Phen)); or tris[1-(2-thenoyl)-3,3,3-trifluoroacetonato](monophenanthroline)europium(III) (abbreviation: Eu(TTA)$_3$(Phen)) performs light emission (electron transition between different multiplicities) from a rare-earth metal ion; therefore, such a rare-earth metal complex can be used as the phosphorescent compound.

When the substance which emits fluorescence is used, a substance having lower singlet excitation energy than that of the triazole derivative which is shown in Embodiment Mode 1 is preferably used. Since the triazole derivative which is shown in Embodiment Mode 1 has high singlet excitation energy, the selection range of the fluorescent compound which is used for the light-emitting layer 113 is extended.

As the fluorescent compound which can be used for the light-emitting layer 113, along with the triazole derivative which is shown in Embodiment Mode 1, for example, as a blue light-emitting material, the following can be given: N,N'-bis[4-(9H-carbazol-9-yl)phenyl]-N,N'-diphenylstilbene-4,4'-diamine (abbreviation: YGA2S); 4-(9H-carbazol- 9-yl)-4'-(10-phenyl-9-anthryl)triphenylamine (abbreviation: YGAPA); and the like. As a green light-emitting material, the following can be given: N-(9,10-diphenyl-2-anthryl)-N, 9-diphenyl-9H-carbazol-3-amine (abbreviation: 2PCAPA); N-[9,10-bis(1,1'-biphenyl-2-yl)-2-anthryl]-N,9-diphenyl-9H-carbazol-3-amine (abbreviation: 2PCABPhA); N-(9,10-diphenyl-2-anthryl)-N,N',N'-triphenyl-1,4-phenylenediamine (abbreviation: 2DPAPA); N-[9,10-bis(1,1'-biphenyl-2-yl)-2-anthryl]-N,N',N'-triphenyl-1,4-phenylenediamine (abbreviation: 2DPABPhA); N-[9,10-bis(1,1'-biphenyl-2-yl)]-N-[4-(9H-carbazol-9-yl)phenyl]-N-phenylanthracen-2-amine (abbreviation: 2YGABPhA); N,N,9-triphenylanthracen-9-amine (abbreviation: DPhAPhA); and the like. As a yellow light-emitting material, the following can be given: rubrene; 5,12-bis(1,1'-biphenyl-4-yl)-6,11-diphenyltetracene (abbreviation: BPT); and the like. As a red light-emitting material, the following can be given; N,N,N',N'-tetrakis(4-methylphenyl)tetracene-5,11-diamine (abbreviation: p-mPhTD); 7,13-diphenyl-N, N,N',N'-tetrakis(4-methylphenyl)acenaphtho[1,2-a]fluoranthene-3,10-diamine (abbreviation: p-mPhAFD); and the like.

An electron-transporting layer 114 is a layer containing a substance having a high electron-transporting property. For example, a metal complex or the like having a quinoline or benzoquinoline skeleton, such as the following, can be used: tris(8-quinolinolato)aluminum(III) (abbreviation: Alq); tris(4-methyl-8-quinoliolato)aluminum(III) (abbreviation: Almq$_3$); bis(10-hydroxybenzo[h]quinolinato)beryllium(II) (abbreviation: BeBq$_2$), or bis(2-methyl-8-quinolinolato)(4-phenylphenolato)aluminum(M) (abbreviation: BAlq). Alternatively, a metal complex or the like having an oxazole-based or thiazole-based ligand, such as bis[2-(2'-hydroxyphenyl)benzoxazolato]zinc(II) (abbreviation: Zn(BOX)$_2$) or bis[2-(2'-hydroxyphenyl)benzothiazolato]zinc(II) (abbreviation: Zn(BTZ)$_2$) can be used. As an alternative to the metal complex, 2-(4-biphenylyl)-5-(4-tert-butylphenyl)-1,3,4-oxadiazole (abbreviation: PBD); 1,3-bis[5-(p-tert-butylphenyl)-1,3,4-oxadiazol-2-yl]benzene (abbreviation; OXD-7), bathophenanthroline (abbreviation: BPhen), bathocuproine (BCP), or the like can be used. The substances described here are mainly substances each having an electron mobility of $10^{-6}$ cm$^2$/Vs or more. Any other substances may also be used as long as it is a substance in which the electron-transporting property is higher than the hole-transporting property. Furthermore, the electron-transporting layer 114 is not limited to a single layer, and may be a stack of two or more layers each containing any of the above-described substances.

For the electron-transporting layer 114, a high molecular compound can be used. For example, poly[(9,9-dihexylfluorene-2,7-diyl)-co-(pyridin-3,5-diyl)] (abbreviation: PF-Py), poly[(9,9-dioctylfluorene-2,7-diyl)-co-(2,2'-bipyridin-6,6'-diyl)] (abbreviation: PF-BPy), or the like can be used.

Note that the electron-transporting layer 114 in contact with the light-emitting layer 113 is preferably formed with a substance having higher excitation energy than that of the light-emitting substance of the light-emitting layer 113. Specifically, when the light-emitting substance is a fluorescent compound, the electron-transporting layer 114 is preferably formed with a substance having higher singlet excitation energy than that of a fluorescent compound. In addition, when the light-emitting substance is a phosphorescent compound, the electron-transporting layer 114 is preferably formed with a substance having higher triplet excitation energy than that of a phosphorescent compound. With such structures, energy transfer from the light-emitting layer 113 to the electron-transporting layer 114 can be suppressed, and high luminous efficiency can be achieved. As a substance having an electron transporting property which is higher than a hole-transporting property and having high triplet excitation energy, the following can be given: 3-(4-biphenylyl)-4-phenyl-5-(4-tert-butylphenyl)-1,2,4-triazole (abbreviation: TAZ01); 2,2',2''-(1,3,5-benzenetriyl)tris(1-phenyl-1H-benzimidazole) (abbreviation: TPBI); 3-(4'-tert-butylphenyl)-4-phenyl-5-(4''-biphenyl)-1,2,4-triazole (abbreviation: TAZ); 3-(4-tert-butylphenyl)-4-(4-ethylphenyl)-5-(4-biphenylyl)-1,2,4-triazole (abbreviation: p-EtTAZ); 9,9',9''-[1,3,5-triazine-2,4,6-triyl]tricarbazole (abbreviation: TCzTRZ); and the like.

An electron-injecting layer 115 may be provided. The electron-injecting layer 115 can be formed with an alkali metal compound or an alkaline earth metal compound such as lithium fluoride (LiF), cesium fluoride (CsF), or calcium fluoride (CaF$_2$). Furthermore, a layer, in which a substance having an electron-transporting property is combined with an alkali metal or an alkaline earth metal, can be employed. For example, it is possible to use a layer made of Alq in which magnesium (Mg) is contained. It is more preferable to use the layer, in which a substance having an electron-transporting property is combined with an alkali metal or an alkaline earth metal, as the electron-injecting layer, because electron injection from the second electrode 102 efficiently proceeds.

The second electrode 102 can be formed with a metal, an alloy, or a conductive compound each having a low work function (specifically less than or equal to 3.8 eV), a mixture of them, or the like. As specific examples of such cathode materials, the following can be given: elements belonging to Group 1 and 2 of the periodic table, in other words, alkali metals such as lithium (Li) or cesium (Cs), alkaline earth metals such as magnesium (Mg), calcium (Ca), or strontium (Sr), or alloys thereof (e.g., MgAg or AlLi); rare earth metals such as europium (Eu) or ytterbium (Yb), or alloys thereof; and the like. Films containing an alkali metal, an alkaline earth metal, or an alloy thereof can be formed by a vacuum evaporation method. Alternatively, films containing an alkali metal, an alkaline earth metal, or an alloy thereof can be formed by a sputtering method. Further alternatively, a film can be formed of a silver paste by an ink-jet method or the like.

When the electron-injecting layer 115 is provided between the second electrode 102 and the electron-transporting layer 114, any of a variety of conductive materials such as Al, Ag, ITO, or ITO containing silicon or silicon oxide can be used for the second electrode 102 regardless of its work function. These conductive materials can be deposited by a sputtering method, an ink-jet method, a spin coating method, or the like.

In the light-emitting element having the above structure, which is described in this embodiment mode, application of voltage between the first electrode 101 and the second electrode 102 makes current flow, whereby holes and electrons are recombined in the light-emitting layer 113 which is a layer containing a substance having a high light-emitting property; thus, light is emitted. That is, a light-emitting region is formed in the light-emitting layer 113.

Light emission is extracted outside through one of or both the first electrode 101 and the second electrode 102. Therefore, one of or both the first electrode 101 and the second electrode 102 are light-transmitting electrodes. When only the first electrode 101 is a light-transmitting electrode, light is extracted from the substrate side through the first electrode 101. In contrast, when only the second electrode 102 is a light-transmitting electrode, light is extracted from a side opposite to the substrate side through the second electrode 102. When both the first electrode 101 and the second electrode 102 are light-transmitting electrodes, light is extracted from both the substrate side and the side opposite to the substrate side through the first electrode 101 and the second electrode 102.

Although FIG. 1 shows a structure in which the first electrode 101 which functions as an anode is provided on the substrate 100 side, the second electrode 102 which functions as a cathode may be provided on the substrate 100 side. FIG. 2 shows a structure in which the second electrode 102 which functions as a cathode, the EL layer 103, and the first electrode 101 which functions as an anode are stacked in this order over the substrate 100. In the EL layer 103, the layers are stacked in the reverse order of that shown in FIG. 1.

Any of a variety of methods can be employed for forming the EL layer regardless of a dry process or a wet process. Further, different deposition methods may be employed for each electrode or layer. A vacuum evaporation method, a sputtering method, or the like can be employed as a dry process. An ink-jet method, a spin-coating method, or the like can be employed as a wet process.

For example, the EL layer may be formed by a wet process with the use of a high molecular compound among the above-described materials. Alternatively, the EL layer can be formed by a wet process with the use of a low molecular organic compound. Further alternatively, the EL layer may be formed by a dry process such as a vacuum evaporation method with the use of a low molecular organic compound.

The electrodes may also be formed by a wet process with the use of a sol-gel process or by a wet process with the use of a metal paste. Alternatively, the electrodes may be formed by a dry process such as a sputtering method or a vacuum evaporation method.

When the light-emitting element shown in this embodiment mode is applied to a display device and its light-emitting layer is separately coated, the light-emitting layer is preferably formed by a wet process. When the light-emitting layer is formed by an ink-jet method, it becomes easy to separately coat the light-emitting layer even on a large-sized substrate, whereby productivity is improved.

A specific method for forming the light-emitting element is described below.

For example, in the structure shown in FIG. 1, the first electrode 101 may be formed by a sputtering method which is a dry process; the hole-injecting layer 111 may be formed by an ink-jet method or a spin coating method which is a wet process; the hole-transporting layer 112 may be formed by a vacuum evaporation method which is a dry process; the light-emitting layer 113 may be formed by an ink-jet method which is a wet process; the electron-transporting layer 114 may be formed by a vacuum evaporation method which is a dry process; the electron-injecting layer 115 may be formed by a vacuum evaporation method which is a dry process; and the second electrode 102 may be formed by an ink-jet method or a spin coating method which is a wet process. Alternatively, in the structure shown in FIG. 1, the first electrode 101 may be formed by an ink-jet method which is a wet process; the hole-injecting layer 111 may be formed by a vacuum evaporation method which is a dry process; the hole-transporting layer 112 may be formed by an ink-jet method or a spin coating method which is a wet process; the light-emitting layer 113 may be formed by an ink-jet method which is a wet process; the electron-transporting layer 114 may be formed by an ink-jet method or a spin coating method which is a wet process; the electron-injecting layer 115 may be formed by an ink-jet method or a spin coating method which is a wet process; and the second electrode 102 may be formed by an ink-jet method or a spin coating method which is a wet process. Note that a wet process and a dry process may be combined, as appropriate, without limitation thereto.

For example, in the structure shown in FIG. 1, the first electrode 101 may be formed by a sputtering method which is a dry process, the hole-injecting layer 111 and the hole-transporting layer 112 may be formed by an ink-jet method or a spin coating method which is a wet process, the light-emitting layer 113 may be formed by an ink-jet method which is a wet process, the electron-transporting layer 114 and the electron-injecting layer 115 may be formed by a vacuum evaporation method which is a dry process, and the second electrode 102 may be formed by a vacuum evaporation method which is a dry process. That is, it is possible to form from the hole-injecting layer 111 to the light-emitting layer 113 each by a wet process over the substrate having the first electrode 101 which has already been formed in a desired shape, and form from the electron-transporting layer 114 to the second electrode 102 thereover each by a dry process. By this method, from the hole-injecting layer 111 to the light-emitting layer 113 can be formed at atmospheric pressure, and it is easy to separately coat the light-emitting layer 113. Further, from the electron-transporting layer 114 to the second electrode 102 can be consecutively formed in vacuum. Therefore, the process can be simplified, and productivity can be improved.

The process is exemplarily described below. First, PEDOT/PSS is deposited as the hole-injecting layer 111 on the first electrode 101. Since PEDOT/PSS is soluble in water, it can be deposited as an aqueous solution by a spin coating method, an ink jet method, or the like. The hole-transporting layer 112 is not provided but the light-emitting layer 113 is provided on the hole-injecting layer 111. The light-emitting layer 113 can be formed by an ink-jet method, with the composition including a solvent (e.g., toluene, dodecylbenzene, a mixed solvent of dodecylbenzene and tetralin, ethers, or alcohols) in which the hole-injecting layer 111 (PEDOT/PSS) which has already been formed is not dissolved, and the triazole derivative which is shown in Embodiment Mode 1. Next, the electron-transporting layer 114 is formed on the light-emitting layer 113. When the electron-transporting layer 114 is formed by a wet process, the electron-transporting layer 114 should be formed with a solvent in which the hole-injecting layer 111 and the light-emitting layer 113 which have already been formed are not dissolved. In that case, the selection range of solvents is limited; therefore, the use of a dry process is easier to form the electron-transporting layer 114. Thus, the process can be simplified by consecutively forming the electron-transporting layer 114 to the second electrode 102 in vacuum by a vacuum evaporation method which is a dry process.

Meanwhile, in the case of a structure shown in FIG. 2, the order is reversed to that of the above-described methods. The second electrode 102 may be formed by a sputtering method or a vacuum evaporation method which is a dry process, the electron-injecting layer 115 and the electron-transporting layer 114 may be formed by a vacuum evaporation method which is a dry process, the light-emitting layer 113 may be formed by an ink-jet method which is a wet process, the hole-transporting layer 112 and the hole-injecting layer 111 may be formed by an ink-jet method or a spin coating method which is a wet process, and the first electrode 101 may be formed by an ink-jet method or a spin coating method which is a wet process. By this method, the second electrode 102 to the electron-transporting layer 114 can be consecutively formed in vacuum by dry processes, and the light-emitting layer 113 to the first electrode 101 can be formed at atmospheric pressure. Therefore, the process can be simplified, and productivity can be improved. The composition which is shown in Embodiment Mode 1 can be applied to a layer formed by an evaporation method or the like, which allows such a manufacturing method.

In this embodiment mode, the light-emitting element is formed over a substrate including glass, plastic, or the like. When a plurality of such light-emitting elements are formed over a substrate, a passive matrix light-emitting device can be manufactured. In addition, it is also possible to form, for example, thin film transistors (TFTs) over a substrate including glass, plastic, or the like, and form light-emitting elements over an electrode that is electrically connected to the TFTs. Accordingly, an active matrix light-emitting device in which drive of the light-emitting elements is controlled by the TFTs can be manufactured. Note that there is no particular limitation on the structure of each TFT, and either a staggered TFT or an inversely staggered TFT may be employed. In addition, a driver circuit formed over a TFT substrate may include both n-channel and p-channel TFTs or one of n-channel and p-channel TFTs. Further, there is no particular limitation on the crystallinity of a semiconductor used for forming the TFTs, and either an amorphous semiconductor or a crystalline semiconductor may be used. Alternatively, a single-crystal semiconductor film may be used. A single-crystal semiconductor film can be formed by Smart Cut (registered trademark) or the like.

Having a bipolar property including an electron-transporting property and a hole-transporting property, the triazole derivative which is shown in Embodiment Mode 1 can be preferably used for a light-emitting layer. In addition, since the triazole derivative which is shown in Embodiment Mode 1 has a bipolar property, a light-emitting region does not exist close to an interface between the light-emitting layer and a hole-transporting layer or an interface between the light-emitting layer and an electron-transporting layer. Accordingly, concentration quenching of a light-emitting substance or quenching due to triplet-triplet annihilation (T-T annihilation) can be suppressed, and high luminous efficiency can be achieved.

Further, since the triazole derivative which is shown in Embodiment Mode 1 has a bipolar property, driving voltage of a light-emitting element can be reduced. Thus, power consumption of a light-emitting element can be reduced.

Furthermore, having high triplet excitation energy, the triazole derivative which is shown in Embodiment Mode 1 can be used for a light-emitting layer, along with a phosphorescent compound. In particular, the triazole derivative which is shown in Embodiment Mode 1 can be used for a full-color display or the like, because it is possible to be used for a light-emitting layer, along with a phosphorescent compound which shows blue light emission of a short wavelength, the light emission peak wavelength of which is greater than or equal to 400 nm and less than or equal to 500 nm. Thus, a full-color display which utilizes the feature of the phosphorescent compound, which is high luminous efficiency, can be achieved.

Still further, the triazole derivative which is shown in Embodiment Mode 1 can manufacture a white light-emitting element with a plurality of light-emitting substances, which are all phosphorescent compounds, because it is possible to be used for a light-emitting layer, along with a phosphorescent compound which shows blue light emission.

Still furthermore, the triazole derivative which is shown in Embodiment Mode 1 shows the above-described feature with one kind of materials. Thus, as compared to the case where the above-described feature is achieved by mixing a plurality of materials, variation in characteristics of each lot can be reduced.

Note that this embodiment mode can be combined with any of other embodiment modes, as appropriate.

Embodiment Mode 3

This embodiment mode will describe a light-emitting element, the structure of which is different from the structure of the light-emitting element shown in Embodiment Mode 2.

Having both an electron-transporting property and a hole-transporting property, the triazole derivative which is shown in Embodiment Mode 1 can be used as a carrier-transporting layer. Specifically, the triazole derivative which is shown in Embodiment Mode 1 can be used as a hole-transporting layer or an electron-transporting layer. In particular, the triazole derivative which is shown in Embodiment Mode 1 has high triplet excitation energy and high singlet excitation energy; therefore, energy transfer from a light-emitting layer does not easily occur in a case where the triazole derivative which is shown in Embodiment Mode 1 is used for a layer in contact with the light-emitting layer. Accordingly, high luminous efficiency can be achieved.

Note that this embodiment mode can be combined with any of other embodiment modes, as appropriate.

Embodiment Mode 4

This embodiment mode will describe a mode of a light-emitting element in which a plurality of light-emitting units related to the present invention are stacked (hereinafter referred to as a stacked-type element) with reference to FIG. 3. The light-emitting element is a stacked-type light-emitting element including a plurality of light-emitting units between a first electrode and a second electrode. The light-emitting units can each have a structure similar to the structure of the EL layer described in Embodiment Mode 2 and/or Embodiment Mode 3. That is, a light-emitting element including one light-emitting unit is shown in Embodiment Modes 2 and 3. In this embodiment mode, a light-emitting element including a plurality of light-emitting units will be described.

Figure 3:
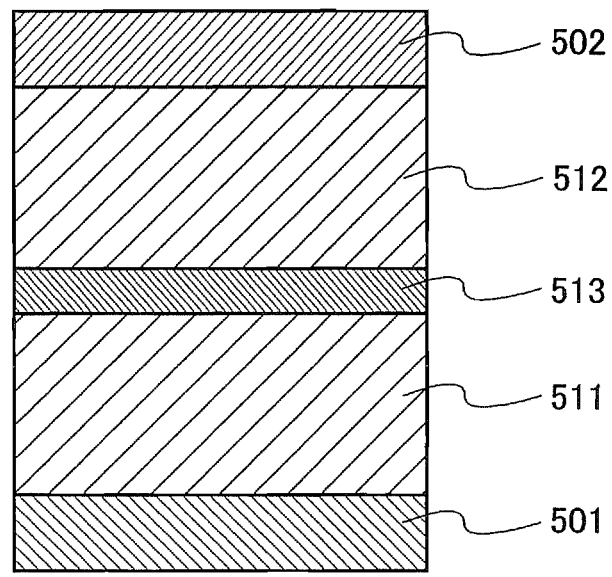
FIG. 3 is a cross-sectional view showing a light-emitting element of the present invention.

In FIG. 3, a first light-emitting unit 511 and a second light-emitting unit 512 are stacked between a first electrode 501 and a second electrode 502. Electrodes which are similar to the first electrode 101 and the second electrode 102 shown in Embodiment Mode 2 can be applied to the first electrode 501 and the second electrode 502. The first light-emitting unit 511 and the second light-emitting unit 512 may have either the same or a different structure, which can be similar to that described in Embodiment Mode 2 and/or Embodiment Mode 3.

A charge generation layer 513 may include a composite material of an organic compound and metal oxide. The composite material of an organic compound and metal oxide is described in Embodiment Mode 2 and contains an organic compound and metal oxide such as vanadium oxide, molybdenum oxide, or tungsten oxide. As the organic compound, any of a variety of compounds such as an aromatic amine compound, a carbazole derivative, aromatic hydrocarbon, or a high molecular compound (e.g., an oligomer, a dendrimer, or a polymer) can be used. The compound having a hole mobility of $1 \times 10^{-6}$ cm$^2$/Vs or more is preferably used as the organic compound having a hole-transporting property. Any other substances may also be used as long as it is a substance in which the hole-transporting property is higher than the electron-transporting property. A composite material of an organic compound with metal oxide is excellent in a carrier-injecting property and a carrier-transporting property, so that low-voltage driving and low-current driving can be achieved.

Note that the charge generation layer 513 may be formed by a combination of the composite material of an organic compound and metal oxide with any other material. For example, the charge generation layer 513 may be formed by a combination of the layer including the composite material of an organic compound and metal oxide with a layer including one compound selected from electron donating substances and a compound having a high electron-transporting property. Alternatively, the charge generation layer 513 may be formed by a combination of a transparent conductive film with a layer including the composite material of an organic compound and metal oxide.

In any case, the charge generation layer 513 interposed between the first light-emitting unit 511 and the second light-emitting unit 512 may have any structure as long as electrons can be injected into the light-emitting unit on one side and holes can be injected into the light-emitting unit on the other side when voltage is applied between the first electrode 501 and the second electrode 502. For example, any acceptable structure is one in which the charge generation layer 513 injects electrons to the first light-emitting unit 511 and injects holes to the second light-emitting unit 512 when voltage is applied so that the potential of the first electrode is higher than that of the second electrode.

Although the light-emitting element having two light-emitting units is described in this embodiment mode, the present invention can be applied in a manner similar to that of a light-emitting element in which three or more light-emitting units are stacked. When a plurality of light-emitting units are arranged between a pair of electrodes so as to partition the two light-emitting units with a charge generation layer therebetween like the light-emitting element related to this embodiment mode, a light-emitting element having a long life in a high luminance region can be achieved with low current density being kept. When the light-emitting element is applied to a lighting system, voltage drop due to resistance of the electrode materials can be suppressed; thus, uniform light emission in a large area becomes possible. Furthermore, a light-emitting device which can be driven at low voltage and consumes low power can be achieved.

Having a bipolar property including an electron-transporting property and a hole-transporting property, the triazole derivative which is shown in Embodiment Mode 1 can be preferably used for a light-emitting layer. In addition, since the triazole derivative which is shown in Embodiment Mode 1 has a bipolar property, a light-emitting region does not exist close to an interface between the light-emitting layer and a hole-transporting layer or an interface between the light-emitting layer and an electron-transporting layer. Accordingly, concentration quenching of a light-emitting substance or quenching due to triplet-triplet annihilation (T-T annihilation) can be suppressed, and high luminous efficiency can be achieved. Further, since the triazole derivative which is shown in Embodiment Mode 1 has a bipolar property, driving voltage of a light-emitting element can be reduced. Thus, power consumption of a light-emitting element can be reduced.

In addition, having high triplet excitation energy, the triazole derivative which is shown in Embodiment Mode 1 can be used for a light-emitting layer, along with a phosphorescent compound. In particular, the triazole derivative which is shown in Embodiment Mode 1 can be applied to the stacked-type light-emitting element which is shown in this embodiment mode because it is possible to be used for a light-emitting layer, along with a phosphorescent compound which shows blue light emission of a short wavelength, the light emission peak wavelength of which is greater than or equal to 400 nm and less than or equal to 500 nm. Accordingly, it is also possible to manufacture a white light-emitting element only with a phosphorescent compound, without a fluorescent compound, as a light-emitting substance. For example, as a light-emitting substance of the first light-emitting unit 511, bis[2-(4',6'-difluorophenyl)pyridinato-N,$C^{2'}$]iridium(III)picolinate (abbreviation: FIrpic) which shows blue light emission is used, and as a light-emitting substance of the second light-emitting unit 512, bis[2,3-bis(4-fluorophenyl)-5,6,7,8-tetrahydroquinoxalinate](picolinato)iridium(III) (abbreviation: Ir(FdpqtH)$_2$(pic)) is used. Accordingly, a white light-emitting element can be obtained. Further, as a light-emitting substance of the first light-emitting unit 511, any of the following phosphorescent compounds, the light emission peak wavelength each of which is greater than or equal to 400 nm and less than or equal to 500 nm, is used: bis[2-(4',6'-difluorophenyl)pyridinato-N,$C^{2'}$]iridium(III)tetrakis(1-pyrazolyl)borate (abbreviation: FIr6); bis[2-(4',6'-difluorophenyl)pyridinato-N,$C^{2'}$]iridium(III)picolinate (abbreviation: FIrpic); bis{2-[3',5'-bis(trifluoromethyl)phenyl]pyridinato-N,$C^{2'}$}iridium (III) picolinate (abbreviation: Ir(CF$_3$ppy)$_2$(pic)); bis[2-(4,6'-difluorophenyl)pyridinato-N,$C^{2'}$]iridium(III)acetylacetonate (abbreviation: FIr(acac)); or the like. As a light-emitting substance of the second light-emitting unit 512, any of the following phosphorescent compounds, the light emission peak wavelength each of which is greater than or equal to 550 nm and less than or equal to 630 nm, is used: (acetylacetonato)bis[2,3-diphenyl-5,6,7,8-tetrahydroquinoxalinate]iridium(III) (abbreviation: Ir(dpqtH)$_2$(acac)); bis[2,3-bis(4-fluorophenyl)-5,6,7,8-tetrahydroquinoxalinate](picolinato)iridium(III) (abbreviation: Ir(FdpqtH)$_2$(pic)); bis[2,3-bis(4-fluorophenyl)-5,6,7,8-tetrahydroquinoxalinato][tetrakis(1-pyrazolyl)borato]iridium(III) (abbreviation: Ir(FdpqtH)$_2$(bpz$_4$)); (acetylacetonato)bis[2,3-bis(4-fluorophenyl)-5,6,7,8-tetrahydroquinoxalinato]iridium(III (abbreviation: Ir(FdpqtH)$_2$(acac)); (acetylacenato)[2,3-bis(4-fluorophenyl)-5,6,7,8-tetrahydroquinoxalinato]platinum(II) (abbreviation: Pt(FdpqtH)(acac)); or the like. Accordingly, a white light-emitting element can be obtained.

Having both an electron-transporting property and a hole-transporting property, the triazole derivative which is shown in Embodiment Mode 1 can be used as a carrier-transporting layer. Specifically, the triazole derivative which is shown in Embodiment Mode 1 can be used as a hole-transporting layer or an electron-transporting layer. In particular, the triazole derivative which is shown in Embodiment Mode 1 has high triplet excitation energy and high singlet excitation energy; therefore, energy transfer from a light-emitting layer does not easily occur in a case where the triazole derivative which is shown in Embodiment Mode 1 is used for a layer in contact with the light-emitting layer. Accordingly, high luminous efficiency can be achieved.

Further, having a bipolar property, the triazole derivative which is shown in Embodiment Mode 1 can be used as a carrier-transporting layer. Energy transfer from a light-emitting layer does not easily occur particularly when the triazole derivative which is shown in Embodiment Mode 1 is used for a layer in contact with the light-emitting layer. Accordingly, high luminous efficiency can be achieved.

Note that this embodiment mode can be combined with any of other embodiment modes, as appropriate.

Embodiment Mode 5

This embodiment mode will describe a light-emitting device which is manufactured using the triazole derivative of the present invention.

This embodiment mode will describe a light-emitting device which is manufactured with the triazole derivative of the present invention with reference to FIGS. 4A and 4B. FIG. 4A is a top view of a light-emitting device, and FIG. 4B is a cross-sectional view taken along lines A-A' and B-B' of FIG. 4A. The light-emitting device includes a driver circuit portion (a source driver circuit) 601; a pixel portion 602; and a driver circuit portion (a gate driver circuit) 603, which are indicated by dotted lines, so as to control light emission from a light-emitting element. Reference numerals 604 and 605 denote a sealing substrate and a sealing material, respectively, and there is a space 607 inside surrounded by the sealing material 605.

Note that a lead wiring 608 is a wiring for transmitting signals which are to be inputted into the source side driver circuit 601 and the gate side driver circuit 603. The lead wiring 608 receives a video signal, a clock signal, a start signal, a reset signal, or the like from a flexible printed circuit (FPC) 609 which is an external input terminal. Although only the FPC is shown here, the FPC may be provided with a printed wiring board (PWB). The light-emitting device in this specification includes not only a light-emitting device itself but also a light-emitting device with an FPC or a PWB attached thereto.

Next, a cross-sectional structure is described with reference to FIG. 4B. The circuit portions and the pixel portion are formed over an element substrate 610. Here, the source side driver circuit 601 which is the driver circuit portion and one pixel in the pixel portion 602 are shown.

A CMOS circuit, which is a combination of an n-channel TFT 623 and a p-channel TFT 624, is formed for the source driver circuit 601. The driver circuit may be formed with various types of circuits, such as CMOS circuits, PMOS circuits, or NMOS circuits. A driver-integration type device, in which a driver circuit is formed over the same substrate as the pixel portion, is shown in this embodiment mode; however, a driver circuit is not necessarily formed over the same substrate as the pixel portion and can also be formed outside the substrate.

The pixel portion 602 is formed of a plurality of pixels, each of which includes a switching TFT 611, a current-controlling TFT 612, and a first electrode 613 which is electrically connected to a drain of the current-controlling TFT 612. Note that an insulator 614 is formed so as to cover an end portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in the case of using a positive photosensitive acrylic resin as a material of the insulator 614, the insulator 614 is preferably formed so as to have a curved surface with a curvature radius (0.2 to 3 µm) only at the upper end portion thereof. Either a negative photoresist which becomes insoluble in an etchant by light irradiation or a positive photoresist which becomes soluble in an etchant by light irradiation can be used for the insulator 614.

Over the first electrode 613, an EL layer 616 and a second electrode 617 are formed. Here, it is preferable to use a material with a high work function as a material for forming the first electrode 613 which functions as an anode. For example, the first electrode 613 can be formed with a single-layer film such as an ITO film, an indium tin oxide film containing silicon, an indium oxide film containing zinc oxide of 2 to 20 wt %, a titanium nitride film, a chromium film, a tungsten film, a Zn film, or a Pt film; a stacked layer of a titanium nitride film and a film containing aluminum as its main component; a three-layer structure of a titanium nitride film, a film containing aluminum as its main component, and a titanium nitride film; or the like. In the case of a stacked-layer structure, the first electrode 613 has low resistance as a wiring, which results in a favorable ohmic contact and can further function as an anode.

In addition, the EL layer 616 is formed by various methods such as an evaporation method with an evaporation mask, an ink-jet method, or a spin coating method. The EL layer 616 contains the triazole derivative which is shown in Embodiment Mode 1. In addition, any of a low molecular compound or a high molecular compound (including an oligomer and a dendrimer) may be used as a material which forms the EL layer 616. In addition, not only an organic compound but also an inorganic compound may be used for the material for forming the EL layer.

Further, as a material which is used for the second electrode 617 which is formed over the EL layer 616 and functions as a cathode, it is preferable to use a material with a low work function (e.g., Al, Mg, Li, Ca, or an alloy or a compound thereof such as MgAg, MgIn, AlLi, LiF, or CaF$_2$). In the case where light generated in the EL layer 616 is transmitted through the second electrode 617, the second electrode 617 may be formed with a stacked layer of a thin metal film having a small thickness and a transparent conductive film (e.g., ITO, indium oxide containing zinc oxide of 2 to 20 wt %, indium tin oxide containing silicon or silicon oxide, or zinc oxide (ZnO)).

The sealing substrate 604 is attached to the element substrate 610 with the sealing material 605. Accordingly, a light-emitting element 618 is provided in the space 607 surrounded by the element substrate 610, the sealing substrate 604, and the sealing material 605. Any of the structures which are shown in Embodiment Modes 2 to 4 can be applied to the light-emitting element 618. Note that the space 607 is filled with a filler, and the space 607 may be filled with an inert gas (e.g., nitrogen or argon) or the sealing material 605.

Note that an epoxy resin is preferably used for the sealing material 605. Such a material preferably allows as little moisture and oxygen as possible to penetrate. As a material for forming the sealing substrate 604, a plastic substrate made of fiberglass-reinforced plastics (FRP), polyvinyl fluoride (PVF), polyester, acrylic, or the like, as well as a glass substrate or a quartz substrate, can be used.

As described above, a light-emitting device which is manufactured using the triazole derivative of the present invention can be obtained.

Since the triazole derivative which is shown in Embodiment Mode 1 is used for the light-emitting device of the present invention, a light-emitting device having favorable characteristics can be obtained. Specifically, a light-emitting device having high luminous efficiency can be obtained.

In addition, a light-emitting device having low power consumption can be obtained with the use of the triazole derivative which is shown in Embodiment Mode 1.

Further, having high triplet excitation energy, the triazole derivative which is shown in Embodiment Mode 1 can be used for a light-emitting layer, along with a phosphorescent compound. In particular, the triazole derivative of the present invention can be used for a full-color display, because it is possible to be used for a light-emitting layer, along with a phosphorescent compound which shows blue light emission of a short wavelength, the light emission peak wavelength of which is greater than or equal to 400 nm and less than or equal to 500 nm. Thus, a full-color display which utilizes the feature of the phosphorescent compound, which is high luminous efficiency, can be achieved.

Figure 5A:
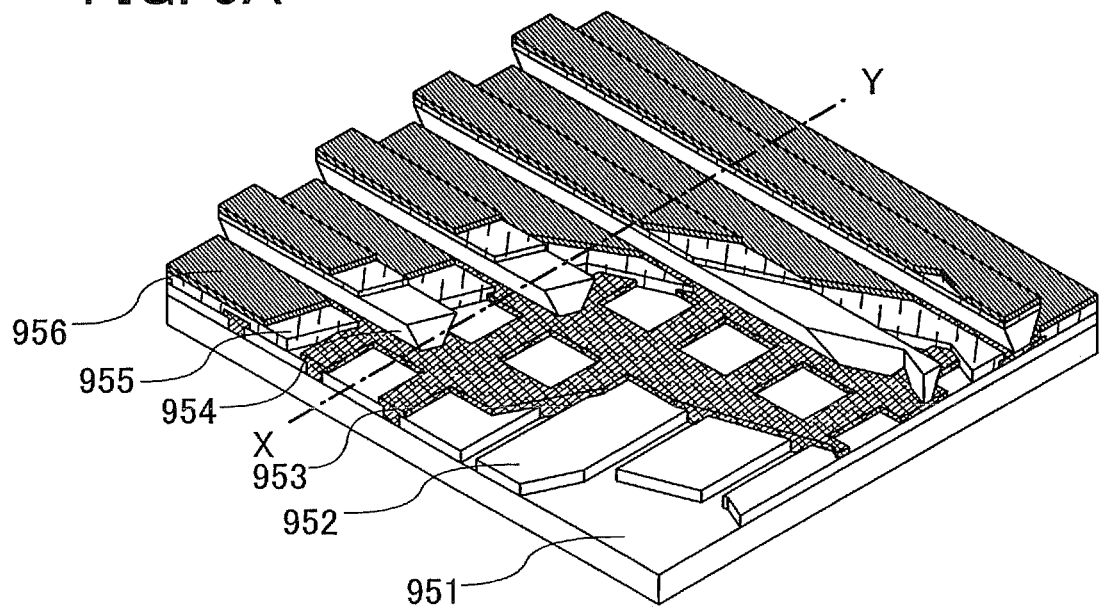
FIGS. 5A and 5B are a perspective view and a cross-sectional view showing a light-emitting device of the present invention, respectively.
Figure 5B:
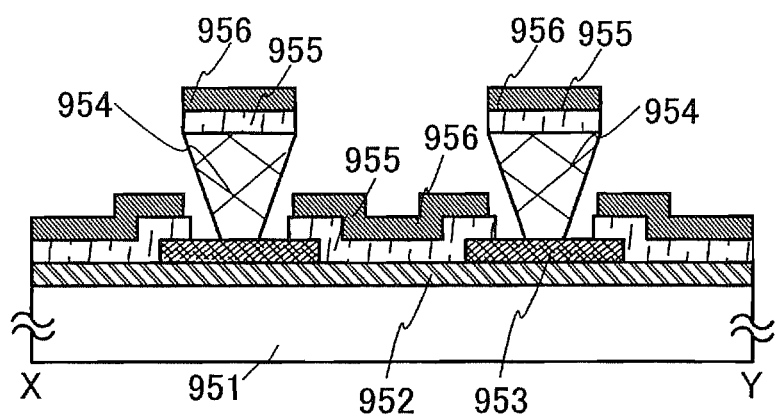

An active matrix light-emitting device in which driving of a light-emitting element is controlled by transistors is described in this embodiment mode as described above. Alternatively, a passive matrix light-emitting device may be used. FIGS. 5A and 5B show a passive matrix light-emitting device which is manufactured by application of the present invention. FIG. 5A is a perspective view of the light-emitting device, and FIG. 5B is a cross-sectional view taken along line X-Y of FIG. 5A. In each of FIGS. 5A and 5B, an EL layer 955 is provided between an electrode 952 and an electrode 956 over a substrate 951. End portions of the electrode 952 are covered with an insulating layer 953. Then, a partition layer 954 is provided over the insulating layer 953. A side wall of the partition layer 954 slopes so that a distance between one side wall and the other side wall becomes narrow toward the substrate surface. That is, a cross section taken along the direction of a shorter side of the partition layer 954 is trapezoidal, and the base of the cross-section (a side facing in the same direction as a plane direction of the insulating layer 953 and in contact with the insulating layer 953) is shorter than the upper side thereof (a side facing in the same direction as the plane direction of the insulating layer 953 and not in contact with the insulating layer 953). Defects of the light-emitting element due to static electricity or the like can be prevented by providing the partition layer 954 in this manner. Also in the passive matrix light-emitting device, a light-emitting element having high luminous efficiency can be obtained by including the light-emitting element of the present invention. Further, a light-emitting device having low power consumption can be obtained.

Embodiment Mode 6

This embodiment mode will describe electronic devices of the present invention, each of which includes the light-emitting device described in Embodiment Mode 5. The electronic devices of the present invention each include a display portion having high luminous efficiency, where the triazole derivative which is described in Embodiment Mode 1 is contained. In addition, each display portion consumes low power.

Examples of the electronic devices each having the light-emitting element manufactured with the triazole derivative of the present invention include cameras such as video cameras or digital cameras, goggle type displays, navigation systems, audio reproducing devices (e.g., car audio components and audio components), computers, game machines, portable information terminals (e.g., mobile computers, cellular phones, portable game machines, and electronic books), and image reproducing devices provided with recording media (specifically, a device capable of reproducing recording media such as digital versatile discs (DVDs) and provided with a display device that can display the image). Specific examples of these electronic devices are shown in FIGS. 6A to 6D.

Figure 6A:
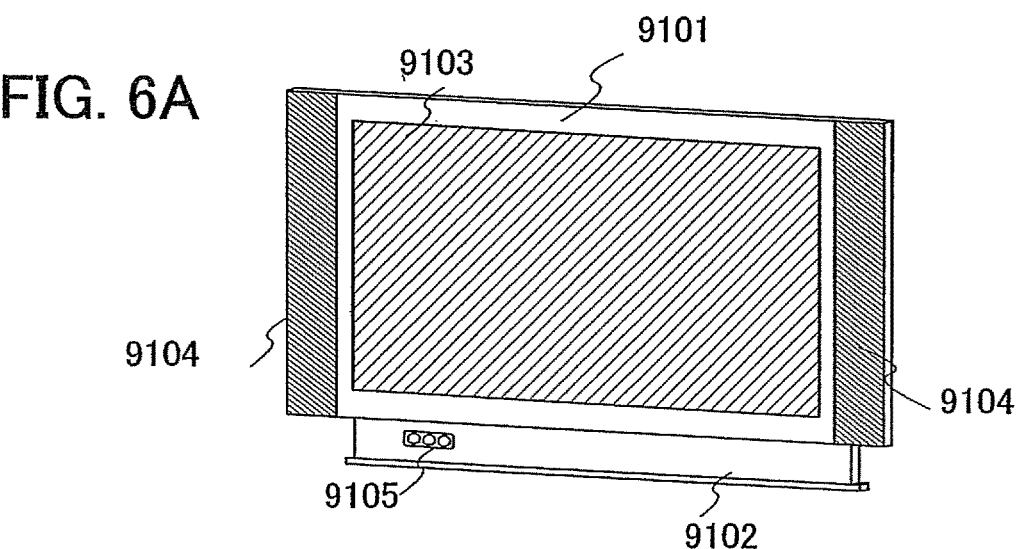
FIGS. 6A to 6D are views each showing an electronic device of the present invention.

FIG. 6A shows a television device according to the present invention, which includes a chassis 9101, a supporting base 9102, a display portion 9103, a speaker portion 9104, a video input terminal 9105, and the like. In the television device, the display portion 9103 includes light-emitting elements similar to those described in Embodiment Mode 2 and/or Embodiment Mode 3, which are arranged in matrix. The light-emitting elements are characterized by high luminous efficiency. The display portion 9103 which includes the light-emitting elements has similar characteristics. Accordingly, the television device consumes low power. Such characteristics can dramatically reduce or downsize deterioration compensation circuits or power supply circuits in the television device, so that the chassis 9101 and the supporting base 9102 can be reduced in size and weight. In the television device according to the present invention, low power consumption, high image quality, and reduced size and weight are achieved; therefore, a product suitable for living environments can be provided.

Figure 6B:
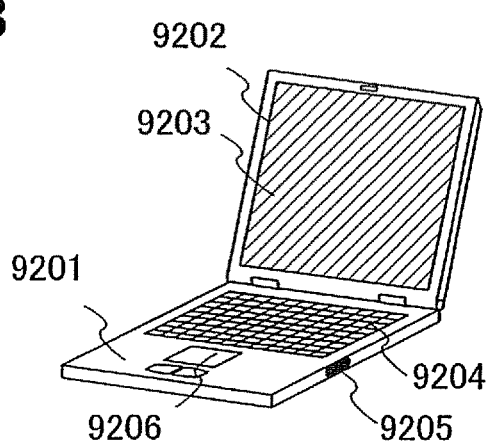

FIG. 6B shows a computer according to the present invention, which includes a main body 9201, a chassis 9202, a display portion 9203, a keyboard 9204, an external connection port 9205, a pointing device 9206, and the like. In the computer, the display portion 9203 includes light-emitting elements similar to those described in Embodiment Mode 2 and/or Embodiment Mode 3, which are arranged in matrix. The light-emitting elements are characterized by high luminous efficiency. The display portion 9203 which includes the light-emitting elements has similar characteristics. Accordingly, the computer consumes low power. Such characteristics can dramatically reduce or downsize deterioration compensation circuits or power supply circuits in the computer, so that the main body 9201 and the chassis 9202 can be reduced in size and weight. In the computer according to the present invention, low power consumption, high image quality, and reduced size and weight are achieved; therefore, a product suitable for the environments can be provided.

Figure 6C:
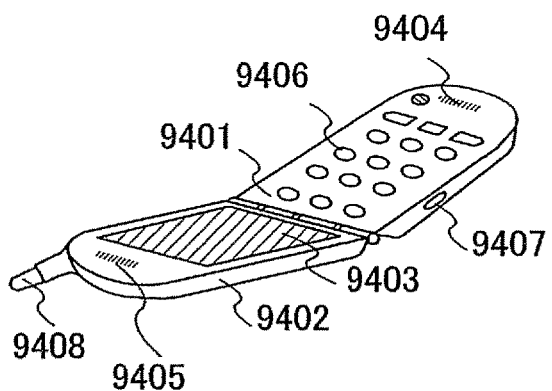

FIG. 6C shows a cellular phone according to the present invention, which includes a main body 9401, a chassis 9402, a display portion 9403, an audio input portion 9404, an audio output portion 9405, operation keys 9406, an external connection port 9407, an antenna 9408, and the like. In the cellular phone, the display portion 9403 includes light-emitting elements similar to those described in Embodiment Mode 2 and/or Embodiment Mode 3, which are arranged in matrix. The light-emitting elements are characterized by high luminous efficiency. The display portion 9403 which includes the light-emitting elements has similar characteristics. Accordingly, the cellular phone consumes low power. Such characteristics can dramatically reduce or downsize deterioration compensation circuits or power supply circuits in the cellular phone, so that the main body 9401 and the chassis 9402 can be reduced in size and weight. In the cellular phone according to the present invention, low power consumption, high image quality, and a small size and light weight are achieved; therefore, a product suitable for carrying can be provided.

Figure 6D:
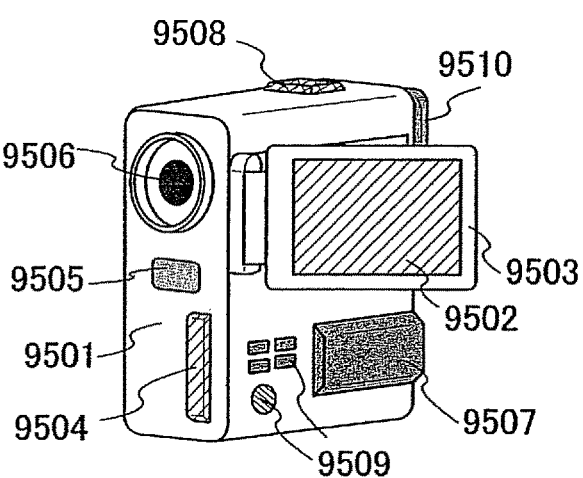

FIG. 6D shows a camera according to the present invention, which includes a main body 9501, a display portion 9502, a chassis 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 includes light-emitting elements similar to those described in Embodiment Mode 2 and/or Embodiment Mode 3, which are arranged in matrix. The light-emitting elements are characterized by high luminous efficiency. The display portion 9502 which includes the light-emitting elements has similar characteristics. Accordingly, the camera consumes low power. Such characteristics can dramatically reduce or downsize deterioration compensation circuits or power supply circuits in the camera, so that the main body 9501 can be reduced in size and weight. In the camera according to the present invention, low power consumption, high image quality, and reduced size and weight are achieved; therefore, a product suitable for carrying can be provided.

As described above, the applicable range of the light-emitting device of the present invention is so wide that the light-emitting device can be applied to electronic devices in various fields. With the use of the triazole derivative of the present invention, an electronic device including a display portion with high luminous efficiency can be provided. Furthermore, the electronic device of the present invention including the display portion with low power consumption can be obtained.

The light-emitting device of the present invention can also be used as a lighting system. One mode in which the light-emitting device of the present invention is used as the lighting system is described with reference to FIG. 7.

Figure 7:
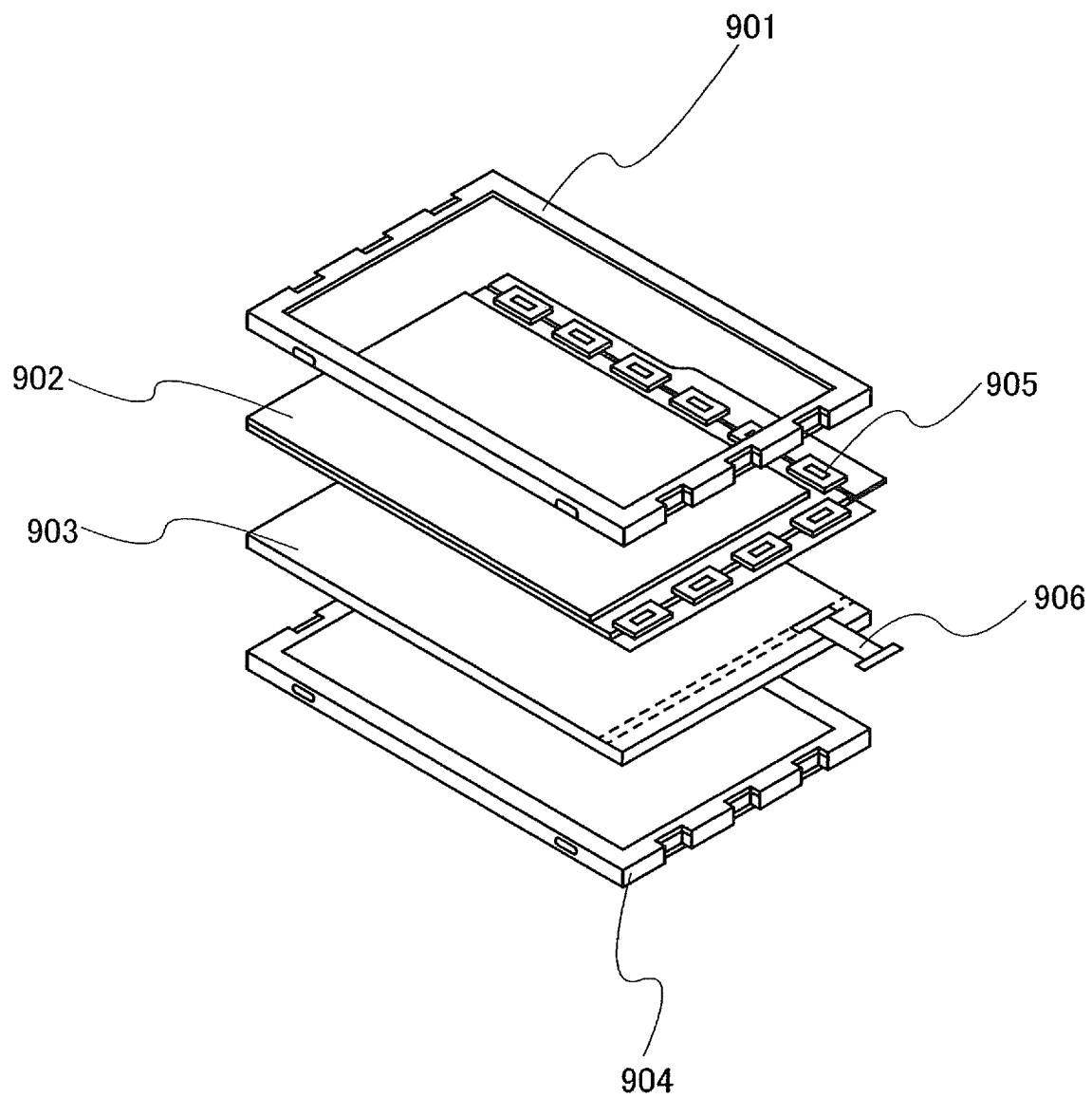
FIG. 7 is a view showing part of an electronic device of the present invention.

FIG. 7 shows an example of a liquid crystal display device in which the light-emitting device of the present invention is used as a backlight. The liquid crystal display device shown in FIG. 7 includes a chassis 901, a liquid crystal layer 902, a backlight 903, and a chassis 904. The liquid crystal layer 902 is connected to a driver IC 905. The light-emitting device of the present invention is used as the backlight 903, and current is supplied through a terminal 906.

When the light-emitting device of the present invention is used as the backlight of the liquid crystal display device, a backlight, the luminous efficiency of which is high and the power consumption of which is reduced, can be obtained. The light-emitting device of the present invention is a plane emission lighting system and can also have a large area; accordingly, it is possible that the backlight have a larger area and the liquid crystal display device have a larger display area. Further, the light-emitting device of the present invention has a thin shape and consumes low power; thus, a display device can also be reduced in thickness and power consumption.

Figure 8:
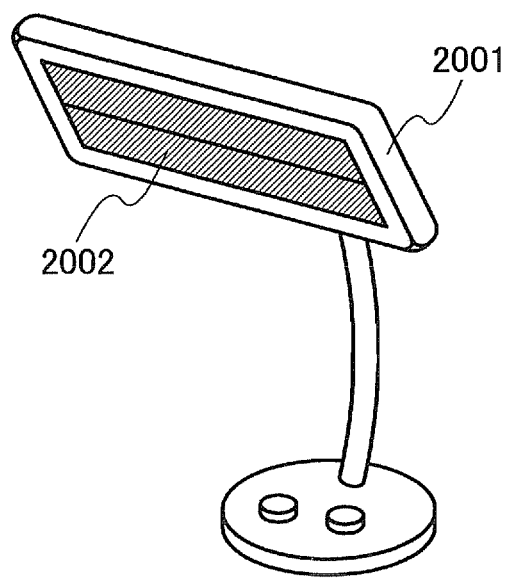
FIG. 8 is a view showing a lighting system of the present invention.

FIG. 8 shows an example in which the light-emitting device to which the present invention is applied is used as a table lamp that is a lighting system. A table lamp shown in FIG. 8 has a chassis 2001 and a light source 2002, and the light-emitting device of the present invention is used as the light source 2002. The light-emitting device of the present invention have high luminous efficiency and low power consumption; thus, the table lamp also has high luminous efficiency and low power consumption.

Figure 9:
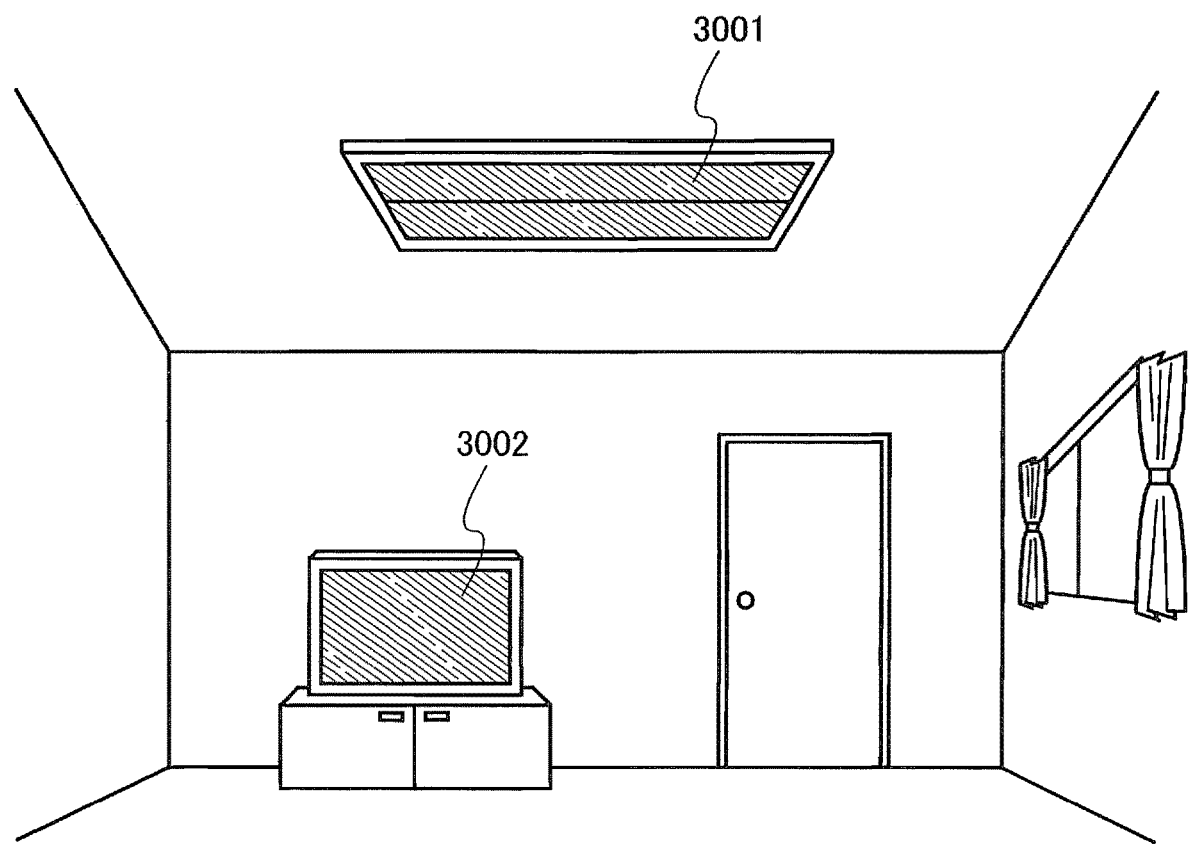
FIG. 9 is a view showing a lighting system of the present invention.

FIG. 9 shows an example in which the light-emitting device to which the present invention is applied is used as an indoor lighting system 3001. Being also possible to have a large area, the light-emitting device of the present invention, can be used as a lighting system having a large area. Further, having a thin shape and low power consumption, the light-emitting device of the present invention can be used as a lighting system having a thin shape and consuming low power. When a television device 3002 related to the present invention as described in FIG. 6A is thus placed in a room in which a light-emitting device to which the present invention is applied is used as the indoor lighting system 3001, public broadcasting and movies can be enjoyed. In such a case, since both of the devices consume low power, a powerful image can be enjoyed in a bright room without concern about electricity charges.

Embodiment 1

This embodiment will describe a synthesis method of 9-[4-(4,5-diphenyl-4H-1,2,4-triazol-3-yl)phenyl]-9H-carbazole (abbreviation: CzTAZ1) which is represented by the structural formula (101).

(101)

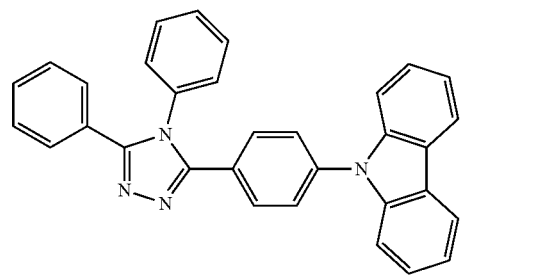

[Step 1] Synthesis of 3-(4-bromophenyl)-4,5-diphenyl-4H-1,2,4-triazole (i) Synthesis of 4-bromobenzoylhydrazine A synthesis scheme of 4-bromobenzoylhydrazine is shown in (B-1).

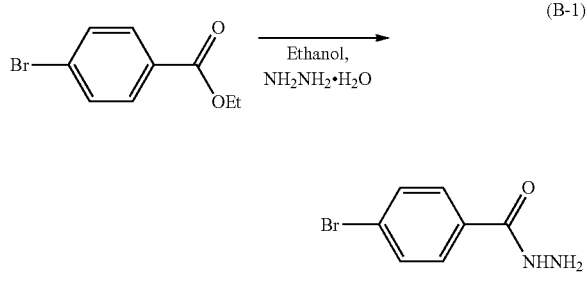

25 g (0.19 mol) of ethyl-4-bromobenzoate was put into a 200 mL three-neck flask, 50 mL of ethanol was added thereto, and the mixture was stirred. After that, 20 mL of hydrazine monohydrate was added, the mixture was stirred at 78° C. for 5 hours, and the contents of the flask were reacted together. After the reaction, water was added to the reactive mixture, and suction filtration was performed on a precipitated solid. The obtained solid was washed and collected by suction filtration, so that 24 g of a white solid, which was the object of the synthesis, was obtained at a yield of 96%.

(ii) Synthesis of N'-benzoyl-4-bromo-benzohydrazide

A synthesis scheme of N'-benzoyl-4-bromo-benzohydrazide is shown in (B-2).

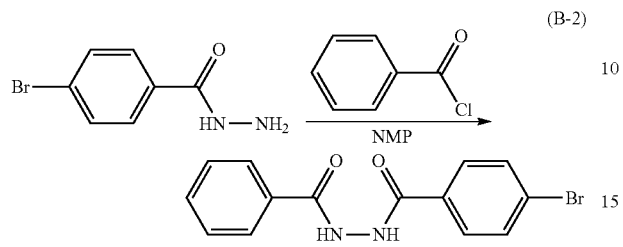

(B-2)

2.0 g (13.9 mmol) of 4-bromobenzoylhydrazine was put into a 300 mL three-neck flask, 7 mL of N-methyl-2-pyrrolidone was added thereto, and the mixture was stirred at a room temperature. A mixed solution of 5.0 mL of N-methyl-2-pyrrolidone and 2.5 mL (21.5 mmol) of benzoyl chloride was dripped into the solution through a 50 mL dropping funnel. The mixture was stirred at 80° C. for 3 hours. After the reaction, a solid was precipitated out with the addition of the reactive mixture to approximately 200 mL of water. The precipitated solid was collected by suction filtration. The collected solid was washed with water, a saturated sodium hydrogen carbonate solution, and saturated saline, in the order given. The obtained solid was recrystallized with a mixed solvent of acetate and hexane, so that 3.6 g of a white solid, which was the object of the synthesis, was obtained at a yield of 80%.

(iii) Synthesis of 1-[(4-bromophenyl) chloromethylidene]-2-[chloro(phenyl)methylidene]hydrazone A synthesis scheme of 1-[(4-bromophenyl) chloromethylidene]-2-[chloro(phenyl)methylidene]hydrazone is shown in (B-3).

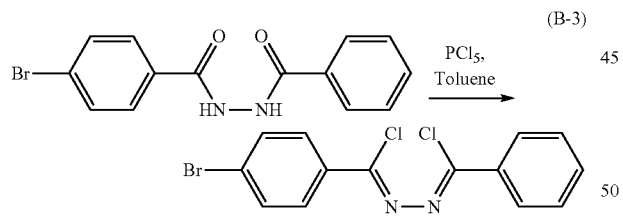

(B-3)

5.0 g (16 mmol) of N'-benzoyl-4-bromo-benzohydrazide and 7.2 g (34 mmol) of phosphorus pentachloride were put into a 200 mL three-neck flask, and 100 mL of toluene was added to the mixture. The mixture was stirred at 120° C. for 3 hours, and the contents of the flask were reacted together. After the reaction, the reactive solution was added to approximately 100 mL of water and the mixture was stirred. An organic layer and an aqueous layer were separated, and the organic layer was washed with a saturated sodium carbonate solution and saturated saline, in the order given. Magnesium sulfate was added to the organic layer, and the mixture was dried. Suction filtration was performed on the mixture to remove the magnesium sulfate, and thus a filtrate was obtained. The solid, which was obtained by condensation of the obtained filtrate, was washed with methanol, so that 4.8 g of a powdery light yellow-colored solid, which was the object of the synthesis, was obtained at a yield of 86%.

(iv) Synthesis of 3-(4-bromophenyl)-4,5-diphenyl-4H-1,2,4-triazole

A synthesis scheme of 3-(4-bromophenyl)-4,5-diphenyl-4H-1,2,4-triazole is shown in (B-4).

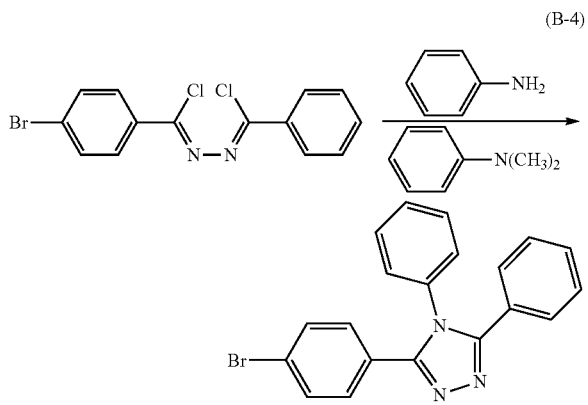

(B-4)

4.5 g (16 mmol) of (8Z,9Z)-1-((4-bromophenyl)chloromethylene)-2-(chloro(phenyl)methylene)hydrazine, 2.0 g (16 mmol) of aniline, and 30 mL of N,N-dimethylaniline were put into a 100 mL three-neck flask, and nitrogen substitution was performed on the contents of the flask. The mixture was stirred at 135° C. for 5 hours. After the reaction, a solid was precipitated out with the reactive solution being added to approximately 100 mL of 1 N diluted hydrochloric acid and the mixture being stirred for 30 minutes. Suction filtration was performed on the precipitated solid, and a solid was obtained. The obtained solid was dissolved in toluene and washed with water and a saturated sodium carbonate solution, in the order given. Magnesium sulfate was added to an organic layer, and the mixture was dried. Suction filtration was performed on the mixture to remove the magnesium sulfate, and thus a filtrate was obtained. The solid, which was obtained by condensation of the obtained filtrate, was recrystallized with a mixed solvent of ethanol and hexane, so that 3.3 g of a powdery light yellow-colored solid, which was the object of the synthesis, was obtained at a yield of 69%.

[Step 2] Synthesis of CzTAZ1

A synthesis scheme of CzTAZ1 is shown in (B-5).

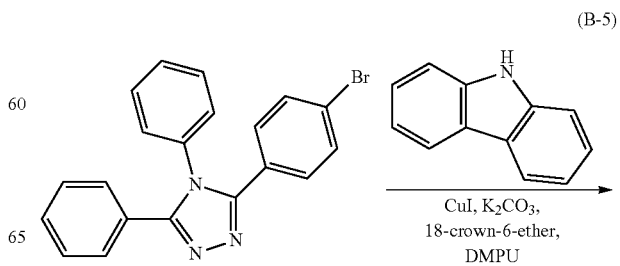

(B-5)

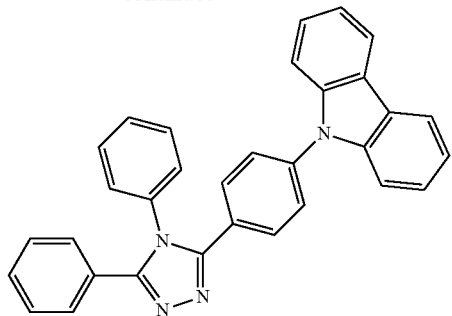

1.5 g (4.0 mmol) of 3-(4-bromophenyl)-4,5-diphenyl-4H-1,2,4-triazole obtained in Step 1, 0.67 g (6.6 mmol) of carbazole, 2.0 g (13 mmol) of potassium carbonate, 0.20 g (1.1 mmol) of copper iodide, and 0.20 g (0.73 mmol) of 18-crown-6-ether were put into a 50 mL three-neck flask, and nitrogen substitution was performed on the contents of the flask. The mixture was added with 1.5 mL of 1,3-dimethyl-3,4,5,6-tetrahydro-2(1H)-pyrimidinone (abbreviation: DMPU) and stirred at 180° C. for 5 hours, and the contents of the flask were reacted together. After the reaction, toluene was added to the reactive mixture, and the suspension was washed with 1 N diluted hydrochloric acid, a saturated sodium carbonate solution, and saturated saline, in the order given. An organic layer was dried with magnesium sulfate. After the drying, suction filtration was performed on the mixture to remove the magnesium sulfate, and thus a filtrate was obtained. Suction filtration was performed with sellite (Wako Pure Chemical Industries. Ltd., catalog number: 531-16855) on the obtained filtrate, and thus a filtrate was obtained. The obtained filtrate was condensed to obtain a solid. The obtained solid was purified by silica gel column chromatography. For the column chromatography, first toluene and then a mixed solvent of toluene and ethyl acetate (toluene:ethyl acetate=4:1) was used as a developing solvent. The obtained fraction was condensed to obtain a solid. The obtained solid was recrystallized with a mixed solvent of chloroform and hexane, so that 1.6 g of a powdery white solid, which was the object of the synthesis, was obtained at a yield of 86%. It was confirmed by a nuclear magnetic resonance (NMR) that the compound was 9-[4-(4,5-diphenyl-4H-1,2,4-triazol-3-yl)phenyl]-9H-carbazole (abbreviation: CzTAZ1).

Sublimation purification of 1.6 g of the obtained white solid was performed by a train sublimation method. Sublimation purification was performed at a reduced pressure of 7.0 Pa, with the argon flow rate of 3 mL/min, at 270° C. for 15 hours. 1.2 g of the white solid was obtained at a yield of 75%.

Figure 10A:
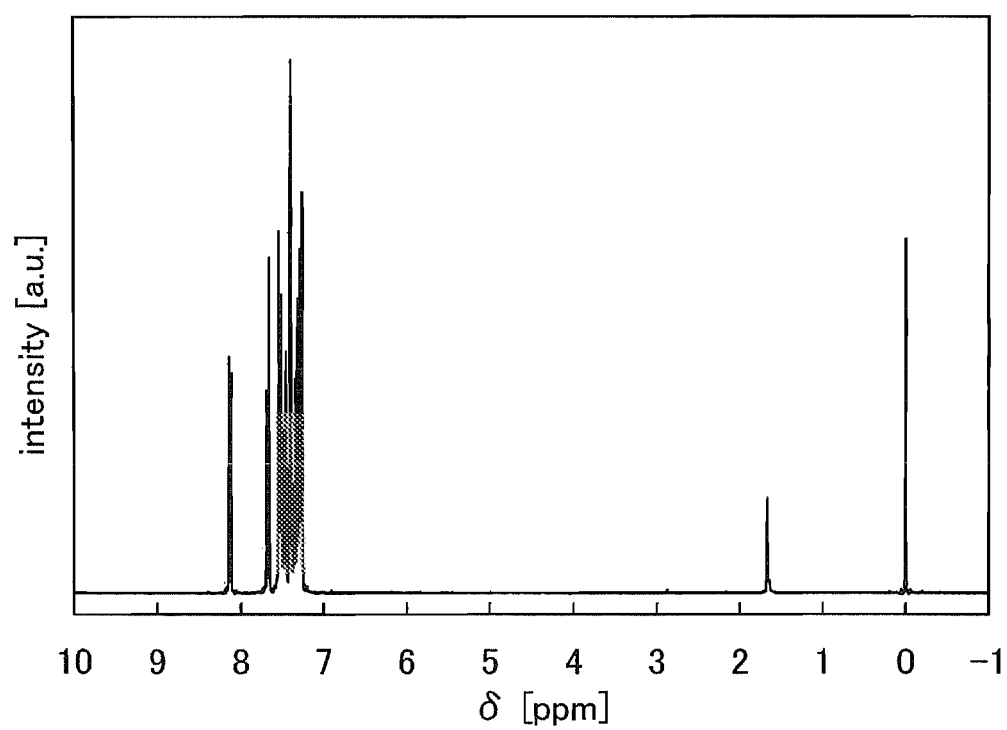
FIGS. 10A and 10B are graphs each showing $^1$H NMR of 9-[4-(4,5-diphenyl-4H-1,2,4-triazol-3-yl)phenyl]-9H-carbazole (abbreviation: CzTAZ1)
Figure 10B:
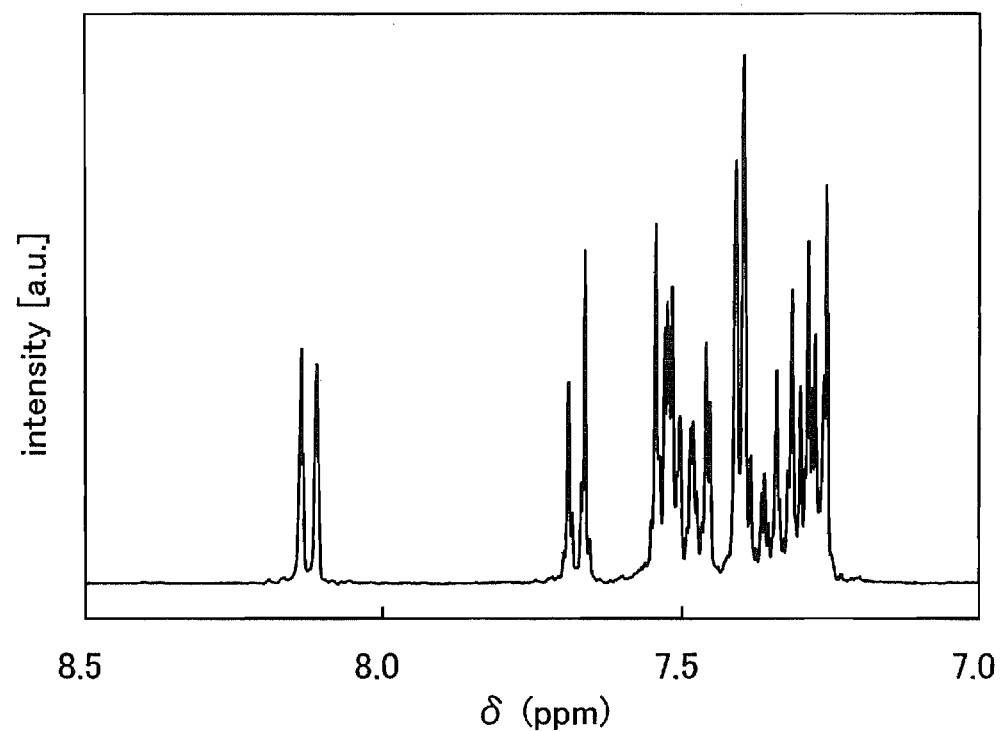

The $^1$H NMR data of CzTAZ1 is given as follows. $^1$H NMR (CDCl$_3$, 300 MHz): δ=7.26-7.56 (m, 18H), 7.68 (d, J=8.3 Hz, 2H), 8.12 (d, J=7.8 Hz, 2H). In addition, charts of $^1$H NMR are shown in FIGS. 10A and 10B. Note that FIG. 10B is a chart showing an enlarged portion of FIG. 10A in a range of from 7.0 to 8.5 ppm.

Figure 11A:
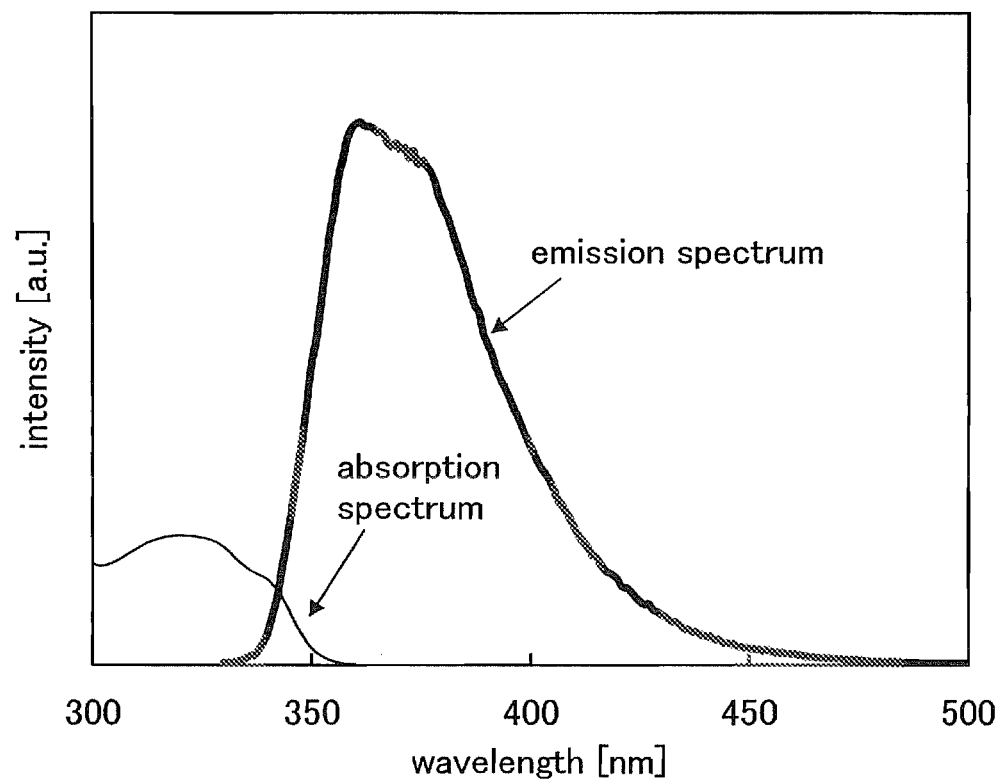
FIGS. 11A and 11B are graphs each showing the absorption spectrum and the emission spectrum of 9-[4-(4,5-diphenyl-4H-1,2,4-triazol-3-yl)phenyl]-9H-carbazole (abbreviation: CzTAZ1)
Figure 11B:
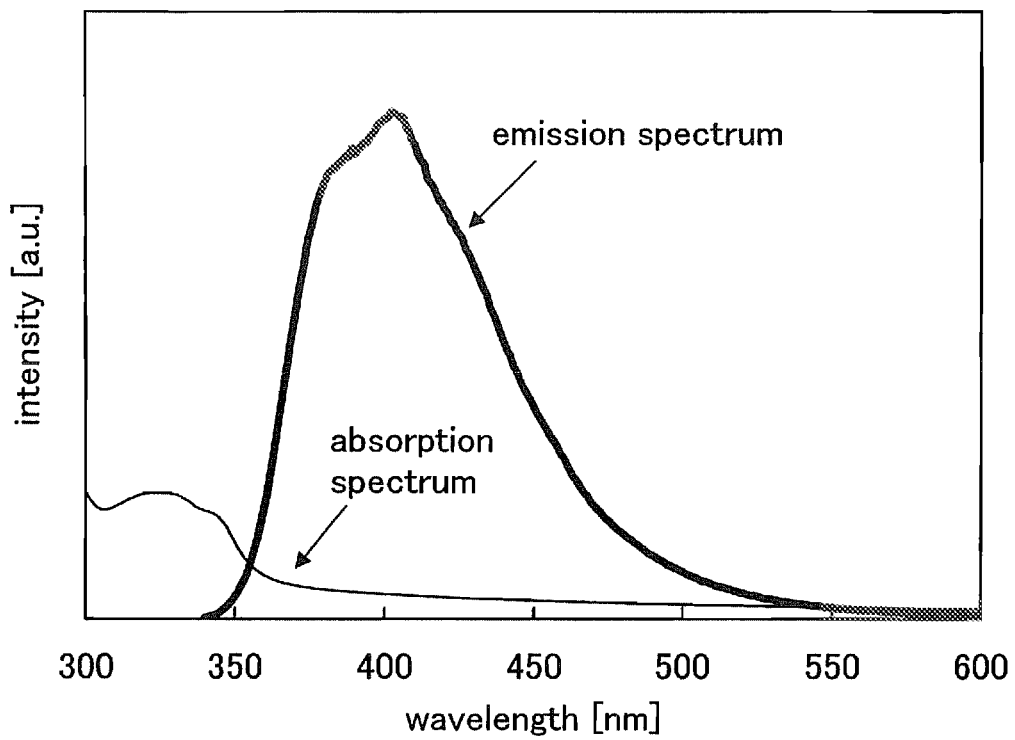

Further, the absorption spectrum and the emission spectrum of a toluene solution of CzTAZ1 are shown in FIG. 11A. The absorption spectrum and the emission spectrum of a thin film of CzTAZ1 are shown in FIG. 11B. Measurements were performed with an ultraviolet-visible light spectrophotometer (V-550, manufactured by JASCO Corporation). The solution was put into a quartz cell as one sample and CzTAZ1 was evaporated over a quartz substrate to form a thin film as another sample, and the absorption spectra of the solution and the thin film, from each of which the absorption spectrum of quartz was subtracted, are shown in FIGS. 11A and 11B. In FIGS. 11A and 11B, the horizontal axis represents wavelength (nm), and the vertical axis represents intensity (arbitrary unit). In the case of the toluene solution of CzTAZ1, the absorption was observed at around 320 nm. In addition, in the case of the toluene solution, the maximum emission wavelength was 360 nm (excitation wavelength: 323 nm). Further, in the case of a thin film of CzTAZ1, the absorption was observed at around 324 nm. In addition, in the case of a thin film, the maximum emission wavelength was 405 nm (excitation wavelength: 324 nm).

Moreover, the result obtained by measurement of the ionized potential of a thin film form of CzTAZ1 by a photoelectron spectrometer (AC-2 photoelectron spectrometer manufactured by Riken Keiki, Co., Ltd.) in the atmosphere was 5.77 eV. As a result, it was understood that the HOMO level was −5.77 eV. The absorption edge was obtained by tauc plot assuming direct transition with the absorption spectrum data of a thin film of CzTAZ1. When the absorption edge was estimated as an optical energy gap, the energy gap was 3.47 eV. A LUMO level of −2.30 eV was obtained from the obtained values of the energy gap value and HOMO level.

Thus, it was understood that CzTAZ1 is a substance having high singlet excitation energy (a band gap).

In addition, the optimal molecular structure in the ground state of CzTAZ1 was estimated by B3LYP/6-311 (d, p) of the density functional theory (DFI). The DFT was employed for the present calculation because the accuracy of calculation is higher than that of the Hartree-Fock (HF) method which does not consider electron correlation and calculation costs are lower than those of the method of perturbation (MP), which has the same level of accuracy of calculation as the DFT. The calculations were performed with a high performance computer (HPC) (Altix 3700 DX manufactured by SGI). When the triplet excitation energy of CzTAZ1 was calculated by application of B3LYP/6-311 (d, p) of the time-dependent density functional theory (TDDFT) in the molecular structure that was structurally optimized by DFT, the triplet excitation energy was found to be 2.98 eV, which corresponds to 416 nm when being converted into the wavelength. Through the above-described results, it was understood that the triazole derivative of the present invention is a substance having high excitation energy. In particular, it was understood that the triazole derivative of the present invention is a substance having high triplet excitation energy.

Embodiment 2

This embodiment will describe a synthesis method of 9-[4-(3,5-diphenyl-4H-1,2,4-triazol-4-yl)phenyl]-9H-carbazole (abbreviation: CzTAZ2) which is represented by the structural formula (201).

(201)

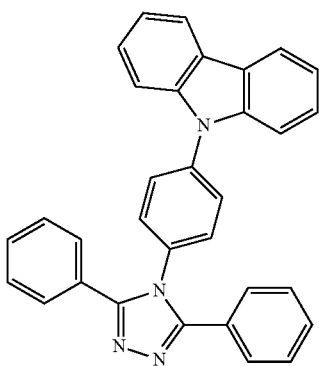

[Step 1] Synthesis of 4-(4-bromophenyl)-3,5-diphenyl-4H-1,2,4-triazole (i) Synthesis of Benzohydrazine A synthesis scheme of benzohydrazine is shown in (B-6).

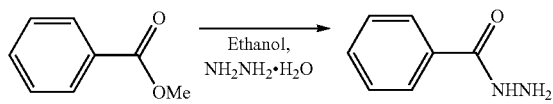
(B-6)

25 g (0.17 mol) of ethyl benzoate was put into a 200 mL three-neck flask, 60 mL of ethanol was added thereto, and the mixture was stirred. After that, 20 mL of hydrazine monohydrate was added, and the mixture was stirred at 78° C. for 8 hours. After the reaction, the reactive solution was added to approximately 500 mL of water and, ethyl acetate was added to the solution to extract the mixture. An organic layer and an aqueous layer were separated, and the organic layer was washed with a saturated sodium hydrogen carbonate solution and saturated saline, in the order given. Magnesium sulfate was added to the organic layer, and the mixture was dried. Suction filtration was performed on the mixture to remove the magnesium sulfate, and thus a filtrate was obtained. The solid, which was obtained by condensation of the obtained filtrate, was recrystallized with a mixed solvent of ethanol and hexane, so that 15 g of a powdery white solid, which was the object of the synthesis, was obtained at a yield of 66%.

(ii) Synthesis of 1,2-dibenzoylhydrazine

A synthesis scheme of 1,2-dibenzoylhydrazine is shown in (B-7).

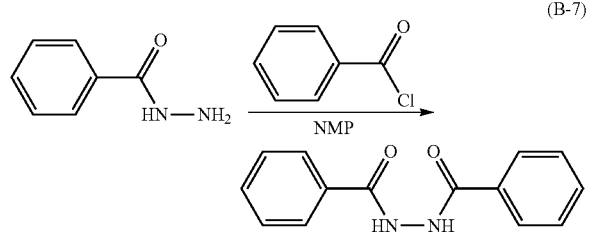
(B-7)

After 10 g (73 mmol) of benzohydrazine was put into a 300 mL three-neck flask, 25 mL of N-methyl-2-pyrrolidone was added thereto, and the mixture was stirred, a mixed solution of 10 mL of N-methyl-2-pyrrolidone and 10 mL (88 mmol) of benzoyl chloride was dripped into the mixture through a 50 mL dropping funnel. The mixture was stirred at 80° C. for 3 hours, and the contents of the flask were reacted together. After the reaction, the reaction solution was added to approximately 500 mL of water and the mixture was stirred, so that a solid was precipitated out. The precipitated solid was collected by suction filtration. The collected solid was washed with water, methanol was added to the obtained solid, and the mixture was washed, so that 10 g of a powdery white solid, which was the object of the synthesis, was obtained at a yield of 57%.

(iii) Synthesis of 1,2-bis[chloro(phenyl)methylidene]hydrazone

A synthesis scheme of 1,2-bis[chloro(phenyl)methylidene]hydrazone is shown in (B-8).

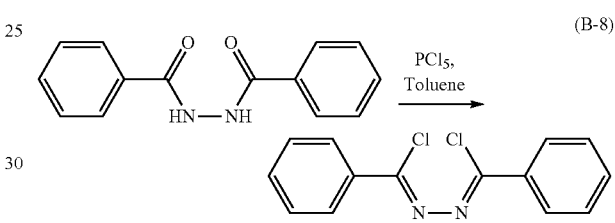
(B-8)

5.0 g (21 mmol) of 1,2-dibenzoylhydrazine and 9.5 g (46 mmol) of phosphorus pentachloride were put into a 200 mL three-neck flask, and 80 mL of toluene was added to the mixture. The mixture was stirred at 120° C. for 3 hours, and the contents of the flask were reacted together. After the reaction, the reactive solution was added to approximately 100 mL of water and the mixture was stirred. An organic layer and an aqueous layer were separated, and the organic layer was washed with water and a saturated sodium hydrogen carbonate solution, in the order given. Magnesium sulfate was added to the organic layer, and the mixture was dried. Suction filtration was performed on the mixture to remove the magnesium sulfate, and thus a filtrate was obtained. The solid, which was obtained by condensation of the obtained filtrate, was washed with methanol, so that 4.9 g of a powdery light yellow-colored solid, which was the object of the synthesis, was obtained at a yield of 85%.

(iv) Synthesis of 4-(4-bromophenyl)-3,5-diphenyl-4H-1,2,4-triazole

A synthesis scheme of 4-(4-bromophenyl)-3,5-diphenyl-4H-1,2,4-triazole is shown in (B-9).

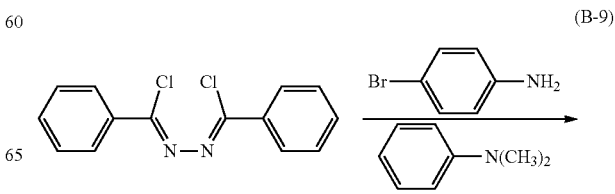
(B-9)

-continued

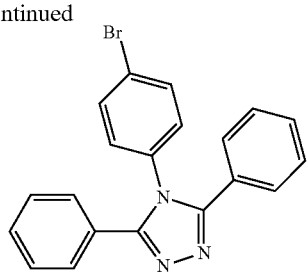

4.5 g (16 mmol) of 1,2-bis(chloro(phenyl)methylene)hydrazine, 2.0 g (16 mmol) of 4-bromoaniline, and 30 mL of N,N-dimethylaniline were put into a 100 mL three-neck flask, and nitrogen substitution was performed on the contents of the flask. The mixture was stirred at 135° C. for 5 hours. After the reaction, a solid was precipitated out with the reactive solution being added to approximately 100 mL of 1 N diluted hydrochloric acid and the mixture being stirred for 30 minutes. Suction filtration was performed on the precipitated solid, and a solid was obtained. The obtained solid was dissolved in toluene and washed with water and a saturated sodium carbonate solution, in the order given. Magnesium sulfate was added to an organic layer, and the mixture was dried. Suction filtration was performed on the mixture to remove the magnesium sulfate, and thus a filtrate was obtained. The solid, which was obtained by condensation of the obtained filtrate, was recrystallized with a mixed solvent of ethanol and hexane, so that 2.3 g of a powdery white solid, which was the object of the synthesis, was obtained at a yield of 38%.

[Step 2] Synthesis of CzTAZ2

A synthesis scheme of CzTAZ2 is shown in (B-10).

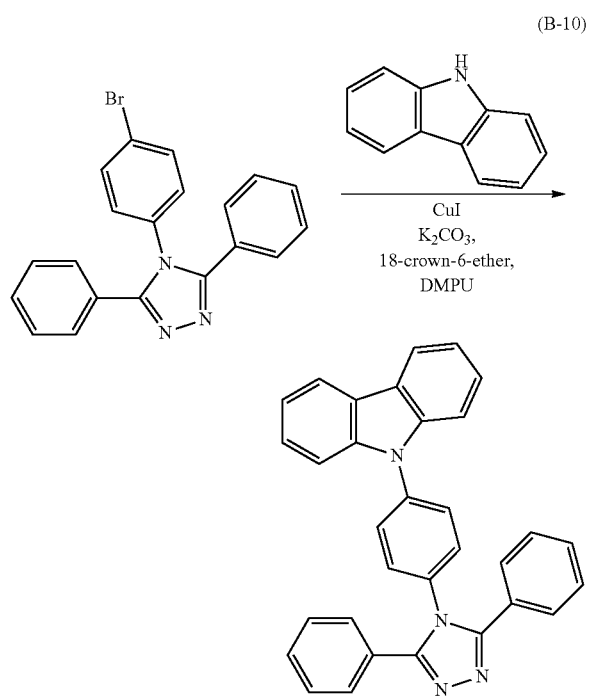

(B-10)

1.5 g (4.0 mmol) of 4-(4-bromophenyl)-3,5-diphenyl-4H-1,2,4-triazole obtained in Step 1, 0.67 g (6.6 mmol) of carbazole, 2.0 g (13 mmol) of potassium carbonate, 0.20 g (1.1 mmol) of copper iodide, and 0.20 g (0.73 mmol) of 18-crown-6-ether were put into a 50 mL three-neck flask, and nitrogen substitution was performed on the contents of the flask. The mixture was added with 3 mL of 1,3-dimethyl-3,4,5,6-tetrahydro-2(1H)-pyrimidinone (abbreviation: DMPU) and stirred at 180° C. for 5 hours, and the contents of the flask were reacted together. After the reaction, chloroform was added to the reactive mixture, and suction filtration was performed with sellite (Wako Pure Chemical Industries. Ltd., catalog number: 531-16855) on the suspension, and thus a filtrate was obtained. The obtained filtrate was washed with water, a saturated sodium hydrogen carbonate solution, and saturated saline, in the order given. An organic layer was dried with magnesium sulfate. After the drying, suction filtration was performed on the mixture to remove the magnesium sulfate, and thus a filtrate was obtained. The obtained filtrate was condensed, and purification by silica gel column chromatography was performed. For the column chromatography, first toluene and then a mixed solvent of toluene and ethyl acetate (toluene:ethyl acetate=2:1) was used as a developing solvent. The obtained fraction was condensed to obtain a solid. The obtained solid was recrystallized with a mixed solvent of chloroform and hexane, so that 0.90 g of a powdery white solid, which was the object of the synthesis, was obtained at a yield of 49%. It was confirmed by a nuclear magnetic resonance (NMR) that the compound was 9-[4-(3,5-diphenyl-4H-1,2,4-triazol-4-yl)phenyl]-9H-carbazole (abbreviation: CzTAZ2).

Sublimation purification of 0.90 g of the obtained white solid was performed by a train sublimation method. Sublimation purification was performed at a reduced pressure of 7.0 Pa, with the argon flow rate of 3 mL/min, at 270° C. for 15 hours. 0.71 g of the white solid was obtained at a yield of 79%.

Figure 12A:
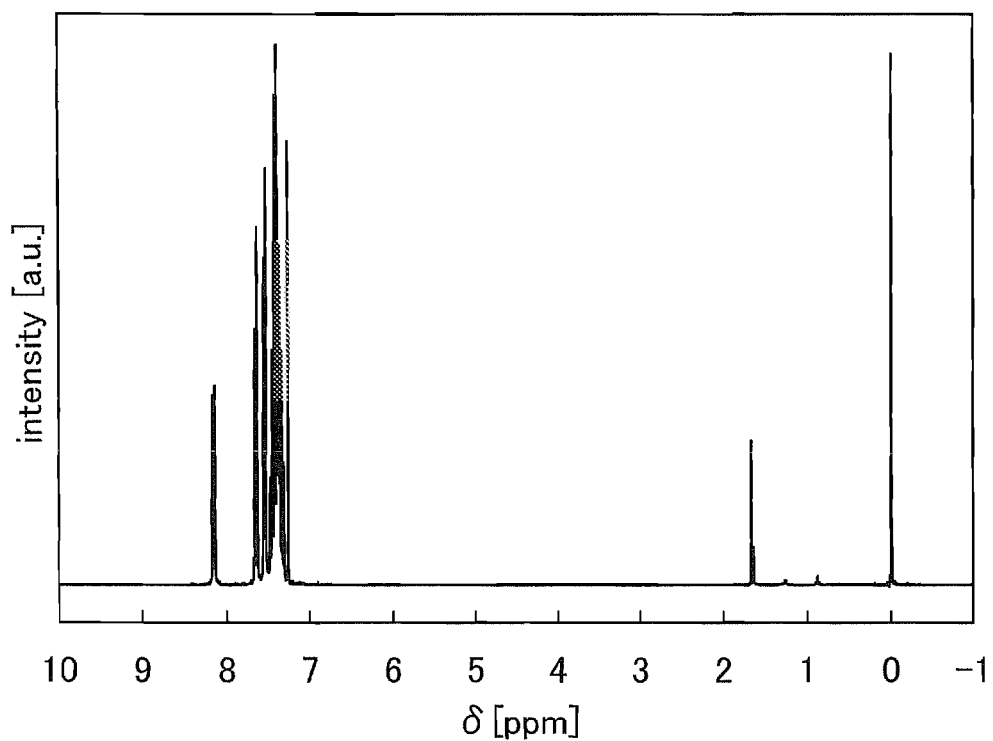
FIGS. 12A and 12B are graphs each showing $^1$H NMR of 9-[4-(3,5-diphenyl-4H-1,2,4-triazol-4-yl)phenyl]-9H-carbazole (abbreviation: CzTAZ2)
Figure 12B:
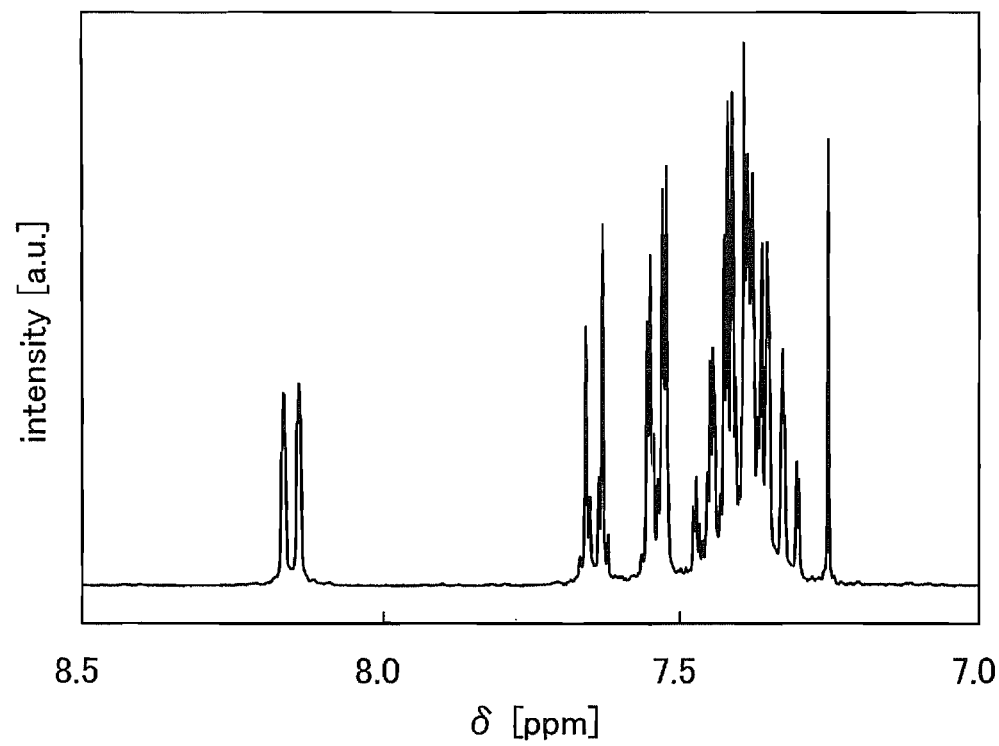

The $^1$H NMR data of CzTAZ2 is given as follows. $^1$H NMR (CDCl$_3$, 300 MHz): δ=7.28-7.48 (m, 14H), 7.49-7.57 (m, 4H), 7.62 (d, J=8.8 Hz, 2H), 8.14 (d, J=7.8 Hz, 2H). In addition, charts of $^1$H NMR are shown in FIGS. 12A and 12B. Note that FIG. 12B is a chart showing an enlarged portion of FIG. 12A in a range of from 7.0 to 8.5 ppm.

Figure 13A:
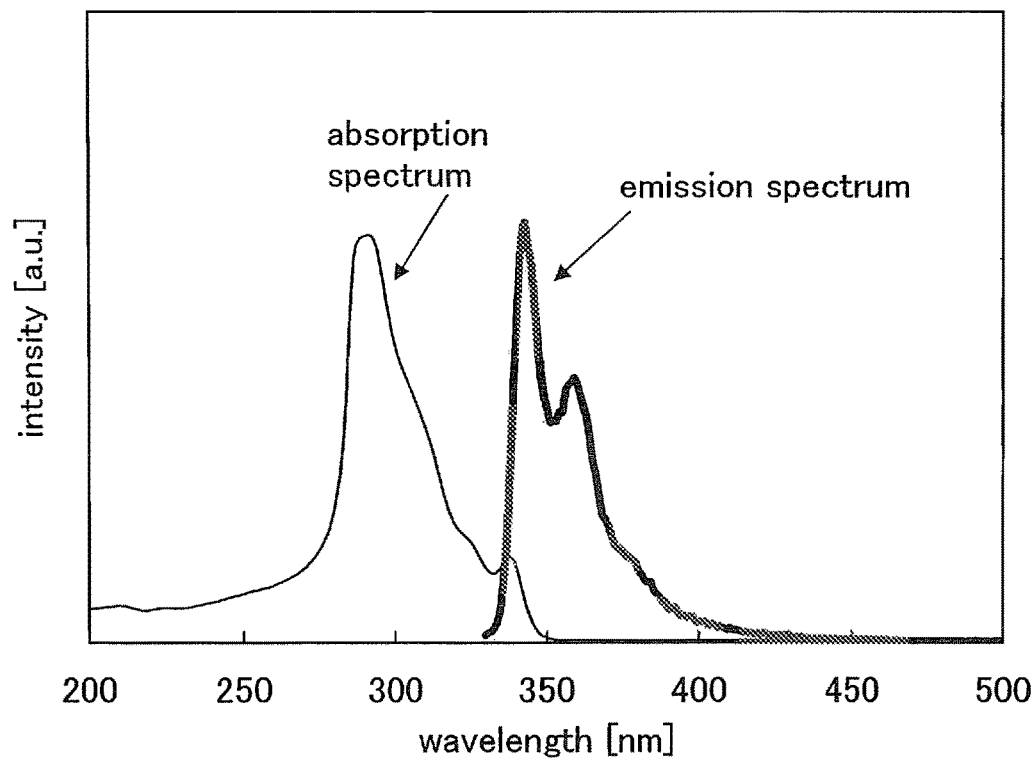
FIGS. 13A and 13B are graphs each showing the absorption spectrum and the emission spectrum of 9-[4-(3,5-diphenyl-4H-1,2,4-triazol-4-yl)phenyl]-9H-carbazole (abbreviation: CzTAZ2)
Figure 13B:
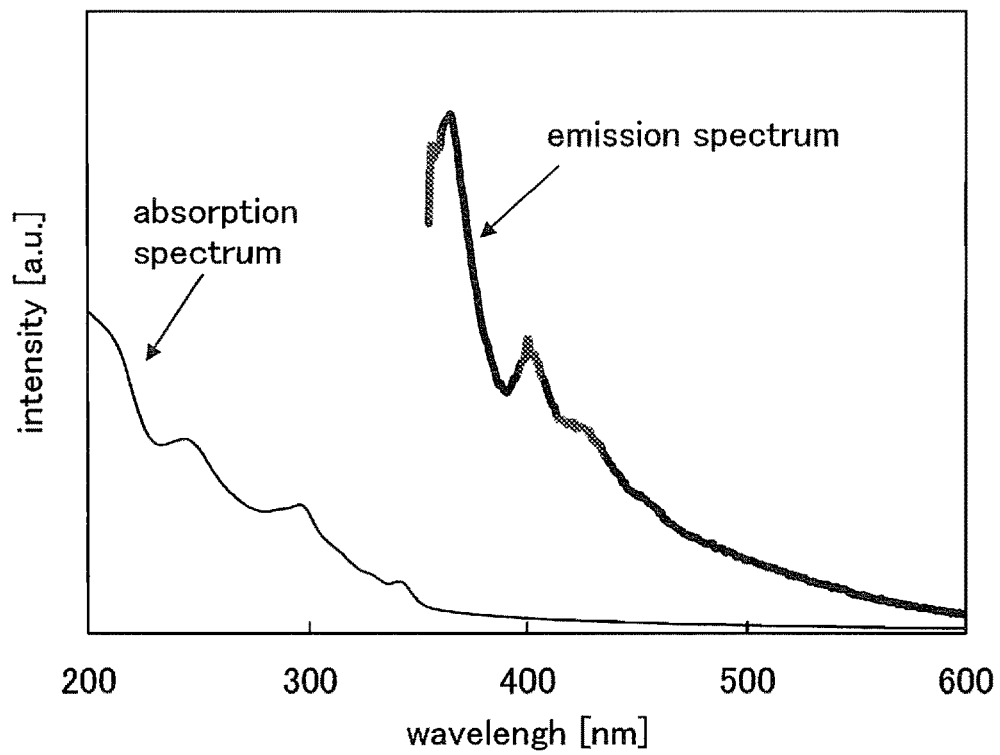

Further, the absorption spectrum and the emission spectrum of a toluene solution of CzTAZ2 are shown in FIG. 13A. The absorption spectrum and the emission spectrum of a thin film of CzTAZ2 are shown in FIG. 13B. Measurements were performed with an ultraviolet-visible light spectrophotometer (V-550, manufactured by JASCO Corporation). The solution was put into a quartz cell as one sample and CzTAZ2 was evaporated over a quartz substrate to form a thin film as another sample, and the absorption spectra of the solution and the thin film, from each of which the absorption spectrum of quartz was subtracted, are shown in FIGS. 13A and 13B. In FIGS. 13A and 13B, the horizontal axis represents wavelength (nm), and the vertical axis represents intensity (arbitrary unit). In the case of the toluene solution of CzTAZ2, the absorption was observed at around 338 nm. In addition, in the case of the toluene solution, the maximum emission wavelength was 343 nm (excitation wavelength: 325 nm). Further, in the case of a thin film of CzTAZ2, the absorption was observed at around 243 nm, around 295 nm, and around 341 nm. In addition, in the case of a thin film, the maximum emission wavelength was 364 nm (excitation wavelength: 341 nm).

Moreover, the result for the ionized potential of a thin film form of CzTAZ2 measured by a photoelectron spectrometer (AC-2 photoelectron spectrometer manufactured by Riken Keiki, Co., Ltd.) in the atmosphere was 5.53 eV. As a result, it was understood that the HOMO level was −5.53 eV. The absorption edge was obtained by tauc plot assuming direct transition with the absorption spectrum data of a thin film of CzTAZ2. When the absorption edge was estimated as an optical energy gap, the energy gap was 3.49 eV. A LUMO level of −2.04 eV was obtained from the obtained values of the energy gap value and HOMO level.

Thus, it was understood that CzTAZ2 is a substance having high singlet excitation energy (a band gap).

In addition, the optimal molecular structure in the ground state of CzTAZ2 was estimated by B3LYP/6-311 (d, p) of the density functional theory (DFT). The DFT was employed for the present calculation because the accuracy of calculation is higher than that of the Hartree-Fock (HF) method which does not consider electron correlation and calculation costs are lower than those of the method of perturbation (MP), which has the same level of accuracy of calculation as the DFT. The calculations were performed with a high performance computer (HPC) (Altix 3700 DX manufactured by SGI). When the triplet excitation energy of CzTAZ2 was calculated by application of B3LYP/6-311 (d, p) of the time-dependent density functional theory (TDDFT) in the molecular structure that was structurally optimized by DFT, the triplet excitation energy was found to be 3.03 eV, which corresponds to 409 nm when being converted into the wavelength. Through the above-described results, it was understood that the triazole derivative of the present invention is a substance having high excitation energy. In particular, it was understood that the triazole derivative of the present invention is a substance having high triplet excitation energy.

Embodiment 3

Figure 14:
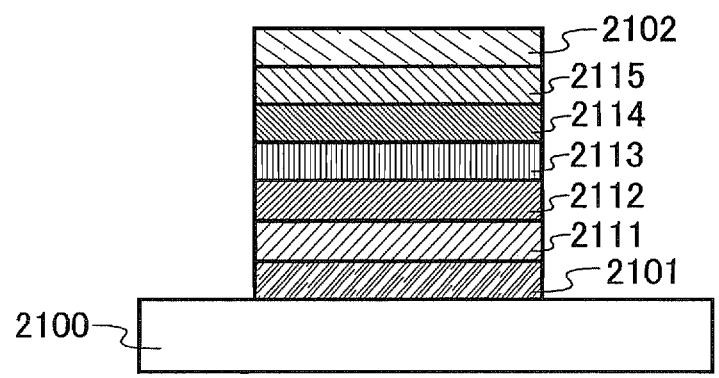
FIG. 14 is a cross-sectional view showing a light-emitting element of embodiments.

This embodiment will describe the light-emitting element of the present invention with reference to FIG. 14. Chemical formulae of the materials used in this embodiment will be shown below.

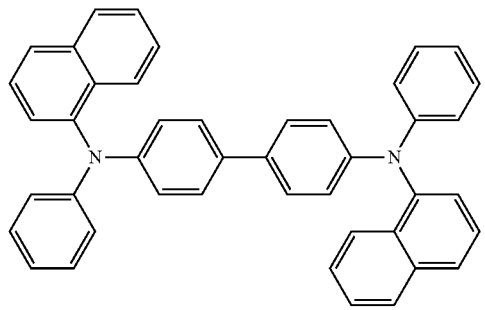

NPB

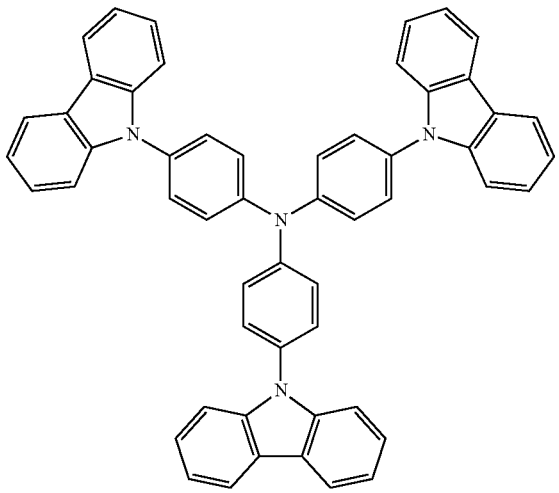

TCTA

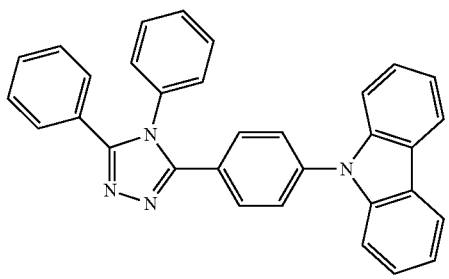

CzTAZ1

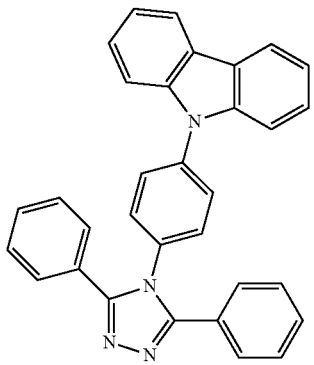

CzTAZ2

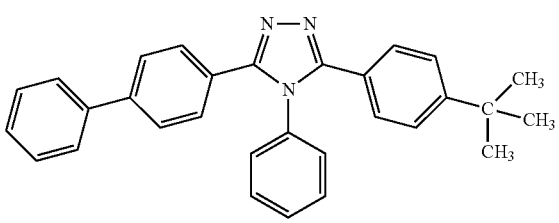

TAZ01

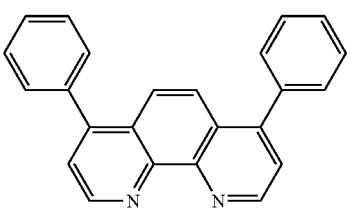

BPhen

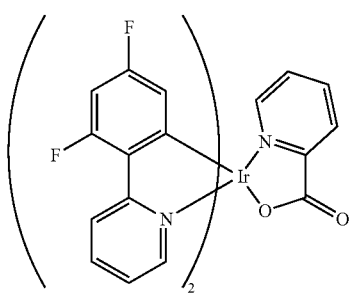
FIrpic

Hereinafter, a method of manufacturing a light-emitting element of this embodiment is described.

(Light-Emitting Element 1)

First, indium tin oxide containing silicon oxide (ITSO) was deposited over a glass substrate 2100 by a sputtering method to form a first electrode 2101. Note that the thickness of the first electrode 2101 was 110 nm and the electrode area was 2 mm×2 mm.

Next, the substrate having the first electrode 2101 was fixed to a substrate holder provided in a vacuum evaporation apparatus in such a way that a surface of the substrate 2100 over which the first electrode 2101 was formed faced downward, and then the pressure was reduced to approximately $10^{-4}$ Pa. Next, 4,4'-bis[N-(1-naphthyl)-N-phenylamino]biphenyl (abbreviation: NPB) and molybdenum (VI) oxide were co-evaporated on the first electrode 2101, whereby a layer 2111 containing a composite material of an organic compound and an inorganic compound was formed. The thickness of the layer 2111 was set to be 40 nm and the weight ratio of NPB to molybdenum(VI) oxide was controlled to 4:1 (=NPB:molybdenum oxide). Note that the co-evaporation method is an evaporation method in which evaporation is performed from a plurality of evaporation sources at the same time in one treatment chamber.

Next, a hole-transporting layer 2112 was formed by depositing 4,4',4''-tris(carbazol-9-yl)triphenylamine (abbreviation: TCTA) to have a thickness of 20 nm on the layer 2111 containing a composite material by an evaporation method using resistance heating.

Furthermore, 9-[4-(4,5-diphenyl-4H-1,2,4-triazol-3-yl)phenyl]-9H-carbazole (abbreviation: CzTAZ1) which is represented by the structural formula (101) and bis[2-(4',6'-difluorophenyl)pyridinato-N,C$^{2'}$]iridium(III)picolinate (abbreviation: FIrpic) were co-evaporated, whereby a 30 nm thick light-emitting layer 2113 was formed on the hole-transportinging layer 2112. Here, the weight ratio of CzTAZ1 to FIrpic was controlled to 1:0.05 (=CzTAZ1:FIrpic).

Then, an electron-transporting layer 2114 was formed by depositing 3-(4-biphenylyl)-4-phenyl-5-(4-tert-butylphenyl)-1,2,4-triazole (abbreviation: TAZ01) to have a thickness of 10 nm on the light-emitting layer 2113 by an evaporation method using resistance heating.

Further, bathophenanthroline (abbreviation: BPhen) and lithium were co-evaporated on the electron-transporting layer 2114, whereby an electron-injecting layer 2115 was formed with a thickness of 20 nm. Here, the weight ratio of BPhen to lithium was controlled to 1:0.01 (=BPhen:lithium).

Finally, a second electrode 2102 was formed by depositing aluminum to have a thickness of 200 nm on the electron-injecting layer 2115 by an evaporation method using resistance heating. Thus, a light-emitting element 1 was formed.

(Light-Emitting Element 2)

Over the same substrate over which the light-emitting element 1 was formed, a light-emitting element 2 was formed in a manner similar to that of the light-emitting element 1 with the use of 9-[4-(3,5-diphenyl-4H-1,2,4-triazol-4-yl)phenyl]-9H-carbazole (abbreviation: CzTAZ2) which is represented by the structural formula (201) as an alternative to CzTAZ1. That is, 9-[4-(3,5-diphenyl-4H-1,2,4-triazol-4-yl)phenyl]-9H-carbazole (abbreviation: CzTAZ2) which is represented by the structural formula (201) and bis[2-(4',6'-difluorophenyl)pyridinato-N,C$^{2'}$]iridium(III)picolinate (abbreviation: FIrpic) were co-evaporated to form the 30 nm thick light-emitting layer 2113 over the hole-transporting layer 2112. Here, the weight ratio of CzTAZ2 to FIrpic was controlled to 1:0.05 (=CzTAZ2:FIrpic). Layers other than the light-emitting layer 2113 were formed in a manner similar to that of the light-emitting element 1.

The light-emitting elements 1 and 2 thus obtained were sealed in a glove box under a nitrogen atmosphere without being exposed to atmospheric air. Then, the operating characteristics of the light-emitting elements were measured. Note that the measurement was performed at a room temperature (atmosphere kept at 25° C.).

Figure 15:
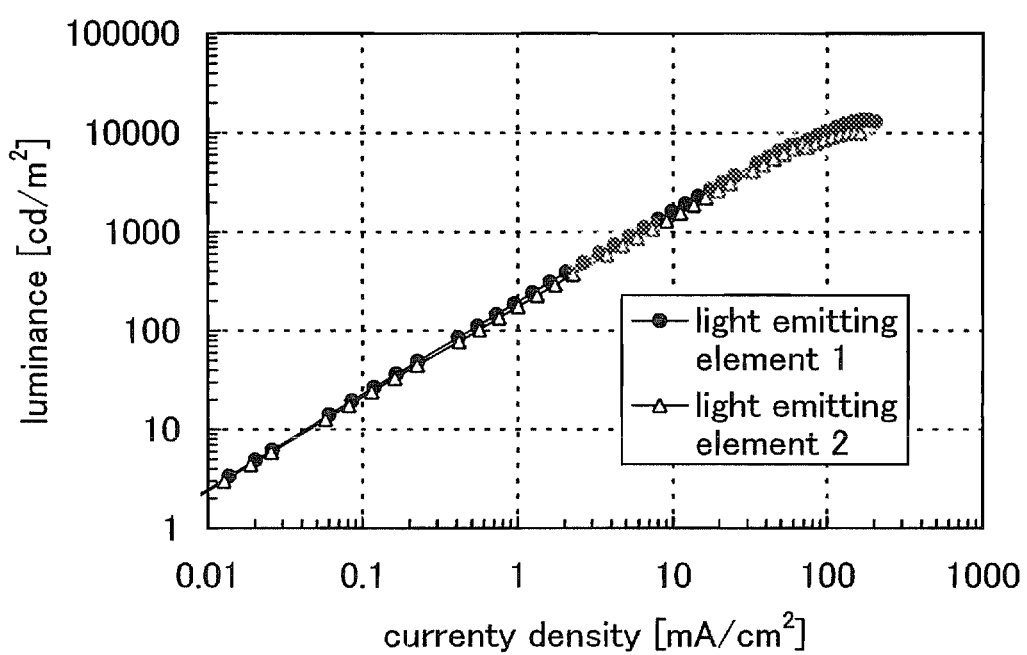
FIG. 15 is a graph showing the current density-luminance characteristics of a light-emitting element manufactured in Embodiment 3.
Figure 16:
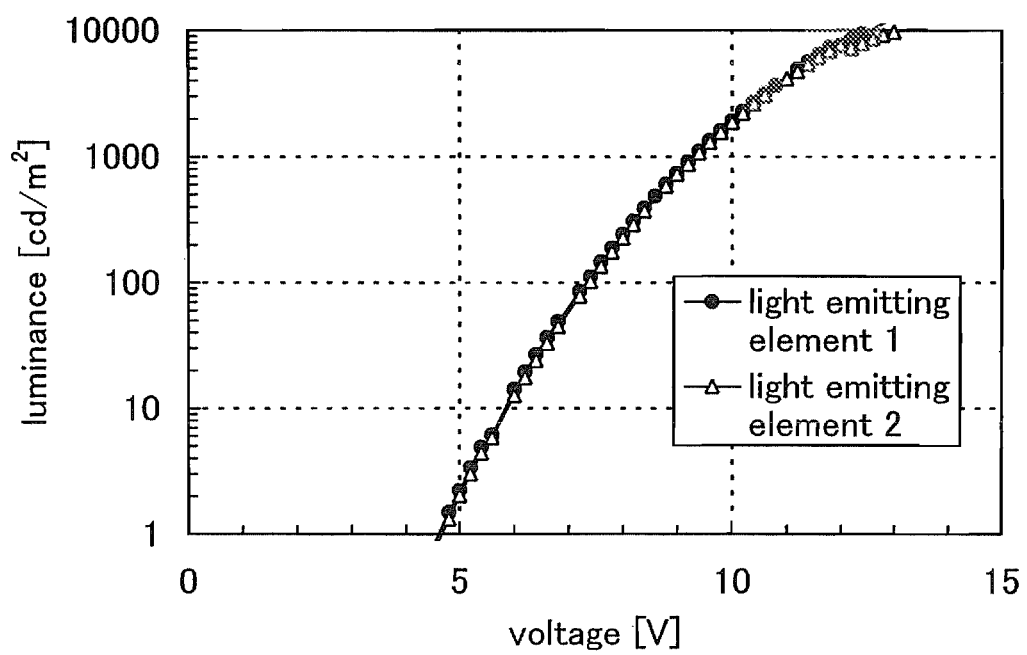
FIG. 16 is a graph showing the voltage-luminance characteristics of a light-emitting element manufactured in Embodiment 3.
Figure 17:
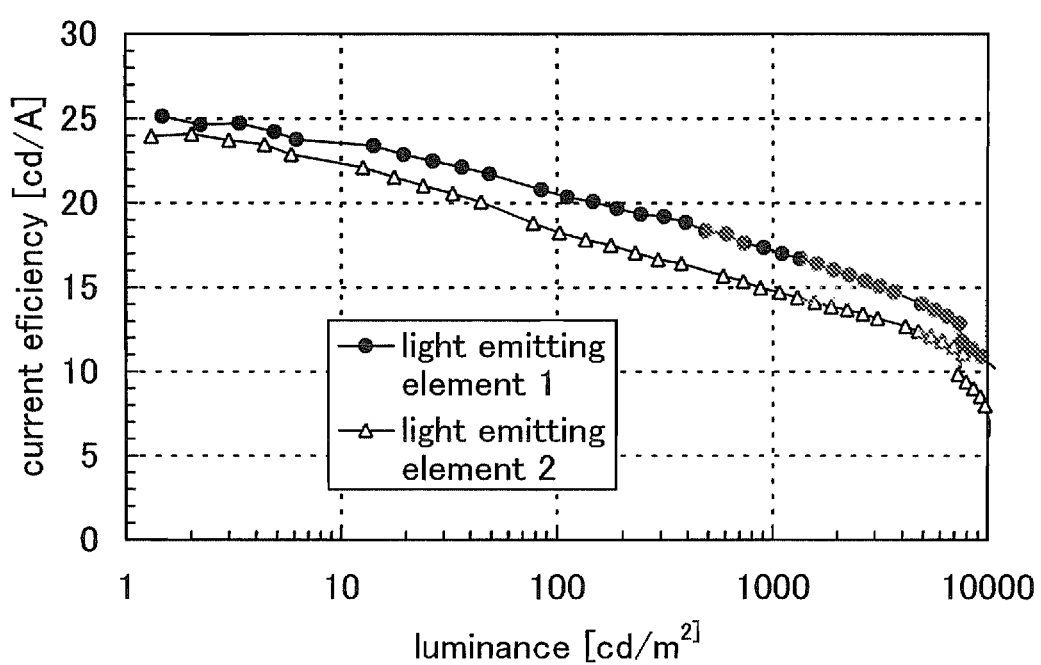
FIG. 17 is a graph showing the luminance-current efficiency characteristics of a light-emitting element manufactured in Embodiment 3.
Figure 18:
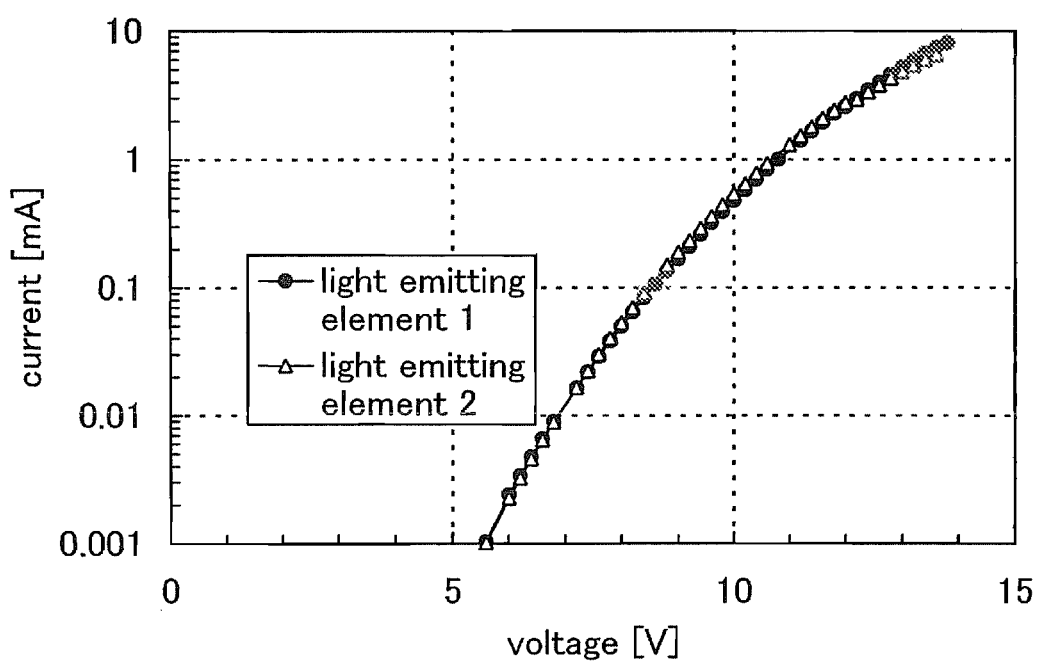
FIG. 18 is a graph showing the voltage-current characteristics of a light-emitting element manufactured in Embodiment 3.
Figure 19:
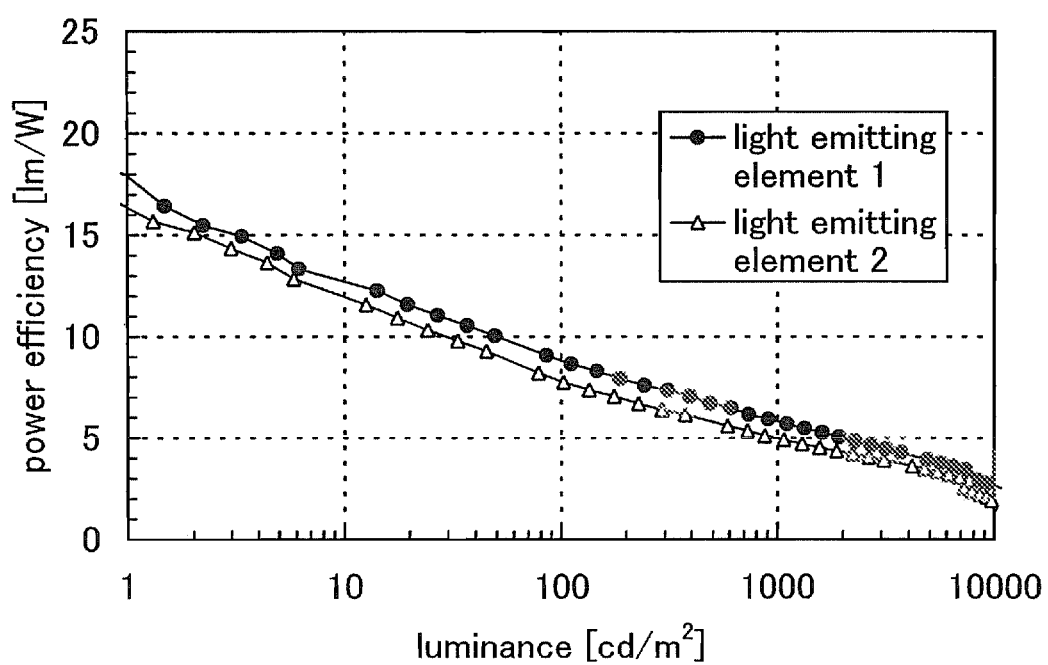
FIG. 19 is a graph showing the luminance-power efficiency characteristics of a light-emitting element manufactured in Embodiment 3.
Figure 20:
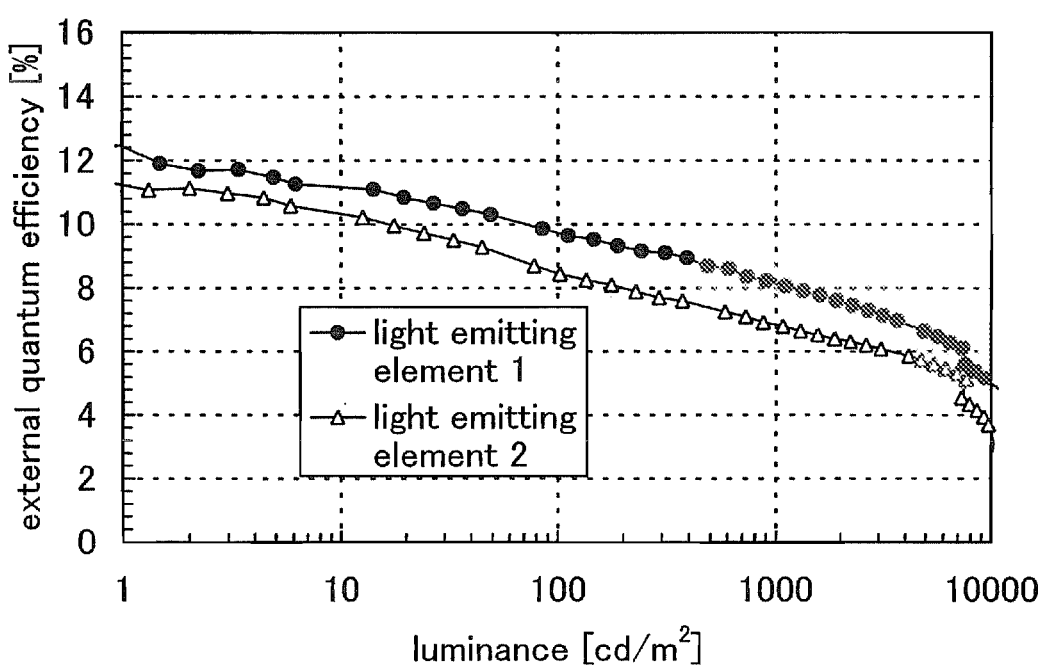
FIG. 20 is a graph showing the luminance-external quantum efficiency characteristics of a light-emitting element manufactured in Embodiment 3.
Figure 21:
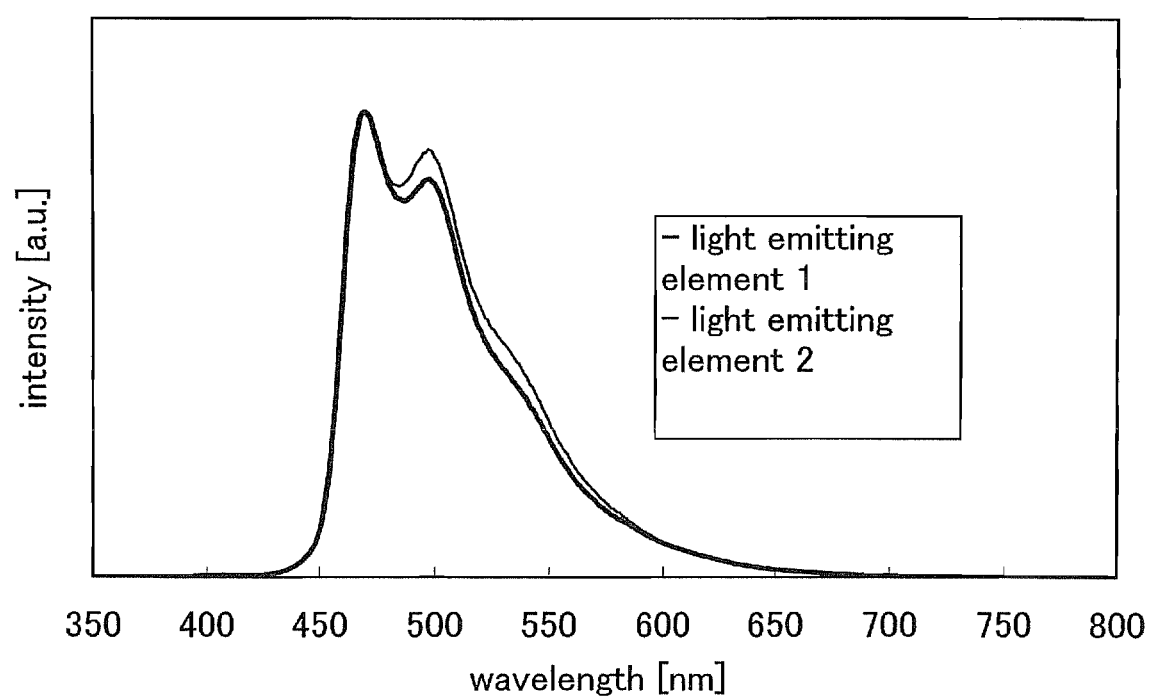
FIG. 21 is a graph showing the emission spectrum of a light-emitting element manufactured in Embodiment 3.

FIG. 15 shows the current density-luminance characteristics of each of the light-emitting elements 1 and 2. FIG. 16 shows the voltage-luminance characteristics of each of the light-emitting elements 1 and 2. FIG. 17 shows the luminance-current efficiency characteristics of each of the light-emitting elements 1 and 2. FIG. 18 shows the voltage-current characteristics of each of the light-emitting elements 1 and 2. FIG. 19 shows the luminance-power efficiency characteristics of each of the light-emitting elements 1 and 2. FIG. 20 shows the luminance-external quantum efficiency of each of the light-emitting elements 1 and 2. FIG. 21 shows the emission spectrum of each of the light-emitting elements 1 and 2 at a current supply of 1 mA.

The emission color of the light-emitting element 1 was located at the CIE chromaticity coordinates of (x=0.19, y=0.36) at a luminance of 910 cd/m$^2$, and was blue. In addition, the current efficiency and external quantum efficiency of the light-emitting element 1 at a luminance of 910 cd/m$^2$ were 17 cd/A and 8.2%, respectively; thus, the light-emitting element 1 had high efficiency. Further, when the luminance was 910 cd/m$^2$, voltage, current density, and power efficiency of the light-emitting element 1 were 9.2 V, 5.2 mA/cm$^2$, and 5.9 lm/W, respectively, and the light-emitting element 1 had high power efficiency.

The emission color of the light-emitting element 2 was located at the CIE chromaticity coordinates of (x=0.19, y=0.36) at a luminance of 1070 cd/m$^2$, and was blue. In addition, the current efficiency and external quantum efficiency of the light-emitting element 2 at a luminance of 1070 cd/m$^2$ were 15 cd/A and 6.8%, respectively; thus, the light-emitting element 2 had high efficiency. Further, when the luminance was 1070 cd/m$^2$, voltage, current density, and power efficiency of the light-emitting element 2 were 9.4 V, 7.3 mA/cm$^2$, and 4.9 lm/W, respectively, and the light-emitting element 2 had high power efficiency.

From the result shown in FIG. 21, it can be seen that light emission of the light-emitting elements 1 and 2 is light emission derived from FIrpic. Thus, it can be seen that, using a tiazole deribvative having high triplet excitation energy, the light-emitting elements of this embodiment each can efficiently emit FIrpic which shows blue light emission of a short wavelength.

By application of the present invention, FIrpic which is a phosphorescent compound which shows light emission of a short wavelength can be emitted efficiently. That is, high luminous efficiency can be achieved even in a case where a phosphorescent compound which shows light emission of a short wavelength is used. Further, a light-emitting element, the power consumption of which is reduced, can be achieved.

Embodiment 4

Figure 22:
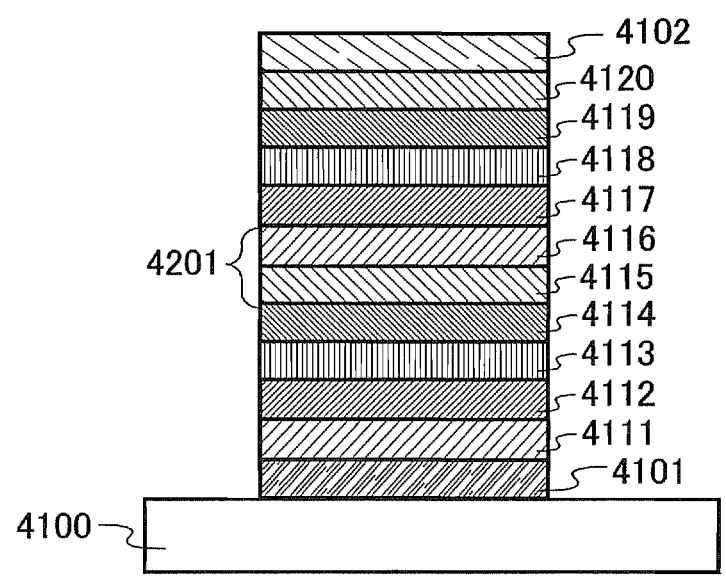
FIG. 22 is a cross-sectional view showing a light-emitting element of embodiments.

This embodiment will describe a light-emitting element of the present invention with reference to FIG. 22. A chemical formula of a material used in this embodiment will be shown below. Note that the materials shown in Embodiment 3 will be omitted.

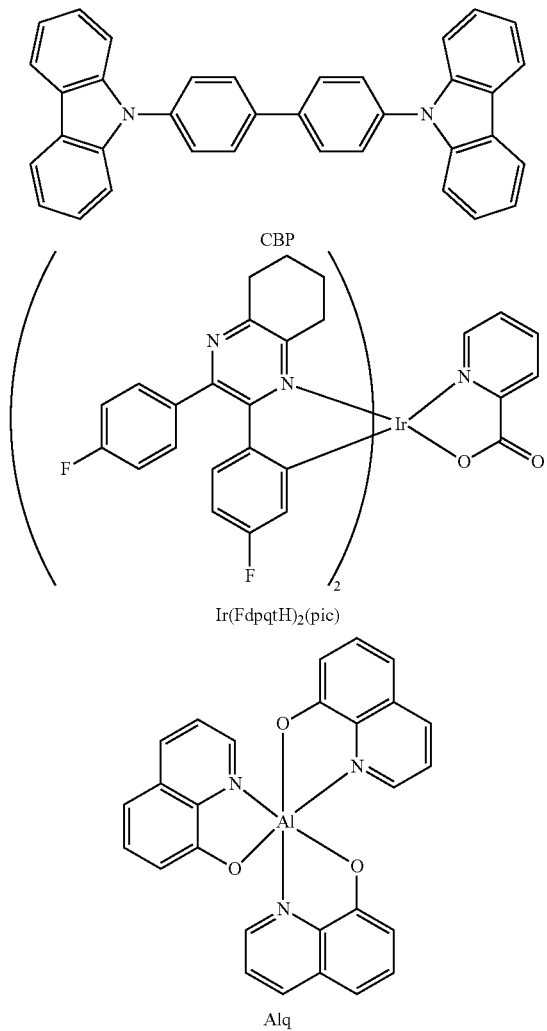

Hereinafter, a method of manufacturing a light-emitting element of this embodiment is described.
(Light-Emitting Element 3)

First, indium tin oxide containing silicon oxide (ITSO) was deposited over a glass substrate 4100 by a sputtering method to form a first electrode 4101. Note that the thickness of the first electrode 4101 was 110 nm and the electrode area was 2 mm×2 mm.

Next, the substrate 4100 having the first electrode 4101 was fixed to a substrate holder provided in a vacuum evaporation apparatus in such a way that a surface of the substrate 4100 over which the first electrode 4101 was formed faced downward, and then the pressure was reduced to approximately $10^{-4}$ Pa. Next, 4,4'-bis[N-(1-naphthyl)-N-phenylamino]biphenyl (abbreviation: NPB) and molybdenum(VI) oxide were co-evaporated on the first electrode 4101, whereby a layer 4111 containing a composite material of an organic compound and an inorganic compound was formed. The thickness of the layer 4111 was set to be 50 nm and the weight ratio of NPB to molybdenum(VI) oxide was controlled to 4:1 (=NPB:molybdenum oxide). Note that the co-evaporation method is an evaporation method in which evaporation is performed from a plurality of evaporation sources at the same time in one treatment chamber.

Next, a hole-transporting layer 4112 was formed by depositing NPB to have a thickness of 10 nm on the layer 4111 containing a composite material by an evaporation method using resistance heating.

Furthermore, 4,4'-di(N-carbazolyl)biphenyl (abbreviation: CBP) and bis[2,3-bis(4-fluorophenyl)-5,6,7,8-tetrahydroquinoxalinate](picolinato)iridium(III) (abbreviation: Ir(FdpqtH)$_2$(pic)) were co-evaporated, whereby a 30 nm thick light-emitting layer 4113 was formed on the hole-transportinging layer 4112. Here, the weight ratio of CBP to Ir(FdpqtH)$_2$(pic) was controlled to 1:0.05 (=CBP:Ir(FdpqtH)$_2$(pic)).

Then, an electron-transporting layer 4114 was formed by depositing bathophenanthroline (abbreviation: BPhen) to have a thickness of 10 nm on the light-emitting layer 4113 by an evaporation method using resistance heating.

Further, tris(8-quinolinolato)aluminum(III) (abbreviation: Alq) and lithium were co-evaporated on the electron-transporting layer 4114, whereby an electron-injecting layer 4115 was formed with a thickness of 30 nm. Here, the weight ratio of Alq to lithium was controlled to 1:0.01 (=Alq:lithium).

Furthermore, NPB and molybdenum(VI) oxide were co-evaporated, whereby a layer 4116 containing a composite material of an organic compound and an inorganic compound was formed with a thickness of 50 am on the electron-injecting layer 4115. Here, the weight ratio of NPB to molybdenum(VI) oxide was controlled to 4:1 (=NPB:molybdenum(VI) oxide).

Note that both the electron-injecting layer 4115 and the layer 4116 containing a composite material together function as a charge-generating layer 4201.

Next, a hole-transporting layer 4117 was formed by depositing 4,4',4''-tris(carbazol-9-yl)triphenylamine (abbreviation: TCTA) to have a thickness of 20 nm on the layer 4116 containing a composite material.

Furthermore, 9-[4-(4,5-diphenyl-4H-1,2,4-triazol-3-yl)phenyl]-9H-carbazole (abbreviation: CzTAZ1) which is represented by the structural formula (101) and bis[2-(4',6'-difluorophenyl)pyridinato-N,C$^{2'}$]iridium(III)picolinate (abbreviation: FIrpic) were co-evaporated, whereby a 30 nm thick light-emitting layer 4118 was formed on the hole-transportinging layer 4117. Here, the weight ratio of CzTAZ1 to FIrpic was controlled to 1:0.05 (=CzTAZ1:FIrpic).

Then, an electron-transporting layer 4119 was formed by depositing 3-(4-biphenylyl)-4-phenyl-5-(4-tert-butylphenyl)-1,2,4-triazole (abbreviation: TAZ01) to have a thickness of 10 nm on the light-emitting layer 4118 by an evaporation method using resistance heating.

Further, bathophenanthroline (abbreviation: BPhen) and lithium were co-evaporated on the electron-transporting layer 4119, whereby an electron-injecting layer 4120 was formed with a thickness of 20 nm. Here, the weight ratio of BPhen to lithium was controlled to 1:0.01 (=BPhen:lithium).

Finally, a second electrode 4102 was formed by depositing aluminum to have a thickness of 200 nm on the electron-injecting layer 4120 by an evaporation method using resistance heating. Thus, a light-emitting element 3 was formed.

The light-emitting element 3 thus obtained was sealed in a glove box under a nitrogen atmosphere without being exposed to atmospheric air. Then, the operating characteristics of the light-emitting element were measured. Note that the measurement was performed at a room temperature (atmosphere kept at 25° C.).

Figure 23:
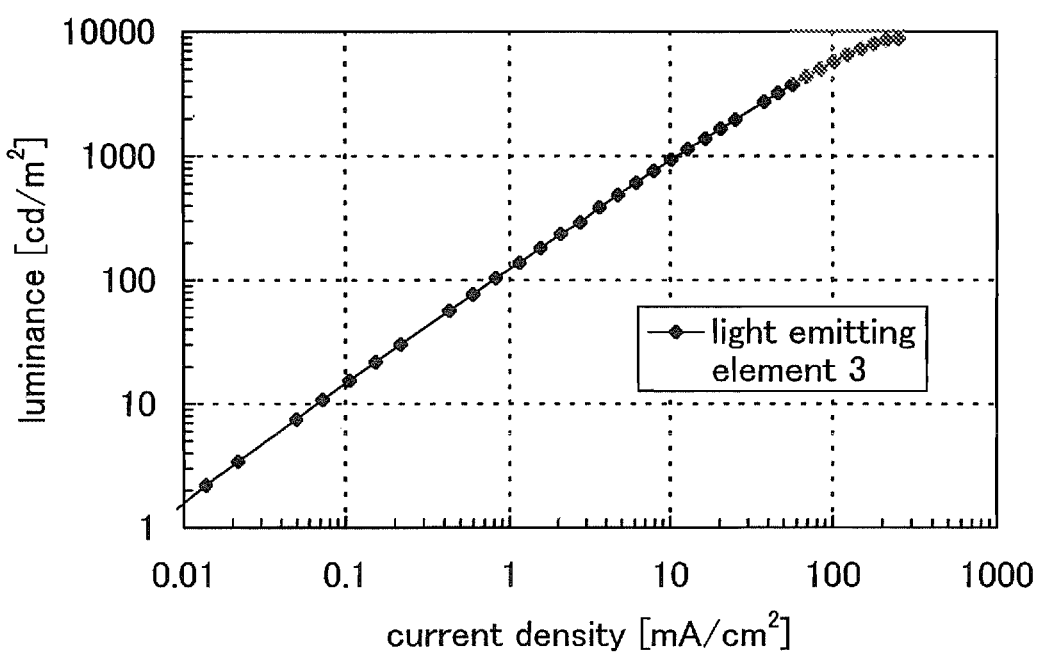
FIG. 23 is a graph showing the current density-luminance characteristics of a light-emitting element manufactured in Embodiment 4.
Figure 24:
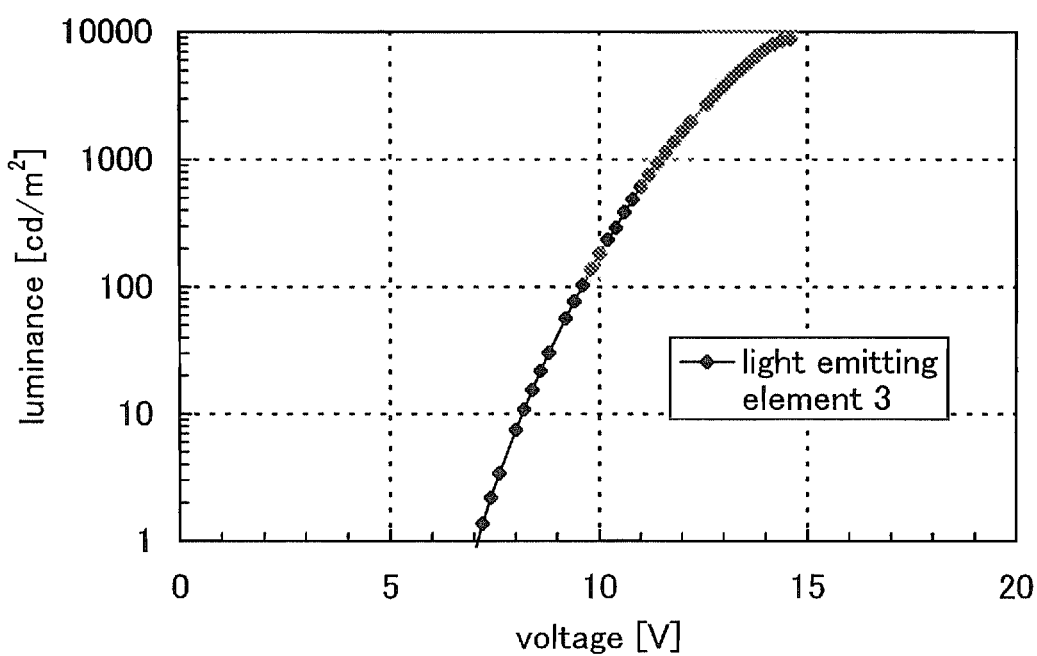
FIG. 24 is a graph showing the voltage-luminance characteristics of a light-emitting element manufactured in Embodiment 4.
Figure 25:
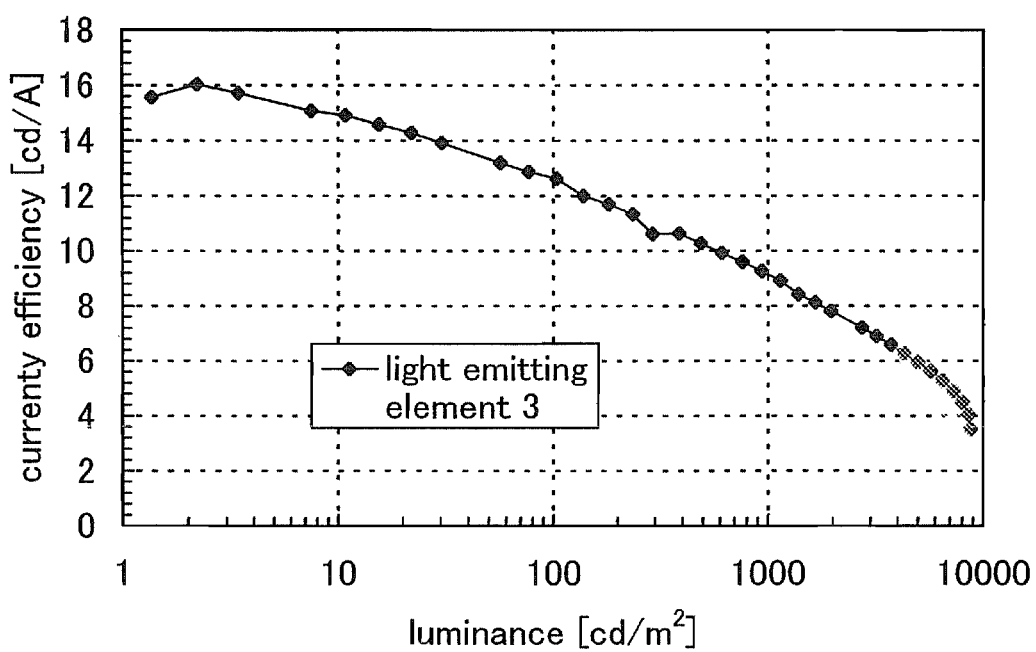
FIG. 25 is a graph showing the luminance-current efficiency characteristics of a light-emitting element manufactured in Embodiment 4.
Figure 26:
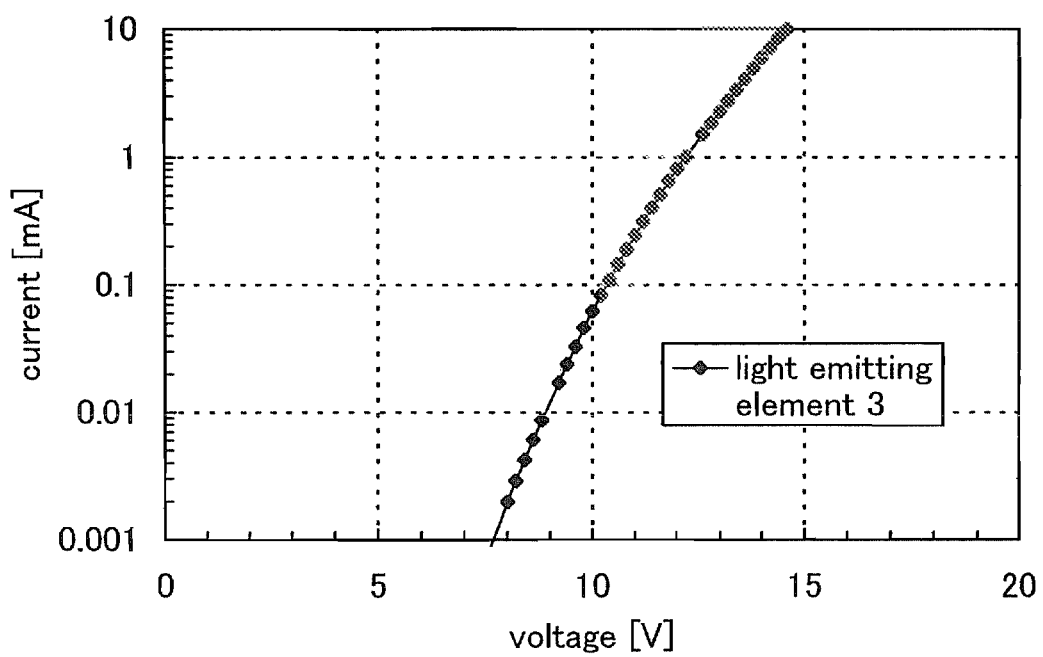
FIG. 26 is a graph showing the voltage-current characteristics of a light-emitting element manufactured in Embodiment 4.
Figure 27:
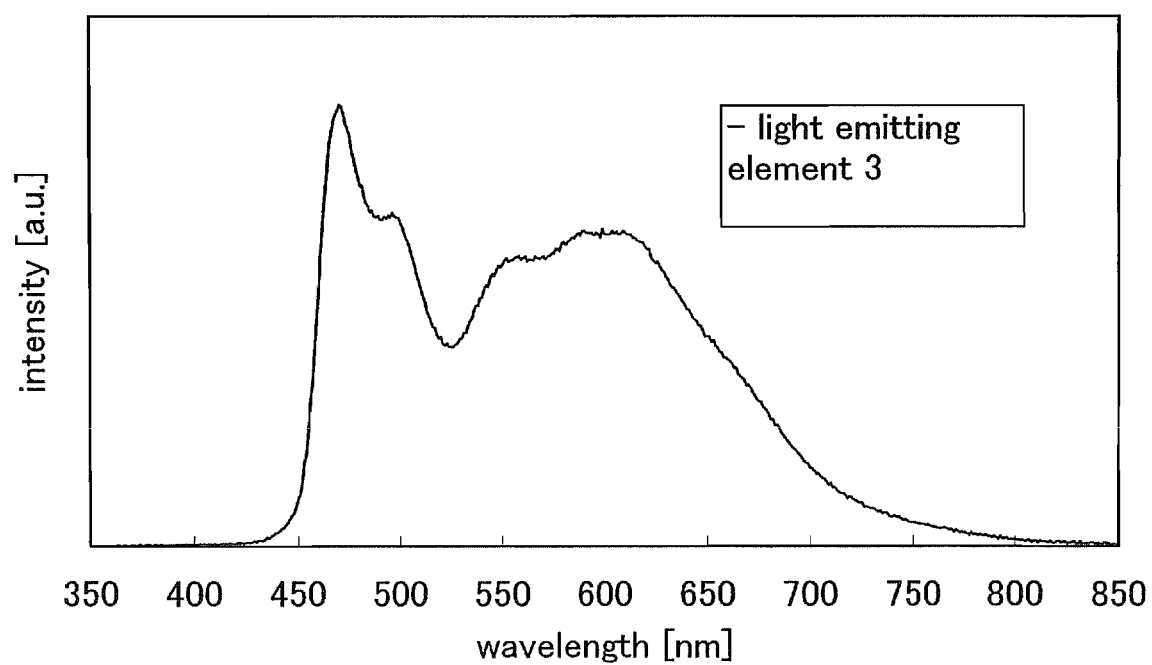
FIG. 27 is a graph showing the emission spectrum of a light-emitting element manufactured in Embodiment 4.

FIG. 23 shows the current density-luminance characteristics of the light-emitting element 3. FIG. 24 shows the voltage-luminance characteristics of the light-emitting element 3. FIG. 25 shows the luminance-current efficiency characteristics of the light-emitting element 3. FIG. 26 shows the voltage-current characteristics of the light-emitting element 3. FIG. 27 shows the emission spectrum of the light-emitting element 3 at a current supply of 1 mA.

The emission color of the light-emitting element 3 was located at the CIE chromaticity coordinates of (x=0.37, y=0.39) at a luminance of 940 cd/m$^2$, and was white. In addition, the current efficiency and external quantum efficiency of the light-emitting element 3 at a luminance of 940 cd/m$^2$ were 9.3 cd/A and 4.6%, respectively; thus, the light-emitting element 3 had high efficiency. Further, when the luminance was 940 cd/m$^2$, voltage, current density, and power efficiency of the light-emitting element 3 were 11.4 V, 10.1 mA/cm$^2$, and 2.6 lm/W, respectively, and the light-emitting element 3 had high power efficiency.

From the result shown in FIG. 27, it can be seen that light emission of the light-emitting element 3 is light emission in which light emission derived from Ir(FdpqtH)$_2$(pic) and light emission derived from FIrpic are mixed. Further, it can be seen that the light-emitting element 3 has a broad emission spectrum and shows white light emission with an excellent color rendering property. Thus, the light-emitting element shown in this embodiment can be preferably used for a lighting system or the like.

Further, it can be seen that, using a tiazole deribvative having high triplet excitation energy, the light-emitting element of this embodiment can efficiently emit FIrpic which shows blue light emission of a short wavelength. Furthermore, the light-emitting element of this embodiment can form a white light-emitting element, which only includes a phosphorescent compound, as a light-emitting substance as in this embodiment, because the light-emitting element of this embodiment can efficiently emit blue light of a short wavelength.

By application of the present invention, FIrpic which is a phosphorescent compound which shows light emission of a short wavelength can be emitted efficiently. That is, high luminous efficiency can be achieved even in a case where a phosphorescent compound which shows light emission of a short wavelength is used.

Further, a white light-emitting element, which only includes a phosphorescent compound, can be formed as a light-emitting substance. Furthermore, a light-emitting element, the power consumption of which is reduced, can be achieved.

Embodiment 5

This embodiment will describe a synthesis method of 9-{4-[4-phenyl-5-(2-pyridyl)-4H-1,2,4-triazol-3-yl]phenyl}-9H-carbazole (abbreviation: CPyTz1) which is represented by the structural formula (125).

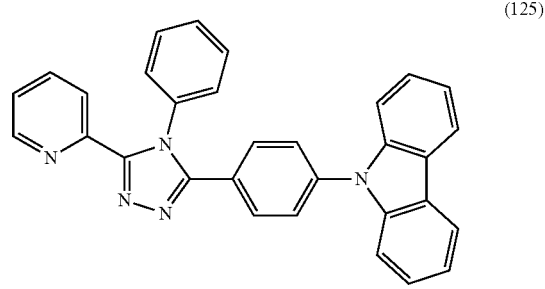 [SMILES: c1ccc(-n2c(-c3ccc(-n4c5ccccc5c5ccccc54)cc3)nnc2-c2ccccn2)cc1]

(125)

[Step 1] Synthesis of 2-[5-(4-bromophenyl)-4-phenyl-4H-1,2,4-triazol-3-yl]pyridine (i) Synthesis of N-phenylpyridine-2-thioamide A synthesis scheme of N-phenylpyridine-2-thioamide is shown in (B-11).

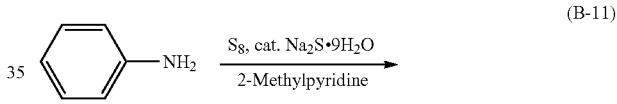

(B-11)

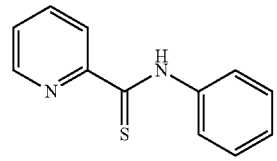

5.0 g (53 mmol) of aniline, 5.11 g (0.16 mol) of sulfur powder, 0.26 g (1.1 mmol) of sodium sulfide nonahydrate, and 2-picoline were put into a 100 mL three-neck flask, and the mixture was stirred at 130° C. for 16 hours. After the reaction, with a solvent of the reactive mixture being distilled off under reduced pressure, dichloromethane was added to the mixture. Suction filtration was performed with sellite (Wako Pure Chemical Industries. Ltd., catalog number: 531-16855) and silica gel on the mixture, and thus a filtrate was obtained. The obtained filtrate was washed with a saturated sodium hydrogen carbonate solution and saturated saline, in the order given. Magnesium sulfate was added to an organic layer, and the mixture was dried. After the drying, suction filtration was performed on the mixture, and thus a filtrate was obtained. The obtained filtrate was condensed and dried, so that 6.0 g of an orange oily substance, which was the object of the synthesis, was obtained at a yield of 53%.

(ii) Synthesis of ethyl N-phenylpyridine-2-carboximidothioate

A synthesis scheme of ethyl N-phenylpyridine-2-carboximidothioate is shown in (B-12).

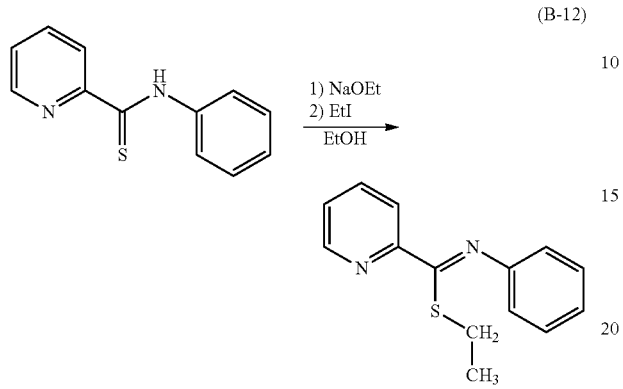

(B-12)

3.65 g (53.6 mmol) of natrium ethoxide and 11.5 g (53.6 mmol) of N-phenylpyridine-2-thiocarboxyamido were put into a 100 mL three-neck flask, and the contents of the flask was added with 100 mL of ethanol and stirred at a room temperature for 1 hour. After being stirred, the mixture was added with 4.3 mL of ethyl iodide and stirred at 50° C. for 8 hours. After the reaction, a solvent of the reactive mixture was distilled off to obtain a solid. Dichloromethane was added to the obtained solid. The suspension was washed with water, a saturated sodium hydrogen carbonate solution, and saturated saline, in the order given. An organic layer was added with magnesium sulfate and dried. After the drying, suction filtration was performed on the mixture to remove the magnesium sulfate, and thus a filtrate was obtained. The obtained filtrate was condensed and the obtained solid was washed with methanol, so that 10 g of an orange oily substance, which was the object of the synthesis, was obtained at a yield of 77%.

(iii) Synthesis of 2-[5-(4-bromophenyl)-4-phenyl-4H-1,2,4-triazol-3-yl]pyridine A synthesis scheme of 2-[5-(4-bromophenyl)-4-phenyl-4H-1,2,4-triazol-3-yl]pyridine is shown in (B-13).

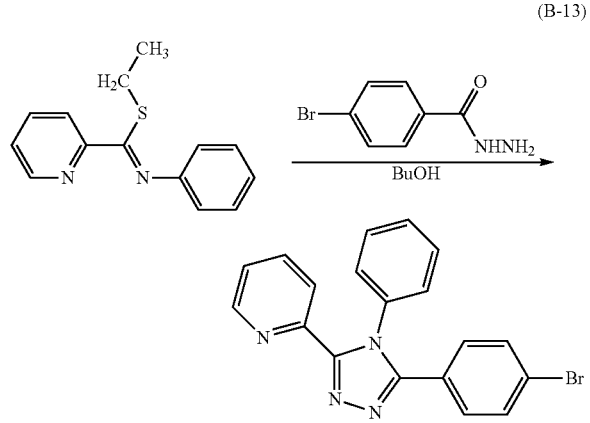

(B-13)

10 g (41 mmol) of ethyl N-phenylpyridine-2-carboximidothioate and 11 g (49 mmol) of 4-bromobenzohydrazine were put into a 100 mL three-neck flask, and 30 mL of butanol was added to the mixture. The mixture was stirred at 120° C. for 11 hours, and the contents of the flask were reacted together. After the reaction, 10 mL of ethanol was added to the reactive mixture, and the mixture was stirred. After being stirred, the contents of the flask were added with methanol and stirred with being cooled with ice. After the stirring, suction filtration was performed on the mixture, and a solid was obtained. The obtained solid was washed with methanol, so that 7.5 g of a powdery white solid, which was the object of the synthesis, was obtained at a yield of 48%.

[Step 2] Synthesis of CPyTz1

A synthesis scheme of CPyTz1 is shown in (B-14).

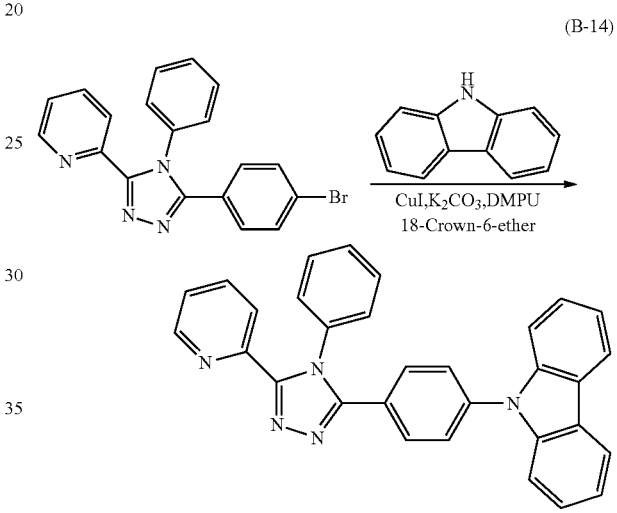

(B-14)

2.0 g (5.3 mmol) of 2-[5-(4-bromophenyl)-4-phenyl-4H-1,2,4-triazol-3-yl]pyridine obtained in Step 1, 1.33 g (8.0 mmol) of carbazole, 3.0 g (22 mmol) of potassium carbonate, 0.3 g of copper iodide, and 0.30 g of 18-crown-6-ether were put into a 50 mL three-neck flask, and 1.5 mL of 1,3-dimethyl-3,4,5,6-tetrahydro-2(1H)-pyrimidinone (abbreviation: DMPU) was added to the contents of the flask, on which nitrogen substitution was performed. The mixture was stirred at 170° C. for 6 hours. After the reaction, chloroform was added to the reactive mixture. The suspension was washed with 1 N diluted hydrochloric acid, a saturated sodium hydrogen carbonate solution, and saturated saline, in the order given. Suction filtration was performed with sellite (Wako Pure Chemical Industries. Ltd., catalog number: 531-16855) on an organic layer, and thus a filtrate was obtained. The obtained filtrate was condensed, and purification by silica gel column chromatography was performed. For the column chromatography, first chloroform and then a mixed solvent of chloroform and ethyl acetate (chloroform:ethyl acetate=1:3) was used as a developing solvent. The obtained fraction was condensed to obtain a solid. When a solution, in which the obtained solid is dissolved, was examined with TLC, spots around the origin had come out along with objective spots; therefore, purification by silica gel column chromatography was performed again. For the column chromatography, first toluene and then a mixed solvent of toluene and ethyl acetate (toluene:

ethyl acetate=1:3) was used as a developing solvent. The obtained fraction was condensed to obtain a solid. The obtained solid was recrystallized with a mixed solvent of chloroform and ethanol, so that 1.2 g of a white solid, which was the object of the synthesis, was obtained. It was confirmed by a nuclear magnetic resonance (NMR) that the compound was 9-{4-[4-phenyl-5-(2-pyridyl)-4H-1,2,4-triazol-3-yl]phenyl}-9H-carbazole (abbreviation: CPyTz1).

Sublimation purification of 0.89 g of the obtained white solid was performed by a train sublimation method. The sublimiation purification was performed at a reduced pressure of 7.0 Pa, with the argon flow rate of 3 mL/min, at 270° C. for 15 hours. 0.50 g of the white solid was obtained at a yield of 56%.

Figure 28A:
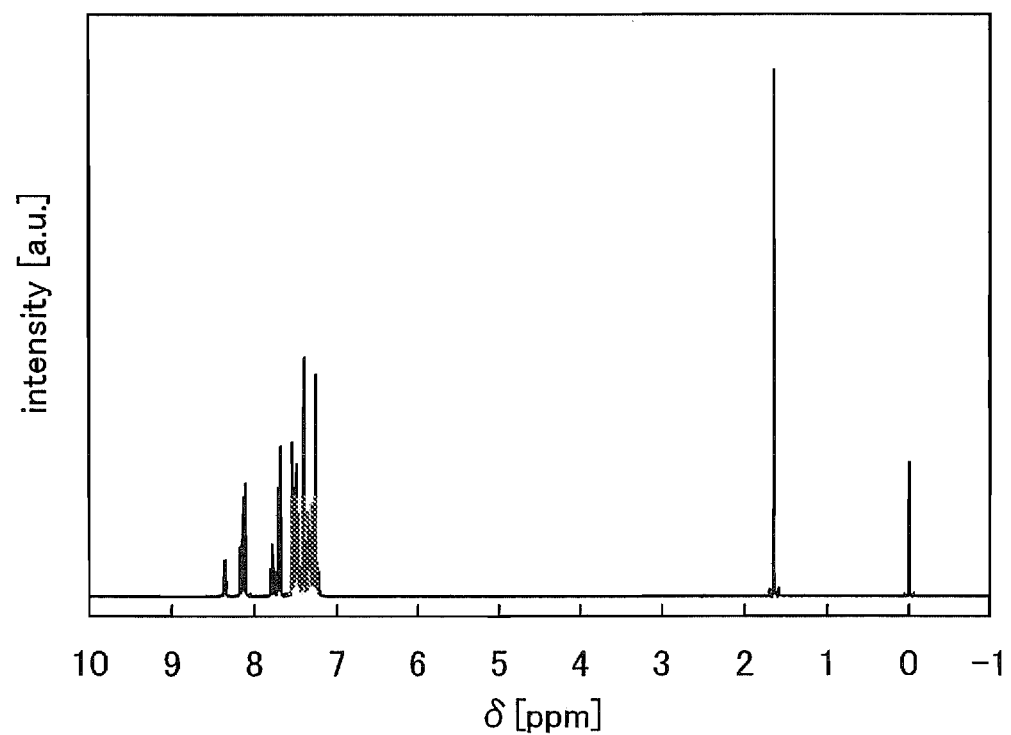
FIGS. 28A and 28B are graphs each showing $^1$H NMR of 9-{4-[4-phenyl-5-(2-pyridyl)-4H-1,2,4-triazol-3-yl]phenyl}-9H-carbazole (abbreviation: CPyTz1)
Figure 28B:
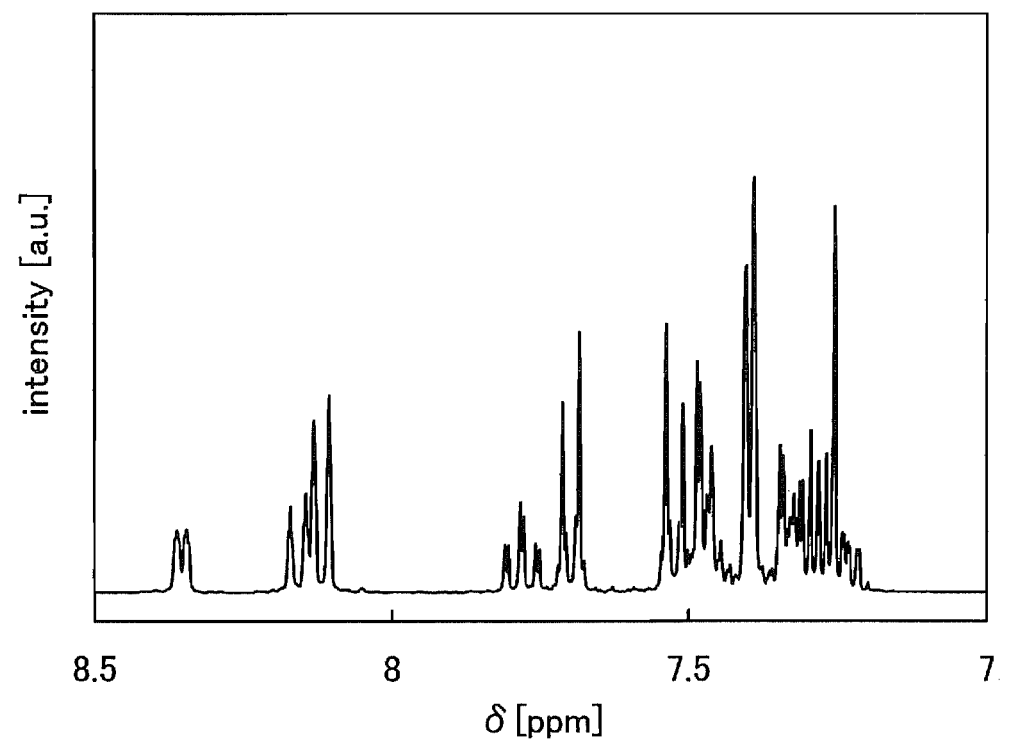

The $^1$H NMR data of CPyTz1 is given as follows. $^1$H NMR (CDCl$_3$, 300 MHz): δ=7.19-7.50 (m, 12H), 7.52 (d, J=8.3 Hz, 2H), 7.70 (d, J=8.3 Hz, 2H), 7.78 (td, J=7.8, 2.0 Hz, 1H), 8.12 (d, J=7.8 Hz, 2H), 8.16 (d, J=7.8 Hz, 1H), 8.35 (d, J=5.4 Hz, 1H). In addition, charts of $^1$H NMR are shown in FIGS. 28A and 28B. Note that FIG. 28B is a chart showing an enlarged portion of FIG. 28A in a range of from 7.0 to 8.5 ppm.

Figure 29A:
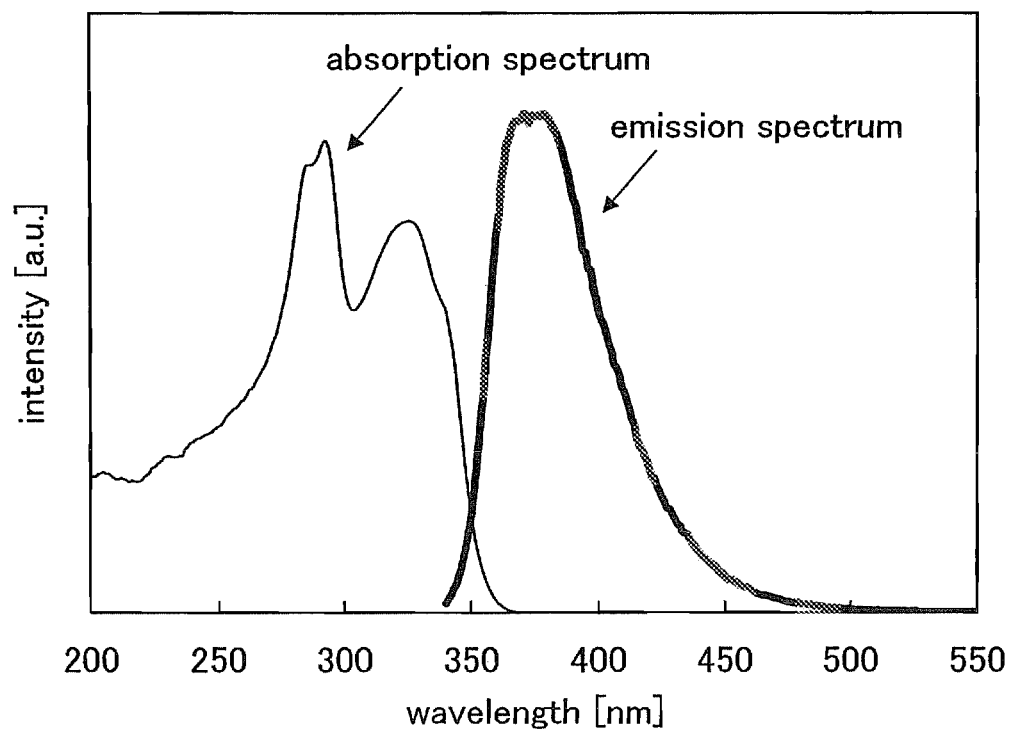
FIGS. 29A and 29B are graphs each showing the absorption spectrum and the emission spectrum of 9-{4-[4-phenyl-5-(2-pyridyl)-4H-1,2,4-triazol-3-yl]phenyl}-9H-carbazole (abbreviation: CPyTz1)
Figure 29B:
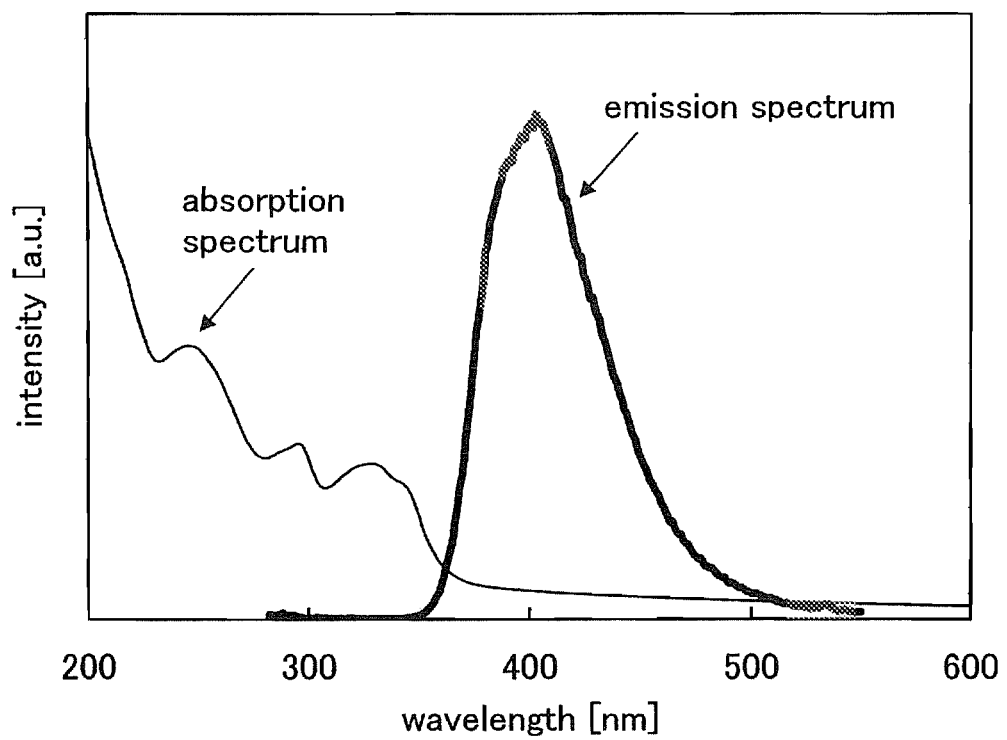

Further, the absorption spectrum and the emission spectrum of a toluene solution of CPyTz1 are shown in FIG. 29A. The absorption spectrum and the emission spectrum of a thin film of CPyTz1 are shown in FIG. 29B. Measurements were performed with an ultraviolet-visible light spectrophotometer (V-550, manufactured by JASCO Corporation). The solution was put into a quartz cell as one sample and CPyTz1 was evaporated over a quartz substrate to form a thin film as another sample, and the absorption spectra of the solution and the thin film, from each of which the absorption spectrum of quartz was subtracted, are shown in FIGS. 29A and 29B. In FIGS. 29A and 29B, the horizontal axis represents wavelength (nm), and the vertical axis represents intensity (arbitrary unit). In the case of the toluene solution of CPyTz1, the absorption was observed at around 324 nm. In addition, in the case of the toluene solution, the maximum emission wavelength was 377 nm (excitation wavelength: 324 nm). Further, in the case of a thin film of CPyTz1, the absorption was observed at around 246 nm, around 295 nm, and around 328 nm. In addition, in the case of a thin film, the maximum emission wavelength was 403 nm (excitation wavelength: 267 nm).

Moreover, the result for the ionized potential of a thin film form of CPyTz1 measured by a photoelectron spectrometer (AC-2 photoelectron spectrometer manufactured by Riken Keiki, Co., Ltd.) in the atmosphere was 5.76 eV. As a result, it was understood that the HOMO level was −5.76 eV. The absorption edge was obtained by tauc plot assuming direct transition with the absorption spectrum data of a thin film of CPyTz1. When the absorption edge was estimated as an optical energy gap, the energy gap was 3.46 eV. A LUMO level of −2.30 eV was obtained from the obtained values of the energy gap value and HOMO level.

Thus, it was understood that CPyTz1 is a substance having high singlet excitation energy (a band gap).

Embodiment 6

This embodiment will describe a synthesis method of 9-{4-[4-(4-pyridyl)-5-(2-pyridyl)-4H-1,2,4-triazol-3-yl]phenyl}-9H-carbazole (abbreviation: CPy2Tz1) which is represented by the structural formula (137).

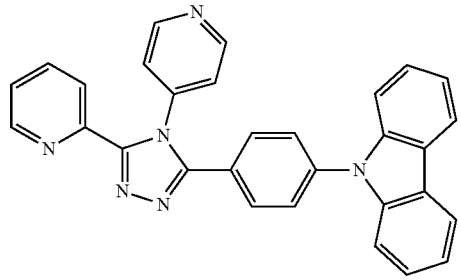

(137)

[Step 1] Synthesis of 2-[5-(4-bromophenyl)-4-(4-pyridyl)-4H-1,2,4-triazol-3-yl]pyridine (i) Synthesis of N-(4-pyridyl)pyridine-2-thioamide A synthesis scheme of N-(4-pyridyl)pyridine-2-thioamide is shown in (B-15).

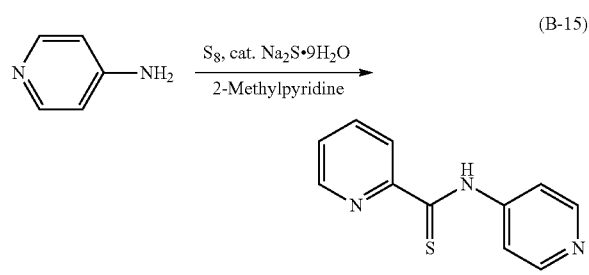

(B-15)

5.0 g (53 mmol) of 4-aminopyridine, 5.11 g (0.16 mmol) of sulfur powder, 0.26 g (1.1 mmol) of sodium sulfide nonahydrate, and 2-methylpyridine were put into a 100 mL three-neck flask, and the mixture was stirred at 130° C. for 20 hours. After the reaction, a solvent of the reactive mixture was distilled off under reduced pressure. 1 N sodium hydroxide solution was added to the mixture. Suction filtration was performed on the suspension to remove the solid, and thus a filtrate was obtained. The obtained filtrate was slowly added with 1 N diluted hydrochloric acid to have a degree of acid at pH5, so that a yellow solid was precipitated out. Suction filtration was performed on the precipitated solid, and a solid was obtained. The obtained solid was washed with water, so that 3.0 g of an ocher solid, which was the object of the synthesis, was obtained at a yield of 26%.

(ii) Synthesis of 2-[5-(4-bromophenyl)-4-(4-pyridyl)-4H-1,2,4-triazol-3-yl]pyridine A synthesis scheme of 2-[5-(4-bromophenyl)-4-(4-pyridyl)-4H-1,2,4-triazol-3-yl]pyridine is shown in (B-16).

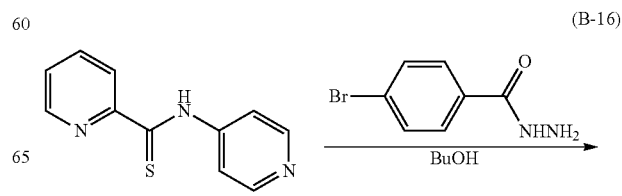

(B-16)

-continued

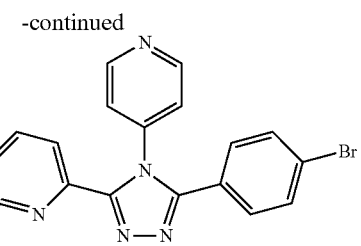

3.8 g (17 mmol) of N-(4-pyridyl)pyridine-2-thiocarboxamido and 4.0 g (19 mmol) of 4-bromobenzohydrazine were put into a 100 mL three-neck flask, and 30 mL of butanol was added to the mixture. The mixture was stirred at 120° C. for 6 hours, and the contents of the flask were reacted together. After the reaction, 10 mL of ethanol was added to the reactive mixture, and the mixture was stirred. After being stirred, the contents of the flask were added with methanol and stirred with being cooled with ice. After the stirring, suction filtration was performed on the mixture, and a solid was obtained. The obtained solid was washed with methanol, so that 3.0 g of a white solid, which was the object of the synthesis, was obtained at a yield of 42%.

[Step 2] Synthesis of CPy2Tz1

A synthesis scheme of CPy2Tz1 is shown in (B-17).

(B-17)

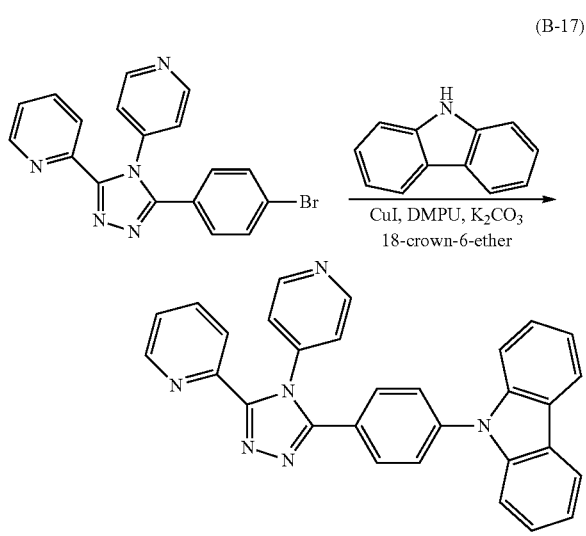

2.0 g (5.3 mmol) of 2-[5-(4-bromophenyl)-4-(4-pyridyl)-4H-1,2,4-triazol-3-yl]pyridine obtained in Step 1, 1.3 g (8.0 mmol) of carbazole, 2.0 g (13 mmol) of potassium carbonate, 0.20 g (1.1 mmol) of copper iodide, and 0.20 g (0.73 mmol) of 18-crown-6-ether were put into a 50 mL three-neck flask, and nitrogen substitution was performed on the contents of the flask. The mixture was added with 3 mL of 1,3-dimethyl-3,4,5,6-tetrahydro-2(1H)-pyrimidinone (abbreviation: DMPU) and stirred at 180° C. for 5 hours, and the contents of the flask were reacted together. After the reaction, chloroform was added to the reactive mixture. The suspension was washed with 1 N diluted hydrochloric acid, a saturated sodium hydrogen carbonate solution, and saturated saline, in the order given. Suction filtration was performed with sellite (Wako Pure Chemical Industries. Ltd., catalog number: 531-16855) on an organic layer, and thus a filtrate was obtained. The obtained filtrate was condensed, and purification by silica gel column chromatography was performed. For the column chromatography, first chloroform and then a mixed solvent of chloroform and ethyl acetate (chloroform:ethyl acetate=1:3) was used as a developing solvent. The obtained fraction was condensed to obtain a solid. The obtained solid was recrystallized with a mixed solvent of chloroform and ethanol, so that 1.2 g of a white solid, which was the object of the synthesis, was obtained at a yield of 49%. It was confirmed by a nuclear magnetic resonance (NMR) that the compound was 9-{4-[4-(4-pyridyl)-5-(2-pyridyl)-4H-1,2,4-triazol-3-yl]phenyl}-9H-carbazole (abbreviation: CPy2Tz1).

Sublimation purification of 1.2 g of the obtained white solid was performed by a train sublimation method. The sublimation purification was performed at a reduced pressure of 7.0 Pa, with the argon flow rate of 3 mL/min, at 270° C. for 15 hours. 0.90 g of the white solid was obtained at a yield of 75%.

Figure 30A:
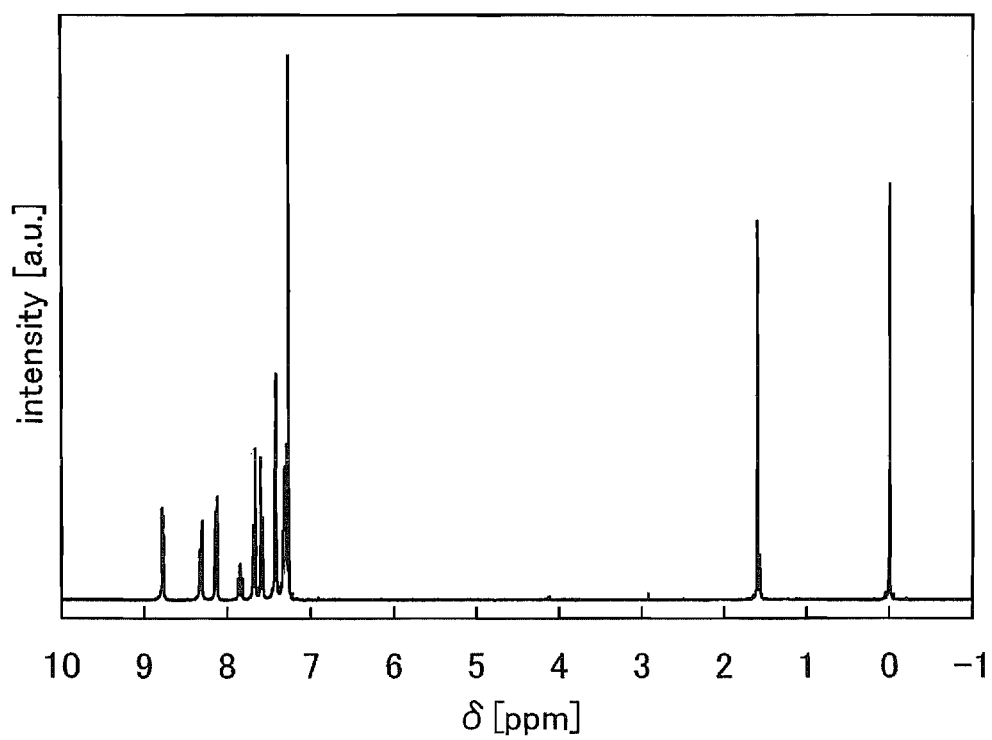
FIGS. 30A and 30B are graphs each showing $^1$H NMR of 9-{4-[4-(4-pyridyl)-5-(2-pyridyl)-4H-1,2,4-triazol-3-yl]phenyl}-9H-carbazole (abbreviation: CPy2Tz1)
Figure 30B:
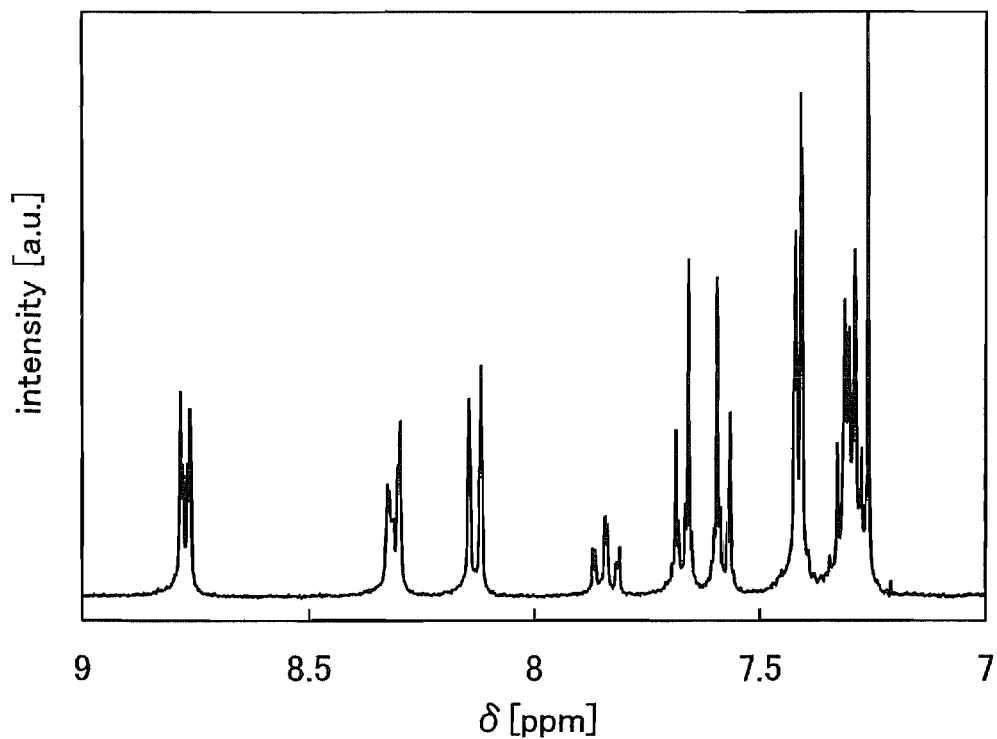

The $^1$H NMR data of CPy2Tz1 is given as follows. $^1$H NMR (CDCl$_3$, 300 MHz): δ=7.27-7.36 (m, 5H), 7.37-7.48 (m, 4H), 7.58 (d, J=8.8 Hz, 2H), 7.68 (d, J=8.8 Hz, 2H), 7.84 (td, J=7.3, 2.0 Hz, 1H), 8.13 (d, J=7.8 Hz, 2H), 8.26-8.37 (m, 2H), 8.77 (dd, J=4.4, 2.0 Hz, 2H). In addition, charts of $^1$H NMR are shown in FIGS. 30A and 30B. Note that FIG. 30B is a chart showing an enlarged portion of FIG. 30A in a range of from 7.0 to 9.0 ppm.

Figure 31A:
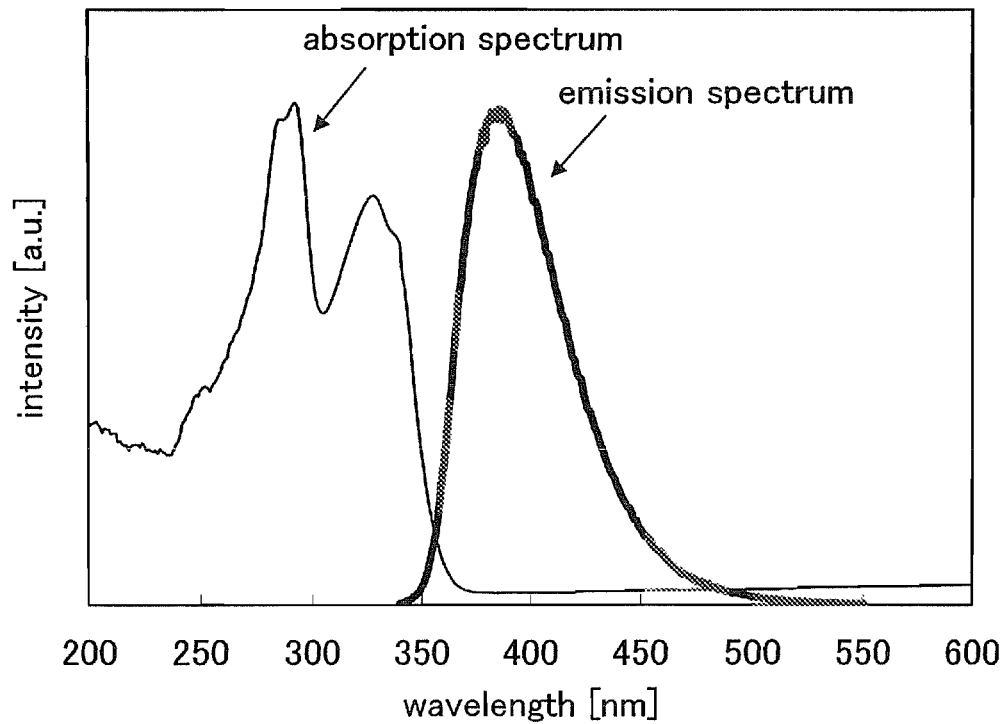
FIGS. 31A and 31B are graphs each showing the absorption spectrum and the emission spectrum of 9-{4-[4-(4-pyridyl)-5-(2-pyridyl)-4H-1,2,4-triazol-3-yl]phenyl}-9H-carbazole (abbreviation: CPy2Tz1)
Figure 31B:
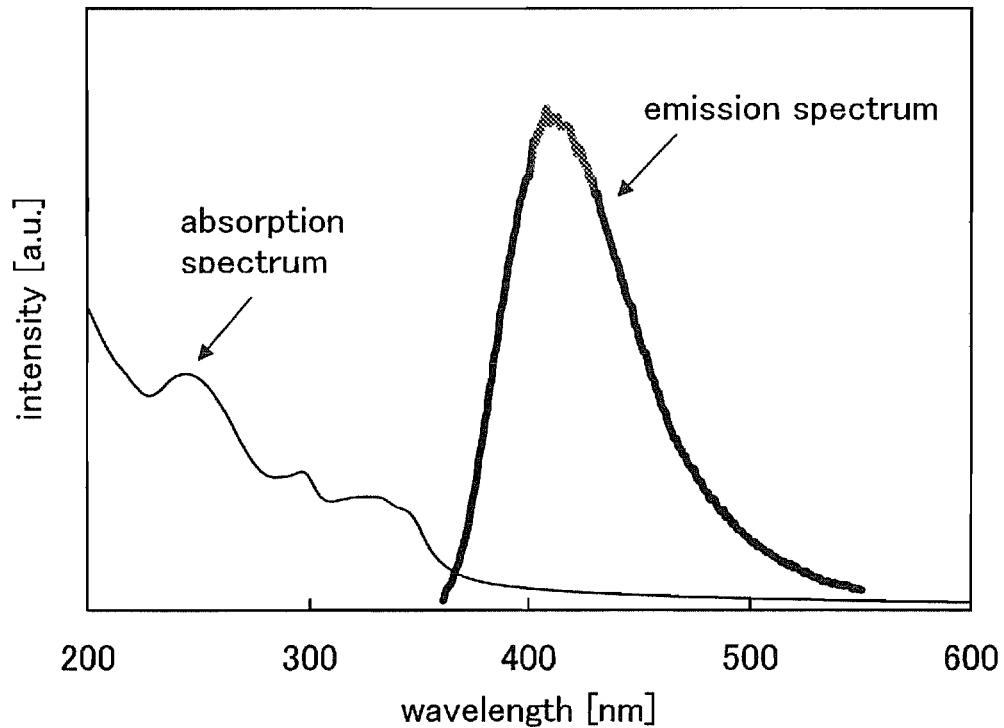

Further, the absorption spectrum and the emission spectrum of a toluene solution of CPy2Tz1 are shown in FIG. 31A. The absorption spectrum and the emission spectrum of a thin film of CPy2Tz1 are shown in FIG. 31B. Measurements were performed with an ultraviolet-visible light spectrophotometer (V-550, manufactured by JASCO Corporation). The solution was put into a quartz cell as one sample and Cpy2Tz1 was evaporated over a quartz substrate to form a thin film as another sample, and the absorption spectra of the solution and the thin film, from each of which the absorption spectrum of quartz was subtracted, are shown in FIGS. 31A and 31B. In FIGS. 31A and 31B, the horizontal axis represents wavelength (nm), and the vertical axis represents intensity (arbitrary unit). In the case of the toluene solution of CPy2Tz1, the absorption was observed at around 325 nm. In addition, in the case of the toluene solution, the maximum emission wavelength was 388 nm (excitation wavelength: 325 nm). Further, in the case of a thin film of CPy2Tz1, the absorption was observed at around 244 nm, around 296 nm, and around 329 nm. In addition, in the case of a thin film, the maximum emission wavelength was 411 nm (excitation wavelength: 346 nm).

Moreover, the result for the ionized potential of a thin film form of CPy2Tz1 measured by a photoelectron spectrometer (AC-2 photoelectron spectrometer manufactured by Riken Keiki, Co., Ltd.) in the atmosphere was 5.62 eV. As a result, it was understood that the HOMO level was −5.62 eV. The absorption edge was obtained by tauc plot assuming direct transition with the absorption spectrum data of a thin film of CPy2Tz1. When the absorption edge was estimated as an optical energy gap, the energy gap was 3.43 eV. A LUMO level of −2.19 eV was obtained from the obtained values of the energy gap value and HOMO level.

Thus, it was understood that CPy2Tz1 is a substance having high singlet excitation energy (a band gap).

Embodiment 7

This embodiment will describe a synthesis method of 9-{4-[5-phenyl-4-(4-pyridyl)-4H-1,2,4-triazol-3-yl]phenyl}-9H-carbazole (abbreviation: CPyTz2) which is represented by the structural formula (142).

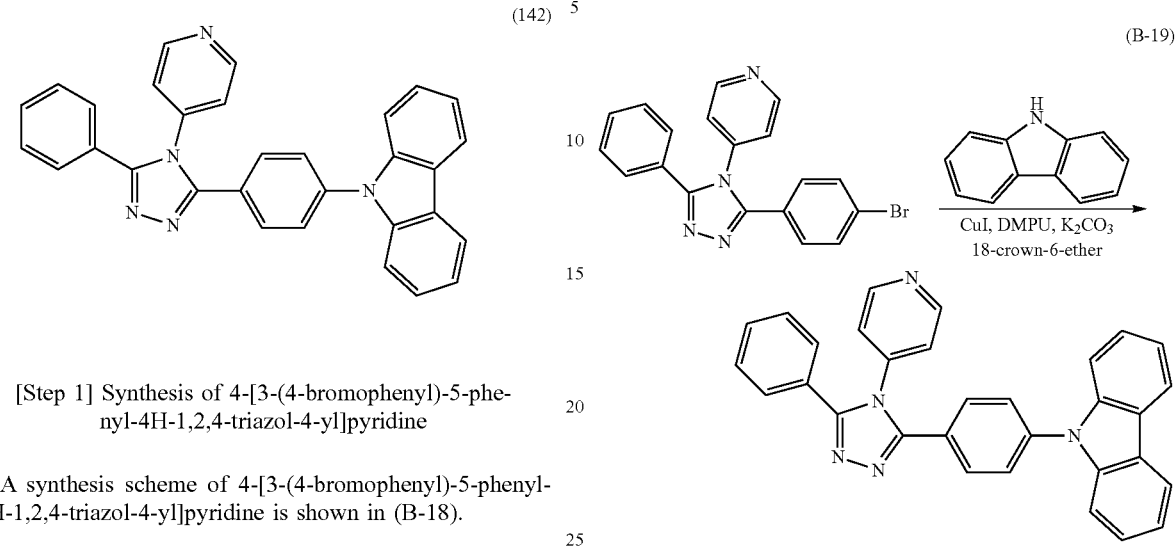

[Step 1] Synthesis of 4-[3-(4-bromophenyl)-5-phenyl-4H-1,2,4-triazol-4-yl]pyridine A synthesis scheme of 4-[3-(4-bromophenyl)-5-phenyl-4H-1,2,4-triazol-4-yl]pyridine is shown in (B-18).

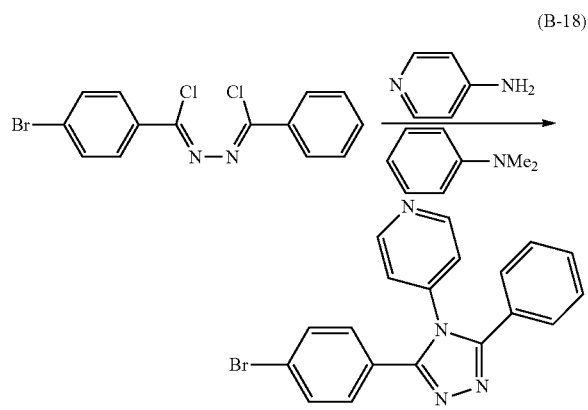

5.0 g (14 mmol) of 1-[(4-bromophenyl)chloromethylidene]-2-[chloro(phenyl)methylidene]hydrazone and 1.6 g (17 mmol) of 4-aminopyridine were put into a 50 mL three-neck flask. The mixture was added with 20 mL of N,N-dimethylaniline and stirred at 135° C. for 5 hours, and the contents of the flask were reacted together. After the reaction, toluene was added to the reactive mixture. The suspension was washed with 1 N diluted hydrochloric acid, a saturated sodium carbonate solution, and saturated saline, in the order given. An organic layer and an aqueous layer were separated, and the organic layer was dried with magnesium sulfate. After the drying, suction filtration was performed on the mixture to remove the magnesium sulfate, and thus a filtrate was obtained. Suction filtration was performed with sellite (Wako Pure Chemical Industries. Ltd., catalog number: 531-16855) on the obtained filtrate, and thus a filtrate was obtained. The obtained filtrate was condensed to obtain a solid. The obtained solid was recrystallized with a mixed solvent of chloroform and methanol, so that 1.1 g of a powdery light-brown solid, which was the object of the synthesis, was obtained at a yield of 73%.

[Step 2] Synthesis of CPyTz2

A synthesis scheme of CPyTz2 is shown in (B-19).

1.2 g (3.2 mmol) of 4-[3-(4-bromophenyl)-5-phenyl-4H-1,2,4-triazol-4-yl]pyridine obtained in Step 1, 0.70 g (4.2 mmol) of carbazole, 1.0 g (7.2 mmol) of potassium carbonate, 0.10 g (0.52 mmol) of copper iodide, and 0.10 g (0.37 mmol) of 18-crown-6-ether were put into a 50 mL three-neck flask, and nitrogen substitution was performed on the contents of the flask. The mixture was added with 1.0 mL of 1,3-dimethyl-3,4,5,6-tetrahydro-2(1H)-pyrimidinone (abbreviation: DMPU) and stirred at 180° C. for 5 hours, and the contents of the flask were reacted together. After the reaction, toluene was added to the reactive mixture, and the suspension was washed with 1 N diluted hydrochloric acid, a saturated sodium carbonate solution, and saturated saline, in the order given. An organic layer was dried with magnesium sulfate. After the drying, suction filtration was performed on the mixture to remove the magnesium sulfate, and thus a filtrate was obtained. Suction filtration was performed with sellite (Wako Pure Chemical Industries. Ltd., catalog number: 531-16855) on the obtained filtrate, and thus a filtrate was obtained. The obtained filtrate was condensed to obtain a solid. Purification by silica gel column chromatography was performed on the obtained solid. For the column chromatography, first toluene and then a mixed solvent of toluene and ethyl acetate (toluene:ethyl acetate=4:1) was used as a developing solvent. The obtained fraction was condensed to obtain a solid. The obtained solid was recrystallized with a mixed solvent of chloroform and hexane, so that 0.62 g of a powdery white solid, which was the object of the synthesis, was obtained at a yield of 43%. It was confirmed by a nuclear magnetic resonance (NMR) that the compound was 9-{4-[5-phenyl-4-(4-pyridyl)-4H-1,2,4-triazol-3-yl]phenyl}-9H-carbazole (abbreviation: CPyTz2).

Sublimation purification of 0.62 g of the obtained white solid was performed by a train sublimation method. The sublimiation purification was performed at a reduced pressure of 7.0 Pa, with the argon flow rage of 3 mL/min, at 270° C. for 15 hours. 0.40 g of the white solid was obtained at a yield of 65%.

Figure 32A:
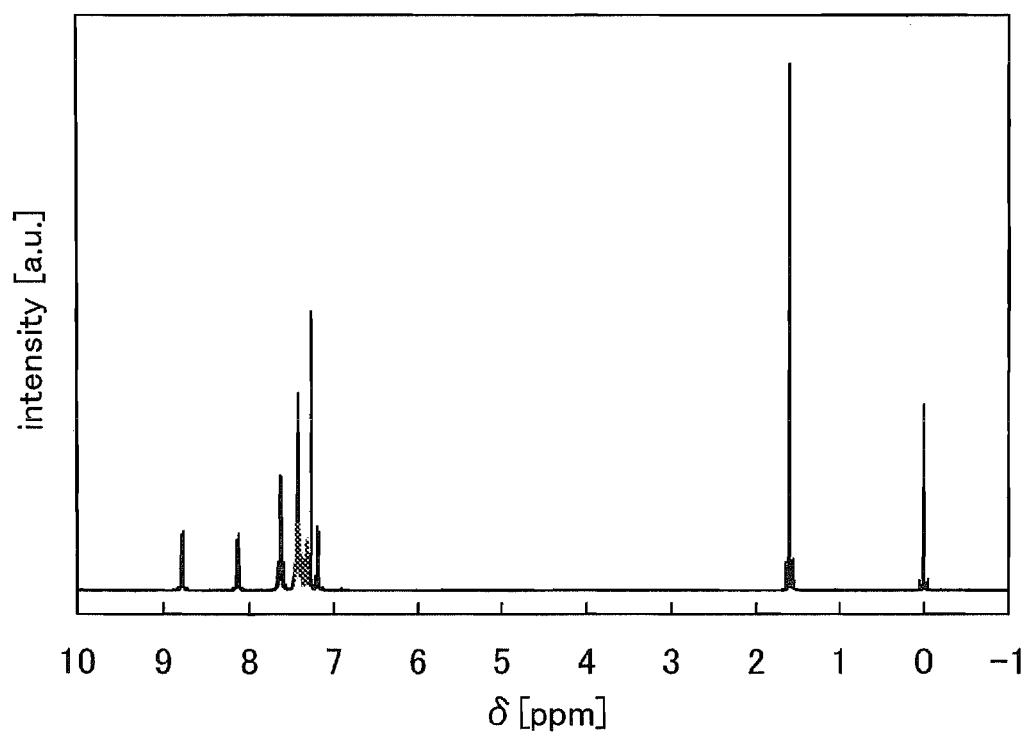
FIGS. 32A and 32B are graphs each showing $^1$H NMR of 9-{4-[5-phenyl-4-(4-pyridyl)-4H-1,2,4-triazol-3-yl]phenyl}-9H-carbazole (abbreviation: CPyTz2)
Figure 32B:
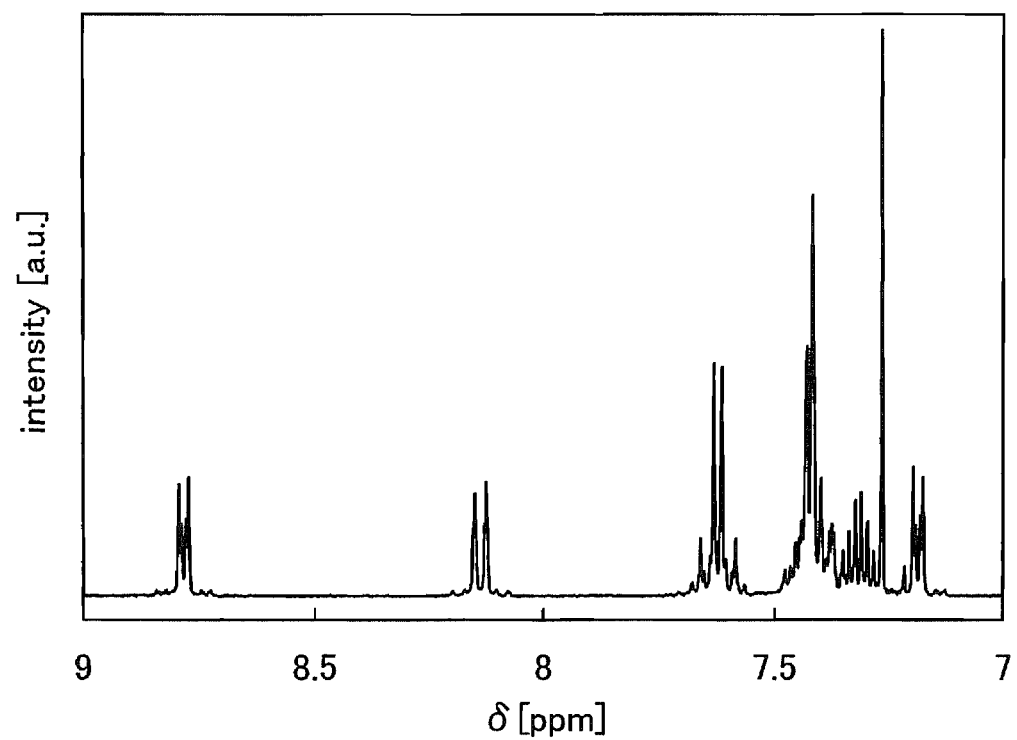

The $^1$H NMR data of CPyTz2 is given as follows. $^1$H NMR (CDCl$_3$, 300 MHz): δ=7.18 (dd, J=4.4, 2.0 Hz, 2H), 7.28-7.53 (m, 11H), 7.60 (d, J=8.8 Hz, 2H), 7.64 (d, J=8.8 Hz, 2H), 8.14 (d, J=6.8 Hz, 2H), 8.78 (dd, J=4.4, 2.0 Hz, 2H). In addition, charts of $^1$H NMR are shown in FIGS. 32A and 32B. Note that FIG. 32B is a chart showing an enlarged portion of FIG. 32A in a range of from 7.0 to 9.0 ppm.

Figure 33A:
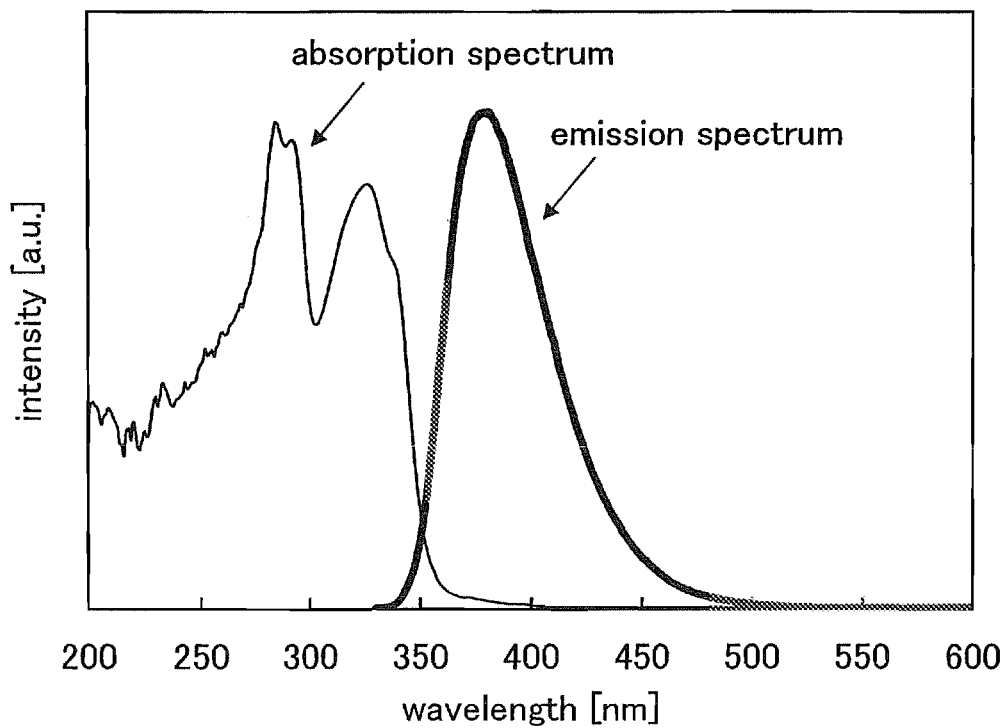
FIGS. 33A and 33B are graphs each showing the absorption spectrum and the emission spectrum of 9-{4-[5-phenyl-4-(4-pyridyl)-4H-1,2,4-triazol-3-yl]phenyl}-9H-carbazole (abbreviation: CPyTz2)
Figure 33B:
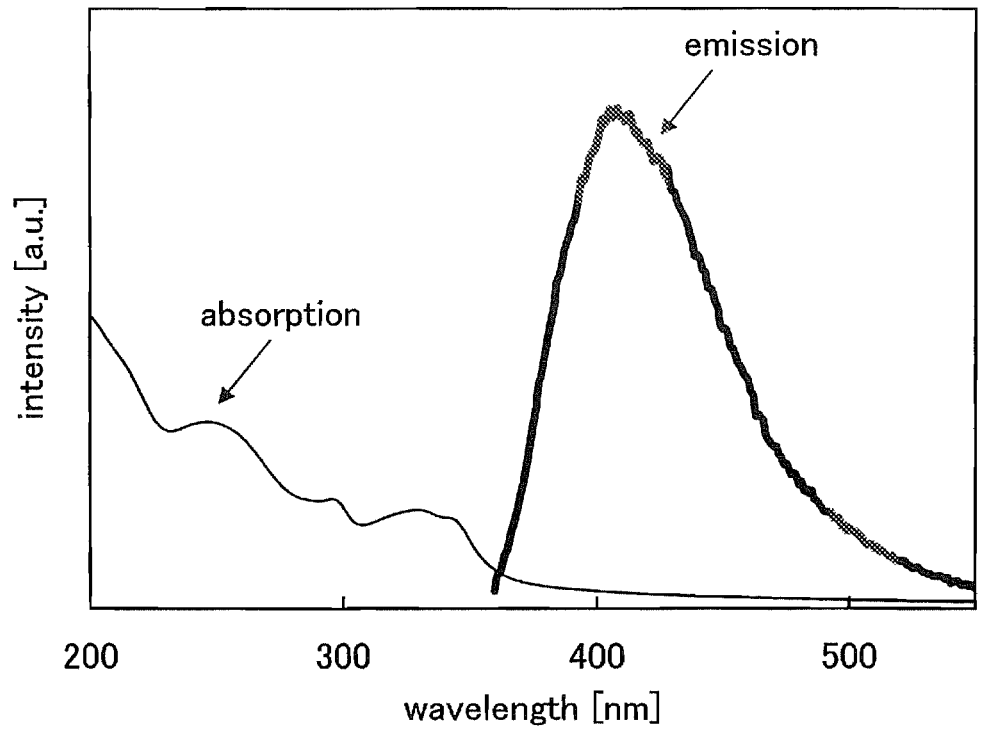

Further, the absorption spectrum and the emission spectrum of a toluene solution of CPyTz2 are shown in FIG. 33A. The absorption spectrum and the emission spectrum of a thin film of CPyTz2 are shown in FIG. 33B. Measurements were performed with an ultraviolet-visible light spectrophotometer (V-550, manufactured by JASCO Corporation). The solution was put into a quartz cell as one sample and CPyTz2 was evaporated over a quartz substrate to form a thin film as another sample, and the absorption spectra of the solution and the thin film, from each of which the absorption spectrum of quartz was subtracted, are shown in FIGS. 33A and 33B. In FIGS. 33A and 33B, the horizontal axis represents wavelength (nm), and the vertical axis represents intensity (arbitrary unit). In the case of the toluene solution of CPyTz2, the absorption was observed at around 325 nm. In addition, in the case of the toluene solution, the maximum emission wavelength was 382 nm (excitation wavelength: 325 nm). Further; in the case of a thin film of CPyTz2, the absorption was observed at around 246 nm, around 296 nm, and around 330 nm. In addition, in the case of a thin film, the maximum emission wavelength was 408 nm (excitation wavelength: 345 nm).

Moreover, the result for the ionized potential of a thin film form of CPyTz2 measured by a photoelectron spectrometer (AC-2 photoelectron spectrometer manufactured by Riken Keiki, Co., Ltd.) in the atmosphere was 5.72 eV. As a result, it was understood that the HOMO level was −5.72 eV. The absorption edge was obtained by tauc plot assuming direct transition with the absorption spectrum data of a thin film of CPyTz2. When the absorption edge was estimated as an optical energy gap, the energy gap was 3.46 eV. A LUMO level of −2.26 eV was obtained from the obtained values of the energy gap value and HOMO level.

Thus, it was understood that CPyTz2 is a substance having high singlet excitation energy (a band gap).

Embodiment 8

This embodiment will describe a synthesis method of 9-{4-[5-phenyl-4-(8-quinolyl)-4H-1,2,4-triazol-3-yl]phenyl}-9H-carbazole (abbreviation: CQTZ1) which is represented by the structural formula (146).

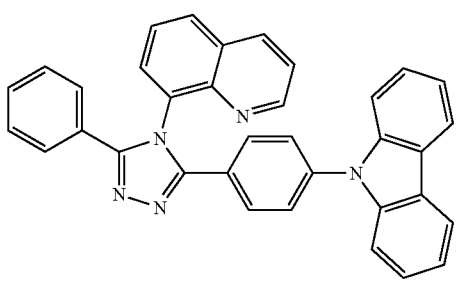
(146)

[Step 1] Synthesis of 8-[3-(4-bromophenyl)-5-phenyl-4H-1,2,4-triazol-4-yl]quinoline A synthesis scheme of 8-[3-(4-bromophenyl)-5-phenyl-4H-1,2,4-triazol-4-yl]quinoline is shown in (B-20).

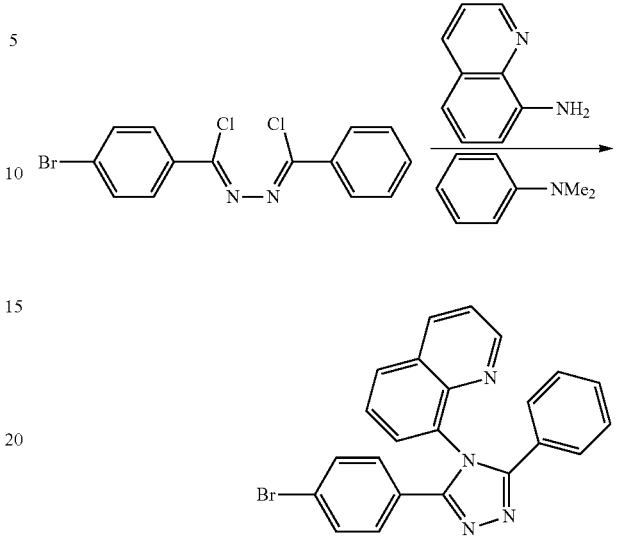
(B-20)

3.0 g (8.4 mmol) of 1-[(4-bromophenyl)chloromethylidene]-2-[chloro(phenyl)methylidene]hydrazone and 1.5 g (10 mmol) of 8-aminoquinoline were put into a 50 mL three-neck flask. The mixture was added with 15 mL of N,N-dimethylaniline and stirred at 135° C. for 5 hours, and the contents of the flask were reacted together. After the reaction, toluene was added to the reactive mixture, and the mixture was stirred for 1 hour. The solution was washed with 1 N diluted hydrochloric acid, a saturated sodium hydrogen carbonate solution, and saturated saline, in the order given. An organic layer and an aqueous layer were separated, and the organic layer was dried with magnesium sulfate. After the drying, suction filtration was performed on the mixture to remove the magnesium sulfate, and thus a filtrate was obtained. Suction filtration was performed with sellite (Wako Pure Chemical Industries. Ltd., catalog number: 531-16855) on the obtained filtrate, and thus a filtrate was obtained. The obtained filtrate was condensed to obtain a solid. The obtained solid was washed with methanol, so that 2.0 g of a powdery light-brown solid, which was the object of the synthesis, was obtained at a yield of 55%.

[Step 2] Synthesis of CQTZ1

A synthesis scheme of CQTZ1 is shown in (B-21).

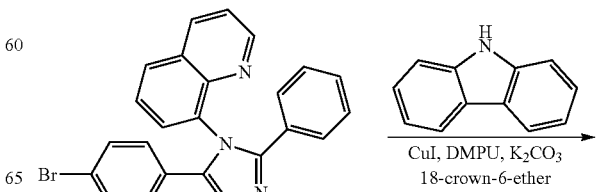
(B-21)

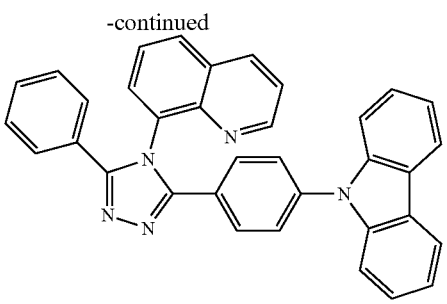

1.7 g (4.0 mmol) of 8-[3-(4-bromophenyl)-5-phenyl-4H-1,2,4-triazol-4-yl]quinoline obtained in Step 1, 1.0 g (6.0 mmol) of carbazole, 2.0 g (13 mmol) of potassium carbonate, 0.20 g (1.1 mmol) of copper iodide, and 0.20 g (0.73 mmol) of 18-crown-6-ether were put into a 50 mL three-neck flask, and nitrogen substitution was performed on the contents of the flask. The mixture was added with 1.5 mL of 1,3-dimethyl-3,4,5,6-tetrahydro-2(1H)-pyrimidinone (abbreviation: DMPU) and stirred at 180° C. for 5 hours, and the contents of the flask were reacted together. After the reaction, the reactive mixture was returned to a room temperature and then dichloromethane was added thereto. The suspension was washed with 1 N diluted hydrochloric acid, a saturated sodium carbonate solution, and saturated saline, in the order given. An organic layer was dried with magnesium sulfate. After the drying, suction filtration was performed on the mixture to remove the magnesium sulfate, and thus a filtrate was obtained. Suction filtration was performed with sellite (Wako Pure Chemical Industries. Ltd., catalog number: 531-16855) on the obtained filtrate, and thus a filtrate was obtained. The obtained filtrate was condensed to obtain a solid. Purification by silica gel column chromatography was performed on the obtained solid. For the column chromatography, first toluene and then a mixed solvent of toluene and ethyl acetate (toluene:ethyl acetate=4:1) was used as a developing solvent. The obtained fraction was condensed to obtain a solid. The obtained solid was recrystallized with a mixed solvent of chloroform and hexane, so that 1.5 g of a powdery white solid, which was the object of the synthesis, was obtained at a yield of 73%. It was confirmed by a nuclear magnetic resonance (NMR) that the compound was 9-{4-[5-phenyl-4-(8-quinolyl)-4H-1,2,4-triazol-3-yl]phenyl}-9H-carbazole (abbreviation: CQTZ1).

Sublimation purification of 1.5 g of the obtained white solid was performed by a train sublimation method. The sublimiation purification was performed at a reduced pressure of 7.0 Pa, with the argon flow rate of 3 mL/min, at 270° C. for 15 hours. 1.1 g of the white solid was obtained at a yield of 73%.

Figure 34A:
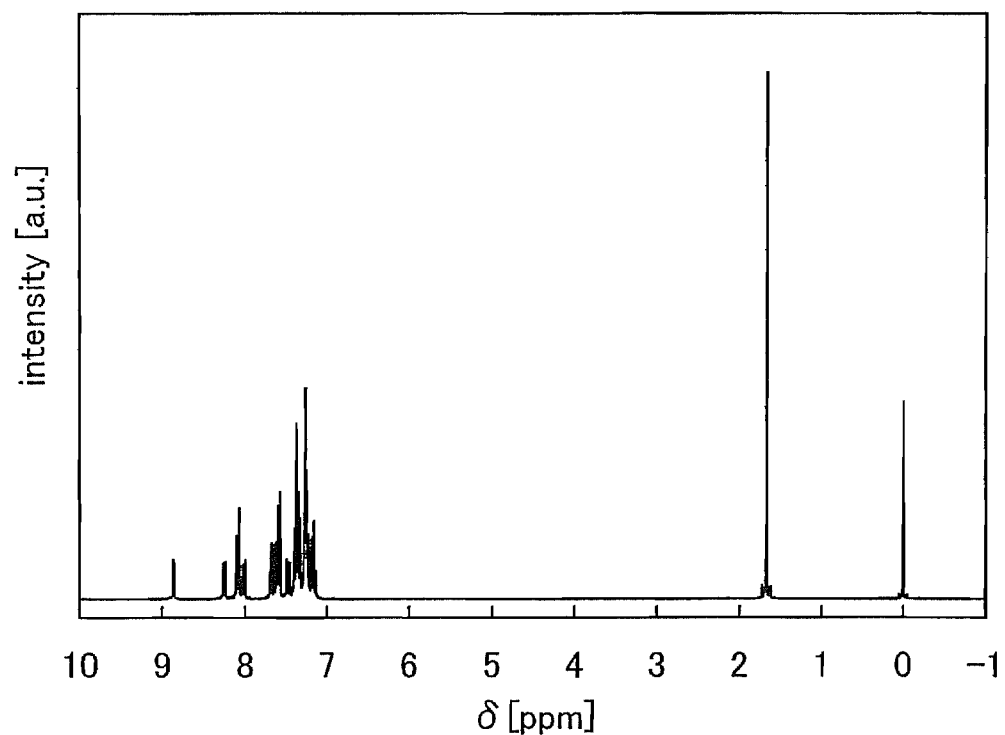
FIGS. 34A and 34B are graphs each showing $^1$H NMR of 9-{4-[5-phenyl-4-(8-quinolyl)-4H-1,2,4-triazol-3-yl]phenyl}-9H-carbazole (abbreviation: CQTZ1)
Figure 34B:
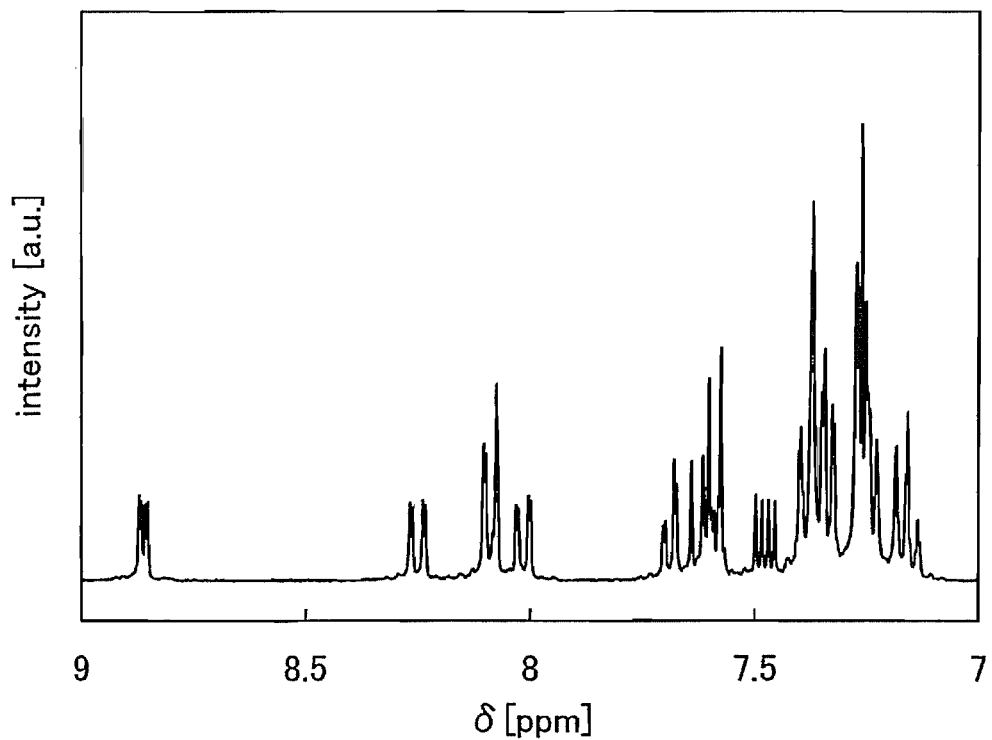

The $^1$H NMR data of CQTZ1 is given as follows. $^1$H NMR (CDCl$_3$, 300 MHz): δ=7.12-7.72 (m, 15H), 8.01 (dd, J=8.3, 1.5 Hz, 1H), 8.1 (d, J=7.8 Hz, 2H), 8.24 (dd, J=8.3, 2.0 Hz, 1H), 8.86 (dd, J=3.9, 1.5 Hz, 1H). In addition, charts of $^1$H NMR are shown in FIGS. 34A and 34B. Note that FIG. 34B is a chart showing an enlarged portion of FIG. 34A in a range of from 7.0 to 9.0 ppm.

Figure 35A:
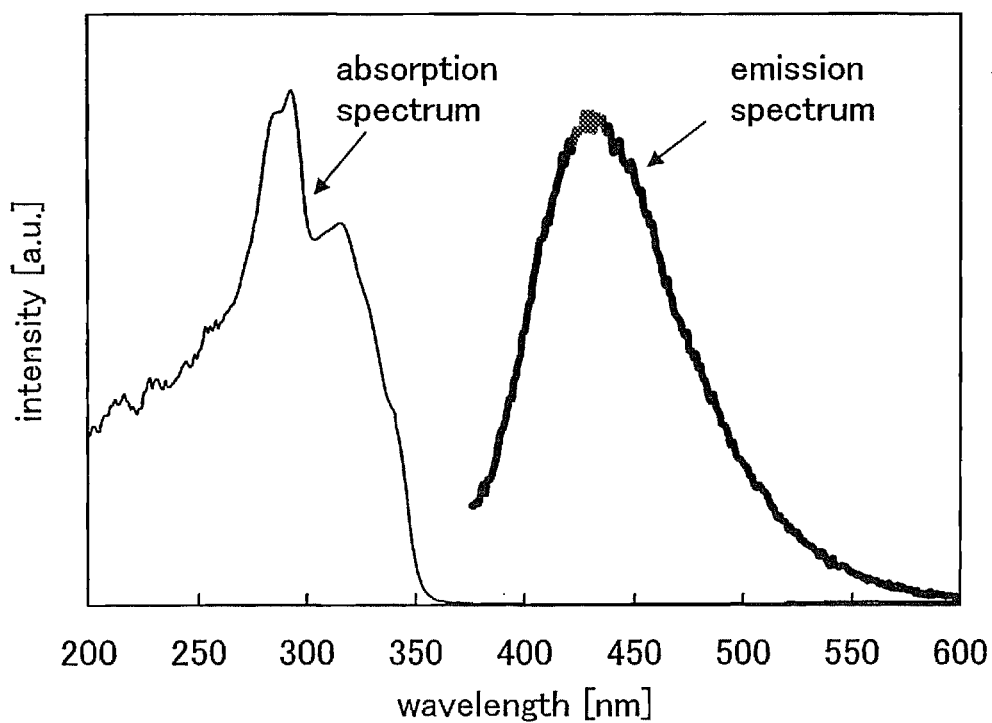
FIGS. 35A and 35B are graphs each showing the absorption spectrum and the emission spectrum of 9-{4-[5-phenyl-4-(8-quinolyl)-4H-1,2,4-triazol-3-yl]phenyl}-9H-carbazole (abbreviation: CQTZ1)
Figure 35B:
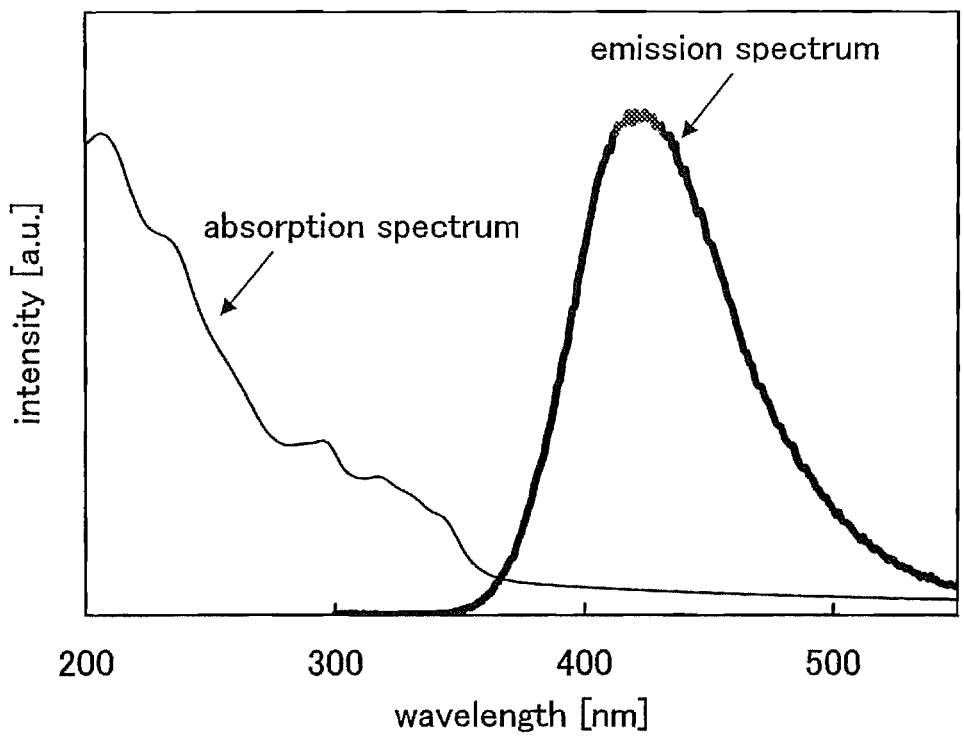

Further, the absorption spectrum and the emission spectrum of a toluene solution of CQTZ1 are shown in FIG. 35A. The absorption spectrum and the emission spectrum of a thin film of CATZ1 are shown in FIG. 35B. Measurements were performed with an ultraviolet-visible light spectrophotometer (V-550, manufactured by JASCO Corporation). The solution was put into a quartz cell as one sample and CQTZ1 was evaporated over a quartz substrate to form a thin film as another sample, and the absorption spectra of the solution and the thin film, from each of which the absorption spectrum of quartz was subtracted, are shown in FIGS. 35A and 35B. In FIGS. 35A and 35B, the horizontal axis represents wavelength (nm), and the vertical axis represents intensity (arbitrary unit). In the case of the toluene solution of CQTZ1, the absorption was observed at around 314 nm and around 341 nm. In addition, in the case of the toluene solution, the maximum emission wavelength was 434 nm (excitation wavelength: 341 nm). Further, in the case of a thin film of CQTZ1, the absorption was observed at around 206 nm, around 295 nm, and around 317 nm. In addition, in the case of a thin film, the maximum emission wavelength was 424 nm (excitation wavelength: 282 nm).

Moreover, the result for the ionized potential of a thin film form of CQTZ1 measured by a photoelectron spectrometer (AC-2 photoelectron spectrometer manufactured by Riken Keiki, Co., Ltd.) in the atmosphere was 5.73 eV. As a result, it was understood that the HOMO level was −5.73 eV. The absorption edge was obtained by tauc plot assuming direct transition with the absorption spectrum data of a thin film of CQTZ1. When the absorption edge was estimated as an optical energy gap, the energy gap was 3.46 eV. A LUMO level of −2.27 eV was obtained from the obtained values of the energy gap value and HOMO level.

Thus, it was understood that CQTZ1 is a substance having high singlet excitation energy (a band gap).

Embodiment 9

This embodiment will describe a synthesis method of 9-{4-[4-(sec-butylphenyl)-5-phenyl-4H-1,2,4-triazol-3-yl]phenyl}-9H-carbazole (abbreviation: sBCTAZ1) which is represented by the structural formula (169).

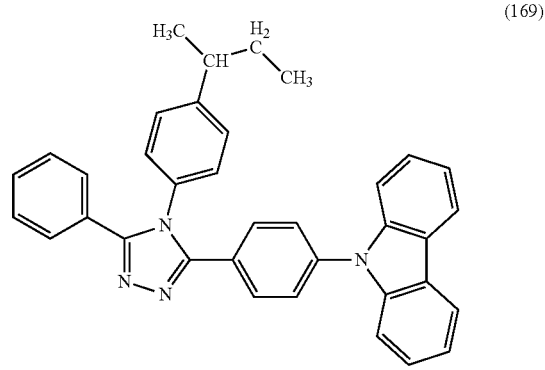 [SMILES: CCC(C)c1ccc(-n2c(-c3ccccc3)nnc2-c2ccc(-n3c4ccccc4c4ccccc43)cc2)cc1]

(169)

[Step 1] Synthesis of 3-(4-bromophenyl)-4-(4-sec-butylphenyl)-5-phenyl-4H-1,2,4-triazole A synthesis scheme of 3-(4-bromophenyl)-4-(4-sec-butylphenyl)-5-phenyl-4H-1,2,4-triazole is shown in (B-22).

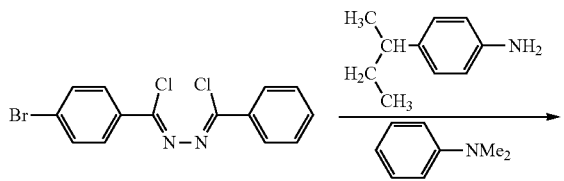

(B-22)

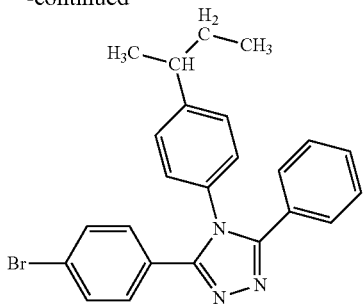

2.9 g (8.1 mmol) of 1-[(4-bromophenyl)chloromethylidene]-2-[chloro(phenyl)methylidene]hydrazone and 1.2 g (8.1 mmol) of 4-sec-butylaniline were put into a 50 mL three-neck flask. The mixture was added with 20 mL of N,N-dimethylaniline and stirred at 135° C. for 5 hours, and the contents of the flask were reacted together. After the reaction, toluene was added to the reactive mixture, and the mixture was stirred. The suspension was washed with 1 N diluted hydrochloric acid, a saturated sodium carbonate solution, and saturated saline, in the order given. An organic layer and an aqueous layer were separated, and the organic layer was dried with magnesium sulfate. After the drying, suction filtration was performed on the mixture to remove the magnesium sulfate, and thus a filtrate was obtained. Suction filtration was performed with sellite (Wako Pure Chemical Industries. Ltd., catalog number: 531-16855) on the obtained filtrate, and thus a filtrate was obtained. The obtained filtrate was condensed to obtain a solid. The obtained solid was washed with methanol, so that 1.3 g of a powdery white solid, which was the object of the synthesis, was obtained at a yield of 37%.

[Step 2] Synthesis of sBCTAZ1

A synthesis scheme of sBCTAZ1 is shown in (B-23).

(B-23)

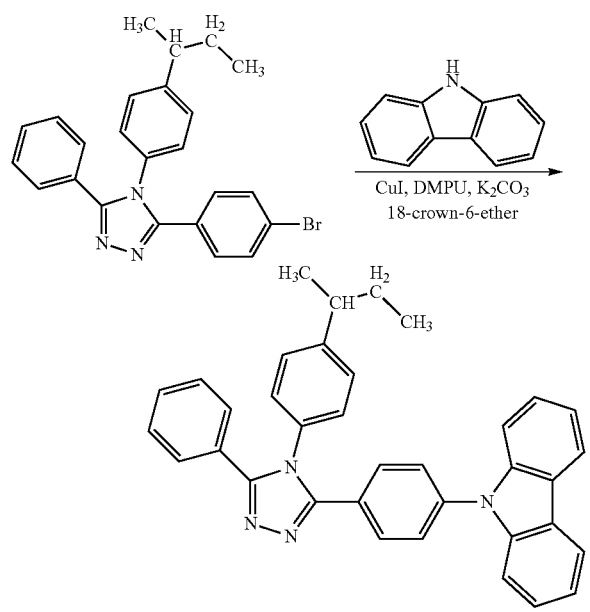

1.0 g (2.3 mmol) of 3-(4-bromophenyl)-4-(4-sec-butylphenyl)-5-phenyl-4H-1,2,4-triazole obtained in Step 1, 0.39 g (2.3 mmol) of carbazole, 2.0 g (13 mmol) of potassium carbonate, 0.20 g (1.1 mmol) of copper iodide, and 0.20 g (0.73 mmol) of 18-crown-6-ether were put into a 50 mL three-neck flask, and nitrogen substitution was performed on the contents of the flask. The mixture was added with 1.5 mL of 1,3-dimethyl-3,4,5,6-tetrahydro-2(1H)-pyrimidinone (abbreviation: DMPU) and stirred at 180° C. for 5 hours, and the contents of the flask were reacted together. After the reaction, the reactive mixture was cooled to a room temperature and then dichloromethane was added thereto. The suspension was washed with 1 N diluted hydrochloric acid, a saturated sodium carbonate solution, and saturated saline, in the order given. An organic layer was dried with magnesium sulfate. After the drying, suction filtration was performed on the mixture to remove the magnesium sulfate, and thus a filtrate was obtained. Suction filtration was performed with sellite (Wako Pure Chemical Industries. Ltd., catalog number: 531-16855) on the obtained filtrate, and thus a filtrate was obtained. The obtained filtrate was condensed to obtain a solid. Purification by silica gel column chromatography was performed on the obtained solid. For the column chromatography, first toluene and then a mixed solvent of toluene and ethyl acetate (toluene:ethyl acetate=4:1) was used as a developing solvent. The obtained fraction was condensed to obtain a solid. The obtained solid was recrystallized with a mixed solvent of chloroform and hexane, so that 0.90 g of a powdery white solid, which was the object of the synthesis, was obtained at a yield of 75%. It was confirmed by a nuclear magnetic resonance (NMR) that the compound was 9-{4-[4-(sec-butylphenyl)-5-phenyl-4H-1,2,4-triazol-3-yl]phenyl}-9H-carbazole (abbreviation: sBCTAZ1).

Sublimation purification of 0.90 g of the obtained white solid was performed by a train sublimation method. The sublimation purification was performed at a reduced pressure of 7.0 Pa, with the argon flow rate of 3 mL/min, at 250° C. for 15 hours. 0.70 g of the white solid was obtained at a yield of 78%.

Figure 36A:
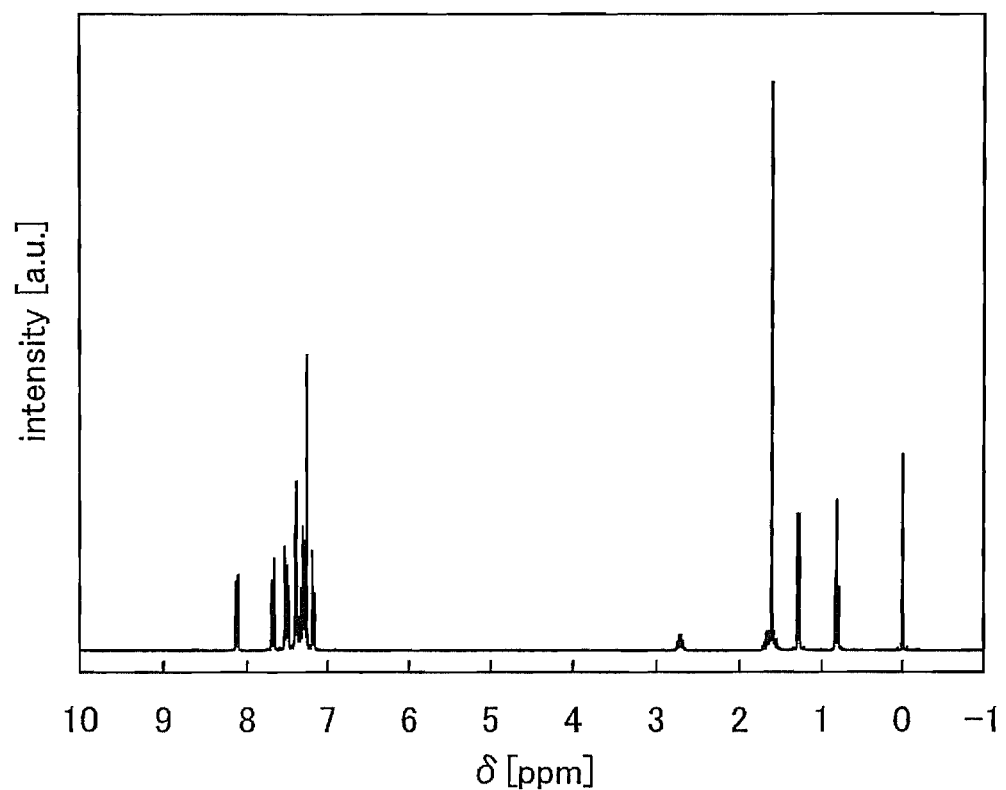
FIGS. 36A and 36B are graphs each showing $^1$H NMR of 9-{4-[4-(sec-butylphenyl)-5-phenyl-4H-1,2,4-triazol-3-yl]phenyl}-9H-carbazole (abbreviation: sBCTAZ1)
Figure 36B:
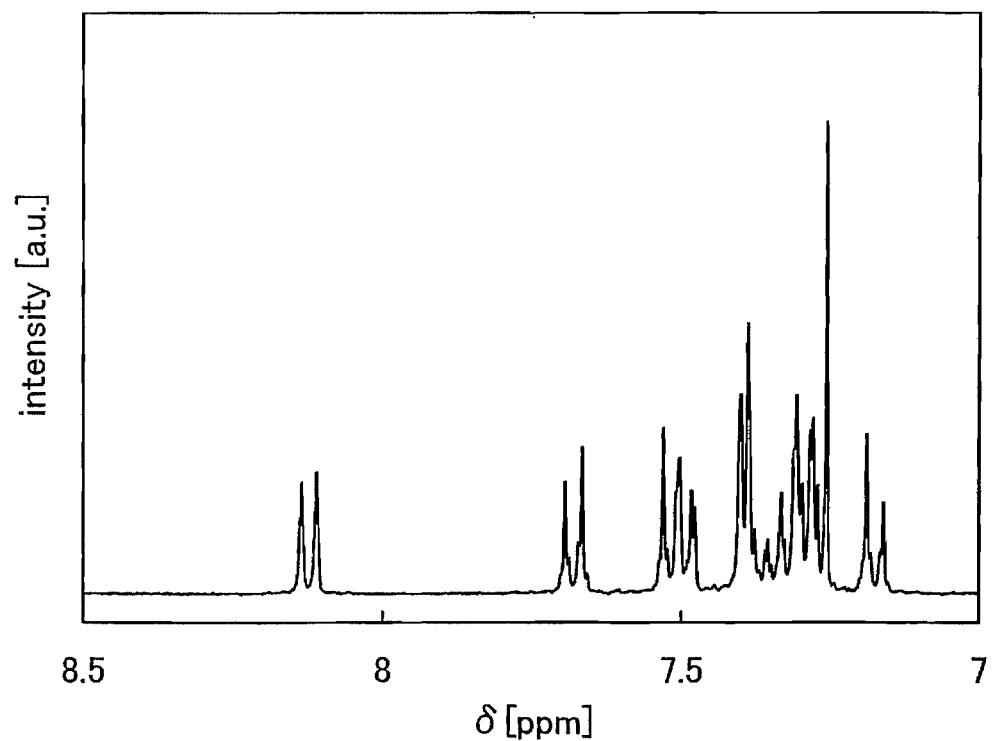

The $^1$H NMR data of sBCTAZ1 is given as follows. $^1$H NMR (CDCl$_3$, 300 MHz): δ=0.80 (t, J=7.3 Hz, 3H), 1.29 (d, J=7.3 Hz, 3H), 1.51-1.74 (m, 2H), 2.70 (q, J=6.8 Hz, 1H), 7.18 (d, J=8.3 Hz, 2H), 7.26-7.44 (m, 11H), 7.46-7.56 (m, 4H), 7.68 (d, J=8.3 Hz, 2H), 8.13 (d, J=7.3 Hz, 2H). In addition, charts of $^1$H NMR are shown in FIGS. 36A and 36B. Note that FIG. 36B is a chart showing an enlarged portion of FIG. 36A in a range of from 7.0 to 8.5 ppm.

Figure 37A:
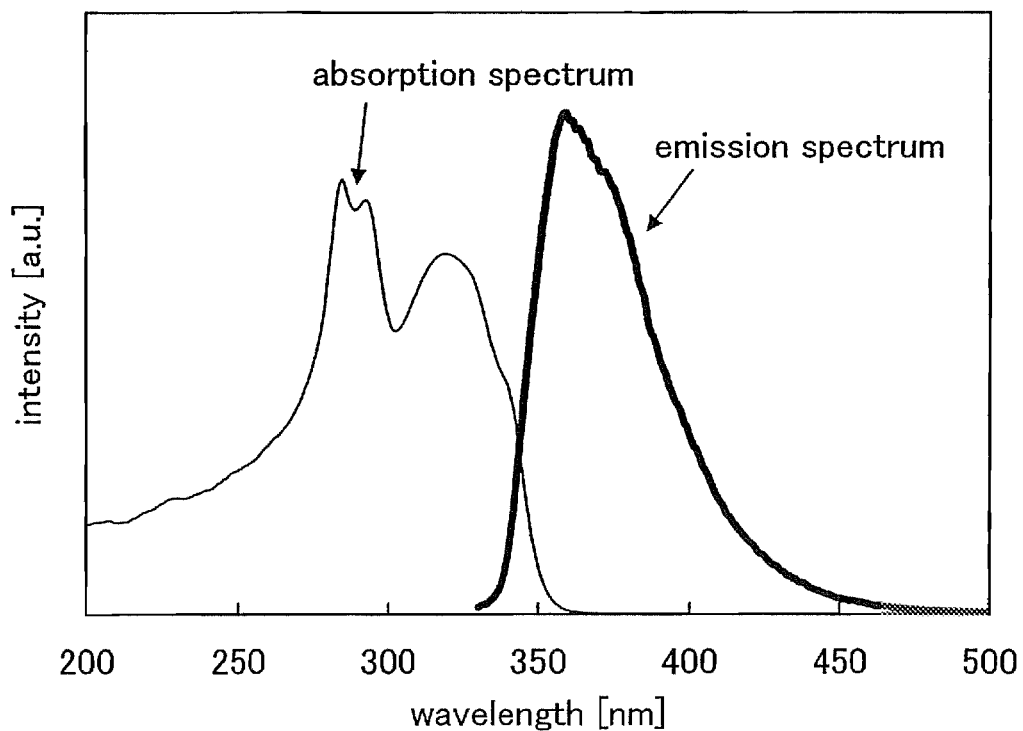
FIGS. 37A and 37B are graphs each showing the absorption spectrum and emission spectrum of 9-{4-[4-(sec-butylphenyl)-5-phenyl-4H-1,2,4-triazol-3-yl]phenyl}-9H-carbazole (abbreviation: sBCTAZ1)
Figure 37B:
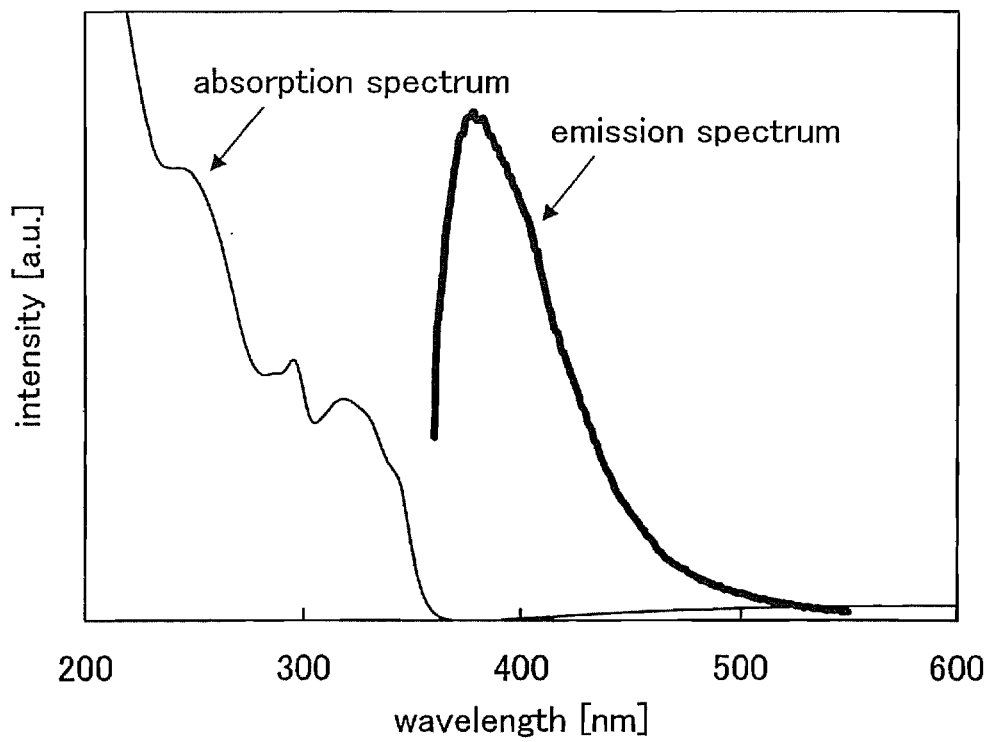

Further, the absorption spectrum and the emission spectrum of a toluene solution of sBCTAZ1 are shown in FIG. 37A. The absorption spectrum and the emission spectrum of a thin film of sBCTAZ1 are shown in FIG. 37B. Measurements were performed with an ultraviolet-visible light spectrophotometer (V-550, manufactured by JASCO Corporation). The solution was put into a quartz cell as one sample and sBCTAZ1 was evaporated over a quartz substrate to form a thin film as another sample, and the absorption spectra of the solution and the thin film, from each of which the absorption spectrum of quartz was subtracted, are shown in FIGS. 37A and 37B. In FIGS. 37A and 37B, the horizontal axis represents wavelength (nm), and the vertical axis represents intensity (arbitrary unit). In the case of the toluene solution of sBCTAZ1, the absorption was observed at around 319 nm. In addition, in the case of the toluene solution, the maximum emission wavelength was 359 nm (excitation wavelength: 319 nm). Further, in the case of a thin film of sBCTAZ1, the absorption was observed at around 319 nm. In addition, in the case of a thin film, the maximum emission wavelength was 377 nm (excitation wavelength: 347 nm).

Moreover, the result for the ionized potential of a thin film form of sBCTAZ1 measured by a photoelectron spectrometer (AC-2 photoelectron spectrometer manufactured by Riken Keiki, Co., Ltd.) in the atmosphere was 5.58 eV. As a result, it was understood that the HOMO level was −5.58 eV. The absorption edge was obtained by tauc plot assuming direct transition with the absorption spectrum data of a thin film of sBCTAZ1. When the absorption edge was estimated as an optical energy gap, the energy gap was 3.53 eV. A LUMO level of −2.05 eV was obtained from the obtained values of the energy gap value and HOMO level.

Thus, it was understood that sBCTAZ1 is a substance having high singlet excitation energy (a band gap).

Embodiment 10

This embodiment will describe a light-emitting element of the present invention with reference to FIG. 14. Hereinafter, a method of manufacturing a light-emitting element of this embodiment is described.
(Light-Emitting Element 4)

First, indium tin oxide containing silicon oxide (ITSO) was deposited over a glass substrate 2100 by a sputtering method to form a first electrode 2101. Note that the thickness of the first electrode 2101 was 110 nm and the electrode area was 2 mm×2 mm.

Next, the substrate having the first electrode 2101 was fixed to a substrate holder provided in a vacuum evaporation apparatus in such a way that a surface of the substrate 2100 over which the first electrode 2101 was formed faced downward, and then the pressure was reduced to approximately $10^{-4}$ Pa. Next, 4,4'-bis[N-(1-naphthyl)-N-phenylamino]biphenyl (abbreviation: NPB) and molybdenum (VI) oxide were co-evaporated on the first electrode 2101, whereby a layer 2111 containing a composite material of an organic compound and an inorganic compound was formed. The thickness of the layer 2111 was set to be 40 nm and the weight ratio of NPB to molybdenum(VI) oxide was controlled to 4:1 (=NPB:molybdenum oxide). Note that the co-evaporation method is an evaporation method in which evaporation is performed from a plurality of evaporation sources at the same time in one treatment chamber.

Next, a hole-transporting layer 2112 was formed by depositing 4,4',4''-tris(carbazol-9-yl)triphenylamine (abbreviation: TCTA) to have a thickness of 10 nm on the layer 2111 containing a composite material by an evaporation method using resistance heating.

Furthermore, 9-{4-[4-phenyl-5-(2-pyridyl)-4H-1,2,4-triazole-3-yl]phenyl}-9H-carbazole (abbreviation: CPyTz1) which is represented by the structural formula (125) and bis[2-(4',6'-difluorophenyl)pyridinato-N,C$^{2'}$]iridium(III)picolinate (abbreviation: FIrpic) were co-evaporated, whereby a 30 nm thick light-emitting layer 2113 was formed on the hole-transportinging layer 2112. Here, the weight ratio of CPyTz1 to FIrpic was controlled to 1:0.05 (=CPyTz1:FIrpic).

Then, an electron-transporting layer 2114 was formed by depositing 3-(4-biphenylyl)-4-phenyl-5-(4-tert-butylphenyl)-1,2,4-triazole (abbreviation: TAZ01) to have a thickness of 10 nm on the light-emitting layer 2113 by an evaporation method using resistance heating.

Further, bathophenanthroline (abbreviation: BPhen) and lithium were co-evaporated on the electron-transporting layer 2114, whereby an electron-injecting layer 2115 was formed with a thickness of 20 nm. Here, the weight ratio of BPhen to lithium was controlled to 1:0.01 (=BPhen:lithium).

Finally, a second electrode 2102 was formed by depositing aluminum to have a thickness of 200 nm on the electron-injecting layer 2115 by an evaporation method using resistance heating. Thus, a light-emitting element 4 was formed.

The light-emitting element 4 thus obtained was sealed in a glove box under a nitrogen atmosphere without being exposed to atmospheric air. Then, the operating characteristics of the light-emitting element were measured. Note that the measurement was performed at a room temperature (atmosphere kept at 25° C.).

Figure 38:
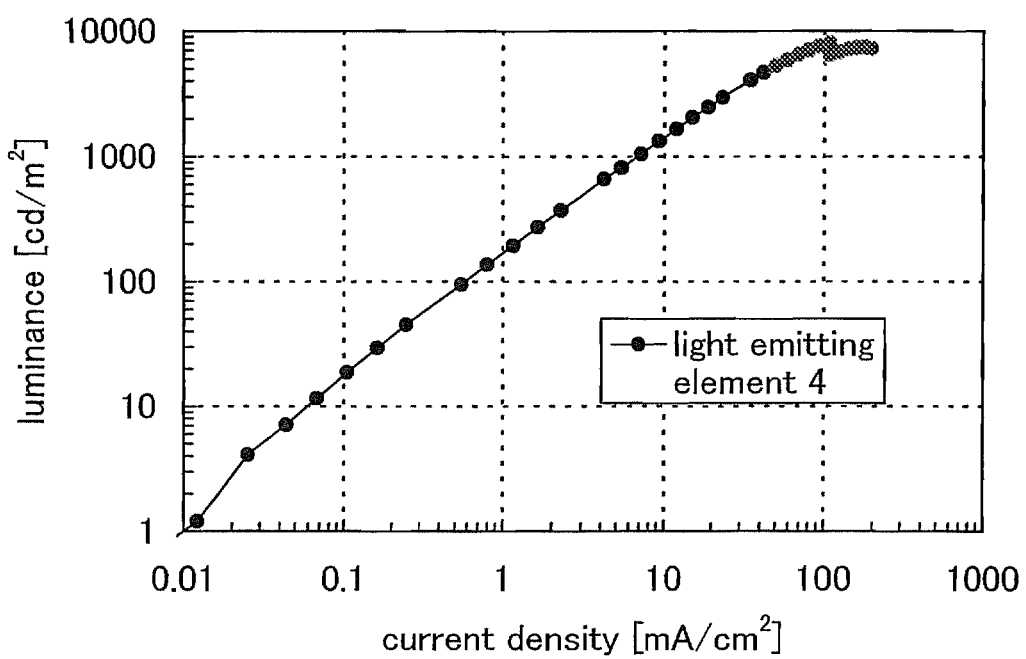
FIG. 38 is a graph showing the current density-luminance characteristics of a light-emitting element manufactured in Embodiment 10.
Figure 39:
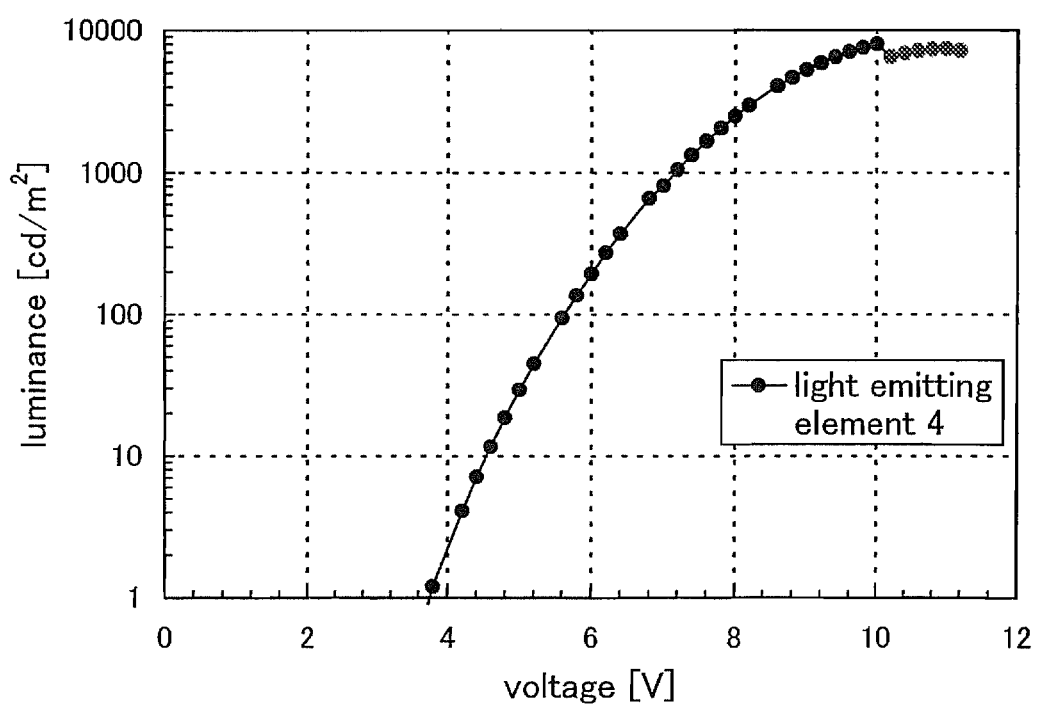
FIG. 39 is a graph showing the voltage-luminance characteristics of a light-emitting element manufactured in Embodiment 10.
Figure 40:
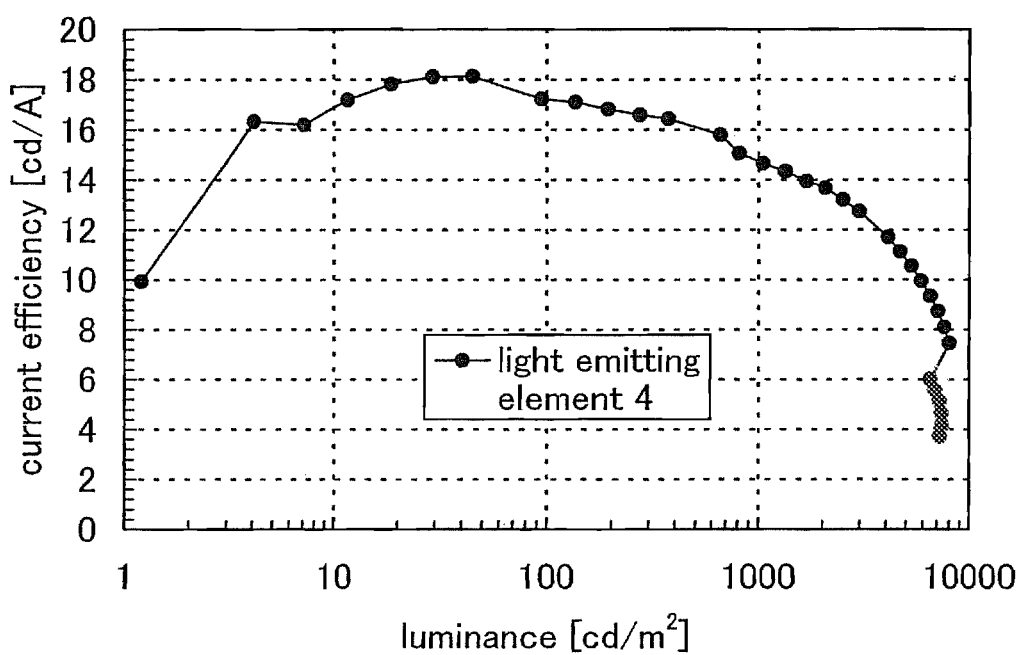
FIG. 40 is a graph showing the luminance-current efficiency characteristics of a light-emitting element manufactured in Embodiment 10.
Figure 41:
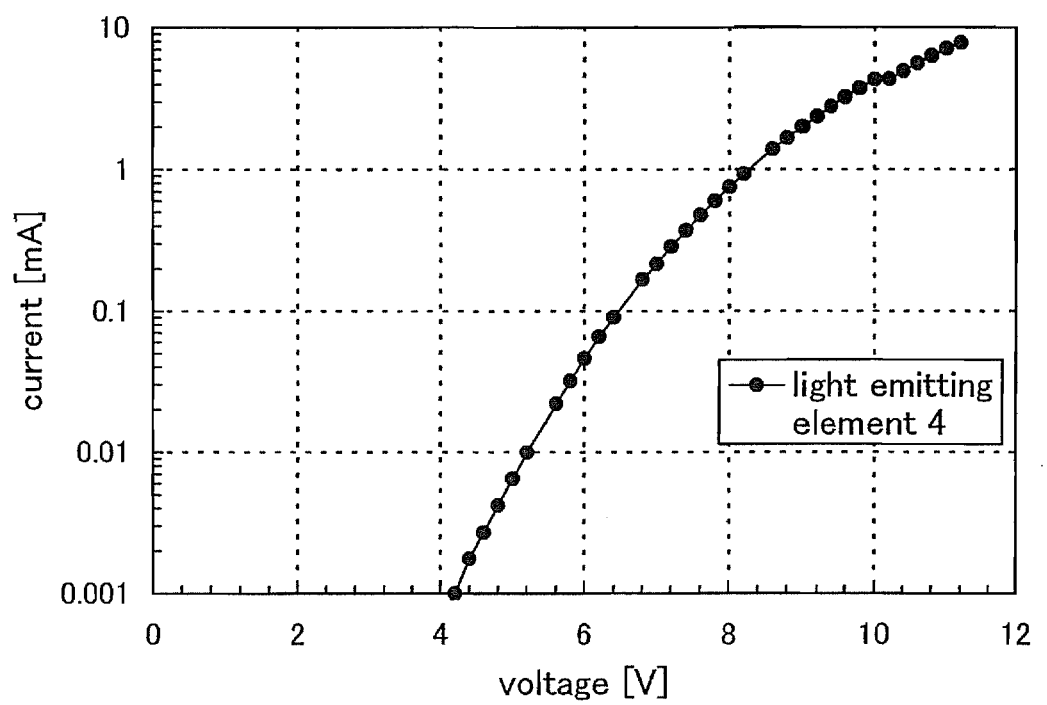
FIG. 41 is a graph showing the voltage-current characteristics of a light-emitting element manufactured in Embodiment 10.
Figure 42:
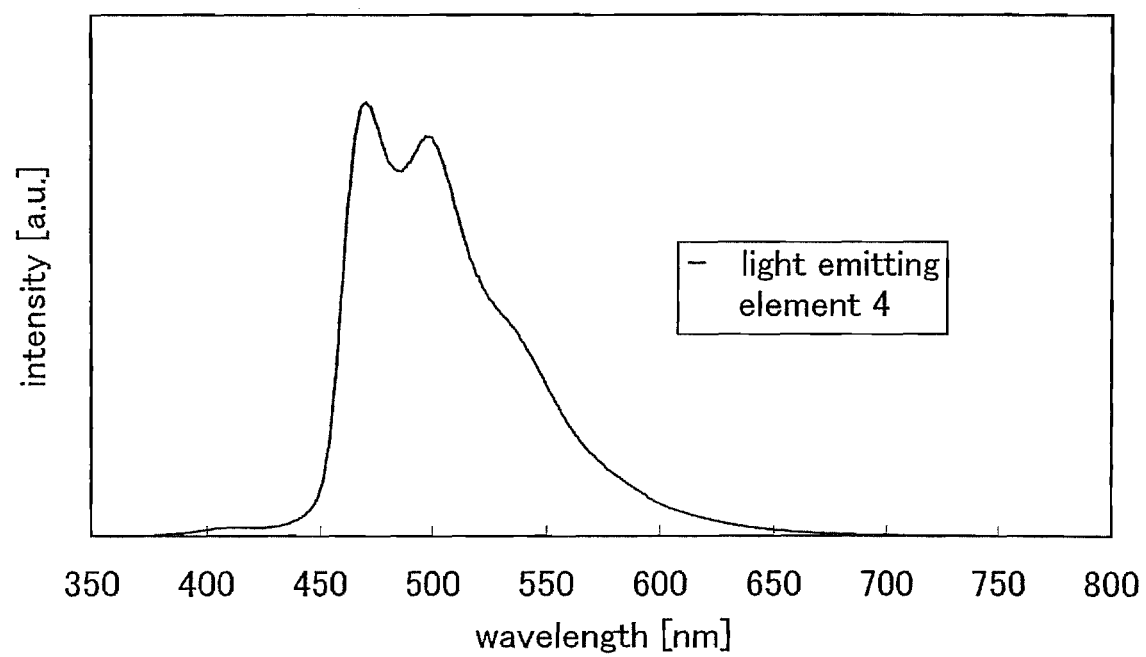
FIG. 42 is a graph showing the emission spectrum of a light-emitting element manufactured in Embodiment 10.

FIG. 38 shows the current density-luminance characteristics of the light-emitting element 4. FIG. 39 shows the voltage-luminance characteristics of the light-emitting element 4. FIG. 40 shows the luminance-current efficiency characteristics of the light-emitting element 4. FIG. 41 shows the voltage-current characteristics of the light-emitting element 4. FIG. 42 shows the emission spectrum of the light-emitting element 4 at a current supply of 1 mA.

The emission color of the light-emitting element 4 was located at the CIE chromaticity coordinates of (x=0.19, y=0.36) at a luminance of 1050 cd/m$^2$, and was blue. In addition, the current efficiency and external quantum efficiency of the light-emitting element 4 at a luminance of 1050 cd/m$^2$ were 15 cd/A and 6.7%, respectively; thus, the light-emitting element 4 had high efficiency. Further, when the luminance was 1050 cd/m$^2$, voltage, current density, and power efficiency of the light-emitting element 4 were 7.2 V, 7.1 mA/cm$^2$, and 6.4 lm/W, respectively, and the light-emitting element 4 had high power efficiency.

From the result shown in FIG. 42, it can be seen that light emission of the light-emitting element 4 is light emission derived from FIrpic. Thus, it can be seen that, using a tiazole deribvative having high triplet excitation energy, the light-emitting element of this embodiment can efficiently emit FIrpic which shows blue light emission of a short wavelength.

By application of the present invention, FIrpic which is a phosphorescent compound which shows light emission of a short wavelength can be emitted efficiently. That is, high luminous efficiency can be achieved even in a case where a phosphorescent compound which shows light emission of a short wavelength is used. Further, a light-emitting element, the power consumption of which is reduced, can be achieved.

Embodiment 11

This embodiment will describe a light-emitting element of the present invention with reference to FIG. 14. Hereinafter, a method of manufacturing a light-emitting element of this embodiment is described.
(Light-Emitting Element 5)

First, indium tin oxide containing silicon oxide (ITSO) was deposited over a glass substrate 2100 by a sputtering method to form a first electrode 2101. Note that the thickness of the first electrode 2101 was 110 nm and the electrode area was 2 mm×2 mm.

Next, the substrate having the first electrode 2101 was fixed to a substrate holder provided in a vacuum evaporation apparatus in such a way that a surface of the substrate 2100 over which the first electrode 2101 was formed faced downward, and then the pressure was reduced to approximately $10^{-4}$ Pa. Next, 4,4'-bis[N-(1-naphthyl)-N-phenylamino]biphenyl (abbreviation: NPB) and molybdenum (VI) oxide were co-evaporated on the first electrode 2101, whereby a layer 2111 containing a composite material of an organic compound and an inorganic compound was formed. The thickness of the layer 2111 was set to be 40 nm and the weight ratio of NPB to molybdenum(VI) oxide was controlled to 4:1 (=NPB:molybdenum oxide). Note that the co-evaporation method is an evaporation method in which evaporation is performed from a plurality of evaporation sources at the same time in one treatment chamber.

Next, a hole-transporting layer 2112 was formed by depositing 4,4',4"-tris(carbazol-9-yl)triphenylamine (abbreviation: TCTA) to have a thickness of 20 nm on the layer 2111 containing a composite material by an evaporation method using resistance heating.

Furthermore, 9-{4-[4-(4-pyridyl)-5-(2-pyridyl)-4H-1,2,4-triazol-3-yl]phenyl}-9H-carbazole (abbreviation: CPy2Tz1) which is represented by the structural formula (137) and bis[2-(4',6'-difluorophenyl)pyridinato-N,$C^{2'}$]iridium(III)picolinate (abbreviation: FIrpic) were co-evaporated, whereby a 30 nm thick light-emitting layer 2113 was formed on the hole-transportinging layer 2112. Here, the weight ratio of CPy2Tz1 to FIrpic was controlled to 1:0.05 (=CPy2Tz1:FIrpic).

Then, an electron-transporting layer 2114 which is a layer in contact with the light-emitting layer 2113 was formed by depositing CPy2Tz1 to have a thickness of 10 nm on the light-emitting layer 2113 by an evaporation method using resistance heating.

Further, bathophenanthroline (abbreviation: BPhen) and lithium were co-evaporated on the electron-transporting layer 2114, whereby an electron-injecting layer 2115 was formed with a thickness of 20 nm. Here, the weight ratio of BPhen to lithium was controlled to 1:0.01 (=BPhen:lithium).

Finally, a second electrode 2102 was formed by depositing aluminum to have a thickness of 200 nm on the electron-injecting layer 2115 by an evaporation method using resistance heating. Thus, a light-emitting element 5 was formed.

The light-emitting element 5 thus obtained was sealed in a glove box under a nitrogen atmosphere without being exposed to atmospheric air. Then, the operating characteristics of the light-emitting element were measured. Note that the measurement was performed at a room temperature (atmosphere kept at 25° C.).

Figure 43:
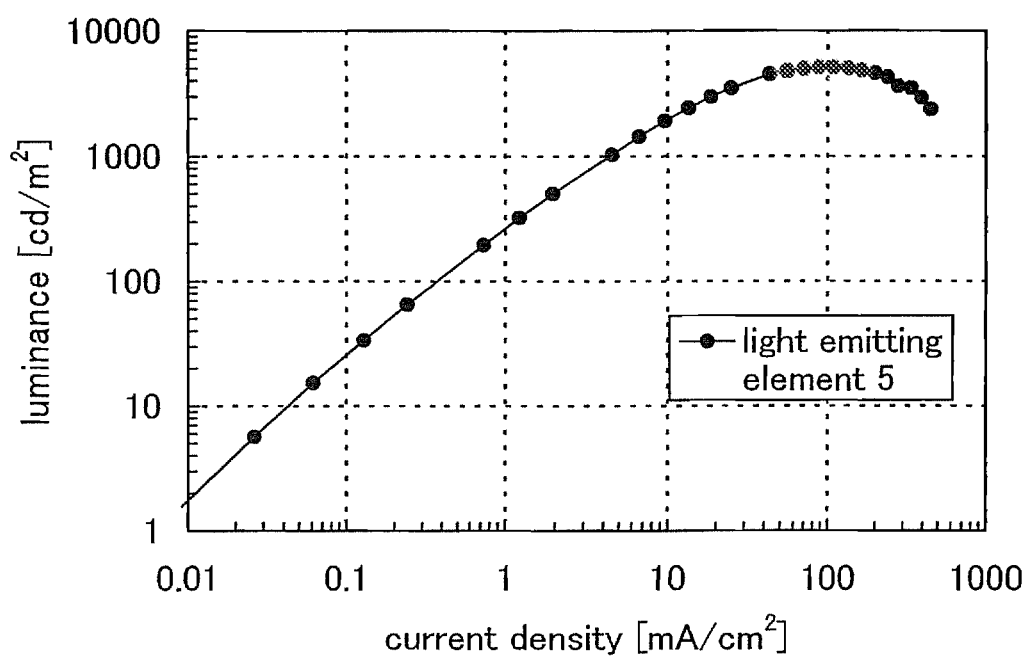
FIG. 43 is a graph showing the current density-luminance characteristics of a light-emitting element manufactured in Embodiment 11.
Figure 44:
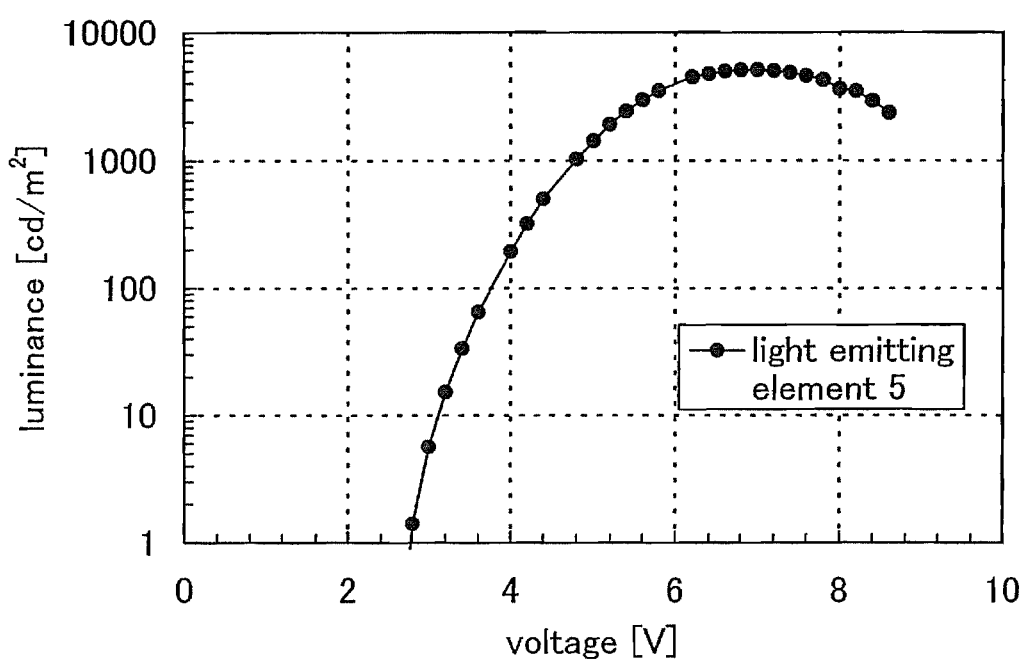
FIG. 44 is a graph showing the voltage-luminance characteristics of a light-emitting element manufactured in Embodiment 11.
Figure 45:
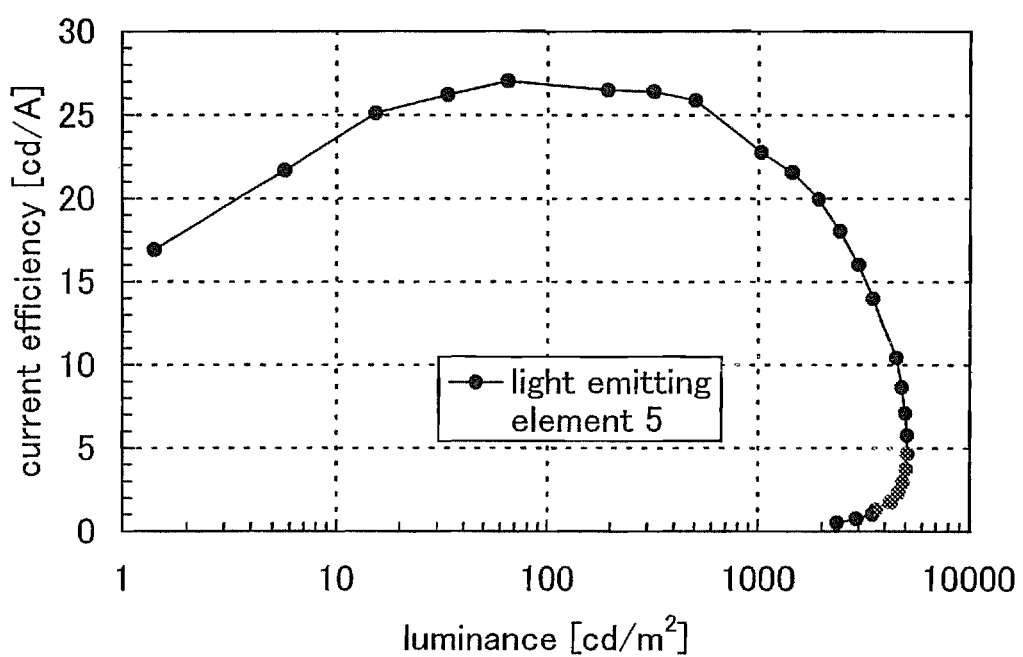
FIG. 45 is a graph showing the luminance-current efficiency characteristics of a light-emitting element manufactured in Embodiment 11.
Figure 46:
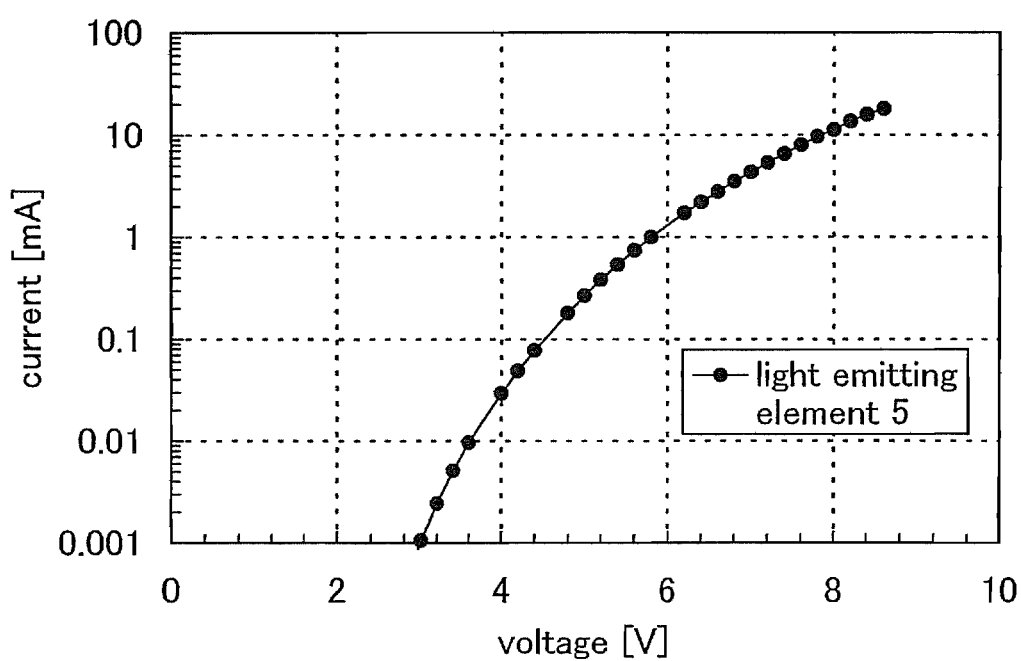
FIG. 46 is a graph showing the voltage-current characteristics of a light-emitting element manufactured in Embodiment 11.
Figure 47:
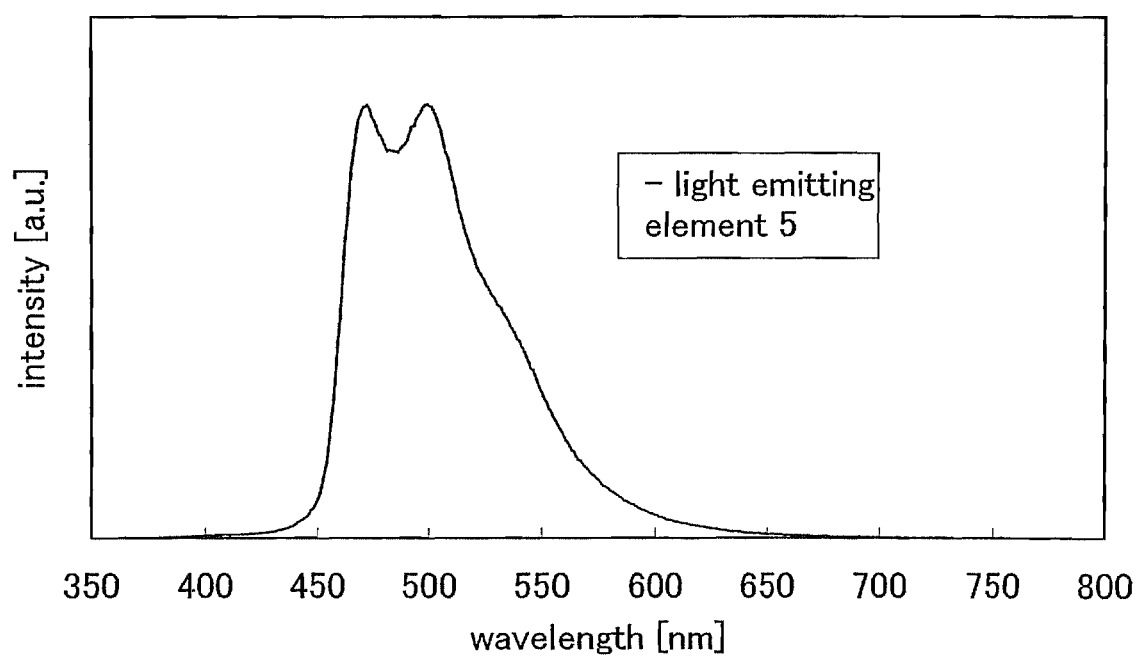
FIG. 47 is a graph showing the emission spectrum of a light-emitting element manufactured in Embodiment 11.

FIG. 43 shows the current density-luminance characteristics of the light-emitting element 5. FIG. 44 shows the voltage-luminance characteristics of the light-emitting element 5. FIG. 45 shows the luminance-current efficiency characteristics of the light-emitting element 5. FIG. 46 shows the voltage-current characteristics of the light-emitting element 5. FIG. 47 shows the emission spectrum of the light-emitting element 5 at a current supply of 1 mA.

The emission color of the light-emitting element 5 was located at the CIE chromaticity coordinates of (x=0.18, y=0.38) at a luminance of 1030 cd/m², and was blue. In addition, the current efficiency and external quantum efficiency of the light-emitting element 5 at a luminance of 1030 cd/m² were 23 cd/A and 10%, respectively; thus, the light-emitting element 5 had extremely high efficiency as a light-emitting element which shows blue light emission. Further, when the luminance was 1030 cd/m², voltage, current density, and power efficiency of the light-emitting element 5 were 4.8 V, 4.5 mA/cm², and 15 lm/W, respectively, and the light-emitting element 5 had extremely high power efficiency.

From the result shown in FIG. 47, it can be seen that light emission of the light-emitting element 5 is light emission derived from FIrpic. Thus, it can be seen that, using a tiazole deribvative having high triplet excitation energy, the light-emitting element of this embodiment can efficiently emit FIrpic which shows blue light emission of a short wavelength.

In addition, in the light-emitting element of this embodiment, the triazole derivative of the present invention is used for the electron-transporting layer which is a layer in contact with the light-emitting layer. The triazole derivative of the present invention has high triplet excitation energy; therefore, energy transfer from the light-emitting layer does not easily occur in a case where the triazole derivative of the present invention is used for a layer in contact with the light-emitting layer. Accordingly, high luminous efficiency can be achieved.

By application of the present invention, FIrpic which is a phosphorescent compound which shows light emission of a short wavelength can be emitted efficiently. That is, high luminous efficiency can be achieved even in a case where a phosphorescent compound which shows light emission of a short wavelength is used. Further, a light-emitting element, the power consumption of which is reduced, can be achieved. In particular, higher luminous efficiency can be obtained with the use of the triazole derivative of the present invention for a light-emitting layer and a layer in contact with the light-emitting layer.

Embodiment 12

This embodiment will describe a light-emitting element of the present invention with reference to FIG. 14. Hereinafter, a method of manufacturing a light-emitting element of this embodiment is described.

(Light-Emitting Element 6)

First, indium tin oxide containing silicon oxide (ITSO) was deposited over a glass substrate 2100 by a sputtering method to form a first electrode 2101. Note that the thickness of the first electrode 2101 was 110 nm and the electrode area was 2 mm×2 mm.

Next, the substrate having the first electrode 2101 was fixed to a substrate holder provided in a vacuum evaporation apparatus in such a way that a surface of the substrate 2100 over which the first electrode 2101 was formed faced downward, and then the pressure was reduced to approximately $10^{-4}$ Pa. Next, 4,4'-bis[N-(1-naphthyl)-N-phenylamino]biphenyl (abbreviation: NPB) and molybdenum (VI) oxide were co-evaporated on the first electrode 2101, whereby a layer 2111 containing a composite material of an organic compound and an inorganic compound was formed. The thickness of the layer 2111 was set to be 40 nm and the weight ratio of NPB to molybdenum(VI) oxide was controlled to 4:1 (=NPB:molybdenum oxide). Note that the co-evaporation method is an evaporation method in which evaporation is performed from a plurality of evaporation sources at the same time in one treatment chamber.

Next, a hole-transporting layer 2112 was formed by depositing 4,4',4"-tris(carbazol-9-yl)triphenylamine (abbreviation: TCTA) to have a thickness of 10 nm on the layer 2111 containing a composite material by an evaporation method using resistance heating.

Furthermore, 9-{4-[4-phenyl-5-(2-pyridyl)-4H-1,2,4-triazole-3-yl]phenyl}-9H-carbazole (abbreviation: CPyTz1) which is represented by the structural formula (125) and bis(2-phenylpyridinato-N,$C^{2'}$)iridium(III)acetylacetonate (abbreviation: Ir(ppy)$_2$(acac)) were co-evaporated, whereby a 40 nm thick light-emitting layer 2113 was formed on the hole-transportinging layer 2112. Here, the weight ratio of CPyTz1 to Ir(ppy)$_2$(acac) was controlled to 1:0.05 (=CPyTz1:Ir(ppy)$_2$(acac)).

Then, an electron-transporting layer 2114 was formed by depositing bathophenanthroline (abbreviation: BPhen) to have a thickness of 10 nm on the light-emitting layer 2113 by an evaporation method using resistance heating.

Further, bathophenanthroline (abbreviation: BPhen) and lithium were co-evaporated on the electron-transporting layer 2114, whereby an electron-injecting layer 2115 was formed with a thickness of 20 nm. Here, the weight ratio of BPhen to lithium was controlled to 1:0.01 (=BPhen:lithium).

Finally, a second electrode 2102 was formed by depositing aluminum to have a thickness of 200 nm on the electron-injecting layer 2115 by an evaporation method using resistance heating. Thus, a light-emitting element 6 was formed.

(Light-Emitting Element 7)

Over the same substrate over which the light-emitting element 6 was formed, a light-emitting element 7 was formed in a manner similar to that of the light-emitting element 6 with the use of 9-{4-[5-phenyl-4-(8-quinolyl)-4H-1,2,4-triazol-3-yl]phenyl}-9H-carbazole (abbreviation: CQTZ1) which is represented by the structural formula (146) as an alternative to CPyTz1. That is, 9-{4-[5-phenyl-4-(8-quinolyl)-4H-1,2,4-triazol-3-yl]phenyl}-9H-carbazole (abbreviation: CQTZ1) which is represented by the structural formula (146) and bis(2-phenylpyridinato-N,C$^{2'}$)iridium(III)acetylacetonate (abbreviation: Ir(ppy)$_2$(acac)) were co-evaporated to form the 40 nm thick light-emitting layer 2113 on the hole-transporting layer 2112. Here, the weight ratio of CQTZ1 to Ir(ppy)$_2$(acac) was controlled to 1:0.05 (=CQTZ1:Ir(ppy)$_2$(acac)). Layers other than the light-emitting layer 2113 were formed in a manner similar to that of the light-emitting element 6.

(Light-Emitting Element 8)

Over the same substrate over which the light-emitting element 6 was formed, a light-emitting element 8 was formed in a manner similar to that of the light-emitting element 6 with the use of 9-{4-[4-(4-pyridyl)-5-(2-pyridyl)-4H-1,2,4-triazol-3-yl]phenyl}-9H-carbazole (abbreviation: CPy2Tz1) which is represented by the structural formula (137) as an alternative to CPyTz1. That is, 9-{4-[4-(4-pyridyl)-5-(2-pyridyl)-4H-1,2,4-triazol-3-yl]phenyl}-9H-carbazole (abbreviation: CPy2Tz1) which is represented by the structural formula (137) and bis(2-phenylpyridinato-N,C$^{2'}$)iridium(III)acetylacetonate (abbreviation: Ir(ppy)$_2$(acac)) were co-evaporated to form the 40 nm thick light-emitting layer 2113 on the hole-transporting layer 2112. Here, the weight ratio of CPy2Tz1 to Ir(ppy)$_2$(acac) was controlled to 1:0.05 (=CPy2Tz1:Ir(ppy)$_2$(acac)). Layers other than the light-emitting layer 2113 were formed in a manner similar to that of the light-emitting element 6.

(Light-Emitting Element 9)

Over the same substrate over which the light-emitting element 6 was formed, a light-emitting element 9 was formed in a manner similar to that of the light-emitting element 6 with the use of 9-[4-(3,5-diphenyl-4H-1,2,4-triazol-4-yl)phenyl]-9H-carbazole (abbreviation: CzTAZ2) which is represented by the structural formula (201) as an alternative to CPyTz1. That is, 9-[4-(3,5-diphenyl-4H-1,2,4-triazol-4-yl)phenyl]-9H-carbazole (abbreviation: CzTAZ2) which is represented by the structural formula (201) and bis(2-phenylpyridinato-N,C$^{2'}$)iridium(III)acetylacetonate (abbreviation: Ir(ppy)$_2$(acac)) were co-evaporated to form the 40 nm thick light-emitting layer 2113 on the hole-transporting layer 2112. Here, the weight ratio of CzTAZ2 to Ir(ppy)$_2$(acac) was controlled to 1:0.05 (=CzTAZ2:Ir(ppy)$_2$(acac)). Other than the light-emitting layer 2113 were formed in a manner similar to that of the light-emitting element 6.

The light-emitting elements 6 to 9 thus obtained were each sealed in a glove box under a nitrogen atmosphere without being exposed to atmospheric air. Then, the operating characteristics of each of the light-emitting elements were measured. Note that the measurement was performed at a room temperature (atmosphere kept at 25° C.).

Figure 48:
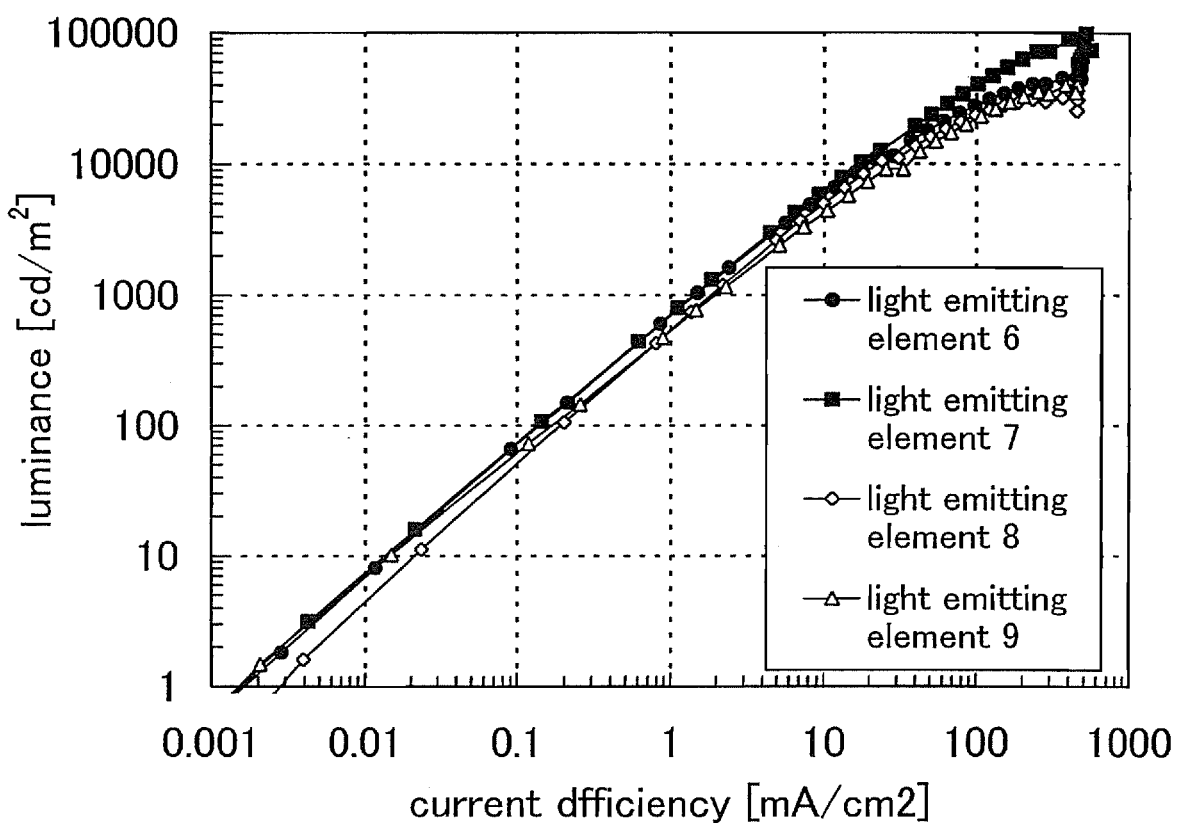
FIG. 48 is a graph showing the current density-luminance characteristics of a light-emitting element manufactured in Embodiment 12.
Figure 49:
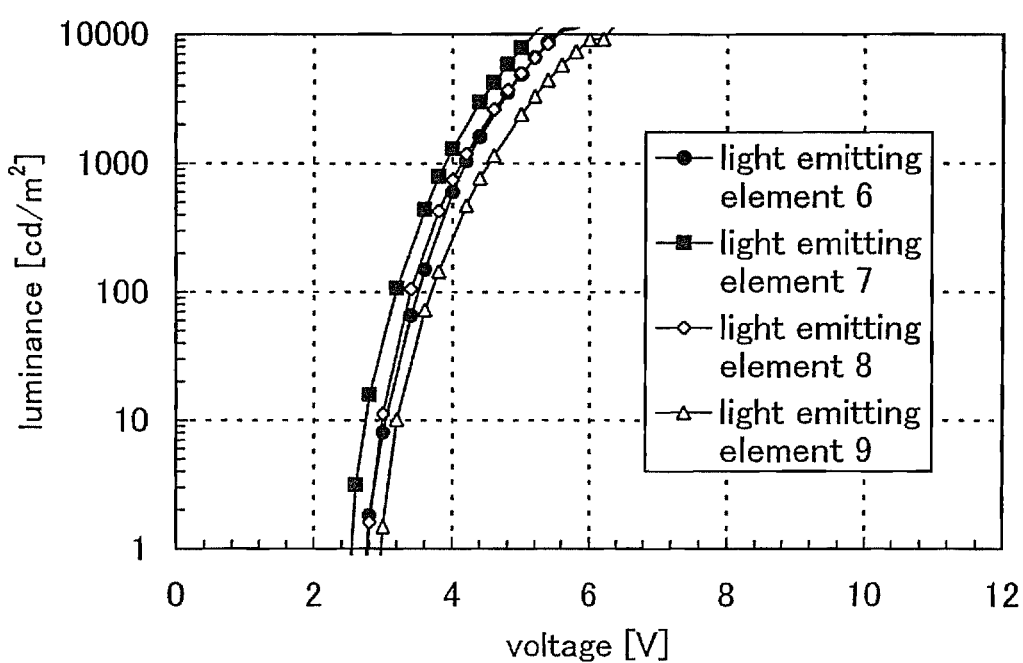
FIG. 49 is a graph showing the voltage-luminance characteristics of a light-emitting element manufactured in Embodiment 12.
Figure 50:
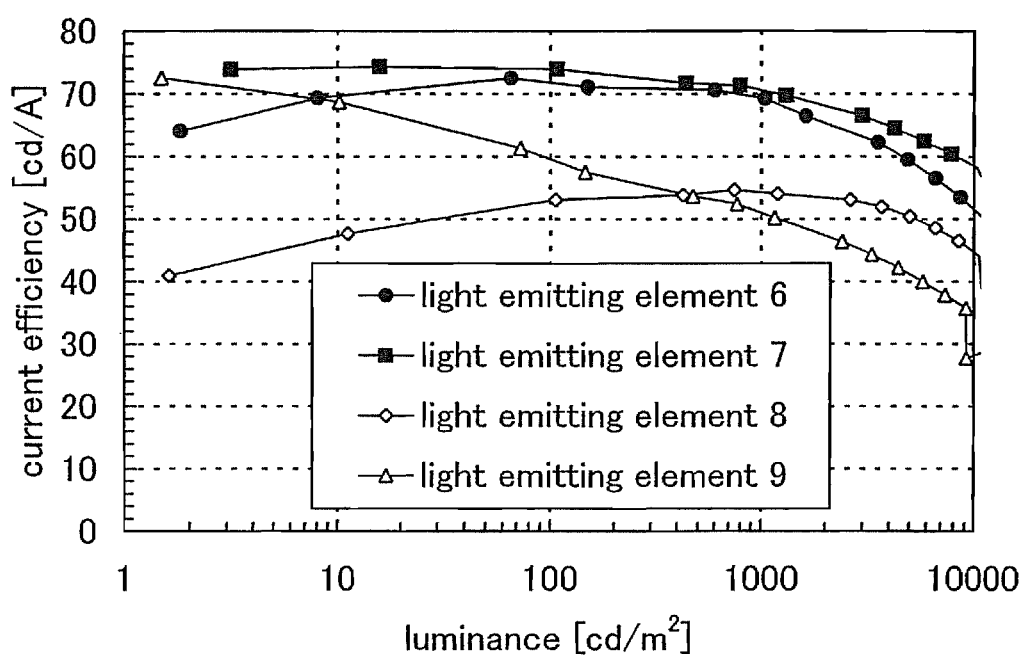
FIG. 50 is a graph showing the luminance-current efficiency characteristics of a light-emitting element manufactured in Embodiment 12.
Figure 51:
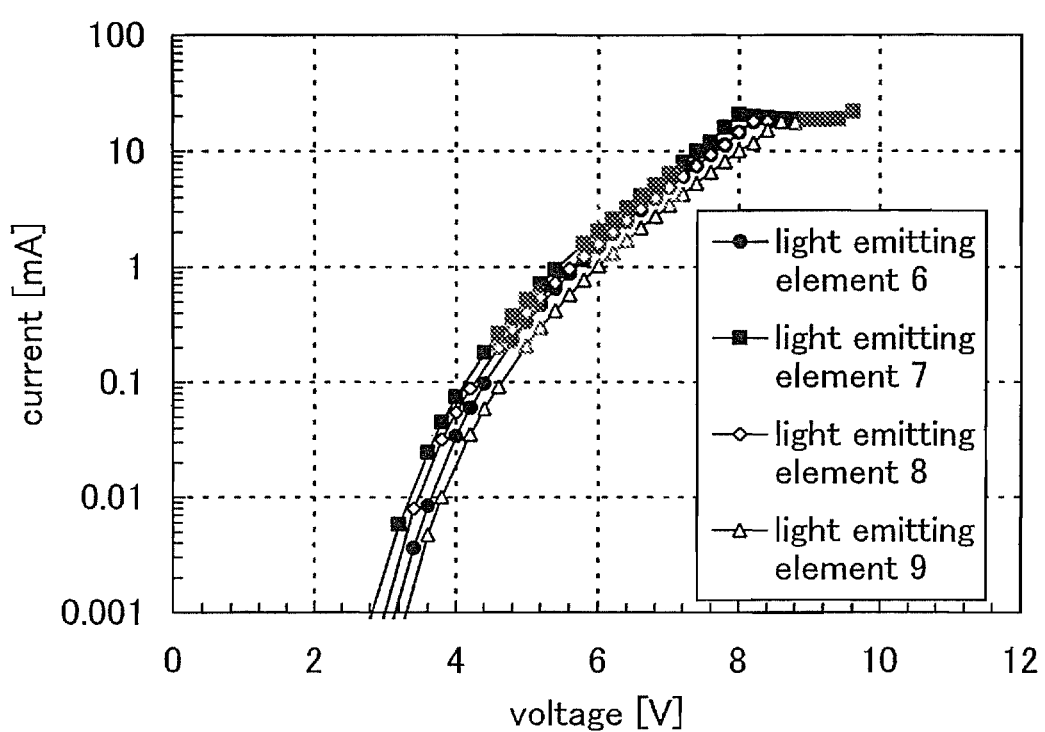
FIG. 51 is a graph showing the voltage-current characteristics of a light-emitting element manufactured in Embodiment 12.
Figure 52:
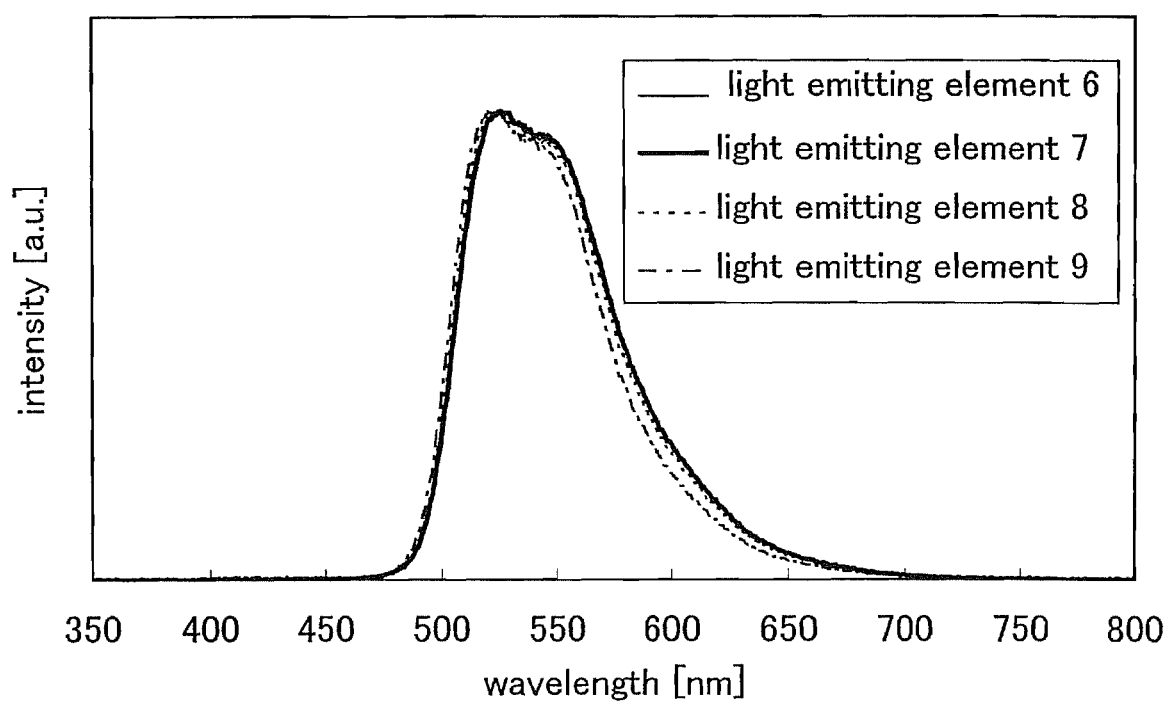
FIG. 52 is a graph showing the emission spectrum of a light-emitting element manufactured in Embodiment 12.

FIG. 48 shows the current density-luminance characteristics of each of the light-emitting elements 6 to 9. FIG. 49 shows the voltage-luminance characteristics of each of the light-emitting elements 6 to 9. FIG. 50 shows the luminance-current efficiency characteristics of each of the light-emitting elements 6 to 9. FIG. 51 shows the voltage-current characteristics of each of the light-emitting elements 6 to 9. FIG. 52 shows the emission spectrum of each of the light-emitting elements 6 to 9 at a current supply of 1 mA.

From the result shown in FIG. 52, it can be seen that light emission of the light-emitting elements 6 to 9 is light emission derived from Ir(ppy)$_2$(acac). Thus, it can be seen that, using a tiazole deribvative having high triplet excitation energy, the light-emitting elements of this embodiment can efficiently emit Ir(ppy)$_2$(acac) which shows green light emission.

The emission color of the light-emitting element 6 was located at the CIE chromaticity coordinates of (x=0.34, y=0.62) at a luminance of 1040 cd/m$^2$, and was green. In addition, the current efficiency and external quantum efficiency of the light-emitting element 6 at a luminance of 1040 cd/m$^2$ were 69 cd/A and 19%, respectively; thus, the light-emitting element 6 had extremely high efficiency. Further, when the luminance was 1040 cd/m$^2$, voltage, current density, and power efficiency of the light-emitting element 6 were 4.2 V, 1.5 mA/cm$^2$, and 52 lm/W, respectively, and the light-emitting element 6 had extremely high power efficiency.

The emission color of the light-emitting element 7 was located at the CIE chromaticity coordinates of (x=0.34, y=0.63) at a luminance of 800 cd/m$^2$, and was green. In addition, the current efficiency and external quantum efficiency of the light-emitting element 7 at a luminance of 800 cd/m$^2$ were 71 cd/A and 19%, respectively; thus, the light-emitting element 7 had extremely high efficiency. Further, when the luminance was 800 cd/m$^2$, voltage, current density, and power efficiency of the light-emitting element 5 were 3.8 V, 1.1 mA/cm$^2$, and 59 lm/W, respectively, and the light-emitting element 7 had extremely high power efficiency.

The emission color of the light-emitting element 8 was located at the CIE chromaticity coordinates of (x=0.34, y=0.63) at a luminance of 1190 cd/m$^2$, and was green. In addition, the current efficiency and external quantum efficiency of the light-emitting element 8 at a luminance of 1190 cd/m$^2$ were 54 cd/A and 15%, respectively; thus, the light-emitting element 8 had extremely high efficiency. Further, when the luminance was 1190 cd/m$^2$, voltage, current density, and power efficiency of the light-emitting element 8 were 4.2 V, 2.2 mA/cm$^2$, and 40 lm/W, respectively, and the light-emitting element 8 had extremely high power efficiency.

The emission color of the light-emitting element 9 was located at the CIE chromaticity coordinates of (x=0.32, y=0.64) at a luminance of 1150 cd/m$^2$, and was green. In addition, the current efficiency and external quantum efficiency of the light-emitting element 9 at a luminance of 1150 cd/m$^2$ were 50 cd/A and 14%, respectively; thus, the light-emitting element 9 had extremely high efficiency. Further, when the luminance was 1150 cd/m$^2$, voltage, current density, and power efficiency of the light-emitting element 9 were 4.6 V, 2.3 mA/cm², and 34 lm/W, respectively, and the light-emitting element 9 had extremely high power efficiency.

By application of the present invention, Ir(ppy)$_2$(acac) which is a phosphorescent compound which shows green light emission can be emitted efficiently. That is, high luminous efficiency can be achieved even in a case where a phosphorescent compound which shows light emission of a relatively short wavelength is used. Further, a light-emitting element, the power consumption of which is reduced, can be achieved.

Embodiment 13

This embodiment will describe a light-emitting element of the present invention with reference to FIG. 14. Hereinafter, a method of manufacturing a light-emitting element of this embodiment is described.
(Light-Emitting Element 10)

First, indium tin oxide containing silicon oxide (ITSO) was deposited over a glass substrate 2100 by a sputtering method to form a first electrode 2101. Note that the thickness of the first electrode 2101 was 110 nm and the electrode area was 2 mm×2 mm.

Next, the substrate having the first electrode 2101 was fixed to a substrate holder provided in a vacuum evaporation apparatus in such a way that a surface of the substrate 2100 over which the first electrode 2101 was formed faced downward, and then the pressure was reduced to approximately 10$^{-4}$ Pa. Next, 4,4'-bis[N-(1-naphthyl)-N-phenylamino]biphenyl (abbreviation: NPB) and molybdenum (VI) oxide were co-evaporated on the first electrode 2101, whereby a layer 2111 containing a composite material of an organic compound and an inorganic compound was formed. The thickness of the layer 2111 was set to be 40 nm and the weight ratio of NPB to molybdenum(VI) oxide was controlled to 4:1 (=NPB:molybdenum oxide). Note that the co-evaporation method is an evaporation method in which evaporation is performed from a plurality of evaporation sources at the same time in one treatment chamber.

Next, a hole-transporting layer 2112 was formed by depositing 4,4',4"-tris(carbazol-9-yl)triphenylamine (abbreviation: TCTA) to have a thickness of 10 nm on the layer 2111 containing a composite material by an evaporation method using resistance heating.

Furthermore, 9-{4-[4-phenyl-5-(2-pyridyl)-4H-1,2,4-triazole-3-yl]phenyl}-9H-carbazole (abbreviation: CPyTz1) which is represented by the structural formula (125) and bis(2-phenylpyridinato-N,C$^{2'}$)iridium(III)acetylacetonate (abbreviation: Ir(ppy)$_2$(acac)) were co-evaporated, whereby a 40 nm thick light-emitting layer 2113 was formed on the hole-transportinging layer 2112. Here, the weight ratio of CPyTz1 to Ir(ppy)$_2$(acac) was controlled to 1:0.05 (=CPyTz1:Ir(ppy)$_2$(acac)).

Then, an electron-transporting layer 2114 which is a layer in contact with the light-emitting layer 2113 was formed by depositing CPyTz1 to have a thickness of 10 nm on the light-emitting layer 2113 by an evaporation method using resistance heating.

Further, bathophenanthroline (abbreviation: BPhen) and lithium were co-evaporated on the electron-transporting layer 2114, whereby an electron-injecting layer 2115 was formed with a thickness of 20 nm. Here, the weight ratio of BPhen to lithium was controlled to 1:0.01 (=BPhen:lithium).

Finally, a second electrode 2102 was formed by depositing aluminum to have a thickness of 200 nm on the electron-injecting layer 2115 by an evaporation method using resistance heating. Thus, a light-emitting element 10 was formed.
(Light-Emitting Element 11)

Over the same substrate over which the light-emitting element 10 was formed, a light-emitting element 11 was formed in a manner similar to that of the light-emitting element 10 with the use of 9-{4-[5-phenyl-4-(8-quinolyl)-4H-1,2,4-triazol-3-yl]phenyl}-9H-carbazole (abbreviation: CQTZ1) which is represented by the structural formula (146) as an alternative to CPyTz1.

That is, 9-{4-[5-phenyl-4-(8-quinolyl)-4H-1,2,4-triazol-3-yl]phenyl}-9H-carbazole (abbreviation: CQTZ1) which is represented by the structural formula (146) and bis(2-phenylpyridinato-N,C$^{2'}$)iridium(III)acetylacetonate (abbreviation: Ir(ppy)$_2$(acac)) were co-evaporated, whereby the 40 nm thick light-emitting layer 2113 was formed on the hole-transporting layer 2112. Here, the weight ratio of CQTZ1 to Ir(ppy)$_2$(acac) was controlled to 1:0.05 (=CQTZ1:Ir(ppy)$_2$(acac)). After that, CQTZ1 was deposited over the light-emitting layer 2113 to have a thickness of 10 nm, and the electron-transporting layer 2114 which is a layer in contact with the light-emitting layer 2113 was formed.

Layers other than the light-emitting layer 2113 and the electron-transporting layer 2114 were formed in a manner similar to that of the light-emitting element 10.
(Light-Emitting Element 12)

Over the same substrate over which the light-emitting element 10 was formed, a light-emitting element 12 was formed in a manner similar to that of the light-emitting element 10 with the use of 9-{4-[4-(4-pyridyl)-5-(2-pyridyl)-4H-1,2,4-triazol-3-yl]phenyl}-9H-carbazole (abbreviation: CPy2Tz1) which is represented by the structural formula (137) as an alternative to CPyTz1.

That is, 9-{4-[4-(4-pyridyl)-5-(2-pyridyl)-4H-1,2,4-triazol-3-yl]phenyl}-9H-carbazole (abbreviation: CPy2Tz1) which is represented by the structural formula (137) and bis(2-phenylpyridinato-N,C$^{2'}$)iridium(III)acetylacetonate (abbreviation: Ir(ppy)$_2$(acac)) were co-evaporated to form the 40 nm thick light-emitting layer 2113 on the hole-transporting layer 2112. Here, the weight ratio of CPy2Tz1 to Ir(ppy)$_2$(acac) was controlled to 1:0.05 (=CPy2Tz1:Ir(ppy)$_2$(acac)). After that, CPy2Tz1 was deposited on the light-emitting layer 2113 to have a thickness of 10 nm, and the electron-transporting layer 2114 which is a layer in contact with the light-emitting layer 2113 was formed.

Layers other than the light-emitting layer 2113 and the electron-transporting layer 2114 were formed in a manner similar to that of the light-emitting element 10.
(Light-Emitting Element 13)

Over the same substrate over which the light-emitting element 10 was formed, a light-emitting element 13 was formed in a manner similar to that of the light-emitting element 10 with the use of 9-[4-(3,5-diphenyl-4H-1,2,4-triazol-4-yl)phenyl]-9H-carbazole (abbreviation: CzTAZ2) which is represented by the structural formula (201) as an alternative to CPyTz1.

That is, 9-[4-(3,5-diphenyl-4H-1,2,4-triazol-4-yl)phenyl]-9H-carbazole (abbreviation: CzTAZ2) which is represented by the structural formula (201) and bis(2-phenylpyridinato-N,C$^{2'}$)iridium(III)acetylacetonate (abbreviation: Ir(ppy)$_2$(acac)) were co-evaporated to form the 40 nm thick light-emitting layer 2113 on the hole-transporting layer 2112. Here, the weight ratio of CzTAZ2 to Ir(ppy)$_2$(acac) was controlled to 1:0.05 (=CzTAZ2:Ir(ppy)$_2$(acac)). After that, CzTAZ2 was deposited on the light-emitting layer 2113 to have a thickness of 10 nm, and the electron-transporting layer 2114 which is a layer in contact with the light-emitting layer 2113 was formed.

Layers other than the light-emitting layer 2113 and the electron-transporting layer 2114 were formed in a manner similar to that of the light-emitting element 10.

The light-emitting elements 10 to 13 thus obtained were each sealed in a glove box under a nitrogen atmosphere without being exposed to atmospheric air. Then, the operating characteristics of each of the light-emitting elements were measured. Note that the measurement was performed at a room temperature (atmosphere kept at 25° C.).

Figure 53:
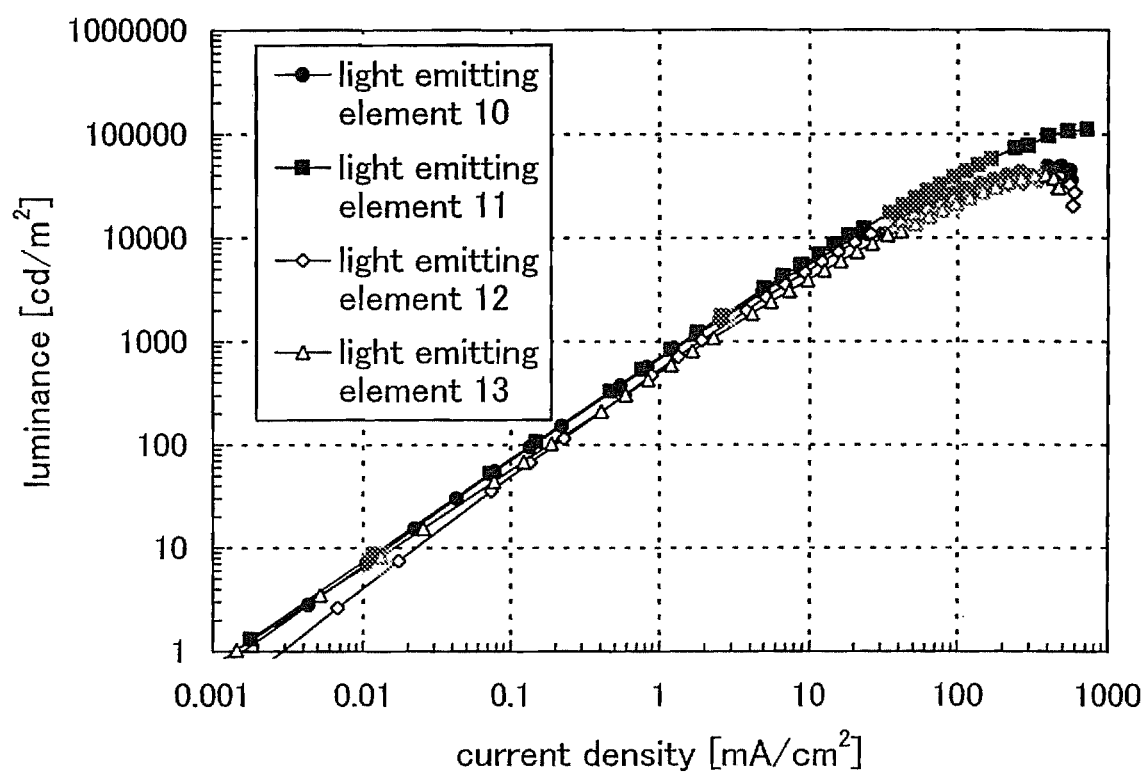
FIG. 53 is a graph showing the current density-luminance characteristics of a light-emitting element manufactured in Embodiment 13.
Figure 54:
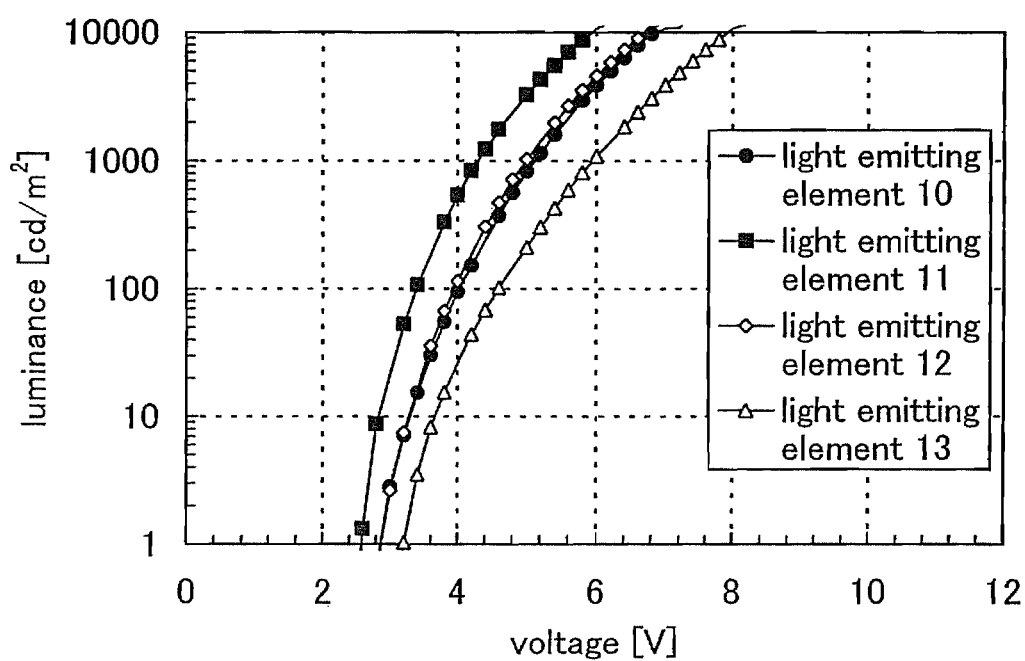
FIG. 54 is a graph showing the voltage-luminance characteristics of a light-emitting element manufactured in Embodiment 13.
Figure 55:
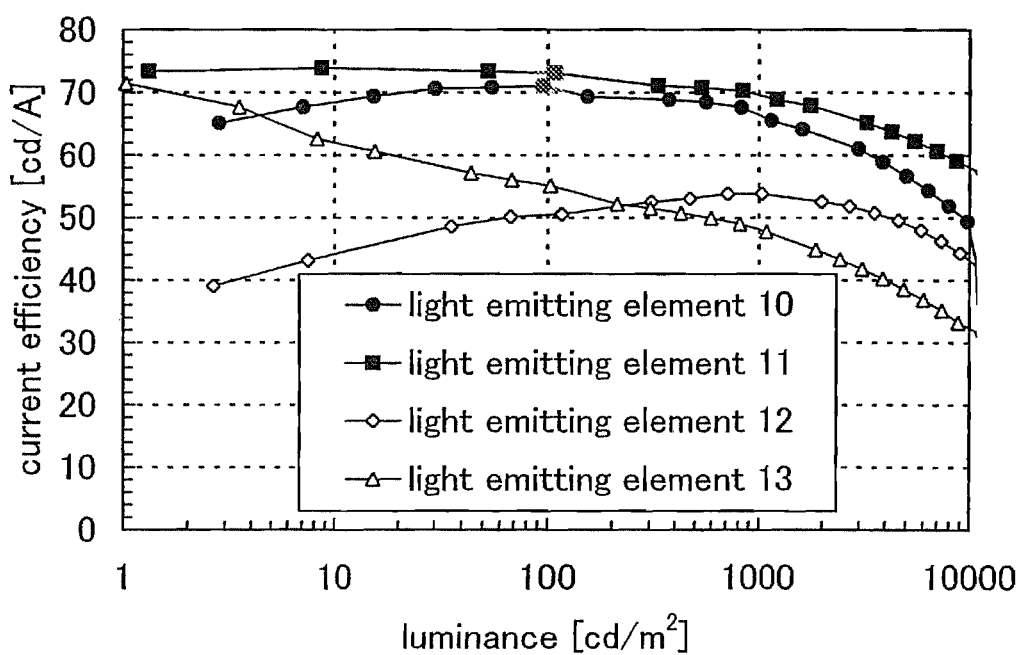
FIG. 55 is a graph showing the luminance-current efficiency characteristics of a light-emitting element manufactured in Embodiment 13.
Figure 56:
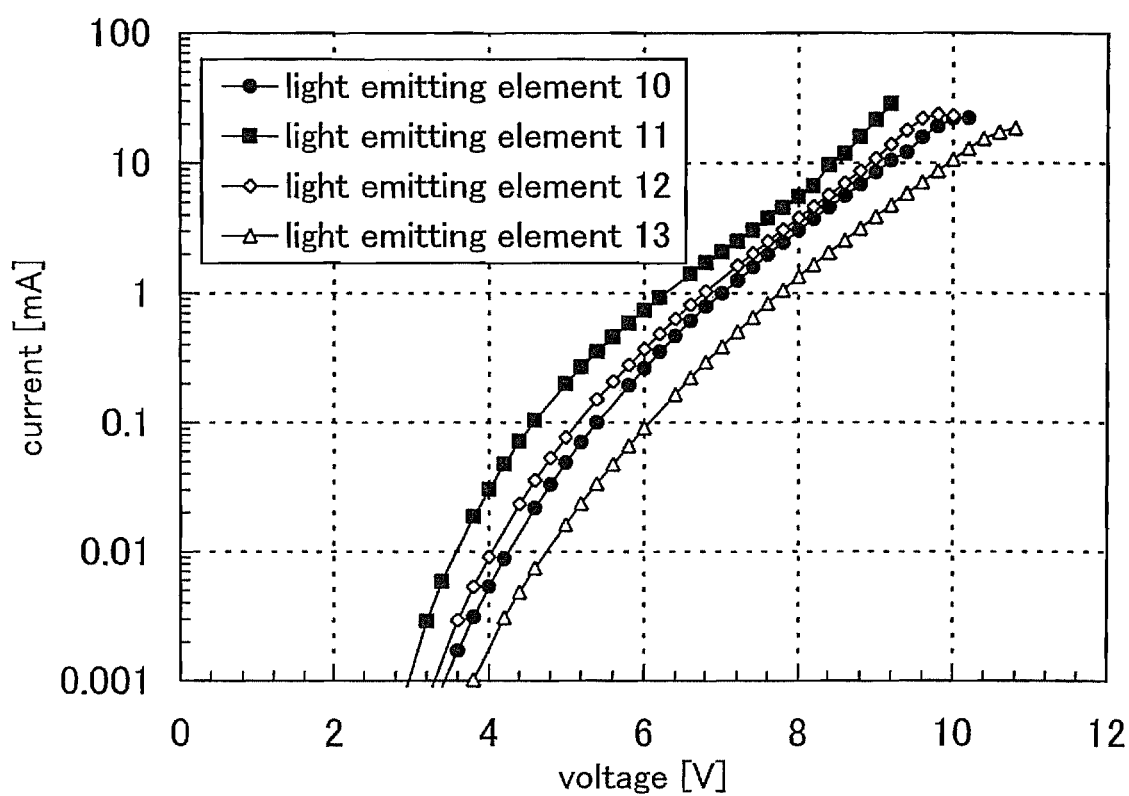
FIG. 56 is a graph showing the voltage-current characteristics of a light-emitting element manufactured in Embodiment 13.
Figure 57:
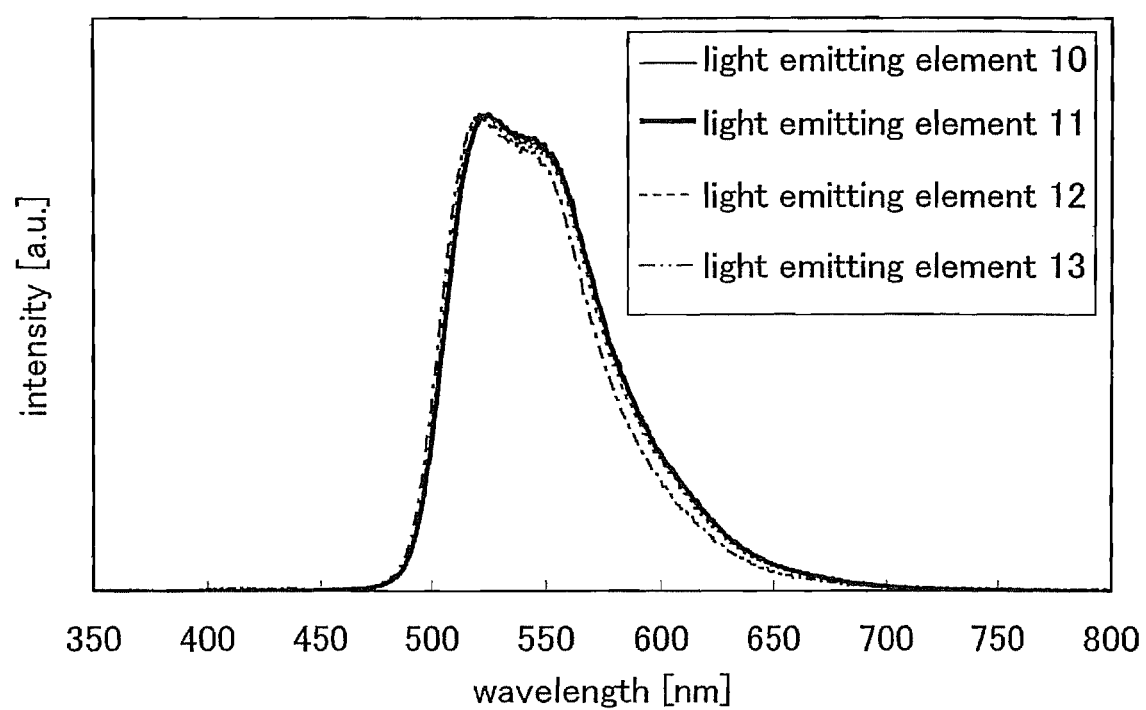
FIG. 57 is a graph showing the emission spectrum of a light-emitting element manufactured in Embodiment 13.

FIG. 53 shows the current density-luminance characteristics of each of the light-emitting elements 10 to 13. FIG. 54 shows the voltage-luminance characteristics of each of the light-emitting elements 10 to 13. FIG. 55 shows the luminance-current efficiency characteristics of each of the light-emitting elements 10 to 13. FIG. 56 shows the voltage-current characteristics of each of the light-emitting elements 10 to 13. FIG. 57 shows the emission spectrum of each of the light-emitting elements 10 to 13 at a current supply of 1 mA.

From the result shown in FIG. 57, it can be seen that light emission of the light-emitting elements 10 to 13 is light emission derived from Ir(ppy)$_2$(acac). Thus, it can be seen that, using a tiazole deribvative having high triplet excitation energy, the light-emitting elements of this embodiment can efficiently emit Ir(ppy)$_2$(acac) which shows green light emission.

The emission color of the light-emitting element 10 was located at the CIE chromaticity coordinates of (x=0.34, y=0.63) at a luminance of 1050 cd/m$^2$, and was green. In addition, the current efficiency and external quantum efficiency of the light-emitting element 10 at a luminance of 1050 cd/m$^2$ were 66 cd/A and 18%, respectively; thus, the light-emitting element 10 had extremely high efficiency. Further, when the luminance was 1050 cd/m$^2$, voltage, current density, and power efficiency of the light-emitting element 10 were 5.2 V, 1.8 mA/cm$^2$, and 40 lm/W, respectively, and the light-emitting element 10 had extremely high power efficiency.

The emission color of the light-emitting element 11 was located at the CIE chromaticity coordinates of (x=0.34, y=0.63) at a luminance of 840 cd/m$^2$, and was green. In addition, the current efficiency and external quantum efficiency of the light-emitting element 11 at a luminance of 840 cd/m$^2$ were 70 cd/A and 19%, respectively; thus, the light-emitting element 11 had extremely high efficiency. Further, when the luminance was 840 cd/m$^2$, voltage, current density, and power efficiency of the light-emitting element 11 were 4.2 V, 1.2 mA/cm$^2$, and 53 lm/W, respectively, and the light-emitting element 11 had extremely high power efficiency.

The emission color of the light-emitting element 12 was located at the CIE chromaticity coordinates of (x=0.33, y=0.63) at a luminance of 1030 cd/m$^2$, and was green. In addition, the current efficiency and external quantum efficiency of the light-emitting element 12 at a luminance of 1030 cd/m$^2$ were 54 cd/A and 15%, respectively; thus, the light-emitting element 12 had extremely high efficiency. Further, when the luminance was 1030 cd/m$^2$, voltage, current density, and power efficiency of the light-emitting element 12 were 5.0 V, 1.9 mA/cm$^2$, and 34 lm/W, respectively, and the light-emitting element 12 had extremely high power efficiency.

The emission color of the light-emitting element 13 was located at the CIE chromaticity coordinates of (x=0.32, y=0.64) at a luminance of 1090 cd/m$^2$, and was green. In addition, the current efficiency and external quantum efficiency of the light-emitting element 13 at a luminance of 1090 cd/m$^2$ were 48 cd/A and 13%, respectively; thus, the light-emitting element 13 had extremely high efficiency. Further, when the luminance was 1090 cd/m$^2$, voltage, current density, and power efficiency of the light-emitting element 13 were 6.0 V, 2.3 mA/cm$^2$, and 25 lm/W, respectively, and the light-emitting element 13 had extremely high power efficiency.

In addition, in the light-emitting elements of this embodiment, the triazole derivative of the present invention is used for the electron-transporting layer which is a layer in contact with the light-emitting layer. The triazole derivative of the present invention has high triplet excitation energy; therefore, energy transfer from the light-emitting layer does not easily occur in a case where the triazole derivative of the present invention is used for a layer in contact with the light-emitting layer. Accordingly, high luminous efficiency can be achieved.

By application of the present invention, Ir(ppy)$_2$(acac) which is a phosphorescent compound which shows green light emission can be emitted efficiently. That is, high luminous efficiency can be achieved even in a case where phosphorescent compound which shows light emission of a relatively short wavelength is used. Further, a light-emitting element, the power consumption of which is reduced, can be achieved.

The present application is based on Japanese Patent Application serial No. 2007-131228 filed with Japan Patent Office on May 17, 2007, the entire contents of which are hereby incorporated by reference.

EXPLANATION OF REFERENCE

100. substrate, 101. first electrode, 102. second electrode, 103. EL layer, 111. hole-injecting layer, 112. hole-transporting layer, 113. light-emitting layer, 114. electron-transporting layer, 115. hole-injecting layer, 501. first electrode, 502. second electrode, 511. first light-emitting unit, 512. second light-emitting unit, 513. charge generation layer, 601. driver circuit portion (source driver circuit), 602. pixel portion, 603. driver circuit portion (gate driver circuit), 604. sealing substrate, 605. sealing material, 607. space, 608. wiring, 609. flexible printed circuit (FPC), 610. element substrate, 611. switching TFT, 612. current-controlling TFT, 613. first electrode, 614. insulator, 616. EL layer, 617. second electrode, 618. light-emitting element, 623. n-channel TFT, 624. p-channel TFT, 901. chassis, 902. liquid crystal layer, 903. backlight, 904. chassis, 905. driver IC, 906. terminal, 951. substrate, 952. electrode, 953. insulating layer, 954. partition layer, 955. EL layer, 956. electrode, 2001. chassis, 2002. light source, 2100. glass substrate, 2101. first electrode, 2102. second electrode, 2111. layer containing composite material, 2112. hole-transporting layer, 2113. light-emitting layer, 2114. electron-transporting layer, 2115. electron-injecting layer, 3001. lighting system, 3002. television device, 4100. glass substrate, 4101. first electrode, 4102. second electrode, 4111. layer containing composite material, 4112. hole-transporting layer, 4113. light-emitting layer, 4114. electron-transporting layer, 4115. electron-injecting layer, 4116. layer containing composite material, 4117. hole-transporting layer, 4118. light-emitting layer, 4119. electron-transporting layer, 4120. electron-injecting layer, 4201. charge generation layer, 9101. chassis, 9102. supporting base, 9103. display portion, 9104. speaker portion, 9105. video input terminal, 9201. main body, 9202. chassis, 9203. display portion, 9204. keyboard, 9205. external connection port, 9206. pointing device, 9401. main body, 9402. chassis, 9403. display portion, 9404. audio input portion, 9405. audio output portion, 9406. operation key, 9407. external connection port, 9408. antenna, 9501. main body, 9502. display portion, 9503. chassis, 9504. external connection port, 9505. remote control receiving portion, 9506. image receiving portion, 9507. battery, 9508. audio input portion, 9509. operation key, and 9510. eye piece portion.

What is claimed is:

1. A triazole derivative represented by formula (TAZ-1),

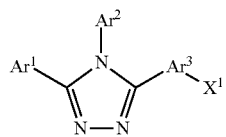

(TAZ-1)

wherein $Ar^1$ represents an aryl group having 6 to 25 carbon atoms or a heteroaryl group having 3 to 9 carbon atoms, wherein $Ar^3$ represents an arylene group having 6 to 25 carbon atoms or a heteroarylene group having 3 to 9 carbon atoms, wherein $Ar^2$ represents a heteroaryl group, and wherein $X^1$ represents a bromo group or an iodo group.

2. The triazole derivative according to claim 1, wherein $Ar^1$ represents a phenyl group, an o-tolyl group, a m-tolyl group, a p-tolyl group, a 4-tert-butylphenyl group, a 1-naphthyl group, a 2-naphthyl group, a 2-biphenyl group, a 3-biphenyl group, a 4-biphenylyl group, a 9,9-dimethylfluoren-2-yl group, a spiro-9,9'-bifluoren-2-yl group, a 1,3,5-triazin-2-yl group, a 1,2,4-triazin-3-yl group, a pyrimidin-4-yl group, a pyrazin-2-yl group, a 2-pyridyl group, a 3-pyridyl group, or a 4-pyridyl group, and wherein $Ar^2$ represents a 1,3,5-triazin-2-yl group, a 1,2,4-triazin-3-yl group, a pyrimidin-4-yl group, a pyrazin-2-yl group, a 2-pyridyl group, a 3-pyridyl group, or a 4-pyridyl group.

3. The triazole derivative according to claim 1, wherein $Ar^3$ represents a 1,2-phenylene group, a 1,3-phenylene group, a 1,4-phenylene group, a 2,5-dimethyl-1,4-phenylene group, a 1,4-naphthylene group, a 1,5-naphthylene group, a 4,4'-biphenylene group, a 9,9-dimethylfluorene-2,7-diyl group, a spiro-9,9'-bifluorene-2,7-diyl group, a pyridin-2,5-diyl group, or a pyridin-2,6-diyl group.

4. The triazole derivative according to claim 2, wherein $Ar^3$ represents a 1,2-phenylene group, a 1,3-phenylene group, a 1,4-phenylene group, a 2,5-dimethyl-1,4-phenylene group, a 1,4-naphthylene group, a 1,5-naphthylene group, a 4,4'-biphenylene group, a 9,9-dimethylfluorene-2,7-diyl group, a spiro-9,9'-bifluorene-2,7-diyl group, a pyridin-2,5-diyl group, or a pyridin-2,6-diyl group.

5. A triazole derivative represented by formula (TAZ-2),

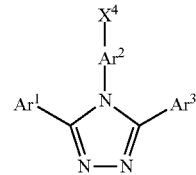

(TAZ-2)

wherein $Ar^1$ and $Ar^3$ each represent an aryl group having 6 to 25 carbon atoms, wherein $Ar^2$ represents a heteroarylene group having 3 to 9 carbon atoms, and wherein $X^4$ represents a bromo group or an iodo group.

6. The triazole derivative according to claim 5, wherein $Ar^1$ and $Ar^3$ each represent a phenyl group, an o-tolyl group, a m-tolyl group, a p-tolyl group, a 4-tert-butylphenyl group, a 1-naphthyl group, a 2-naphthyl group, a 2-biphenyl group, a 3-biphenyl group, a 4-biphenylyl group, a 9,9-dimethylfluoren-2-yl group, or a spiro-9,9'-bifluoren-2-yl group.

7. The triazole derivative according to claim 5, wherein $Ar^2$ represents a pyridin-2,5-diyl group or a pyridin-2,6-diyl group.

8. A triazole derivative represented by any one of formulae (B-13), (B-16), (B-18), (B-20), and (B-22),

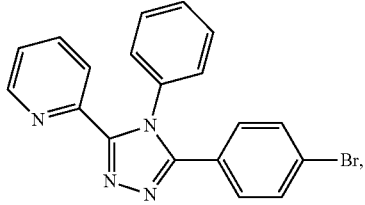

(B-13)

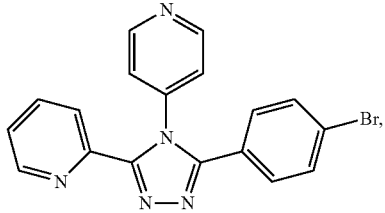

(B-16)

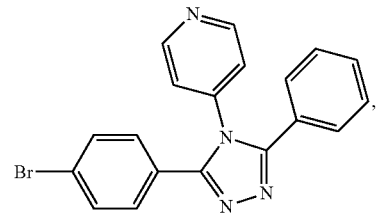

(B-18)

-continued (B-20)
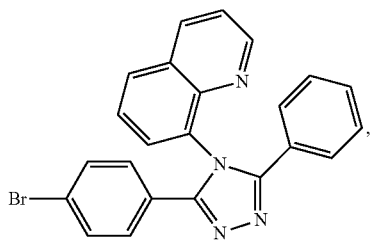

(B-22)
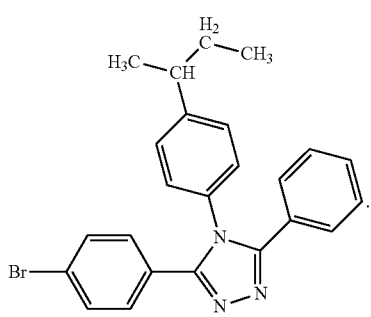

9. A triazole derivative represented by formula (TAZ-2), (TAZ-2)
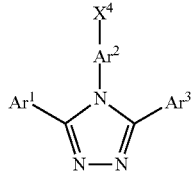

wherein $Ar^1$ and $Ar^3$ each represent an aryl group having 6 to 25 carbon atoms, wherein $Ar^2$ represents a 2,5-dimethyl-1,4-phenylene group, a 1,4-naphthylene group, a 1,5-naphthylene group, a 4,4'-biphenylene group, a 9,9-dimethylfluorene-2,7-diyl group, a spiro-9,9'-bifluorene-2,7-diyl group, a pyridin-2,5-diyl group, or a pyridin-2,6-diyl group, and wherein $X^4$ represents a chloro group.

10. The triazole derivative according to claim 9, wherein $Ar^1$ and $Ar^3$ each represent a phenyl group, an o-tolyl group, a m-tolyl group, a p-tolyl group, a 4-tert-butylphenyl group, a 1-naphthyl group, a 2-naphthyl group, a 2-biphenyl group, a 3-biphenyl group, a 4-biphenylyl group, a 9,9-dimethylfluoren-2-yl group, or a spiro-9,9'-bifluoren-2-yl group.

* * * * *